United States Patent
Bagley et al.

(10) Patent No.: US 11,661,419 B2
(45) Date of Patent: May 30, 2023

(54) BENZIMIDAZOLE DERIVATIVE COMPOUNDS AND USES THEREOF

(71) Applicant: Pfizer Inc., New York, NY (US)

(72) Inventors: Scott William Bagley, Mystic, CT (US); Agustin Casimiro-Garcia, Concord, MA (US); Xiayun Cheng, Old Saybrook, CT (US); Jennifer Elizabeth Davoren, Cambridge, MA (US); Rajiah Aldrin Denny, Sharon, MA (US); Brian Stephen Gerstenberger, Cambridge, MA (US); Frank Eldridge Lovering, Acton, MA (US); Mihir Dineshkumar Parikh, East Greenwich, RI (US); Joseph Walter Strohbach, Wentzville, MO (US); John Isidro Trujillo, Ledyard, CT (US)

(73) Assignee: Pfizer Inc., New York, NY (US)

( * ) Notice: Subject to any disclaimer, the term of this patent is extended or adjusted under 35 U.S.C. 154(b) by 97 days.

(21) Appl. No.: 17/126,358

(22) Filed: Dec. 18, 2020

(65) Prior Publication Data

US 2021/0188829 A1 Jun. 24, 2021

Related U.S. Application Data

(60) Provisional application No. 63/108,602, filed on Nov. 2, 2020, provisional application No. 62/951,030, filed on Dec. 20, 2019.

(51) Int. Cl.
| | | |
|---|---|---|
| *C07D 413/14* | (2006.01) | |
| *A61P 17/00* | (2006.01) | |
| *A61K 45/06* | (2006.01) | |

(52) U.S. Cl.
CPC ............ *C07D 413/14* (2013.01); *A61K 45/06* (2013.01); *A61P 17/00* (2018.01)

(58) Field of Classification Search
CPC .................................................. C07D 413/14
See application file for complete search history.

(56) References Cited

U.S. PATENT DOCUMENTS

2014/0088117 A1   3/2014   Burch et al.

FOREIGN PATENT DOCUMENTS

| CN | 103800327 A | 5/2014 |
|---|---|---|
| CN | 103800328 A | 5/2014 |
| CN | 103800337 A | 5/2014 |
| CN | 103800340 A | 5/2014 |
| CN | 103804272 A | 5/2014 |
| CN | 103804291 A | 5/2014 |
| CN | 103804302 A | 5/2014 |
| CN | 103804351 A | 5/2014 |
| CN | 103804361 A | 5/2014 |
| CN | 103804363 A | 5/2014 |
| CN | 103804364 A | 5/2014 |
| CN | 104628657 A | 5/2015 |
| EP | 2505586 A1 | 3/2012 |
| EP | 2455080 A1 | 5/2012 |
| EP | 2455081 A1 | 5/2012 |
| EP | 3165525 A1 | 5/2017 |
| JP | 2003231687 A2 | 8/2003 |
| WO | 2000069846 A1 | 11/2000 |
| WO | 2003035065 | 5/2003 |
| WO | 2003035065 A1 | 5/2003 |
| WO | 2003035644 A1 | 5/2003 |
| WO | 2005105788 A1 | 11/2005 |
| WO | 2006108488 A1 | 10/2006 |
| WO | 2007088401 A1 | 8/2007 |
| WO | 2008024981 A1 | 2/2008 |

(Continued)

OTHER PUBLICATIONS

Overview of Atopic Dermatitis [online] retrieved from interneton Nov. 18, 2022 URL: https://www.niams.nih.gov/health-topics/atopic-dermatitis.*
Atopic Dermatitis Treatment Options [online] retrieved from internet on Nov. 18, 2022 URL: https://www.healthline.com/health/atopic-dermatitis/treatment-option.*
No new references cited by the Examiner.*
Podlipnik et al., "Structural elements of TRK receptors and directives for development of their inhibitors", Slovenski Kemijski Dnevi, Maribor, Slovenia, Sep. 23-24, 2010 (2010), podi1/1-podi1/17.

(Continued)

*Primary Examiner* — Shawquia Jackson
(74) *Attorney, Agent, or Firm* — Young-In Julia Oh

(57) ABSTRACT

The invention relates to benzimidazoles of Formula (I)

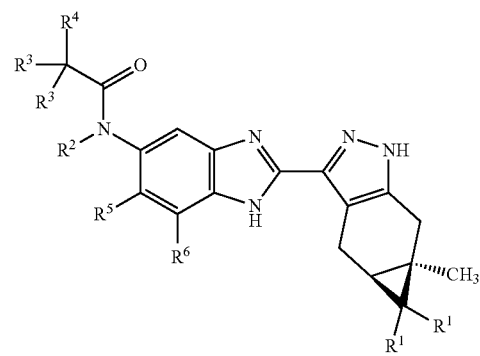

and pharmaceutically acceptable salts thereof, wherein $R^1$ to $R^6$ are as defined in the description; to their use in medicine; to compositions containing them; to processes for their preparation; and to intermediates used in such processes.
The benzimidazoles of Formula (I) are ITK inhibitors and are therefore potentially useful in the treatment of a wide range of disorders including, atopic dermatitis.

23 Claims, 7 Drawing Sheets

(56) References Cited

FOREIGN PATENT DOCUMENTS

| | | |
|---|---|---|
| WO | 2009106441 A1 | 9/2009 |
| WO | 2009106442 A1 | 9/2009 |
| WO | 2009106443 A1 | 9/2009 |
| WO | 2009106444 A1 | 9/2009 |
| WO | 2009106445 A1 | 9/2009 |
| WO | 2010066829 A1 | 6/2010 |
| WO | 2010072352 A1 | 7/2010 |
| WO | 2011018488 A1 | 2/2011 |
| WO | 2011065402 A1 | 3/2011 |
| WO | 2011113578 A1 | 9/2011 |
| WO | 2011117160 A1 | 9/2011 |
| WO | 2011144584 A1 | 11/2011 |
| WO | 2012036997 A1 | 3/2012 |
| WO | 2012109075 A1 | 8/2012 |
| WO | 2013024011 A1 | 2/2013 |
| WO | 2013030138 A1 | 3/2013 |
| WO | 2014023258 A1 | 2/2014 |
| WO | 2014041518 A1 | 3/2014 |
| WO | 16002918 | 1/2016 |
| WO | 16010108 | 1/2016 |
| WO | 2016001341 A1 | 1/2016 |
| WO | 16045598 A1 | 3/2016 |
| WO | 2016091916 A1 | 6/2016 |
| WO | 16115455 A2 | 7/2016 |
| WO | 2017004500 A1 | 1/2017 |
| WO | 19225740 A1 | 11/2019 |
| WO | 19225741 A1 | 11/2019 |
| WO | 19225768 A1 | 11/2019 |

OTHER PUBLICATIONS

Podlipnik et al., "DFG-in and DFG-out homology models of TrkB kinase receptor Induced-fit and ensemble docking", Journal of Molecular Graphics and Modelling, 2010, 309-320, 29, 3.

Boatman et al., "Potent tricyclic pyrazole tetrazole agonists of the nicotinic acid receptor (GPR109a)", Bioorganic & Medicinal Chemistry Letters, 2010, 2797-2800, 20, 9.

Tonkikh et al., "4(3H)-Quinazolinones containing heterocyclic group in position 3", Chemistry of Heterocyclic Compounds, 2000, 822-829, 36, 7.

Trani et al., "Design, synthesis and structure-activity relationships of a novel class of sulfonylpyridine inhibitors of interleukin-2 inducible T-cell kinase (ITK)", Bioorganic & Medicinal Chemistry Letters, 2014, 5818-5823, 24.

Burch et al., "Property- and Structure-Guided Discovery of a Tetrahydroindazole Series of Interleukin-2 Inducible T-Cell Kinase Inhibitors", Journal of Medicinal Chemistry, 2014, 5714-5727, 57.

Burch et al., "Tetrahydroindazoles as Interleukin-2 Inducible T-Cell Kinase Inhibitors. Part II. Second-Generation Analogues with Enhanced Potency, Selectivity, and Pharmacodynamic Modulation in Vivo", Journal of Medicinal Chemistry, 2015, 3806-3816, 58.

Lo et al., "Itk inhibitors: a patent review", Expert Opinion on Therapeutic Patents, 2010, 459-469, 20(4).

International Search Report and Written Opinion dated Feb. 17, 2021 for International application No. PCT/IB2020/062036, filed Dec. 16, 2020.

International Preliminary Report on Patentability, dated May 17, 2022; for International application No. PCT/IB2020/062036, filed Dec. 16, 2020, 7 pages.

* cited by examiner

BENZIMIDAZOLE DERIVATIVE COMPOUNDS AND USES THEREOF

The invention relates to benzimidazole derivatives, to their use in medicine, to compositions containing them, to processes for their preparation and to intermediates used in such processes. More especially the invention relates to inhibitors of interleukin-2-inducible T cell kinase (ITK) and their use in the treatment of diseases mediated by ITK, in particular skin diseases, such as dermatitis (e.g. atopic dermatitis).

Atopic dermatitis (AD) is a common chronic inflammatory skin disease with a prevalence to in both children and adults. AD patients suffer from dry and pruritic skin lesions which can greatly affect their quality of life. Genetic and environmental factors can contribute to skin barrier disruption and immune hyper-activation which are key drivers of AD pathogenesis.

The pathogenic role for T cells and the Th2 cell-derived cytokines, IL-4 and IL-13, in AD has been shown through the clinical development of dupilumab, an antibody to the IL-4 receptor that blocks the activity of both IL-4 and IL-13. The important activity of these cytokines is also consistent with the early clinical efficacy that has been observed with Janus kinase (JAK) inhibitors, which block signaling of IL-4 and IL-13 as well as additional inflammatory cytokines produced in the skin. A therapeutic strategy that can effectively control the production of IL-4 and IL-13 is an alternative approach to modulate this pathway. Additionally, Th1 cells, Th22 cells, and Th17 cells and the cytokines which they produce, IFNγ, IL-22, and IL-17, respectively, also contribute to AD pathogenesis.

An effective anti-inflammatory for AD would modulate the predominant T cell driven inflammatory response. Interleukin-2-inducible T cell kinase (ITK) is a member of the Tec family of tyrosine kinases. ITK expression is largely limited to immune cells such as T, natural killer (NK), natural killer T (NKT), and mast cells. In T cells, ITK amplifies T cell receptor (TCR)-dependent signals to promote T cell activation, cytokine production, and T cell proliferation. ITK deletion or inhibition of ITK activity in T cells results in suppression of TCR-induced IL-4 and IL-13 production, which plays a central role in contributing to the pathophysiology of AD. An ITK inhibitor is expected to have additional efficacy compared to an antagonist of the IL-4 receptor, as ITK also contributes to TCR-dependent production of numerous pro-inflammatory cytokines such as IL-2, IL-17, IL-22, IL-31, IFNγ, and TNF-α. Additionally, ITK deficient CD8+ T cells demonstrate impaired cytotoxic T lymphocyte expansion, reduced degranulation and defective cytolytic capacity. ITK deficient mice and/or mice treated with an ITK inhibitor demonstrate reduced disease in models of type I diabetes, lymphoproliferative disease, allergy/asthma, and airway hyperresponsiveness. Moreover, ITK-deficient mice or mice treated with an ITK inhibitor demonstrate reduced skin inflammation in models of dermatitis. Elevated levels of ITK were described in peripheral T cells from patients with moderate to severe AD, and ITK expression is elevated in skin lesions from AD patients.

Additionally, tropomyosin receptor kinases (TRKs) are expressed by cells in the skin such as keratinocytes, neurons, mast cells, and basophils. Both TRKA and its ligand, nerve growth factor (NGF), are present in the skin and their expression is enhanced in AD skin lesions. Levels of NGF in skin lesions from AD patients have been demonstrated to correlate with itch severity. Cytokines IL-4 and IL-13 which contribute to AD pathogenesis have been demonstrated to enhance TRKA expression by keratinocytes. In addition to regulating development and maintenance of neurons, NGF can sensitize nociceptors and promote pruritis in the skin. Pruritis is a major factor contributing to reduced quality of life for AD patients. A therapy which can suppress pruritis would not only provide relief for patients, but may also break the itch-scratch cycle which contributes to the barrier disruption and thus reduce the course and chronicity of the disease.

NGF is also expressed by and has effects on non-neuronal cells. NGF induces keratinocyte proliferation, promotes basophil activation, stimulates mast cell degranulation, and contributes to neurogenic itch and inflammation. Furthermore, TRKA expression has been reported on TCR-stimulated peripheral blood T cells and T cells collected from synovial fluid from arthritis patients, and NGF induces proliferation of T cells. Thus, inhibiting TRKA in the skin may suppress dermal inflammation in addition to reducing pruritis.

These data suggest that an ITK inhibitor will suppress pathogenic T cell responses and reduce cytokine production, and therefore have therapeutic value in the treatment of a variety of inflammatory and autoimmune diseases, including dermatological conditions, such as atopic dermatitis, contact dermatitis, psoriasis, alopecia areata, and vitiligo. Moreover an inhibitor of both ITK and TRKA activity should be of particular advantage in the treatment of dermatological conditions, such as those just mentioned (e.g. atopic dermatitis).

REFERENCES

Benecke H, et al. Expert Opin. Invest. Drugs. 2013; 22:1167-1179;
Bissonette R, Papp K A, et al. Brit. J. Derm. 2016; 175: 902-911;
Botchkarev V A, Yaar M, Peters E M J et al. J. Invest. Dermatology. 2006; 126:1719-1727;
Brunner P M, et al. J Allergy Clin Immunol. 2017; 139(4S): S65-S76;
Kapnick S M, Stinchcombe J C, et al. Immunol. 2017; 198:2699-2711;
Lin T A, McIntyre K W, et al. Biochemistry 2004; 43:11056-11062;
Matsumura S, Terao M, et al. J. Derm. Science 2015; 78:215-223;
Otsuka A, Nomura T, et al. Immunological Reviews. 2017; 278:246-262;
Raychaudhuri S P, Raychaudhuri S K, et al. Arthritis & Rheumatism 2011; 63:3243-3252;
Sabat R, Wolk K, et al. Seminars in Immunopathology 2019; 41:359-377;
Sahu N, and August A. Curr. Top. Med. Chem. 2009; 9:690-703;
Von Bonin A, Rausch A, et al. Exp. Derm. 2010; 20:41-47;
Yamaguchi J, Aihara M, et al. J. Dermatol. Science. 2008; 53:48-54

According to a first aspect of the invention there is provided a compound of Formula (I)

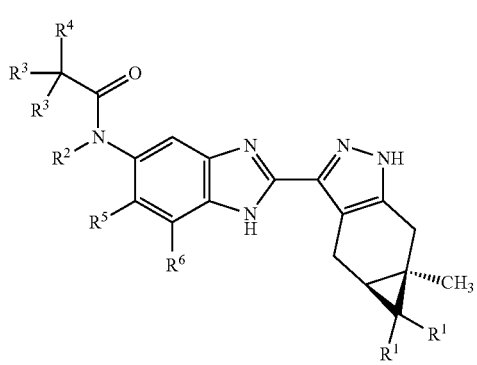

or a pharmaceutically acceptable salt thereof, or a pharmaceutically acceptable solvate of said compound or said salt, wherein each $R^1$ is independently H or F;

$R^2$ is H, $(C_1-C_4)$alkyl, hydroxy$(C_1-C_4)$alkyl, $(C_1-C_4)$alkoxy$(C_1-C_4)$alkyl or $(C_1-C_4)$alkyl substituted by one, two or three F;

each $R^3$ is independently H, F, $(C_3-C_5)$cycloalkyl, $(C_1-C_4)$alkyl or $(C_1-C_4)$alkyl substituted by one, two or three F; or both $R^3$ taken together with the carbon atom to which they are attached form $(C_3-C_5)$cycloalkyl;

$R^4$ is

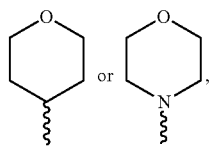

wherein each heterocycle is optionally substituted by one or two substituents independently selected from oxo, $(C_1-C_4)$alkyl, hydroxy$(C_1-C_4)$alkyl and $(C_1-C_4)$alkyl substituted by one, two or three F; and $R^5$ and $R^6$ are independently H; halogen; OH; CN; $(C_1-C_6)$alkyl; hydroxy$(C_1-C_6)$alkyl; $(C_1-C_4)$alkoxy$(C_1-C_6)$alkyl; $(C_1-C_6)$alkyl substituted by one, two or three F; $(C_1-C_6)$alkoxy; or $(C_1-C_6)$alkoxy substituted by $(C_1-C_4)$alkoxy.

Described below are embodiments of this first aspect of the invention, where for convenience E1 is identical thereto.

E1 A compound of Formula (I) or a pharmaceutically acceptable salt thereof, or a pharmaceutically acceptable solvate of said compound or said salt, as defined above.

E2 A compound according to embodiment E1 or a pharmaceutically acceptable salt thereof, or a pharmaceutically acceptable solvate of said compound or said salt, wherein each $R^1$ is H or F.

E3 A compound according to embodiment E2 or a pharmaceutically acceptable salt thereof, or a pharmaceutically acceptable solvate of said compound or said salt, wherein each $R^1$ is H.

E4 A compound according to any one of embodiments E1 to E3 or a pharmaceutically acceptable salt thereof, or a pharmaceutically acceptable solvate of said compound or said salt, wherein $R^2$ is H or $(C_1-C_4)$alkyl.

E5 A compound according to embodiment E4 or a pharmaceutically acceptable salt thereof, or a pharmaceutically acceptable solvate of said compound or said salt, wherein $R^2$ is H.

E6 A compound according to embodiment E4 or a pharmaceutically acceptable salt thereof, or a pharmaceutically acceptable solvate of said compound or said salt, wherein $R^2$ is methyl or ethyl.

E7 A compound according to embodiment E6 or a pharmaceutically acceptable salt thereof, or a pharmaceutically acceptable solvate of said compound or said salt, wherein $R^2$ is methyl.

E8 A compound according to embodiment E6 or a pharmaceutically acceptable salt thereof, or a pharmaceutically acceptable solvate of said compound or said salt, wherein $R^2$ is ethyl.

E9 A compound according to any one of embodiments E1 to E8 or a pharmaceutically acceptable salt thereof, or a pharmaceutically acceptable solvate of said compound or said salt, wherein each $R^3$ is independently H, F or $(C_1-C_4)$alkyl.

E10 A compound according to embodiment E9 or a pharmaceutically acceptable salt thereof, or a pharmaceutically acceptable solvate of said compound or said salt, wherein each $R^3$ is independently H, F or methyl.

E11 A compound according to embodiment E10 or a pharmaceutically acceptable salt thereof, or a pharmaceutically acceptable solvate of said compound or said salt, wherein each $R^3$ is F.

E12 A compound according to embodiment E10 or a pharmaceutically acceptable salt thereof, or a pharmaceutically acceptable solvate of said compound or said salt, wherein each $R^3$ is H.

E13 A compound according to embodiment E10 or a pharmaceutically acceptable salt thereof, or a pharmaceutically acceptable solvate of said compound or said salt, wherein one $R^3$ is H and the other $R^3$ is methyl.

E14 A compound according to embodiment E13 of Formula (Ia)

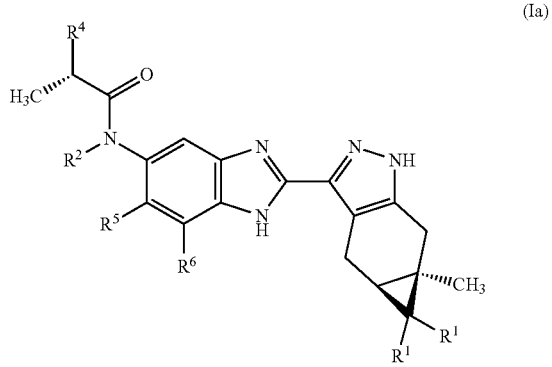

or a pharmaceutically acceptable salt thereof, or a pharmaceutically acceptable solvate of said compound or said salt.

E15 A compound according to any one of embodiments E1 to E14 or a pharmaceutically acceptable salt thereof, or a pharmaceutically acceptable solvate of said compound or said salt, wherein $R^4$ is

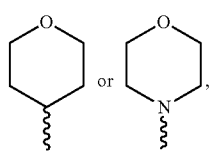

optionally substituted by one or two substituents independently selected from oxo, (C₁-C₄)alkyl and hydroxy(C₁-C₄)alkyl.

E16 A compound according to embodiment E15 or a pharmaceutically acceptable salt thereof, or a pharmaceutically acceptable solvate of said compound or said salt, wherein R⁴ is

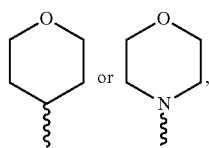

optionally substituted by one or two substituents independently selected from oxo, methyl and hydroxymethyl.

E17 A compound according to embodiment E16 or a pharmaceutically acceptable salt thereof, or a pharmaceutically acceptable solvate of said compound or said salt, wherein R⁴ is

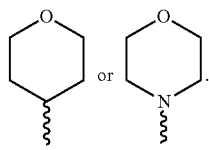

E18 A compound according to embodiment E17 or a pharmaceutically acceptable salt thereof, or a pharmaceutically acceptable solvate of said compound or said salt, wherein R⁴ is

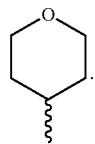

E19 A compound according to embodiment E16 or a pharmaceutically acceptable salt thereof, or a pharmaceutically acceptable solvate of said compound or said salt, wherein R⁴ is

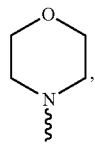

to optionally substituted by one or two substituents independently selected from oxo, methyl and hydroxymethyl.

E20 A compound according to embodiment E19 or a pharmaceutically acceptable salt thereof, or a pharmaceutically acceptable solvate of said compound or said salt, wherein R⁴ is

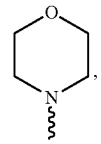

optionally substituted by oxo.

E21 A compound according to embodiment E19 or a pharmaceutically acceptable salt thereof, or a pharmaceutically acceptable solvate of said compound or said salt, wherein R⁴ is

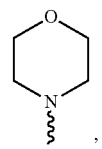

optionally substituted by one or two methyl.

E22 A compound according to embodiment E19 or a pharmaceutically acceptable salt thereof, or a pharmaceutically acceptable solvate of said compound or said salt, wherein R⁴ is

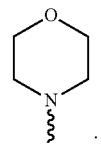

E23 A compound according to any one of embodiments E1 to E22 or a pharmaceutically acceptable salt thereof, or a pharmaceutically acceptable solvate of said compound or said salt, wherein R⁵ and R⁶ are independently H; halogen; OH; CN; (C₁-C₃)alkyl; hydroxy(C₁-C₃)alkyl; (C₁-C₃)alkoxy(C₁-C₃)alkyl; (C₁-C₃)alkyl substituted by one, two or three F; (C₁-C₃)alkoxy; or (C₁-C₃)alkoxy substituted by (C₁-C₃)alkoxy.

E24 A compound according to embodiment E23 or a pharmaceutically acceptable salt thereof, or a pharmaceutically acceptable solvate of said compound or said salt, wherein R⁵ is H, halogen, CN, (C₁-C₆)alkyl, (C₁-C₆)alkoxy or (C₁-C₆)alkoxy substituted by (C₁-C₄)alkoxy.

E25 A compound according to embodiment E24 or a pharmaceutically acceptable salt thereof, or a pharmaceutically acceptable solvate of said compound or said salt, wherein R⁵ is H, halogen, CN, (C₁-C₃)alkyl, (C₁-C₃)alkoxy or (C₁-C₃)alkoxy substituted by (C₁-C₃)alkoxy.

E26 A compound according to embodiment E25 or a pharmaceutically acceptable salt thereof, or a pharmaceutically acceptable solvate of said compound or said salt, wherein R⁵ is H, F, Br, CN, methyl, ethyl, methoxy or CH₃O—CH₂—CH₂O—.

E27 A compound according to any one of embodiments E1 to E26 or a pharmaceutically acceptable salt thereof, or a pharmaceutically acceptable solvate of said compound or said salt, wherein $R^6$ is H; halogen; OH; CN; $(C_1-C_6)$ alkyl; hydroxy$(C_1-C_6)$alkyl; $(C_1-C_4)$alkoxy$(C_1-C_6)$alkyl; $(C_1-C_6)$alkyl substituted by one, two or three F; or $(C_1-C_6)$alkoxy.

E28 A compound according to embodiment E27 or a pharmaceutically acceptable salt thereof, or a pharmaceutically acceptable solvate of said compound or said salt, wherein $R^6$ is H; halogen; OH; CN; $(C_1-C_3)$alkyl; hydroxy$(C_1-C_3)$alkyl; $(C_1-C_3)$alkoxy$(C_1-C_3)$alkyl; $(C_1-C_3)$alkyl substituted by one, two or three F; or $(C_1-C_3)$alkoxy.

E29 A compound according to embodiment E28, or a pharmaceutically acceptable salt thereof, or a pharmaceutically acceptable solvate of said compound or said salt, wherein $R^6$ is H, F, Cl, Br, OH, CN, methyl, ethyl, hydroxymethyl, methoxymethyl, CHF$_2$, CF$_3$ or methoxy.

E30 A compound according to embodiment E1 or a pharmaceutically acceptable salt thereof, or a pharmaceutically acceptable solvate of said compound or said salt, selected from:

Example 1: (S)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide;

Example 2: N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide;

Example 3: (R)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide;

Example 4: (R)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide;

Example 5: N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide;

Example 6: (S)—N-ethyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide;

Example 7: (R)—N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide;

Example 8: N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide;

Example 9: (S)—N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide;

Example 10: N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)acetamide;

Example 11: 2,2-difluoro-N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)acetamide;

Example 12: (R)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-(tetrahydro-2H-pyran-4-yl)propanamide;

Example 13: (S)—N-(2-((4aS,5aR)-5,5-difluoro-5a-methyl-1,4,4a,5,5a,6-hexahydrocyclopropa[f]indazol-3-yl)-1H-benzo[d]imidazol-5-yl)-N-methyl-2-morpholinopropanamide;

Example 14: (S)—N-methyl-N-(2-((4aS,5aR)-5a-methyl-1,4,4a,5,5a,6-hexahydrocyclopropa[f]indazol-3-yl)-1H-benzo[d]imidazol-5-yl)-2-morpholinopropanamide;

Example 15: (S)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 16: (S)—N-ethyl-N-(7-fluoro-2-((4aS,5aR)-5a-methyl-1,4,4a,5,5a,6-hexahydrocyclopropa[f]indazol-3-yl)-1H-benzo[d]imidazol-5-yl)-2-morpholinopropanamide;

Example 17: (S)—N-(6-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 18: (S)—N-(6-ethyl-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 19: (S)—N-(6-methoxy-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 20: (S)—N-(6-bromo-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 21: (S)—N-(6-cyano-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 22: (S)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-(3-oxomorpholino)propanamide;

Example 23: (R)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-(3-oxomorpholino)propanamide;

Example 24: (S)—N-(6,7-difluoro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 25: (S)—N-(6,7-difluoro-2-((4aS,5aR)-5a-methyl-1,4,4a,5,5a,6-hexahydrocyclopropa[f]indazol-3-yl)-1H-benzo[d]imidazol-5-yl)-N-ethyl-2-morpholinopropanamide;

Example 26: 2-((S)-2-(hydroxymethyl)morpholino)-N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)acetamide;

Example 27: 2-(2-(Hydroxymethyl)morpholino)-N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)acetamide;

Example 28: 2-((R)-2-(Hydroxymethyl)morpholino)-N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)acetamide;

Example 29: 2-(2,2-Dimethylmorpholino)-N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)acetamide;

Example 30: Methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-((R)-2-methylmorpholino)acetamide;

Example 31: Methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-((S)-2-methylmorpholino)acetamide;

Example 32: 2-((2R,6R)-2,6-Dimethylmorpholino)-N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)acetamide;

Example 33: 2-((2S,6S)-2,6-Dimethylmorpholino)-N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)acetamide;

Example 34: N-Methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinoacetamide;

Example 35: N-Methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)acetamide;

Example 36: N-Methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-(3-oxomorpholino)acetamide;

Example 37: (S)—N-(7-bromo-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 38: (S)—N-(7-cyano-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 39: (S)—N-(7-hydroxy-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 40: (S)—N-(7-methoxy-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 41: (S)—N-methyl-N-(2-((4aS,5aR)-5a-methyl-1,4,4a,5,5a,6-hexahydrocyclopropa[f]indazol-3-yl)-7-(trifluoromethyl)-1H-benzo[d]imidazol-5-yl)-2-morpholinopropanamide;

Example 42: (S)—N-(7-(methoxymethyl)-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 43: (S)—N-(7-chloro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 44: (S)—N-(7-ethyl-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 45: (S)—N-(7-(hydroxymethyl)-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 46: (S)—N-(7-fluoro-6-methyl-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 47: (S)—N-(6-fluoro-7-methyl-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 48: (S)—N-(7-(difluoromethyl)-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 49: (S)—N-(6-(2-methoxyethoxy)-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 50: (S)—N-methyl-N-(7-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide; and Example 51: (S)—N-(2-((4aS,5aR)-5,5-difluoro-5a-methyl-1,4,4a,5,5a,6-hexahydrocyclopropa[f]indazol-3-yl)-7-methyl-1H-benzo[d]imidazol-5-yl)-N-methyl-2-morpholinopropanamide.

E31 A compound according to embodiment E1 or a pharmaceutically acceptable salt thereof, or a pharmaceutically acceptable solvate of said compound or said salt, selected from:

Example 52: (S)—N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide;

Example 53: (S)—N-(2-((4aS,5aR)-5,5-difluoro-5a-methyl-1,4,4a,5,5a,6-hexahydrocyclopropa[f]indazol-3-yl)-5-methyl-1H-benzo[d]imidazol-6-yl)-N-methyl-2-morpholinopropanamide;

Example 54: N-(6-cyano-2-((4aS,5aR)-5a-methyl-1,4,4a,5,5a,6-hexahydrocyclopropa[f]indazol-3-yl)-1H-benzo[d]imidazol-5-yl)-N-methyl-2-(tetrahydro-2H-pyran-4-yl)acetamide;

Example 55: (R)—N-(7-cyano-2-((4aS,5aR)-5a-methyl-1,4,4a,5,5a,6-hexahydrocyclopropa[f]indazol-3-yl)-1H- benzo[d]imidazol-5-yl)-N-methyl-2-(tetrahydro-2H-pyran-4-yl)propenamide; and

Example 56: (S)—N-(methyl-$^{13}$C-d$_3$)-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide.

E32 A compound according to embodiment E1 or a pharmaceutically acceptable salt thereof, or a pharmaceutically acceptable solvate of said compound or said salt, selected from:

Example 1: (S)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide;

Example 7: (R)—N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide;

Example 12: (R)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-(tetrahydro-2H-pyran-4-yl)propanamide;

Example 15: (S)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 16: (S)—N-ethyl-N-(7-fluoro-2-((4aS,5aR)-5a-methyl-1,4,4a,5,5a,6-hexahydrocyclopropa[f]indazol-3-yl)-1H-benzo[d]imidazol-5-yl)-2-morpholinopropanamide;

Example 24: (S)—N-(6,7-difluoro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

Example 25: (S)—N-(6,7-difluoro-2-((4aS,5aR)-5a-methyl-1,4,4a,5,5a,6-hexahydrocyclopropa[f]indazol-3-yl)-1H-benzo[d]imidazol-5-yl)-N-ethyl-2-morpholinopropanamide;

Example 46: (S)—N-(7-fluoro-6-methyl-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide; and Example 50: (S)—N-methyl-N-(7-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide.

E33 The compound according to embodiment E32 which is (S)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide, or a pharmaceutically acceptable salt thereof, or a pharmaceutically acceptable solvate of said compound or said salt.

E34 The compound according to embodiment E32 which is (R)—N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide, or a pharmaceutically acceptable salt thereof, or a pharmaceutically acceptable solvate of said compound or said salt.

E35 The compound according to embodiment E32 which is (R)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-(tetrahydro-2H-pyran-4-yl)propanamide, or a pharmaceutically acceptable salt thereof, or a pharmaceutically acceptable solvate of said compound or said salt.

E36 The compound according to embodiment E32 which is (S)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide, or a pharmaceutically acceptable salt thereof, or a pharmaceutically acceptable solvate of said compound or said salt.

E37 The compound according to embodiment E32 which is (S)—N-ethyl-N-(7-fluoro-2-((4aS,5aR)-5a-methyl-1,4,4a,5,5a,6-hexahydrocyclopropa[f]indazol-3-yl)-1H-benzo[d]imidazol-5-yl)-2-morpholinopropanamide, or a pharmaceutically acceptable salt thereof, or a pharmaceutically acceptable solvate of said compound or said salt.

E38 The compound according to embodiment E32 which is (S)—N-(6,7-difluoro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide, or a pharmaceutically acceptable salt thereof, or a pharmaceutically acceptable solvate of said compound or said salt.

E39 The compound according to embodiment E32 which is (S)—N-(6,7-difluoro-2-((4aS,5aR)-5a-methyl-1,4,4a,5,5a,6-hexahydrocyclopropa[f]indazol-3-yl)-1H-benzo[d]imidazol-5-yl)-N-ethyl-2-morpholinopropanamide, or a pharmaceutically acceptable salt thereof, or a pharmaceutically acceptable solvate of said compound or said salt.

E40 The compound according to embodiment E32 which is (S)—N-(7-fluoro-6-methyl-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide, or a pharmaceutically acceptable salt thereof, or a pharmaceutically acceptable solvate of said compound or said salt.

E41 The compound according to embodiment E32 which is (S)—N-methyl-N-(7-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide, or a pharmaceutically acceptable salt thereof, or a pharmaceutically acceptable solvate of said compound or said salt.

E42 The compound according to embodiment E33 which is (S)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide, or a pharmaceutically acceptable solvate thereof.

E43 The compound according to embodiment E42 which is (S)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide, or a hydrate thereof.

E44 The compound according to embodiment E43 which is (S)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide, dihydrate.

E45 The compound according to embodiment E33 which is

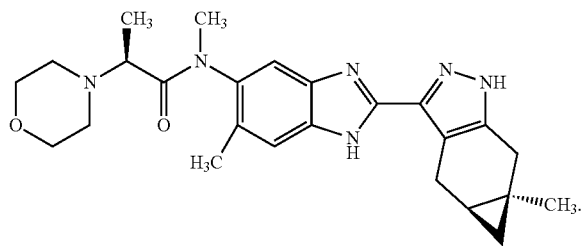 [SMILES: Cc1cc2[nH]c(-c3n[nH]c4c3C[C@@H]3C[C@]3(C)C4)nc2cc1N(C)C(=O)[C@H](C)N1CCOCC1]

E46 A crystalline form of the compound according to embodiment E44.

E47 The crystalline form according to embodiment E46 with one, two, three, four or five PXRD peaks selected from 6.6°±0.2° 2θ, 7.4°±0.2° 2θ, 11.0°±0.2° 2θ, 11.6°±0.2° 2θ, 15.7°±0.2° 2θ and 17.7°±0.2° 2θ.

E48 The crystalline form according to embodiment E47 with PXRD peaks at 6.6°±0.2° 2θ, 11.0°±0.2° 2θ, 15.7°±0.2° 2θ and 17.7°±0.2° 2θ.

E49 The crystalline form according to embodiment E47 with PXRD peaks at 6.6°±0.2° 2θ, 7.4°±0.2° 2θ, 11.0°±0.2° 2θ and 11.6°±0.2° 2θ.

E50 The crystalline form according to embodiment E47 with PXRD peaks at 7.4°±0.2° 2θ, 11.6°±0.2° 2θ, 15.7°±0.2° 2θ and 17.7°±0.2° 2θ.

E51 The crystalline form according to embodiment E47 with PXRD peaks at 6.6°±0.2° 2θ, 7.4°±0.2° 2θ, 11.0°±0.2° 2θ, 11.6°±0.2° 2θ, 15.7°±0.2° 2θ and 17.7°±0.2° 2θ.

E52 The crystalline form according to embodiment E46 with PXRD peaks at 6.6°±0.2° 2θ, 7.4°±0.2° 2θ, 11.0°±0.2° 2θ, 11.6°±0.2° 2θ, 13.3°±0.2° 2θ, 15.7°±0.2° 2θ, 16.2°±0.2° 2θ, 17.7°±0.2° 2θ, 18.8°±0.2° 2θ and 22.9°±0.2° 2θ.

Figure 1:
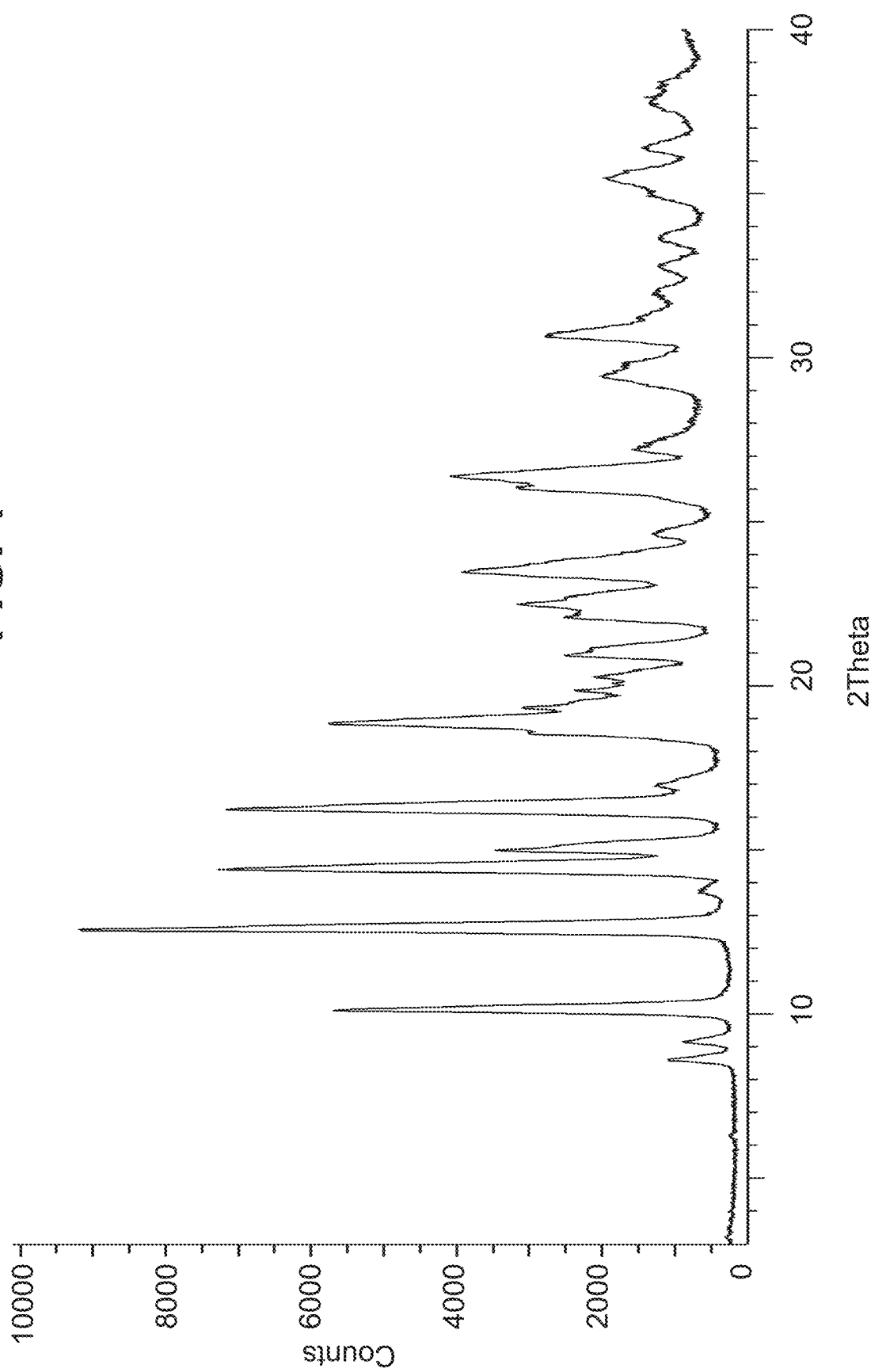
FIG. 1 is the PXRD pattern for the compound of Example 1.1 (crystal Form 1).

In compounds of Formula (I):

Alkyl means a straight or branched chain hydrocarbon group of formula $—C_nH_{(2n+1)}$. Examples of alkyl include methyl, ethyl, n-propyl, i-propyl, n-butyl, i-butyl, sec-butyl and t-butyl.

Alkyloxy means an alkyl substituent attached through an oxygen atom. Examples of alkyloxy include methoxy, ethoxy, n-propoxy, i-propoxy, n-butoxy, i-butoxy, sec-butoxy and t-butoxy.

Cycloalkyl means a cyclic hydrocarbon group of formula $—C_nH_{(2n-1)}$ containing at least three carbon atoms. Examples of Cycloalkyl include cyclopropyl, cyclobutyl nd cyclopentyl.

Examples of halogen include fluoro (F), chloro (Cl), bromo (Br) and iodo (I).

Oxo refers to a double bonded oxygen (═O).

Hereinafter, all references to compounds of the invention include compounds of Formula (I) or pharmaceutically acceptable salts, solvates, or multi-component complexes thereof, or pharmaceutically acceptable solvates or multi-component complexes of pharmaceutically acceptable salts of compounds of Formula (I), as discussed in more detail below.

Preferred compounds of the invention are compounds of Formula (I) or pharmaceutically acceptable salts thereof or pharmaceutically acceptable solvates of said compounds or said salts.

Further preferred compounds of the invention are compounds of Formula (I) or to pharmaceutically acceptable solvates thereof.

Further preferred compounds of the invention are compounds of Formula (I) or pharmaceutically acceptable hydrates thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, 1,5-naphthalenedisulfonate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Hemisalts of acids may also be formed, for example, hemisulphate and hemitartrate salts.

The skilled person will appreciate that the aforementioned salts include ones wherein the counterion is optically active, for example d-lactate, or racemic, for example dl-tartrate.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of Formula (I) may be prepared by one or more of three methods:

(i) by reacting the compound of Formula (I) with the desired acid;

(ii) by removing an acid-labile protecting group from a suitable precursor of the compound of Formula (I) using the desired acid; or (iii) by converting one salt of the compound of Formula (I) to another by reaction with an appropriate acid or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of Formula (I) or pharmaceutically acceptable salts thereof may exist in both unsolvated and solvated forms. The term 'solvate' is used herein to describe a molecular complex comprising a compound of Formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) of compounds of Formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The term '2 theta' or '2θ' refers to the PXRD peak position in degrees along the x-axis.

A typical error associated with PXRD peak position is up to +/−0.2° 2θ (USP-941). The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970), incorporated herein by reference.

The compounds of the invention may be administered as prodrugs. Thus certain derivatives of compounds of Formula (I) which may have little or no pharmacological activity themselves can, when administered into or onto the body, be converted into compounds of Formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of Formula (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of Formula (I), that is, compounds formed in vivo upon administration of the drug. Examples of metabolites in accordance with the invention include, where the compound of Formula (I) contains a morpholinyl moiety according to embodiment E19, hydroxylethyl amines of Formula (Ib), and amines of Formulae (Ic), as shown below.

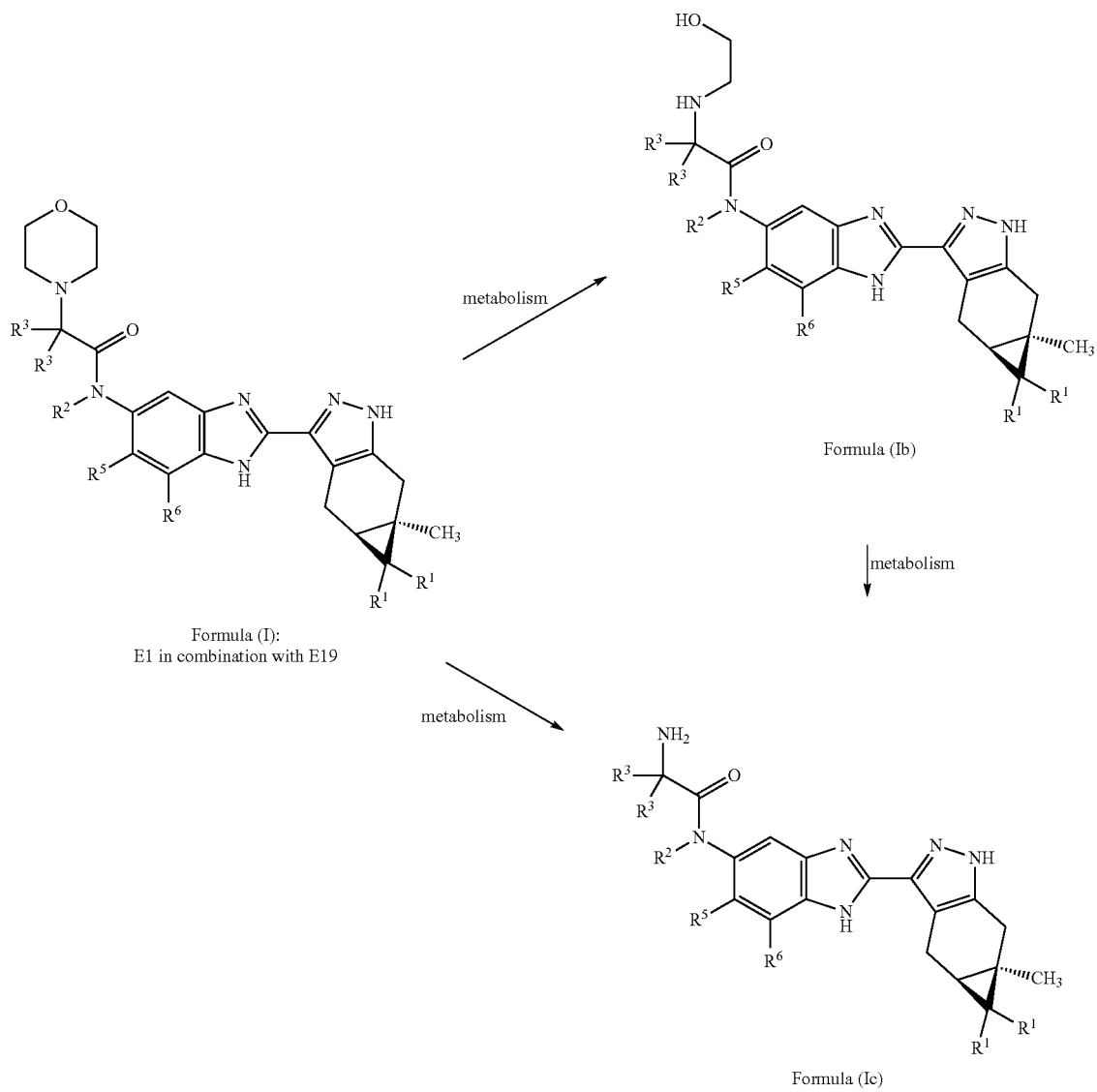

Formula (I):
E1 in combination with E19

Formula (Ib)

Formula (Ic)

The compounds M1 and M2 below, metabolites of the compound of Ex1, illustrate this aspect of the invention and are of particular interest.

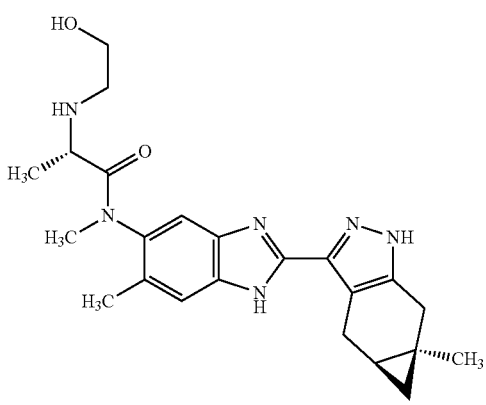

M1

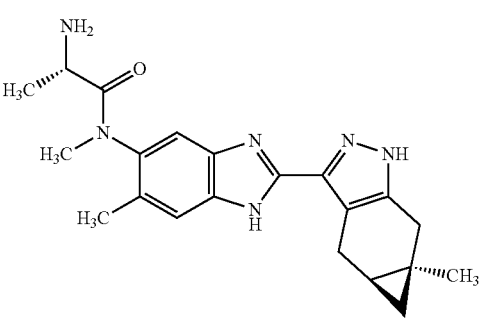

M2

Other examples of metabolites in accordance with the invention include:

(i) hydroxymethyl derivatives (—$CH_3$ → —$CH_2OH$);

(ii) where the compound of Formula (I) contains an alkoxy group, a hydroxy derivative thereof (—($C_1$-$C_6$) alkoxy → —OH); and (iii) where the compound of Formula (I) contains a phenyl moiety, a phenol derivative thereof (-Ph→-PhOH).

Formula (I) contains an asymmetric cyclopropaindazolyl moiety and is stereospecifically defined (as the '4aS,5aR' stereoisomer).

The skilled person will appreciate that one or more substituents in Formula (I) may introduce one or more additional asymmetric centres. An illustration of such an additional asymmetric centre is the asymmetric carbon atom of a compound of Formula (Ia) or a pharmaceutically acceptable salt thereof, or a pharmaceutically acceptable solvate of said compound or said salt, according to Embodiment E14, marked by an asterisk (*) in the representation of Formula (Ia) below:

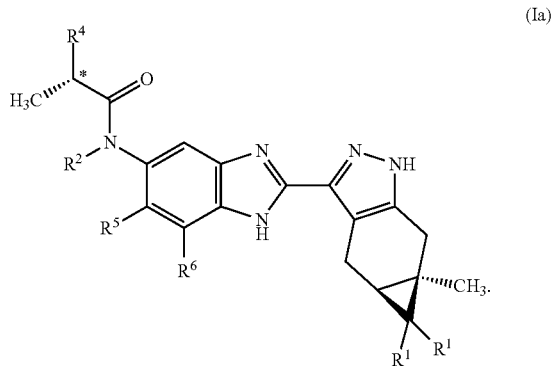

(Ia)

Compounds of the invention containing said one or more additional asymmetric centres can exist as two or more stereoisomers; included within the scope of the invention are all such stereoisomers (including epimers) of the compounds of the invention and mixtures of two or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of Formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Chiral chromatography using sub- and supercritical fluids may be employed. Methods for chiral chromatography useful in some embodiments of the present invention are known; see, for example, Smith, Roger M., Loughborough University, Loughborough, UK; Chromatographic Science Series (1998), 75 (Supercritical Fluid Chromatography with Packed Columns), pp. 223-249 and references cited therein.

Mixtures of stereoisomers may be separated by conventional techniques known to those skilled in the art; see, for example, "Stereochemistry of Organic Compounds" by E. L. Eliel and S. H. Wilen (Wiley, New York, 1994.

Where structural isomers are interconvertible via a low energy barrier, tautomeric isomerism ('tautomerism') and conformational isomerism can occur.

Tautomerism can take the form of proton tautomerism in compounds of Formula (I), as illustrated below in Formula (I) generally, and Example 1 specifically, with respect to the benzimidazole group:

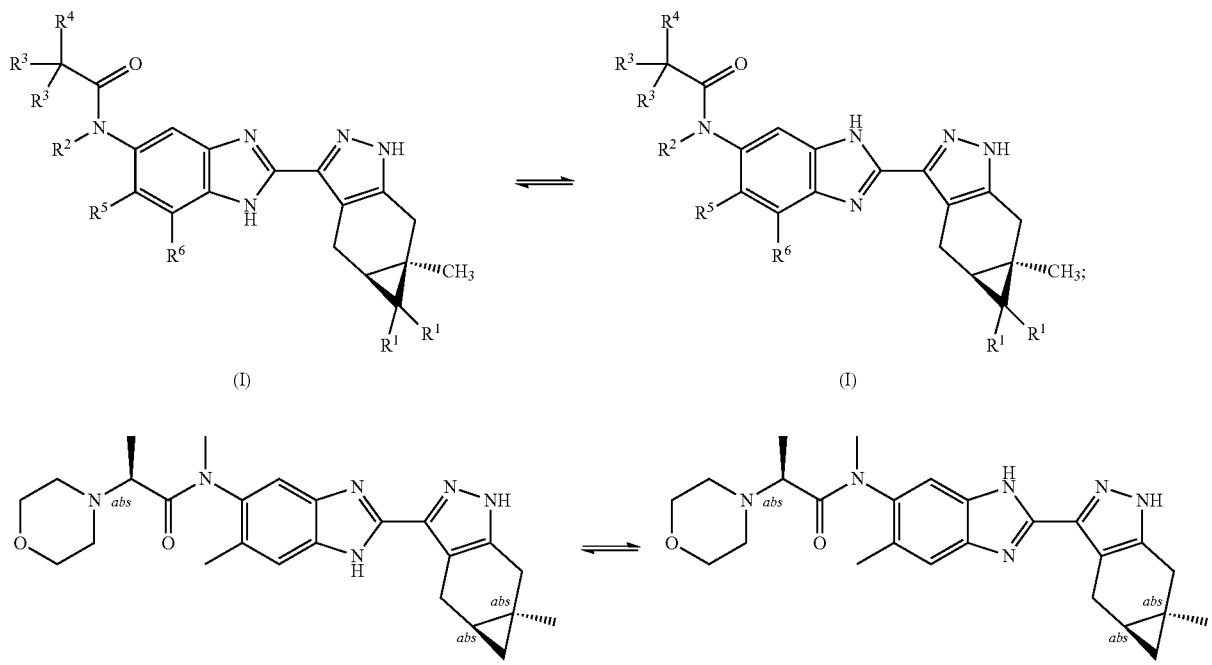

The skilled person will appreciate that proton tautomerism can also take place on the pyrazole ring in compounds of Formula (I).

While, for conciseness, the compounds of Formula (I) have been drawn herein in a single tautomeric form, all possible tautomeric forms, and mixtures thereof, are included within the scope of the invention.

Conformational isomerism is a form of stereoisomerism in which the isomers of a compound can be interconverted exclusively by rotations about single bonds. Such isomers are generally referred to as conformational isomers or conformers and, specifically, as rotamers. A "rotameric mixture", or "mixture of rotamers", describes a compound existing as a mixture of more than one of the possible conformational isomers. While, for conciseness, the compounds of Formula (I) have been drawn in a single conformational form, all possible conformers, and mixtures thereof, are included within the scope of the invention.

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of: hydrogen, such as $^2$H and $^3$H; carbon, such as $^{11}$C, $^{13}$C and $^{14}$C; fluorine, such as $^{18}$F; chlorine, such as $^{36}$Cl; iodine, such as $^{123}$I and $^{125}$I; nitrogen, such as $^{13}$N and $^{15}$N; oxygen, such as $^{15}$O, $^{17}$O and $^{18}$O.

Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium (D), i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{15}$O and $^{13}$N, can be useful in Positron Emission Topography (PET) studies for examining substrate receptor occupancy.

Isotopically-labeled compounds of Formula (I) can generally be prepared by conventional techniques known to those skilled in the art or by processes analogous to those described in the accompanying examples and preparations using an appropriate isotopically-labeled reagent in place of the non-labeled reagent previously employed.

Also within the scope of the invention are intermediate compounds as hereinafter defined, all salts, solvates and complexes thereof, and all solvates and complexes of salts thereof as defined hereinbefore for compounds of Formula (I). The invention includes all polymorphs of the aforementioned species and crystal habits thereof.

When preparing a compound of Formula (I) in accordance with the invention, a person skilled in the art may routinely select the form of intermediate which provides the best combination of features for this purpose. Such features include the melting point, solubility, processability and yield of the intermediate form and the resulting ease with which the product may be purified on isolation.

The compounds of the invention may be prepared by any method known in the art for the preparation of compounds of analogous structure. In particular, the compounds of the invention can be prepared by the procedures described by reference to the schemes that follow, or by the specific methods described in the examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of Formula (I). It will be further appreciated that it may be necessary or desirable to carry out the transformations in a different order from that described in the schemes, or to modify one or more of the transformations, to provide the desired compound of the invention.

Compounds of the present invention contain two or more stereogenic centers, with the stereochemical designation (R) or (S). The skilled person will appreciate that all the synthetic transformations can be conducted on either enantioenriched or racemic compounds, and that the resolution to the desired stereoisomer may take place at any point in the synthesis, using well known methods described herein and/or known in the art.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect hydroxyl, carboxyl and/or amino groups. The protecting groups used in the preparation of the compounds of the invention may be used in conventional manner; see, for example, those described in 'Greene's Protective Groups in Organic Synthesis' by Theodora W Greene and Peter G M Wuts, fifth edition, (John Wiley and Sons, 2014), incorporated herein by reference, and in particular chapters 2, 5 and 7 respectively, which also describes methods for the removal of such groups.

In the following general processes and unless otherwise stated:

$R^1$ to $R^6$ are as previously defined for a compound of Formula (I);

R is alkyl, such as ethyl, or in the case of Formulae 3 and 4, two R may be taken together with the oxygen atoms to which they are attached to form a cyclic acetal;

PG is a suitable amino protecting group, such as a silyl ether (e.g. SEM), an alkoxy carbonyl (e.g. BOC), acetyl (Ac), benzyl (e.g. PMB) or dihydropyran (DHP) protecting group; and X is F or Cl.

A substituted pyrazole of Formula 11 may be prepared as shown in Scheme 1.

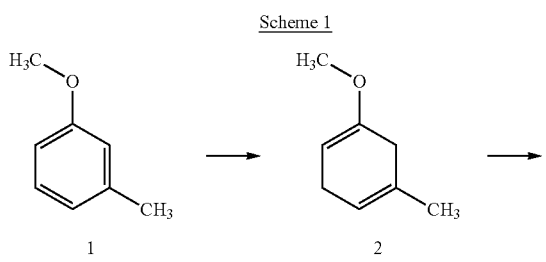

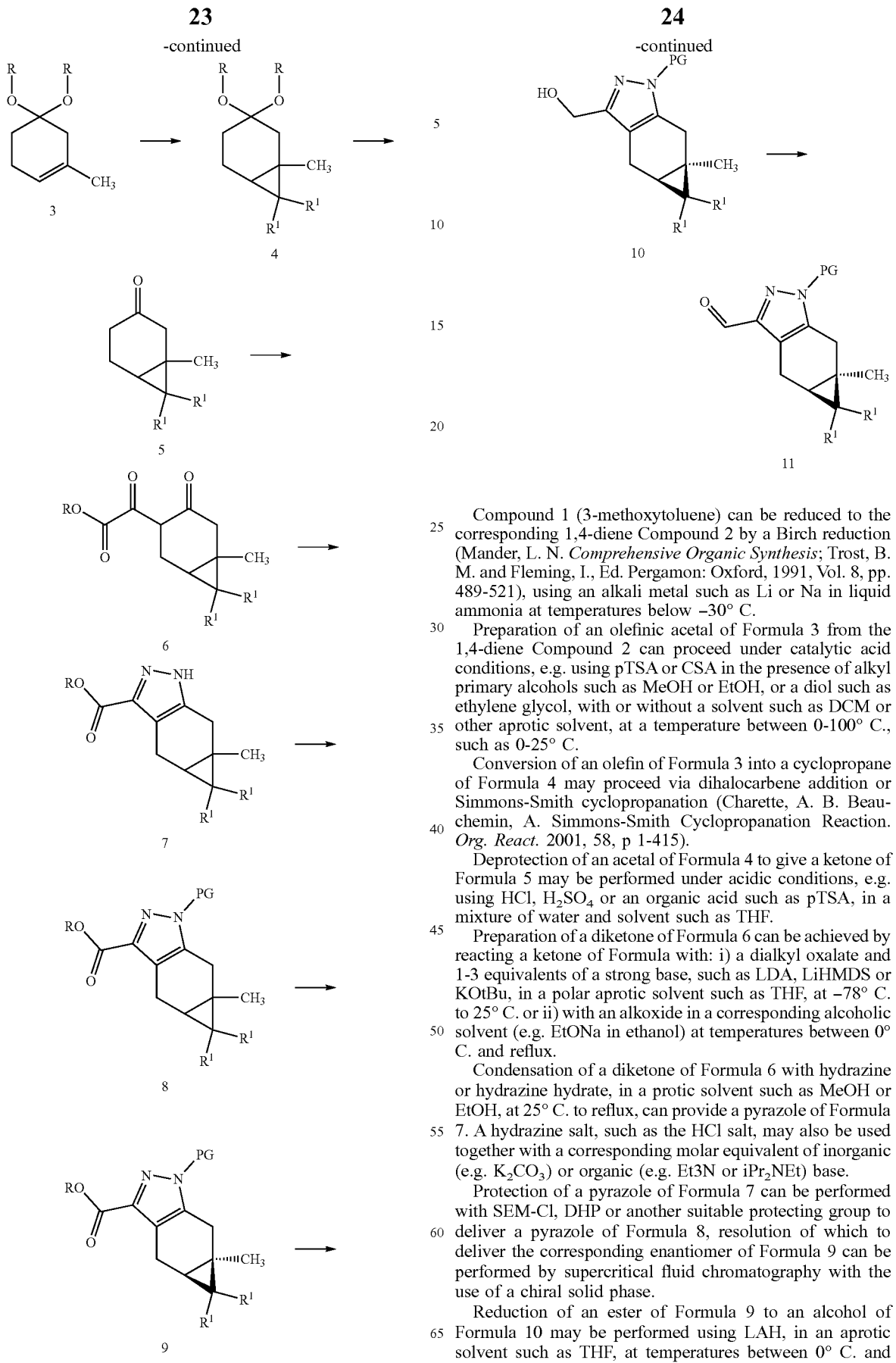

Compound 1 (3-methoxytoluene) can be reduced to the corresponding 1,4-diene Compound 2 by a Birch reduction (Mander, L. N. *Comprehensive Organic Synthesis*; Trost, B. M. and Fleming, I., Ed. Pergamon: Oxford, 1991, Vol. 8, pp. 489-521), using an alkali metal such as Li or Na in liquid ammonia at temperatures below −30° C.

Preparation of an olefinic acetal of Formula 3 from the 1,4-diene Compound 2 can proceed under catalytic acid conditions, e.g. using pTSA or CSA in the presence of alkyl primary alcohols such as MeOH or EtOH, or a diol such as ethylene glycol, with or without a solvent such as DCM or other aprotic solvent, at a temperature between 0-100° C., such as 0-25° C.

Conversion of an olefin of Formula 3 into a cyclopropane of Formula 4 may proceed via dihalocarbene addition or Simmons-Smith cyclopropanation (Charette, A. B. Beauchemin, A. Simmons-Smith Cyclopropanation Reaction. *Org. React.* 2001, 58, p 1-415).

Deprotection of an acetal of Formula 4 to give a ketone of Formula 5 may be performed under acidic conditions, e.g. using HCl, H$_2$SO$_4$ or an organic acid such as pTSA, in a mixture of water and solvent such as THF.

Preparation of a diketone of Formula 6 can be achieved by reacting a ketone of Formula with: i) a dialkyl oxalate and 1-3 equivalents of a strong base, such as LDA, LiHMDS or KOtBu, in a polar aprotic solvent such as THF, at −78° C. to 25° C. or ii) with an alkoxide in a corresponding alcoholic solvent (e.g. EtONa in ethanol) at temperatures between 0° C. and reflux.

Condensation of a diketone of Formula 6 with hydrazine or hydrazine hydrate, in a protic solvent such as MeOH or EtOH, at 25° C. to reflux, can provide a pyrazole of Formula 7. A hydrazine salt, such as the HCl salt, may also be used together with a corresponding molar equivalent of inorganic (e.g. K$_2$CO$_3$) or organic (e.g. Et3N or iPr$_2$NEt) base.

Protection of a pyrazole of Formula 7 can be performed with SEM-Cl, DHP or another suitable protecting group to deliver a pyrazole of Formula 8, resolution of which to deliver the corresponding enantiomer of Formula 9 can be performed by supercritical fluid chromatography with the use of a chiral solid phase.

Reduction of an ester of Formula 9 to an alcohol of Formula 10 may be performed using LAH, in an aprotic solvent such as THF, at temperatures between 0° C. and reflux.

Oxidation of an alcohol of Formula 10 to an aldehyde of Formula 11 can be effected by: i) using an agent, such as PCC, PDC, or MnO$_2$, in an aprotic solvent; or ii) by catalysis, for example by using TEMPO/bleach and TPAP/NMO (Caron, S., Dugger, R. W., Gut Ruggeri, S., Ragan, J. A., Brown Ripin, D. H., Chem. Rev. 2006, 106, 2943-2989) or Swern oxidation conditions.

A compound of Formula (I) may be prepared as shown in Scheme 2, wherein R is H or PG.

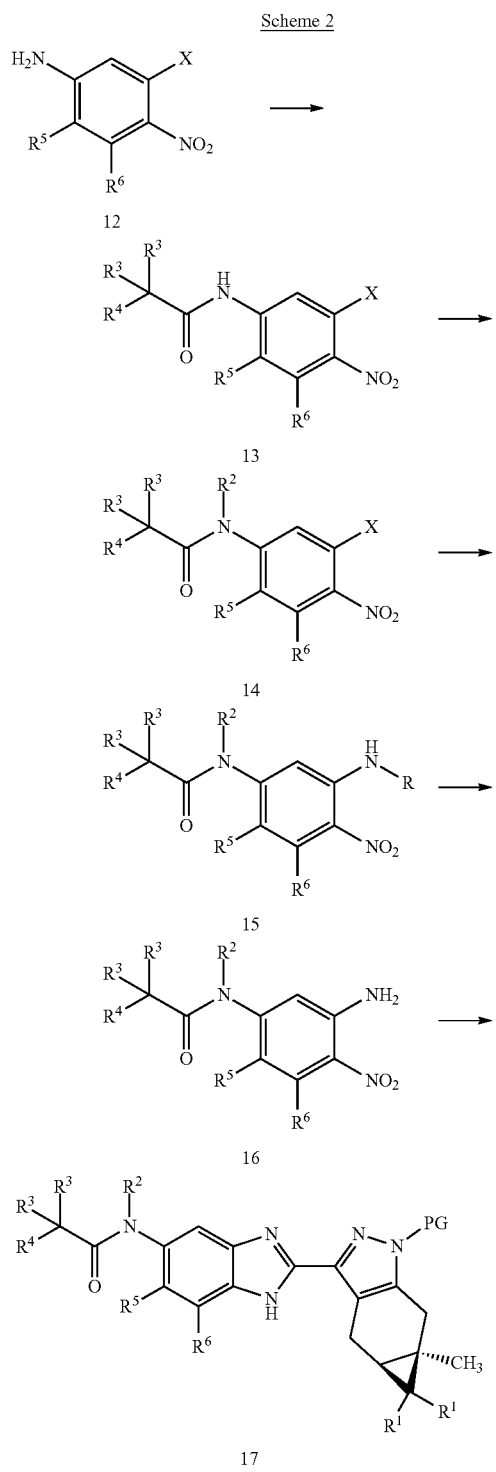

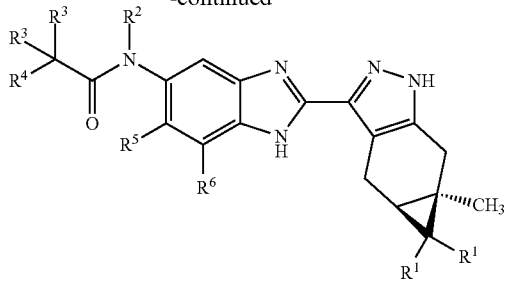

Formula (I)

A 4-nitroaniline of Formula 12 may be acylated to provide an amide of Formula 13 with a carboxylic acid using standard amide coupling reagents such as EDCI, HATU, HBTU, or T3P; or by reaction with an alternate acylating agent, such an acid chloride or acyl imidazole, in a solvent such as DCM or DMF, in the presence of an organic base such as Et3N, at a temperature between 0° C. and reflux.

Alkylation of an amide of Formula 13 to provide an amide of Formula 14 may be effected to with an alkylating agent such as an alkyl halide or tosylate, in the presence of a base such as KOtBu or LiHMDS, in a polar aprotic solvent such as DMF or THF.

A nitro aniline of Formula 15 may be prepared by substitution of X in a compound of Formula 14 with a nitrogen nucleophile, such as ammonia or benzyl or substituted benzyl amine, at 25 to 100° C., either neat or in a solvent such as DMF or THF.

Reduction of a nitro aniline of Formula 15 (with concomitant deprotection, as required) can be performed under hydrogenation conditions with Pd catalyst, such as 10% Pd/C under 1-3 atm H$_2$, in an alcoholic solvent such as MeOH or EtOH, at a temperature between 20 and 60° C., to deliver ortho-diamines of Formula 16. Alternatively, when R=H, reduction of the nitro group can be effected by use of a metal such as Zn or Fe in AcOH, at a temperature between 20-100° C.

A diamine of Formula 16 can be condensed with an aldehyde of Formula 11 in a polar solvent, such as DMF with 2-5 eq DMSO, with an oxidant such as Na$_2$S$_2$O$_5$, at a temperature between 90 and 150° C., to deliver a benzimidazole of Formula 17. Alternatively, the condensation of compounds of Formulae 16 and 11 can proceed in the presence aqueous NaHSO$_3$, and EtOH or other alcoholic solvent, at 60° C. to reflux.

Removal of the protecting group in a compound of Formula 17 to deliver the corresponding compound of Formula (I) may be performed under conditions well known to the skilled person. For instance, when PG=SEM, the protecting group may be removed by use of TFA in DCM, optionally with added Et$_3$SiH.

By processes directly corresponding to those described in Scheme 2, a compound of Formula (I) may also be prepared from a 3-nitro aniline of Formula 18, according to Scheme 3.

Scheme 3

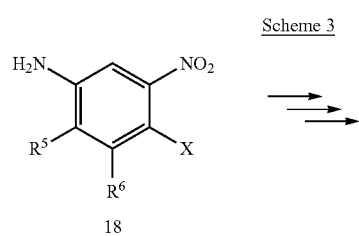

18

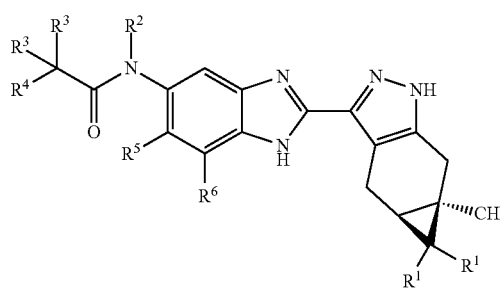

Formula (I)

A compound of Formula (I) may also be synthesized according to Scheme 4, wherein R is H or PG.

Scheme 4

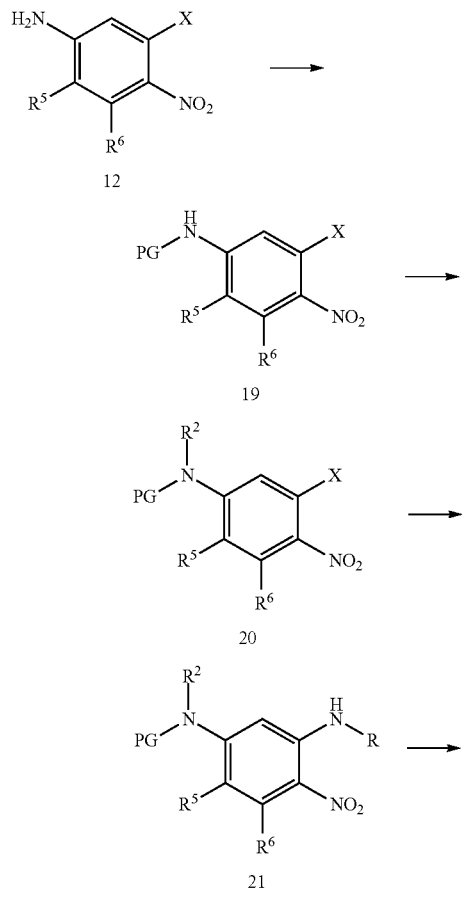

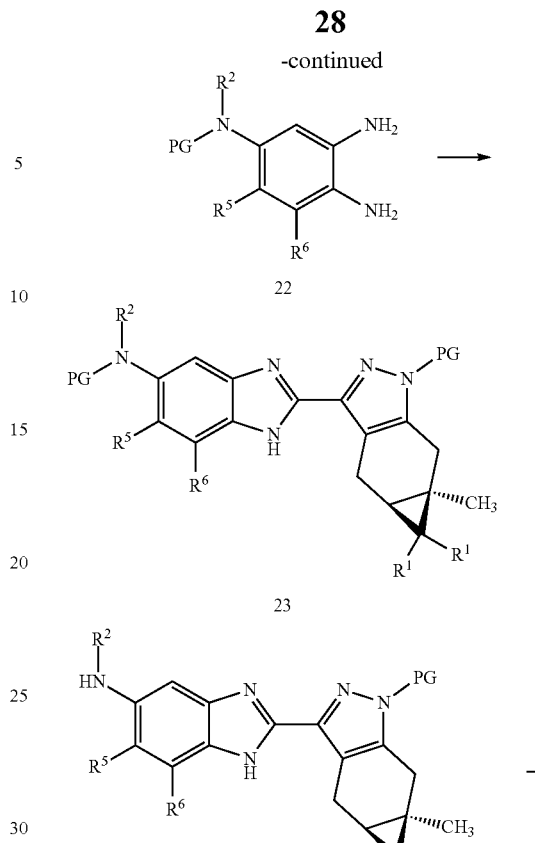

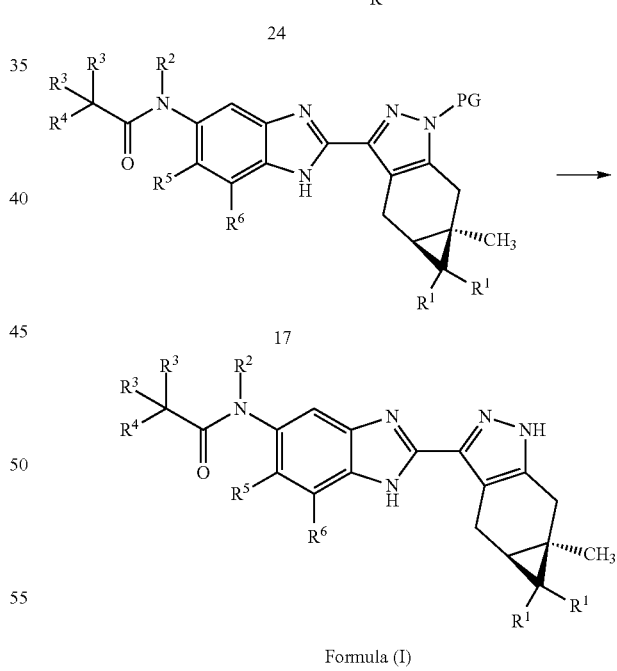

Formula (I)

A 4-nitro aniline of Formula 12 may be N-protected with an appropriate protecting group such as BOC or Ac to deliver a compound of Formula 19, which in turn may be N-alkylated with an alkyl halide, as described in Scheme 2 above for the preparation of a compound of Formula 14, to deliver a compound of Formula 20.

A compound of Formula 20 may be substituted under conditions of aromatic nucleophilic substitution to give a compound of Formula 21; which in turn may be reduced, e.g. under the conditions described above in Scheme 2 for the preparation of a compound of Formula 16, to give a diamine of Formula 22; and the diamine finally condensed with an aldehyde of Formula 11 to deliver an orthogonally protected compound of Formula 23.

Selective deprotection of the aniline protecting group of a compound of Formula 23 to deliver an aniline of Formula 24 can be achieved by reaction with ZnBr₂ or TMSOTf (PG=BOC), in a non-polar solvent such as DCM; or by basic hydrolysis with aq. NaOH or KOH, in MeOH or EtOH, at reflux (PG=Ac).

An aniline of Formula 24 may be acylated under the conditions described above in Scheme 2 for the preparation of a benzimidazole of Formula 17, and the benzimidazole subsequently deprotected to provide a compound of Formula (I) under conditions well known to the skilled person, such as those described in Scheme 2 for the preparation of Formula (I).

Compounds of Formula (I) may also be synthesized according to Scheme 5.

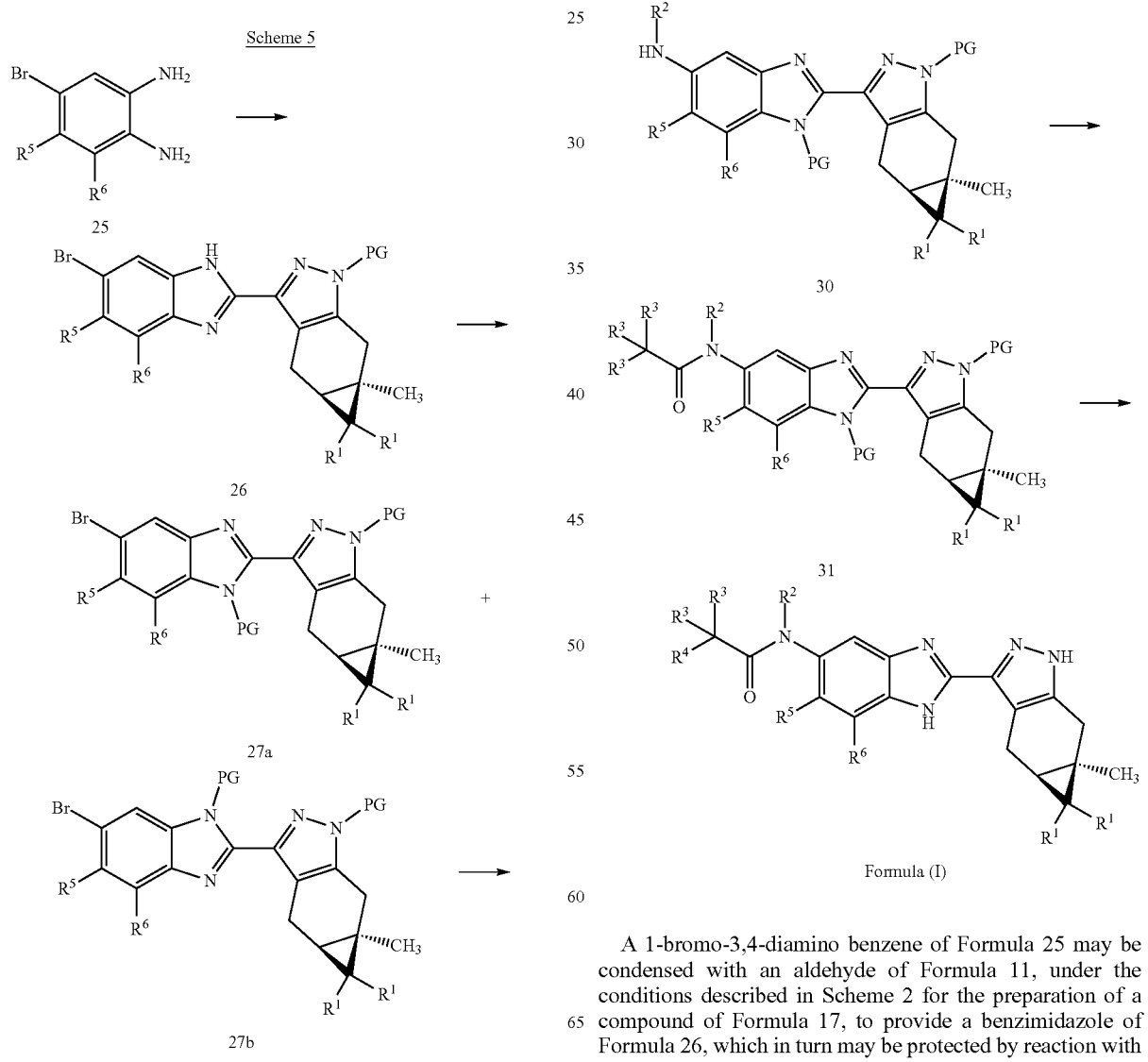

A 1-bromo-3,4-diamino benzene of Formula 25 may be condensed with an aldehyde of Formula 11, under the conditions described in Scheme 2 for the preparation of a compound of Formula 17, to provide a benzimidazole of Formula 26, which in turn may be protected by reaction with SEM-Cl in an aprotic solvent such as THF or DMF, with a base such as NaH, KOtBu or LiHMDS, at a temperature between −78° C. and 60° C., to provide a mixture of regioisomers of Formulae 27a and 27b. The compound of Formula 27b may be isolated therefrom by conventional techniques.

While the description of subsequent transformations is made with reference to Formula 27b, the skilled person will appreciate that:

i. the mixture of regioisomers of Formulae 27a and 27b may be employed in the ultimate preparation of a compound of Formula (I) (leading to the preparation of corresponding pairs of regioisomers of Formulae 29, 30 and 31); and ii. the regioisomers of compounds of Formula 29, 30 or 31 may also be isolated by conventional techniques and used in the ultimate preparation of a compound of Formula (I).

Transition metal catalyzed cross-coupling of a compound of Formula 27b with a protected amine derivative such as t-butyl carbamate, otherwise known as a Buchwald/Hartwig coupling, provides a protected aniline of Formula 28. The cross-coupling reaction may be catalyzed by Pd or Cu metal and appropriate ligands and performed in a solvent such as toluene, t-amyl alcohol or 1,4-dioxane; with a range of bases including $Cs_2CO_3$, LiHMDS, NaOtBu and KOtBu; and at temperatures between 20 and 120° C.

A protected aniline of Formula 28 may be alkylated as described in Scheme 2 for the preparation of a compound of Formula 14 to deliver a compound of Formula 29. The subsequent steps of deprotection to deliver a compound of Formula 30, acylation to deliver a compound of Formula 31 and final deprotection to deliver a compound of Formula (I) may be carried out under conventional conditions, such as those described in Scheme 4 for the preparation of, respectively, compounds of Formulae 24, 17 and (I).

A compound of Formula (I) may also be synthesized according to Scheme 6.

Scheme 6

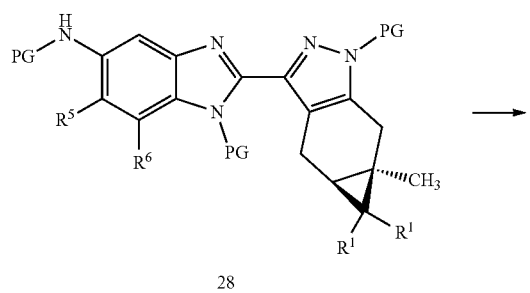

28

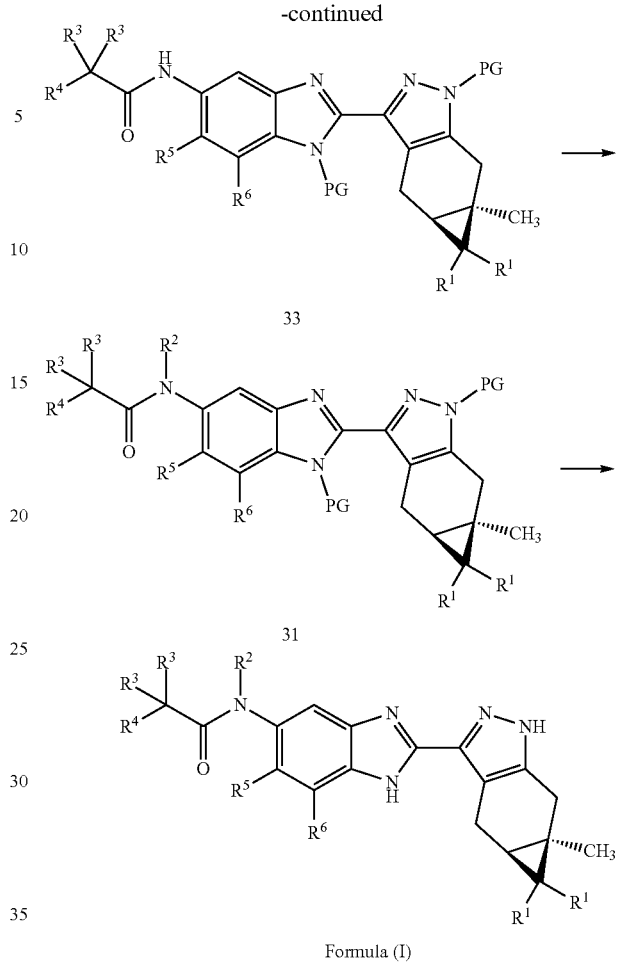

Formula (I)

A compound of Formula 28 may be deprotected, under the conditions described in Scheme 5 for the preparation of a compound of Formula 30, to deliver an aniline of Formula 32, which may be acylated, under the conditions described in Scheme 2 for the preparation of a benzimidazole of Formula 17, to provide an amide of Formula 33.

An amide of Formula 33 may be N-alkylated to provide a compound of Formula 31, and subsequently deprotected to provide a compound of Formula (I), under conventional conditions, such as described in Scheme 2 respectively for the preparation of compounds of Formulae 14 and (I).

A compound of Formula (I) wherein $R^4$ is a morpholinyl substituent may also be synthesized according to Scheme 7.

Scheme 7

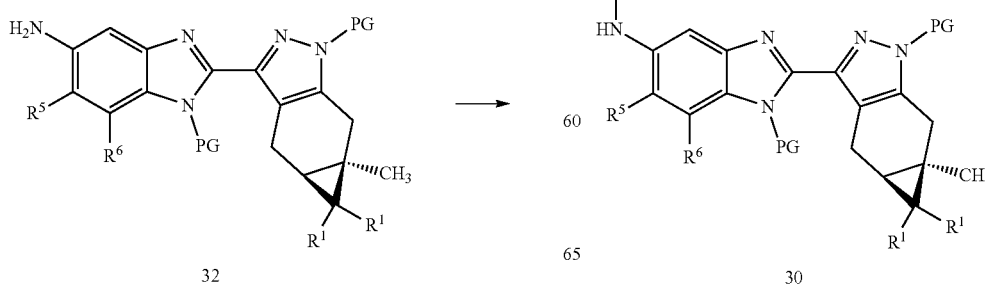

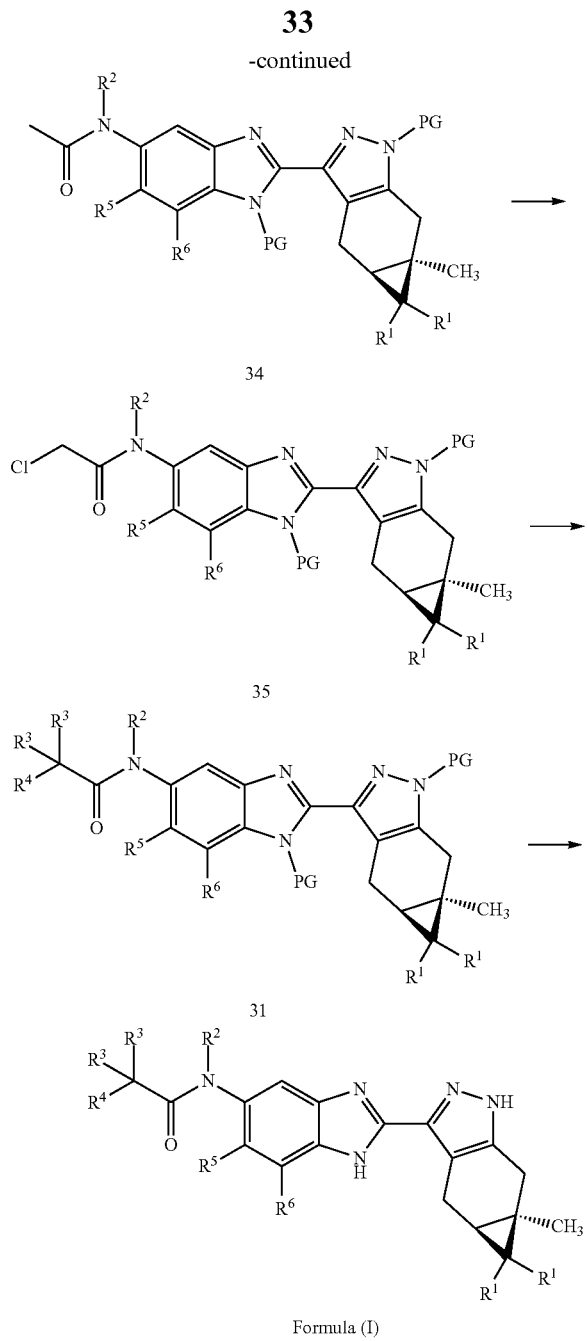

Formula (I)

An aniline of Formula 30 may be acylated by use of acetyl chloride or acetic anhydride, neat or in an aprotic solvent such as DCM, with an organic base such as Et₃N, at a temperature between −20 and 60° C., to deliver an N-acetyl compound of Formula 34.

A compound of Formula 34 may be treated with a strong base such as LDA in an aprotic solvent such as THF, followed by chlorination by a reagent such as benzene sulfonyl chloride, to deliver an α-chloro amide of Formula 35.

An amide of Formula 35 may be treated with the appropriate morpholine, in an aprotic solvent such as DMF or MeCN, in the presence of a base such as $K_2CO_3$ or $Na_2CO_3$, and with addition of NaI, to provide a compound of Formula 31, which may then be deprotected to provide a compound of Formula (I) under conventional conditions, such as those described in Scheme 2 for the preparation of a compound of Formula (I).

A compounds of Formula (I) may be transformed to alternative compound of Formula (I) by functional group interconversions well known to those skilled in the art. For example, when $R^5$ or $R^6$ is halogen, such as Br or Cl, additional transformation is possible using synthetic techniques such as transition metal mediated coupling reactions including Suzuki and Buchwald/Hartwig cross couplings, cyanations and borylations, among other reactions, to manipulate substitution at those positions.

Compounds of Formulae 1, 12, 18 and 25 may be acquired from commercial sources, prepared by analogy with literature methods, or obtained by the methods described in the Experimental section that follows or variations of the same, well known to the skilled person.

All new processes for preparing compounds of Formula (I) or a pharmaceutically acceptable salts thereof, and corresponding new intermediates employed therein, form further aspects of the present invention.

Compounds of the invention intended for pharmaceutical use may be administered in amorphous or crystalline form or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

Compounds of the invention may be administered by any suitable route in the form of a pharmaceutical composition adapted to such a route, and in a dose effective for the treatment intended. Generally, they will be administered as a formulation in association with one or more pharmaceutically acceptable excipients. The term 'excipient' is used herein to describe any ingredient other than the compound(s) of the invention. The choice of excipient will to a large extent depend on factors such as the mode of administration, the effect of the excipient on solubility and stability, and the nature of the dosage form.

Modes of administration for compounds of the invention include oral, parenteral, topical, rectal, vaginal, ocular and aural administration.

Oral administration may involve swallowing, so that a compound of the invention enters the gastrointestinal tract, or buccal or sublingual administration, such that the compound enters the bloodstream directly from the mouth.

Parenteral administration may involve injecting a compound of the invention into the bloodstream, muscle or an internal organ, where the injection may be intravenous, intraarterial, intraperitoneal, intrathecal, intraventricular, intraurethral, intrasternal, intracranial, intramuscular or subcutaneous. Parenteral administration may employ needle (including microneedle) injectors, needle-free injectors and infusion techniques.

Topical administration is preferred and includes:
administration to the skin, nail, hair, claw, hoof, mucosa;
dermal or transdermal administration;
intranasal administration or administration by inhalation;
rectal or vaginal administration; and
administration directly to the eye or ear.

The term "transdermal administration" refers to the diffusion of a compound of the invention across the barrier of the skin, nail, hair, claw or hoof resulting from topical administration or other application of a composition. Transdermal delivery includes delivery through any portion of the skin, nail, hair, claw or hoof and absorption or permeation through the remaining portion.

Topical administration of a compound of the invention can result in distribution of the compound limited to the skin and surrounding tissues or, when the compound is removed from the treatment area by the bloodstream, can result in systemic exposure of the compound of the invention. Preferably, topical administration of a compound of the invention results in distribution of the compound limited to the skin and surrounding tissues. Where systemic exposure of the compound of the invention occurs, preferably the compound is rapidly metabolized so that systemic exposure of compound of the invention is minimized. Minimizing systemic exposure can reduce unwanted biological effects (i.e. side effects).

In another aspect the invention provides a pharmaceutical composition comprising a compound of the invention and a pharmaceutically acceptable excipient.

Pharmaceutical compositions suitable for the delivery of compounds of the invention and methods for their preparation will be readily apparent to those skilled in the art. Such compositions and preparative methods may be found in, for example, "Remington's Pharmaceutical Sciences", 19th Edition (Mack Publishing Company, 1995).

Pharmaceutical compositions are typically prepared by mixing a compound of the invention and one or more excipients. Excipients include materials such as carbohydrates, waxes, water soluble and/or swellable polymers, hydrophilic or to hydrophobic materials, gelatin, oils, solvents, water, buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and the like. Solvents may include water, ethanol, propylene glycol, polyethylene glycols (e.g., PEG400, PEG300), and mixtures thereof. The excipient(s) are chosen to facilitate manufacture, or use, of the pharmaceutical composition.

Pharmaceutical compositions may be prepared by conventional dissolution and mixing. For example, the compound of the invention may be dissolved in a solvent in the presence of one or more of the excipients described above. The dissolution rate of poorly water-soluble compounds may be enhanced by the use of a spray-dried dispersion, such as those described by Takeuchi, H., et al. in "Enhancement of the dissolution rate of a poorly water-soluble drug (tolbutamide) by a spray-drying solvent deposition method and disintegrants" *J. Pharm. Pharmacol.*, 39, 769-773 (1987); and US2002/009494; incorporated herein by reference.

Solid dosage forms for oral administration of compounds of the invention include, for example, tablets, hard or soft capsules, lozenges, granules or powders, each containing at least one compound of the invention. In such solid dosage forms the compound of the invention is ordinarily combined with one or more pharmaceutically acceptable excipients. Solid dosage forms for oral administration such as tablets and capsules may be prepared with enteric coatings.

Liquid dosage forms for oral administration of compounds of the invention include, for example, pharmaceutically acceptable emulsions, solutions, suspensions, syrups, and elixirs containing inert diluents commonly used in the art (e.g. water). Such compositions also may comprise excipients, such as wetting, emulsifying, suspending, flavoring (e.g. sweetening), and/or perfuming agents.

Parenteral formulations of compounds of the invention are typically aqueous solutions which may contain excipients such as salts, carbohydrates and buffers (preferably buffering to a pH of from 3 to 9). Formulations for parenteral administration may also be sterile non-aqueous solutions, or dried (e.g. lyophilised) forms to be administered on reconstitution with a suitable vehicle such as sterile, pyrogen-free water.

Pharmaceutical compositions for topical or transdermal administration of a compound of the invention include ointments, pastes, creams, lotions, gels, suppositories, powders, solutions, sprays, drops, inhalants and patches. The compound of the invention is admixed under sterile conditions with a pharmaceutically acceptable topical carrier and any preservatives or buffers as may be required. Compounds that are volatile may require admixture with formulating agents or with packaging materials to assure proper dosage delivery. Compounds of the invention that have poor skin permeability may require one or more permeation enhancers, whereas compounds rapidly absorbed through the skin may require formulation with absorption-retarding agents or barriers.

The term "pharmaceutically acceptable topical carrier" refers to a carrier medium, suitable for topical application, that provides appropriate delivery of an effective amount of a compound of the invention, such as an inactive liquid or cream vehicle capable of suspending or dissolving the compound. The skilled person will appreciate that this term encompasses carrier materials approved for use in topical cosmetics as well.

The terms "permeation enhancer" relates to an increase in the permeability of the skin, nail, hair, claw or hoof to the compound of the invention, so as to increase the rate and extent of permeation of the compound. The enhanced permeation can be observed, for example, by measuring the rate of diffusion of the drug through animal or human skin, nail, hair, claw or hoof using a diffusion cell apparatus. A diffusion cell is described by Merritt et al. Diffusion Apparatus for Skin Penetration, J of Controlled Release, 1 (1984) pp. 161-162.

The ointments, pastes, creams, lotions, gels, suppositories, powders, solutions, sprays, drops, inhalants and patches for topical administration may contain, in addition to a compound of the invention, one or more pharmaceutically acceptable excipients, such animal or vegetable fats, oils, waxes, paraffins, starch, tragacanth, cellulose derivatives, polyethylene glycols, silicones, bentonites, silicic acid, talc, zinc oxide, preservatives, antioxidants, fragrances, emulsifiers, dyes, inert fillers, anti-irritants, tackifiers, fragrances, opacifiers, antioxidants, gelling agents, stabilizers, surfactants, emollients, coloring agents, preservatives, buffering agents, permeation enhancers. Such excipients should not interfere with the effectiveness of the biological activity of the active agent and not be deleterious to the epithelial cells or their function.

Transdermal administration may be achieved by means of a transdermal patch. The transdermal patch may be of the 'reservoir and porous membrane' type or employ a 'matrix system'.

The solubility of compounds of compounds of the invention used in the preparation of pharmaceutical compositions may be increased by the use of appropriate formulation techniques, such as the incorporation of solubility-enhancing agents.

Pharmaceutical compositions may be formulated to be immediate and/or modified release. Conveniently compounds of the invention are formulated for immediate release Modified release formulations include delayed-, sustained-, pulsed-, controlled-, targeted- and programmed-release. Thus compounds of the invention may be formulated as a solid, semi-solid, or thixotropic liquid for administration as an implanted depot providing modified release of the active compound. Examples of such formulations include poly(dl-lactic-coglycolic)acid (PGLA) microspheres.

The compounds of the invention may be combined with soluble macromolecular entities, such as cyclodextrin and suitable derivatives thereof, or polyethylene glycol-containing polymers, in order to improve their solubility, dissolution rate, taste-masking, bioavailability and/or stability for use in any of the aforementioned modes of administration.

For administration to human patients, the total daily dose of the compounds of the invention is typically in the range 1 mg to 10 g, such as 60 mg to 6 g, for example 100 mg to 1.5 g, depending on the mode of administration and efficacy. For example, administration may require a total daily dose of from 200 mg to 1 g, such as from 250 mg to 750 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

As noted above, the compounds of the invention are useful because they exhibit pharmacological activity in animals, i.e. inhibition of ITK. More particularly, the compounds of the invention are of use in the treatment of disorders for which an ITK inhibitor is indicated.

Preferably the animal is a mammal, more preferably a human.

Preferably the compound of the invention also inhibits TRKA.

In a further aspect of the invention there is provided a compound of the invention for use as a medicament.

In a further aspect of the invention there is provided a compound of the invention for use in the treatment of a disorder for which an ITK inhibitor is indicated.

In a further aspect of the invention there is provided use of a compound of the invention for the preparation of a medicament for the treatment of a disorder for which an ITK inhibitor is indicated.

In a further aspect of the invention there is provided a method of treating a disorder in an animal (preferably a mammal, more preferably a human) for which an ITK inhibitor is indicated, comprising administering to said animal a therapeutically effective amount of a compound of the invention.

Disorders or conditions for which an ITK inhibitor is indicated include inflammatory, autoimmune, dermatologic, eye, respiratory, joint, cardiovascular and neuroinflammatory diseases. The skilled person will appreciate that a given disease, disorder or condition may fall into more than one of the above categories.

More particularly, disorders or conditions for which an ITK inhibitor is indicated include:

inflammatory disorders, such as allergic conjunctivitis, celiac diseases, proctitis, eosinophilic gastroenteritis, mastocytosis, inflammatory bowel disease (e.g. Crohn's disease, ulcerative colitis, microscopic colitis (such as collagenous colitis or to lymphocytic colitis), diversion colitis, Behcet's disease, and indeterminate colitis), nephritis, retinitis, retinopathy, myositis, vasculitis, Sjogren's syndrome, Wegener's granulomatosis, arteritis, sclerosing cholangitis, and eosinophilic esophagitis;

autoimmune disorders, such as lupus nephritis, autoimmune hepatitis, myasthenia gravis, Guillain-Barre syndrome, and Graves' disease;

eye disorders or conditions, including autoimmune diseases of the eye, keratoconjunctivitis, vernal conjunctivitis, non-infectious uveitis (e.g. uveitis associated with Behcet's disease and lens-induced uveitis), keratitis (e.g. herpetic keratitis and conical keratitis), corneal epithelial dystrophy, keratoleukoma, ocular pemphigus, Mooren's ulcer, scleritis, retinitis, retinopathy, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization;

dermatological conditions, such as eczema (e.g. chronic and dyshidrotic eczema), chronic itch, dermatitis (e.g. atopic, irritant contact, allergic contact, occupational, perioral, stasis, nummular, seborrheic, xerotic, eyelid, diaper, and hand dermatitis), vitiligo, alopecia areata, pruritis (e.g. chronic idiopathic pruritus), psoriasis (e.g. plaque, guttate, inverse, pustular, nail, flexural palmoplantar, facial or erythrodermic psoriasis), scleroderma, pemphigus, dermatomyositis, neurodermatitis, skin flushing, urticaria, cutaneous lupus erythematosus (e.g. acute cutaneous lupus (acute skin lupus), subacute cutaneous lupus (subacute lupus), and chronic cutaneous lupus (discoid lupus)), keloid, sunburn, hypertrophic scar, idiopathic thrombocytopenic thrombotic purpura (also known as immune thrombocytopenia purpura (ITP)), ichthyosis (e.g. ichthyosis vulgaris), epidermal hyperplasia, acne, lichen planus, lichen sclerosis, rosacea, epidermolysis bullosa, intertrigo, keratosis pilaris, urticaria (e.g. chronic spontaneous urticaria, chronic idiopathic urticaria, chronic physical urticaria), molluscum contagiosum, Netherton syndrome, Vogt-Koyanagi-Harada syndrome, Sweet's syndrome, *pityriasis* alba, vulvovaginitis, Sutton's nevus/nevi, post inflammatory hypopigmentation, senile leukoderma, chemical/drug-induced leukoderma, palmoplantar pustulosis, pemphigoid, and hidradenitis suppurativa;

respiratory conditions, such as rhinitis (e.g. allergic and perennial rhinitis), rhinorrhoea, nasal congestion, nasal inflammation, asthma (e.g. chronic asthma, inveterate asthma, late asthma, bronchial asthma, allergic asthma, intrinsic asthma, extrinsic asthma, and dust asthma), chronic obstructive pulmonary disease (COPD), chronic and acute bronchoconstriction, chronic bronchitis, emphysema, chronic eosinophilic pneumonia, acute lung injury (ACI), adult respiratory distress syndrome (ARDS), pulmonary vascular disease (PVD), pulmonary arterial hypertension (PAH), bronchiectasis, sinusitis, pulmonary sarcoidosis, and silicosis;

joint disorders, such as arthritis (e.g. osteoarthritis, as well as psoriatic, rheumatoid, juvenile, and gouty arthritis), spondyloarthropathy (e.g. reactive arthritis (also known as Reiter's Syndrome) and axial spondyloarthritis (including ankylosing spondylitis)), cartilage inflammation, bone degradation, and Still's disease;

cardiovascular and metabolic disorders, such as diabetes (type 1 and type 2), diabetic neuropathy, cachexia, and Celiac Sprue; and neuroinflammatory disorders, such as lupus (e.g. CNS, systemic and discoid lupus), diabetic neuropathy, and multiple sclerosis.

Allergic contact dermatitis (ACD) is a contact dermatitis characterised by an allergic response to contact with a substance. An example of ACD is urushiol-induced contact dermatitis (also called *toxicodendron* dermatitis or *Rhus* dermatitis), which is caused by the oil urushiol found in various plants, including poison ivy, poison oak, poison sumac and the Chinese lacquer tree. Other allergens that can induce ACD include chromium, gold and nickel.

Irritant contact dermatitis (ICD) is a form of contact dermatitis that can be divided into forms caused by chemical irritants and those caused by physical irritants. Common chemical irritants include acids, alkalis, latex, oils, perfumes and preservatives in cosmetics, solvents, and surfactants.

Occupational dermatitis is an ACD or ICD arising from exposure to an allergen or irritant in a work environment.

Additionally, an ITK inhibitor may be of use in treating certain viral and bacterial infections, transplant rejection, septic shock, acute or chronic graft-versus-host disease, polymyalgia rheumatica, sarcoidosis, Addison's disease and Raynaud's syndrome.

In one embodiment the disorder or condition for which an ITK inhibitor is indicated is a dermatological condition. In another embodiment the dermatological condition for which an ITK inhibitor is indicated is dermatitis. In another embodiment the dermatitis for which an ITK inhibitor is indicated is atopic dermatitis.

A compound of the invention may usefully be combined with one or more other pharmacologically active compounds. Such combinations offer the possibility of significant advantages, including patient compliance, ease of dosing and synergistic activity.

In a further aspect of the invention there is provided a compound of the invention in combination with another pharmacologically active compound, or with two or more other pharmacologically active compounds.

In such combinations the compound of the invention and other pharmacologically active compound(s) may be administered simultaneously, such as in a single dosage form (e.g. a composition for topical administration, such as a cream or an ointment), sequentially or separately.

The one or more additional therapeutic agents may be selected from any of the agents or types of agent that follow:
- an agent for treating autoimmune and/or inflammatory disorders, such as, sulfasalazine, mesalazine, azathioprine, an antibody (e.g. infliximab, adalimumab, belimumab, tanezumab, ranibizumab, bevacizumab, mepolizumab certolizumab, natalizumab, and vedolizumab), 6-mercaptopurine, hydroxychloroquine, mofetil, sodium mycophenolate, leflunomide, rituxan, solumedrol, dopomedrol, a non-steroidal anti-inflammatory drug (NSAID) (e.g. aspirin, ibuprofen, celecoxib, valdecoxib, WBI-1001 and MRX-6), and a corticosteroid (e.g. betamethasone, dexamethasone, and prednisone);
- an agent for treating dermatological conditions, such as an immunosuppressant (e.g. cyclosporin, tacrolimus, and pimecrolimus), an antibody (e.g. infliximab, adalimumab dupilumab, omalizumab, and efalizumab), a TNF inhibitor (e.g. etanercept), a PDE4 inhibitor (e.g. crisaborole), and a topical corticosteroid (e.g. fluocinonide, mapracorat, hydrocortisone, desonide, alclometasone, triamcinolone, and desoximetasone);
- an agent for treating respiratory conditions, such as oxymetazoline, rifampin, an anti-histamine (e.g. fexofenadine, loratidine, desloratadine, levocetirizine, methapyrilene, cetirizine), a leukotriene receptor antagonist (e.g. montelukast and zafirlukast), a 5-lipoxygenase activating protein (FLAP) antagonist, a muscarinic receptor antagonist (e.g. tiotropium and ipratropium), sodium cromoglycate, sodium nedocromil, a corticosteroid (e.g. budesonide, fluticasone, mometasone, dexamethasone, prednisolone, ciclesonide, and beclomethasone), a beta-2 agonist (e.g. salmeterol, albuterol, salbutamol, fenoterol, and formoterol), and an antibody (e.g. omalizumab);
- an agent for treating joint disorders, such as methotrexate, azathioprine, and an NSAID (e.g. aspirin, ibuprofen, celecoxib, valdecoxib, WBI-1001 and MRX-6);
- an agent for treating cardiovascular and metabolic disorders, such as ursodeoxycholic acid, chloroquine, quinacrine, methylnorephrine, phenylephrine, methoxamine, oxymetazoline, theophylline, a PDE5 inhibitor (e.g. sildenafil, vardenafil, and tadalafil), a PDE4 inhibitor (e.g. crisaborole, ibudilast, cilomilast, roflumilast, and apremilast), and a kinin $B_1$ or $B_2$ receptor antagonist; and
- an agent for treating neuroinflammatory disorder treatments, such as cyclophosphamide.

The one or more additional therapeutic agents may also be selected from any of the agents that follow:
- a JAK inhibitor, such as abrocitinib, baricitinib, brepocitinib cerdulatinib, decernotinib, delgocitinib, fedratinib, filgotinib, gandotinib, ilginatinib, itacitinib, lestaurtinib, momelotinib, oclacitinib pacritinib, peficitinib, ritlecitinib, ruxolitinib, tofacitinib, upadacitinib, ATI-502, BMS-986165, JTE052, PF-06826647, SNA-152, and SHR-0302;
- an aryl hydrocarbon receptor agonist such as, tapinarof;
- an IRAK4 inhibitor such as PF-06650833;
- a vitamin D analog, such as calcipotriene;
- a retinoic acid derivative such as, alitretinoin;
- a liver X receptor (LXR) selective agonist, such as VTP-38543;
- an H4 receptor antagonist, such as, ZPL-389;
- an NK1 receptor antagonist, such as, aprepitant and tradipitant;
- a CRTH2 receptor antagonist, such as, fevipiprant and OC-459;
- a chymase inhibitor, such as SUN 13834;
- a GATA-3 inhibitor, such as SB-011 and GR-MD-02;
- an ROR inverse agonist, such as VTP-43742, ARN6039, TAK-828 and JTE-451;
- an immunomodulator, such as PF-06763809; and
- an inhibitor of SYK and BTK, including but not limited to, R-348, fostamatinib, mastinib, mivavotinib, sperbrutinib, fenebrutinib, cerdulatinib, ibrutinib, entospletinib and tirabrutinib.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms (e.g. topical, oral, parenteral, etc.), for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which an ITK inhibitor is indicated.

It is to be appreciated that all references herein to treatment include curative, palliative and prophylactic treatment.

In the non-limiting Examples and Preparations set out below that illustrate the invention, and in the aforementioned Schemes, the following the abbreviations, definitions and analytical procedures may be referred to:

°2θ is degrees 2-Theta;
AcOH is acetic acid;
$Ac_2O$ is acetic anhydride;
APC is allophycocyanin;
aq. is aqueous;
atm is atmosphere;
ATP is adenosine 5'-triphosphate disodium salt trihydrate;
BINAP is (2,2'-bis(diphenyiphosphino)-1,1'-binaphthyl);
Boc is tert-butoxycarbonyl;
$BOC_2O$ is BOC anhydride, di-tert-butyl dicarbonate;
br is broad;
BTFFH is fluorobis(tetramethylene)formamidinium hexafluorophosphate;
BTK is Bruton's tyrosine kinase;
° C. is degrees celcius;
$CD_3OD$ is deutero-methanol;
$CDCl_3$ is deutero-chloroform;
conc. is concentrated;
CSA is camphor sulphonic acid;
δ is chemical shift;
d is doublet;
dd is doublet of doublets;
ddd is doublet of doublet of doublets;
dt is doublet of triplets;
DAST is diethylaminosulfur trifluoride;
DCM is dichloromethane;
DCE is 1,2-dichloroethane;
Dess-Martin periodinane is 3-oxo-1,3-dihydro-1λ$^5$,2-benziodoxole-1,1,1-triyl triacetate;
DHP is dihydropyran;
DMAP is 4-dimethylaminopyridine;
DMF is N,N-dimethylformamide;
DMSO is dimethyl sulfoxide;
EDCI is 1-ethyl-3-(3-dimethylaminopropyl)carbodiimide hydrochloride;
ee is enantiomeric excess;
EDTA is ethylenediaminetetraacetic acid;
ESI-MS is electrospray ionization mass spectrometry;
EtOAc is ethyl acetate;
EtOH is ethanol;
EtONa is sodium ethoxide;
$Et_3N$ is triethylamine;
$Et_3SiH$ is triethylsilane;
g is gram;
h is hour(s);
HATU is 1-[bis(dimethylamino)methylene]-1H-1,2,3-triazolo[4,5-b]pyridinium 3-oxide, hexafluorophosphate;
HBTU is N,N,N',N'-tetramethyl-O-(1H-benzotriazol-1-yl) uronium hexafluorophosphate;
HEPES is (4-(2-hydroxyethyl)-1-piperazineethanesulfonic acid);
HPLC is high pressure liquid chromatography;
$iPr_2NEt$ is N,N-diisopropylethyl amine, also known as Hunig's base;
KOAc is potassium acetate;
KOtBu is potassium tert-butoxide;
L is liter;
LAH is lithium aluminium hydride;
LCMS is liquid chromatography mass spectrometry;
LDA is lithium diisopropylamide;
LiHMDS is lithium hexamethyldisilazide, also known as lithium bis(trimethylsilyl)amide;
m is multiplet;
M is molar;
MeCN is acetonitrile;
$MeNH_2$ is methyl amine;
MeOH is methanol;
MHz is mega Hertz;
min is minutes;
mL is milliliter;
mm is millimeter;
mmol is millimole;
mol is mole;
MS m/z is mass spectrum peak;
MTBE is methyl tert-butyl ether;
n-BuLi is n-butyl lithium;
NaHMDS is sodium bis(trimethylsilyl) amide;
NaOtBu is sodium tert-butoxide;
NMP is N-Methyl-2-pyrrolidone;
NMR is nuclear magnetic resonance;
ORTEP is Oak Ridge Thermal Ellipsoid Plot;
PCC is pyridinium chlorochromate;
PDC is pyridinium dichromate;
$Pd_2(dba)_3$ is tris(dibenzylideneacetone)dipalladium(0);
Pd/C is palladium on carbon;
$Pd(dppf)Cl_2$ is 1,1'-bis(diphenylphosphino)ferrocene]dichloropalladium(II);
$Pd(OAc)_2$ is palladium(II)acetate;
to $Pd(OH)_2/C$ is palladium(II)hydroxide on carbon;
$Pd(Ph_3P)_4$ is tetrakis(triphenylphosphine)palladium(0);
PE is petroleum ether;
$PhCH_3$ is toluene;
PMB is para-methoxybenzyl;
pTSA is p-toluenesulfonic acid monohydrate;
PXRD is powder X-ray diffraction;
q is quartet;
Qphos is 1,2,3,4,5-pentaphenyl-1'-(di-tert-butylphosphino) ferrocene;
RT is room temperature;
s is singlet;
sat. is saturated;
SEM-Cl is 2-(trimethylsilyl)ethoxymethyl chloride;
SFC is supercritical fluid chromatography;
SPhos is 2-Dicyclohexylphosphino-2',6'-dimethoxybiphenyl;
SXRD is single crystal X-ray diffraction;
t is triplet;
tert-BuDavePhos is 2-di-tert-butylphosphino-2'-(N,N-dimethylamino)biphenyl;
t-BuOH is tert-butanol;
TCEP is tris(2-carboxyethyl)phosphine;
TFA is trifluoroacetic acid;
TFAA is trifluoroacetic anhydride;
TGA is thermogravimetric analysis;
THF is tetrahydrofuran;
$TMSCF_3$ is Trifluoromethyltrimethylsilane;
TMSOTf is Trimethylsilyl trifluoromethanesulfonate;
$T_3P$ is propylphosphonic anhydride;

Tris is tris(hydroxymethyl)aminomethane;
μm is micrometer;
v/v is volume by volume;
w/v is volume by volume;
XantPhos is 4,5-Bis(diphenylphosphino)-9,9-dimethylxanthene; and
ZnEt$_2$ is diethylzinc.

Unless otherwise stated all reactions are run under a nitrogen atmosphere. When sodium hydride is used in the following procedures the weights are corrected to reflect its use as a 60% suspension in mineral oil. RT (room temperature) is generally taken to mean approximately 22° C. (±5° C.). The term "concentrated" refers to the process of removal of volatile compounds, such as solvents, by use of a rotary evaporator under reduced pressure.

$^1$H and $^{19}$F Nuclear NMR spectra were in all cases consistent with the proposed structures. Characteristic δ for $^1$H-NMR are reported relative to residual solvent signals (for CDCl$_3$, δH=7.27 ppm; for DMSO-d$_6$, δH=2.50 ppm, for CD$_3$OD, δH=3.30 ppm, for DMF-d$_7$, δH=8.03 ppm) using conventional abbreviations for designation of major peaks. The skilled person will appreciate that tautomers may be recorded within the NMR data and some exchangeable protons may not be visible. Likewise the skilled person will appreciate that a mixture of rotamers may be recorded within the NMR data.

Mass spectra were recorded using either ESI-MS. Where relevant and unless otherwise stated the m/z data provided are for isotopes $^{19}$F, $^{35}$Cl, $^{79}$Br and/or $^{81}$Br and $^{127}$I.

Where preparative TLC or silica gel chromatography have been used, the skilled person will appreciate that any suitable solvent or solvent combination may be employed to purify the desired compound.

Nomenclature for the compounds of the Preparations and Examples that follow was generated using ChemDraw Professional 18.0, Perkin Elmer, in accordance with the IUPAC (International Union of Pure and Applied Chemistry).

Preparations

Preparation 1:
1-methoxy-5-methylcyclohexa-1,4-diene

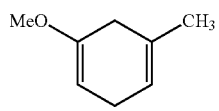

The reaction was carried out in 25 parallel batches. To a solution of 1-methoxy-3-methylbenzene (500 g, 4.09 mol) in t-BuOH (1.5 L) and THF (1 L) was bubbled in anhydrous ammonia (1.4 kg, 82.2 mmol) while the reaction was kept between −60 and −50° C. To the reaction mixture was then added lithium sand (62.5 g, 9.0 mol) by portions while maintaining the temperature between −60 and −50° C. and the reaction was stirred for 2 h. The reaction mixture was warmed slowly to ~20° C. and the ammonia was allowed to evaporate. To the reaction was added NH$_4$Cl (500 g) and water (500 mL). The batches were combined, and the organic layer was separated. The aqueous layer was washed with EtOAc (5 L×2). The combined organic layers were then washed with brine (5 L) and the organic layer was dried (Na$_2$SO$_4$) and concentrated to provide the title compound (10.1 kg, 80%). $^1$H NMR (400 MHz, CDCl$_3$) δ 5.42-5.41 (m, 1H), 4.65-4.63 (m, 1H), 3.56 (s, 3H), 2.79-2.77 (m, 2H), 2.65-2.56 (m, 2H), 1.74-1.68 (m, 3H).

Preparation 2:
7-methyl-1,4-dioxaspiro[4.5]dec-7-ene

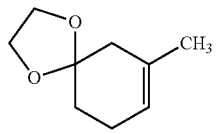

The reaction was carried out in 6 parallel batches. To a solution of Preparation 1 (500 g, 4.03 mol) in DCM (4.0 L) was added with p-toluenesulfonic acid monohydrate (46.8 g, 201 mmol) and ethylene glycol (399 g, 6.04 mol) between −10 and 0° C. The mixture was stirred at approximately 0° C. for 0.5 h. The reaction batches were combined and washed with sat. aq. NaHCO$_3$ (5 L), water (5 L, 2×), dried (Na$_2$SO$_4$), filtered and concentrated to provide the title compound (14.2 kg). $^1$H NMR (400 MHz, CDCl$_3$) δ 5.40-5.34 (m, 1H), 3.98-3.88 (m, 4H), 2.21-2.12 (m, 4H), 1.67 (d, 5H).

Preparation 3: 1-methylspiro[bicyclo[4.1.0]heptane-3,2'-[1,3]dioxolane]

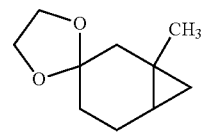

The reaction was carried out in 10 parallel batches. A solution of ZnEt$_2$ (1.00M, 5.14 L) in DCM (2.0 L) was cooled at 0° C. to which was added TFA (380 mL, 5.14 mol) dropwise at 0° C. The mixture was stirred at 0° C. for 30 min after which CH$_2$I$_2$ (414 mL, 5.14 mol) was added dropwise at 0° C. The mixture was stirred at 0° C. for 30 min. Preparation 2 (396 g, 2.57 mol) was added dropwise, maintaining the temperature at 0° C. and the resulting mixture was stirred at 0° C. for 30 min. The reaction mixture was poured into water (1 L) and the batches were combined. The combined mixture was extracted with DCM (3×8 L). The combined organic phases were dried (Na$_2$SO$_4$), filtered and concentrated to provide the title compound (3.0 kg); $^1$H NMR (400 MHz, CDCl$_3$) δ 3.93-3.73 (m, 4H), 2.13-2.01 (m, 1H), 1.84-1.79 (m, 1H), 1.75-1.67 (m, 2H), 1.47-1.36 (m, 1H), 1.27 (m, 1H), 1.03 (s, 3H), 0.73-0.61 (m, 1H), 0.35-0.25 (m, 2H).

Preparation 4: 1-methylbicyclo[4.1.0]heptan-3-one

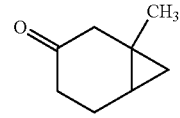

The reaction was carried out in 14 parallel batches. A solution of Preparation 3 (300 g, 1.78 mol) in THF (1.5 L)

and water (300 mL) was treated with pTSA·H$_2$O (34.0 g, 178 mmol). The mixture was stirred at 60° C. for 3 h and then cooled to RT. The 14 batches were combined and treated with sat. aq. NaHCO$_3$ solution until the pH was between 6-7. The mixture was extracted with MTBE (3×8 L), dried (Na$_2$SO$_4$), filtered and concentrated. The residue was purified by chromatography (silica, EtOAc/PE=0-100%) to provide the title compound (1.2 kg, 39%). $^1$H NMR (400 MHz, CDCl$_3$) δ 2.60-2.40 (m, 1H), 2.32-2.18 (m, 1H), 2.11-1.93 (m, 1H), 1.34-1.17 (m, 1H), 1.17-1.05 (m, 4H), 0.95-0.86 (m, 1H), 0.85-0.74 (m, 2H), 0.43-0.33 (m, 1H).

Preparation 5: ethyl 2-(6-methyl-4-oxobicyclo[4.1.0]heptan-3-yl)-2-oxoacetate

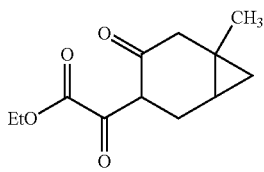 [SMILES: CCOC(=O)C(=O)C1CC2CC2(C)CC1=O]

The reaction was carried out in four parallel batches. A solution of Preparation 4 (200 g, 1.61 mol) in EtOH (1.0 L) was treated with EtONa (126 g, 1.77 mol) at 0° C. Diethyl oxalate (259 g, 1.77 mol, 242 mL) was added at 0° C. and the mixture was slowly warmed to 20° C. and stirred for 1 h. The four batches were combined and the mixture was poured into 1N HCl (5 L) and extracted with DCM (3×3 L). The combined organic extracts were dried (Na$_2$SO$_4$), filtered and concentrated. The residue was purified by chromatography (silica, EtOAc/PE=0-10%) to provide the title compound (1.4 kg, 97%). LC/MS m/z (M+H)$^+$=225.0

Preparation 6: ethyl 5a-methyl-1,4,4a,5,5a,6-hexahydrocyclopropa[f]indazole-3-carboxylate

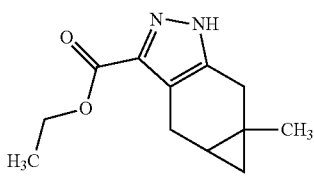 [SMILES: CCOC(=O)c1n[nH]c2c1CC1CC1(C)C2]

The reaction was carried out in four parallel batches. To a solution of Preparation 5 (350 g, 1.56 mol) in EtOH (1.5 L) was added hydrazine hydrate (79.7 g, 1.56 mol) at 0° C. The resulting mixture was stirred at 20° C. for 2 h. The four reaction batches were combined to which was added H$_2$O (10 L) and extracted with DCM (3×8 L). The combined organic layers were dried (Na$_2$SO$_4$), filtered and concentrated. The crude product was purified by chromatography (silica, EtOAc/PE=5-33%) to provide the title compound (800 g, 58%). $^1$H NMR (400 MHz, DMSO-de) δ 13.70-12.78 (m, 1H), 4.25-4.20 (m, 2H), 3.14-3.07 (m, 1H), 2.89-2.82 (m, 2H), 2.68-2.62 (m, 1H), 1.27 (br s, 3H), 1.20 (br s, 3H), 1.04-1.00 (m, 1H), 0.31-0.29 (m, 1H), 0.08-0.02 (m, 1H); LC/MS m/z (M+H)$^+$=221.0.

Preparation 6a: ethyl (4aR,5aS)-5a-methyl-1,4,4a,5,5a,6-hexahydrocyclopropa[f]indazole-3-carboxylate; and Preparation 6b: ethyl (4aS,5aR)-5a-methyl-1,4,4a,5,5a,6-hexahydrocyclopropa[f]indazole-3-carboxylate

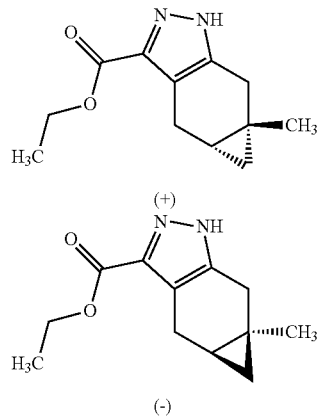

Preparation 6 was separated by chiral SFC (Chiral Tech OZ-H 250 mm×4.6 mm×5 μm column with a mobile phase of CO$_{2(g)}$/MeOH=80:20 with 0.2% NH$_4$$^+$ (7N NH$_3$ in MeOH) and a flow rate of 3.0 mL/min).

6a: retention time=3.89 min, 100% ee, [α]$^{20}_D$=+67.1 (c=4.2, MeOH); LC/MS m/z (M+H)$^+$=221.1.

6b: retention time=4.76 min, 98.9% ee; [α]$^{20}_D$=−80.2 (c=4.7, MeOH); $^1$H NMR (400 MHz, DMSO-d$_6$) δ 13.44-12.80 (m, 1H), 4.20-4.12 (m, 2H), 3.25-3.10 (m, 1H), 3.09-2.99 (m, 1H), 2.96-2.86 (m, 1H), 2.82-2.71 (m, 1H), 2.63-2.52 (m, 1H), 1.25-1.18 (m, 3H), 1.14 (s, 3H), 1.02-0.92 (m, 1H), 0.34-0.20 (br s, 1H), 0.05-0.05 (br s, 1H).

Preparation 7a: ethyl (4aS,5aR)-5a-methyl-2-((2-(trimethylsilyl)ethoxy)methyl)-2,4,4a,5,5a,6-hexahydrocyclopropa[f]indazole-3-carboxylate; and Preparation 7b: ethyl (4aS,5aR)-5a-methyl-1-((2-(trimethylsilyl)ethoxy)methyl)-1,4,4a,5,5a,6-hexahydrocyclopropa[f]indazole-3-carboxylate

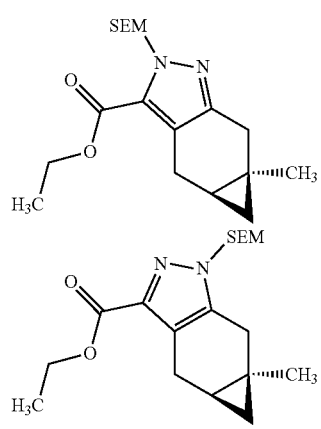

A suspension of NaH (19.3 g, 483 mmol) in THF (500 mL) was treated with a solution of Preparation 6b (103 g, 467.6 mmol) in THF (1.25 L) at 0° C. After 30 min, SEM-Cl (81.9 g, 491 mmol) was added at 0° C. and the mixture was stirred at 0° C. for 3 h. The mixture was treated with sat. aq. NH$_4$Cl (500 mL) at 0° C. The mixture was extracted with EtOAc (3×500 mL), washed with brine (500 mL), dried (MgSO$_4$), filtered and concentrated. The crude product was purified by chromatography (silica, EtOAc/heptanes=7-18%) to provide the title compounds.

7a: (5.5 g, 3.3%); $^1$H NMR (400 MHz, DMSO-d6) δ 5.43 (br. s, 2H), 4.54-4.28 (m, 2H), 3.55-3.50 (m, 2H), 3.27-3.23 (m, 1H), 3.12-3.08 (m, 1H), 2.99-2.97 (m, 1H), 2.71-2.67 (m, 1H), 1.60-1.41 (m, 3H), 1.21 (s, 3H), 1.08-1.05 (m, 1H), 0.89-0.85 (m, 2H), 0.41-0.39 (m, 1H), 0.21-0.19 (m, 1H), −0.03 (s, 9H).

7b: (138 g, 84%); $^1$H NMR (400 MHz, DMSO-d6) δ 5.64 (s, 2H), 4.32-4.25 (m, 2H), 3.49-3.44 (m, 2H), 3.20-3.16 (m, 1H), 2.95-2.88 (m, 2H), 2.67-2.62 (m, 1H), 1.32-1.28 (m, 3H), 1.21 (s, 3H), 1.05-0.95 (m, 1H), 0.76-0.72 (m, 2H), 0.33-0.29 (m, 1H), 0.04-0.01 (m, 1H), −0.1 (s, 9H); LC/MS m/z (M+H)$^+$=351.3.

Preparation 8: ((4aS,5aR)-5a-methyl-1-((2-(trimethylsilyl)ethoxy)methyl)-1,4,4a,5,5a,6-hexahydrocyclopropa[f]indazol-3-yl)methanol

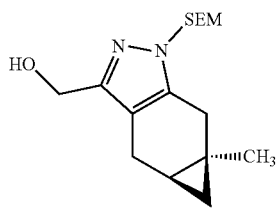 [SMILES: C[C@@]12Cc3c(c(CO)nn3COCC[Si](C)(C)C)C[C@@H]1C2]

A suspension of LiAlH$_4$ (14.94 g, 393.7 mmol) in THF (500 mL) at 0° C. was treated dropwise with a solution of Preparation 7b (138 g, 393.7 mmol) in THF (1 L). The mixture was stirred at 15° C. for 2 h. The mixture was cooled to 0° C. and treated sequentially by dropwise addition of H$_2$O (15 mL), 15% aq. NaOH (15 mL) and H$_2$O (30 mL), followed by addition of MgSO$_4$, and EtOAc (500 mL). The resulting mixture was filtered and the filtrate was concentrated to provide the title compound (110 g, 91%). $^1$H NMR (400 MHz, CDCl$_3$) δ 5.35-5.23 (m, 2H), 4.64-4.55 (m, 2H), 3.53-3.49 (m, 2H), 3.06-3.02 (m, 1H), 2.86-2.81 (m, 2H), 2.67-2.63 (m, 1H), 2.07-1.90 (m, 1H), 1.24 (s, 3H), 1.05-1.03 (m, 1H), 0.91-0.87 (m, 2H), 0.39-0.35 (m, 1H), 0.25-0.22 (m, 1H), −0.03 (d, 9H).

Preparation 9: (4aS,5aR)-5a-methyl-1-((2-(trimethylsilyl)ethoxy)methyl)-1,4,4a,5,5a,6-hexahydrocyclopropa[f]indazole-3-carbaldehyde

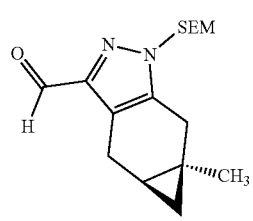 [SMILES: C[C@@]12Cc3c(c(C=O)nn3COCC[Si](C)(C)C)C[C@@H]1C2]

A solution of Preparation 8 (110.13 g, 0.36 mol) in DCM (1.5 L) was treated with activated MnO$_2$ (310 g, 3.57 mol) and the resulting mixture was stirred at 25° C. for 16 h. The mixture was filtered. The filtrate was concentrated, and the crude product was purified by chromatography (silica, EtOAc/PE=3-10%) to provide the title compound (96 g, 88%). SFC method: Chiral Pak AD-3 150 mm×4.6 mm×3 μm, 5-40% (0.05% diethylamine in EtOH/CO$_{2(g)}$) over 1.5 min, 2.5 mL/min, retention time=1.466 min 97.4%, 94.8% ee. $^1$H NMR (400 MHz, DMSO-d6) δ 9.86 (s, 1H), 5.52-5.38 (m, 2H), 3.53-3.49 (m, 2H), 3.16-3.11 (m, 2H), 2.93-2.82 (m, 1H), 2.69-2.65 (m, 1H), 1.22 (s, 3H), 1.08-1.02 (m, 1H), 0.84-0.80 (m, 2H), 0.40-0.39 (m, 1H), 0.10-0.08 (m, 1H), −0.07 (s, 9H); LC/MS m/z (M+H)$^+$=307.3.

Preparation 10. 7,7-difluoro-1-methylspiro[bicyclo[4.1.0]heptane-3,2'-[1,3]dioxolane]

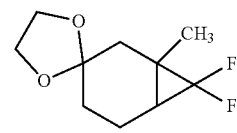

The reaction was carried out in 26 batches in parallel. A solution of Preparation 2 (150 g, 972 mmol) in THF (1.20 L) was treated with TMSCF$_3$ (276 g, 1.95 mol) and NaI (75.8 g, 506 mmol). The mixture was stirred at 70° C. for 16 h. The 26 reaction mixtures were cooled to room temperature and combined. The mixture was diluted with water (10 L) and extracted with MTBE (4×3 L). The organic phase was washed with brine (8 L), dried (Na$_2$SO$_4$), filtered and concentrated to obtain the title compound (4.30 kg, 83% yield).

Preparation 11: 7,7-difluoro-1-methylbicyclo[4.1.0]heptan-3-one

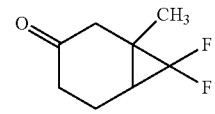

The reaction was carried out 5 batches in parallel. A mixture of Preparation 10 (860 g, 4.21 mol) in THF (10 L) was treated with 3M HCl (2.6 L) at 25° C. The mixture was stirred at 25° C. for 16 hours. The 5 reactions were combined and extracted with MTBE (4×2.5 L), washed with sat. aq. NaHCO$_3$ (5 L) and brine (5 L). The organic phase was dried (Na$_2$SO$_4$), filtered and concentrated to deliver the title compound 11 (3.50 kg); $^1$H NMR (400 MHz, CDCl$_3$) δ: 2.56 (br d, 1H), 2.38-2.13 (m, 4H), 2.01-1.89 (m, 1H), 1.49-1.38 (m, 1H), 1.27 (br s, 3H)

Preparation 12: ethyl 2-(7,7-difluoro-6-methyl-4-oxobicyclo[4.1.0]heptan-3-yl)-2-oxoacetate

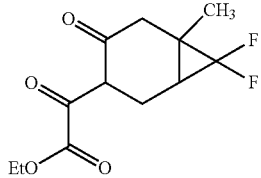 [SMILES: CCOC(=O)C(=O)C1CC2C(F)(F)C2(C)CC1=O]

The reaction was carried out 8 batches in parallel. A solution of Preparation 11 (250 g, 1.56 mol) in EtOH (1.25 L) was treated with EtONa (112 g, 1.65 mol) in portions at 0° C. The resultant mixture was treated with diethyl oxalate (242 g, 1.65 mol) at 0° C. The reaction mixture was stirred at 25° C. for 1 h. The 8 batches were combined. The mixture was poured into 3M HCl solution (8.00 L) and extracted with DCM (3×2 L). The organic extracts were washed with brine (5 L), dried ($Na_2SO_4$), filtered and concentrated to deliver the title compound 12 (3.20 kg, 98% yield)

Preparation 13: ethyl 5,5-difluoro-5a-methyl-1,4,4a,5,5a,6-hexahydrocyclopropa[f]indazole-3-carboxylate

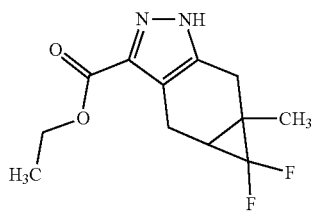 [SMILES: CCOC(=O)c1n[nH]c2c1CC1C(F)(F)C1(C)C2]

The reaction was carried out 8 batches in parallel. A suspension of Preparation 12 (400 g, 1.54 mol) in EtOH (2 L) was treated with hydrazine hydrate (76.9 g, 1.54 mol) at 0° C. The reaction was stirred at RT for 16 h. The eight reactions were combined for workup. The reaction mixture was concentrated and the residue taken up in $H_2O$ (5.00 L) and extracted with EtOAc (5×2 L). The combined organic extracts were dried over ($Na_2SO_4$), filtered and concentrated. The crude product was purified by re-crystallization from 6:1 EtOAc/EtOH (3 L) at 20° C. to deliver the title compound 13 (1.0 Kg). $^1$H NMR (400 MHz, $CDCl_3$) δ: 12.03-10.65 (br m, 1H), 4.38 (q, 2H), 3.30-3.04 (m, 3H), 2.79 (dd, 1H), 1.57 (br dd, 1H), 1.34-1.43 (m, 6H); LC-MS (ES+) e/z [M+H]=257.1

Preparation 14: Chiral SFC Separation of Enantiomers

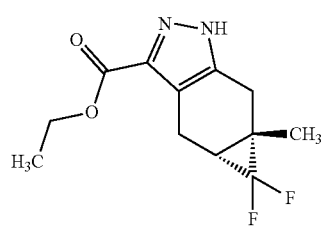

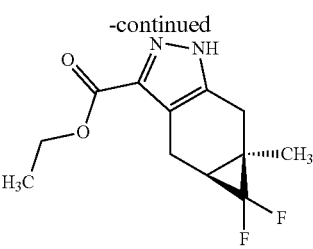

Preparation 13 was separated by chiral SFC using a Chiral Tech AD-H 250 mm×21.2 mm 5 μm column with a mobile phase of $CO_{2(g)}$/MeOH=80:20 with 0.2% 7N $NH_3$ in MeOH and a flow rate of 200 mL/min.

SFC analytical method: Chiral Tech AD-H 250 mm×4.6 mm×5 μm A=$CO_{2(g)}$; B=0.2% $NH_3$ (as 7N $NH_3$ in MeOH) in MeOH; gradient=0-1 min 5% B, 1-9.5 min 5-60% B ramp; 9.5-10 min 60-5% B ramp.

Prep. 14a, ethyl (4aR,5aS)-5,5-difluoro-5a-methyl-1,4,4a,5,5a,6-hexahydrocyclopropa[f]indazole-3-carboxylate, 100% ee by SFC analytical method, retention time=4.605 min Prep. 14b, ethyl (4aS,5aR)-5,5-difluoro-5a-methyl-1,4,4a,5,5a,6-hexahydrocyclopropa[f]indazole-3-carboxylate, 99.85% ee by SFC analytical method, retention time=5.565 min

Preparation 15: ethyl (4aS,5aR)-5,5-difluoro-5a-methyl-1-((2-(trimethylsilyl)ethoxy)methyl)-1,4,4a,5,5a,6-hexahydrocyclopropa[f]indazole-3-carboxylate

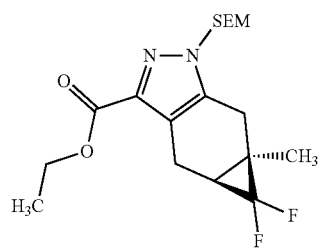 [SMILES: CCOC(=O)c1nn(COCC[Si](C)(C)C)c2c1C[C@@H]1C(F)(F)[C@]1(C)C2]

A mixture of NaH (4.25 g, 106 mmol) in THF (20 mL) cooled to 0° C. was treated dropwise over 45 min with a solution of Preparation 14b (18.16 g, 70.87 mmol) in THF (100 mL). The mixture was stirred at 0° C. for 1 h and then treated dropwise with SEM-Cl (17.7 g, 106 mmol) in THF (80 mL). The resultant mixture was stirred at RT for 48 h. The reaction mixture was poured slowly over ice and extracted 3× with EtOAc. The organic extracts were combined, washed with brine, dried ($MgSO_4$), filtered and concentrated. The crude product was purified by chromatography (silica, EtOAc/heptanes=0-20%) to deliver 25.8 g (94%) of the title compound. $^1$H NMR (400 MHz, $CDCl_3$) δ 5.50-5.40 (m, 2H), 4.40 (q, 2H), 3.55-3.47 (m, 2H), 3.26-3.05 (m, 3H), 2.76 (br dd, 1H), 1.62-1.54 (m, 1H), 1.44-1.35 (m, 6H), 0.94-0.81 (m, 2H), −0.03 (s, 9H); LC-MS m/z (M+H)$^+$=387.4

Preparation 16: ((4aS,5aR)-5,5-difluoro-5a-methyl-1-((2-(trimethylsilyl)ethoxy)methyl)-1,4,4a,5,5a,6-hexahydrocyclopropa[f]indazol-3-yl)methanol

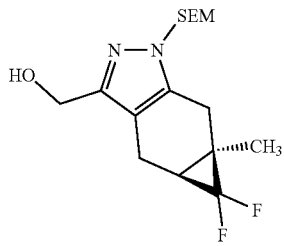 [SMILES: C[C@@]12Cc3c(c(CO)nn3COCC[Si](C)(C)C)C[C@@H]1C2(F)F]

To a solution of Preparation 15 (25.84 g, 66.86 mmol) in THF (100 mL) at approximately −5° C. was added a solution of LiAlH$_4$ (100 mL, 1M in THF) dropwise at such a rate as to control the temperature between 0 and 10° C. The mixture was stirred at 0° C. for additional 1 h and gradually warmed to RT and stirred for an additional 4 h. The mixture was cooled to −10° C. and treated dropwise with 6 N NaOH (45 mL) over 30 min. Additional EtOAc was added to aid stirring of the thick mixture and the slurry was warmed to RT. Anhydrous MgSO$_4$ was added and stirring continued for an additional 30 min. The mixture was filtered and the solids rinsed with EtOAc. The filtrate was concentrated and dried to deliver the title compound (21.89 g, 95%). $^1$H NMR (400 MHz, CDCl$_3$) δ 5.38-5.21 (m, 2H), 4.60 (s, 2H), 3.55-3.41 (m, 2H), 3.08 (br d, 1H), 2.98-2.83 (m, 2H), 2.79-2.65 (m, 1H), 2.24 (br s, 1H), 1.60-1.49 (m, 1H), 1.40 (br s, 3H), 0.94-0.80 (m, 2H), −0.03 (s, 9H); LC-MS m/z (M+H)$^+$=345.5.

Preparation 17: (4aS,5aR)-5,5-difluoro-5a-methyl-1-((2-(trimethylsilyl)ethoxy)methyl)-1,4,4a,5,5a,6-hexahydrocyclopropa[f]indazole-3-carbaldehyde

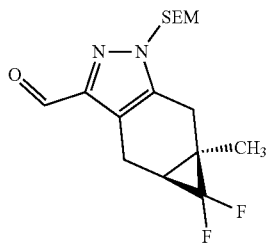 [SMILES: C[C@@]12Cc3c(c(C=O)nn3COCC[Si](C)(C)C)C[C@@H]1C2(F)F]

A solution of Preparation 16 (21.89 g, 63.55 mmol) in DCM (25 mL) was cooled to 0° C. A solution of Dess-Martin periodinane (33.7 g, 79.4 mmol) in DCM (250 mL) was added dropwise at 0° C. over approximately 20 min. The mixture was treated with 2.2% water/DCM (50 mL) added dropwise over 45 min at 0° C. The mixture was warmed to RT and stirred for 4 h. The mixture was treated with 1 N NaOH (380 mL) and stirred for 30 min. The biphasic mixture was separated. The organic phase was washed with brine, dried (MgSO$_4$), filtered and concentrated. The crude product was purified by chromatography (silica, EtOAc/heptanes=0-50%) to deliver the title compound (17.8 g, 82%). $^1$H NMR (400 MHz, CDCl$_3$) d 9.98 (s, 1H), 5.52-5.35 (m, 2H), 3.61-3.43 (m, 2H), 3.27-3.05 (m, 4H), 2.82-2.66 (m, 1H), 1.42 (m., 3H), 0.98-0.80 (m, 2H), 0.08--0.13 (m, 9H); LC-MS m/z (M+H)$^+$=343.3.

Preparation 18: Benzyl (S)-2-morpholinopropanoate

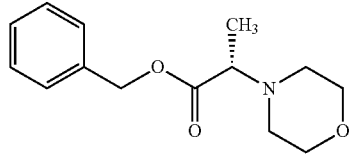 [SMILES: C[C@@H](C(=O)OCc1ccccc1)N1CCOCC1]

A solution of benzyl L-alaninate 4-methylbenzenesulfonate (500 g, 1.42 mol) in DMSO (3 L) was treated with Et$_3$N (624 g, 6.165 mol) and the mixture was cooled to 0° C. A solution of 1-bromo-2-(2-bromoethoxy)ethane (429 g, 1.849 mol) in DMSO (1 L) was slowly added to the reaction. The resulting mixture was stirred at 25° C. for 36 h. Water (3 L) and EtOAc (2 L) were added to the mixture. The aqueous phase was extracted with EtOAc (2×1 L). The combined organic extracts were dried (Na$_2$SO$_4$), filtered and concentrated. The crude product was purified by chromatography (silica, EtOAc/PE=11%) to provide the title compound (290 g, 82%). $^1$H NMR (400 MHz, DMSO-de) δ 7.42-7.31 (m, 5H), 5.19 (s, 2H), 3.79-3.66 (m, 4H), 3.35-3.30 (m, 1H), 2.69-2.56 (m, 4H), 1.32-1.29 (m, 3H).

Preparation 19: (S)-2-morpholinepropanoic acid

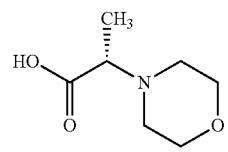

A solution of Preparation 18 (290 g, 1.56 mol) in MeOH (2.9 L) was treated with 10% Pd(OH)$_2$/C (29 g) at 25° C. The mixture was degassed and purged with N$_2$ (3 times) and then stirred under an atmosphere of H$_2$ for 36 h. The solid was removed by filtration and the filtrate concentrated. The resulting residue was washed with MTBE (200 mL×2) to provide the title compound (146 g, 79%). SFC analytical method: Chiral Tech IC 250 mm×4.6 mm×5 μm, 5 to 60% with 0.2% NH$_4$$^+$ (7 N in MeOH) in MeOH/CO$_{2(g)}$, 3.0 mL/min, retention time=5.88 min, 100% ee; $^1$H NMR (400 MHz, DMSO-de) δ 3.56 (s, 4H), 3.18-3.16 (m, 1H), 2.54-2.53 (m, 4H), 1.17-1.15 (m, 3H); LC/MS m/z (M+H)$^+$=160.1.

Preparation 20: 2-(tetrahydro-2H-pyran-4-yl)acetyl chloride

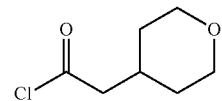

A solution of 2-(tetrahydro-2H-pyran-4-yl)acetic acid (17.3 g, 120 mmol) in DCM (400 mL) and DMF (1 mL) at 0° C. was treated with oxalyl chloride (30.5 g, 240 mmol).

The mixture was then warmed to 20° C. and stirred for 16 h. The mixture was concentrated to give the title compound (19.5 g, quant.).

Preparation 21: (R)-4-benzyl-3-(2-(tetrahydro-2H-pyran-4-yl)acetyl)oxazolidin-2-one

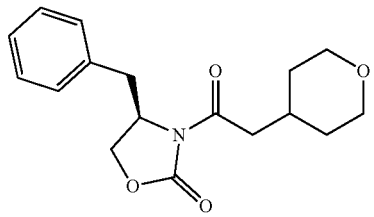 [SMILES: O=C(CC1CCOCC1)N1C(=O)OC[C@H]1Cc1ccccc1]

A solution of 20 (14.2 g, 79.9 mmol) in THF (500 mL) at −78° C. was treated with n-BuLi (47.9 mL, 120 mmol). The mixture was then stirred at −78° C. for 2 h. A solution of 2-(tetrahydro-2H-pyran-4-yl)acetyl chloride (19.5 g, 120 mmol) in THF (100 mL) was added at −78° C. and stirred for an additional 2 h. The mixture was then warmed to 20° C. and then stirred for 16 h. The reaction was treated with sat. aq. NH$_4$Cl (400 mL) and the resulting biphasic mixture separated. The organic phase was dried (Na$_2$SO$_4$) and concentrated. The residue was suspended in DCM/PE (50 mL/300 mL) and stirred at −50° C. for 30 min. The solids were collected and dried to give the title compound (21.5 g, 89% yield). LC/MS m/z (M+H)=303.8.

Preparation 21a: (R)-4-benzyl-3-((R)-2-(tetrahydro-2H-pyran-4-yl)propanoyl)oxazolidin-2-one

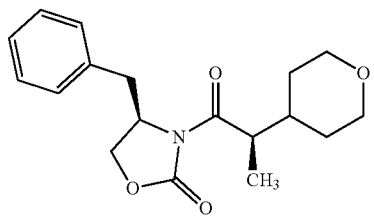 [SMILES: C[C@@H](C(=O)N1C(=O)OC[C@H]1Cc1ccccc1)C1CCOCC1]

A solution of Preparation 21 (21.5 g, 70.8 mmol) in THF (200 mL) at −78° C. was treated with NaHMDS (1M in THF, 106 mL). The mixture was stirred for 1 h and treated with methyl iodide (50.3 g, 354 mmol) at −78° C. The reaction mixture was stirred at −78° C. for 2 h and then gradually warmed to 20° C. over 16 h. The reaction mixture was treated with sat. aq. NH$_4$Cl (300 mL) and the biphasic mixture separated. The organic layer was washed with brine, dried (MgSO$_4$), filtered and concentrated. The crude product was purified by chromatography (silica, EtOAc/PE: 0-100%) to give the title compound (15.5 g, 69%). $^1$H NMR (400 MHz, CDCl$_3$) δ 7.32-7.11 (m, 5H), 4.62 (ddt, 1H), 4.20-4.07 (m, 2H), 4.02 (dd, 1H), 3.94 (dd, 1H), 3.65-3.54 (m, 1H), 3.33 (tt, 2H), 3.22 (dd, 1H), 2.72 (dd, 1H), 1.97-1.87 (m, 1H), 1.64-1.56 (m, 1H), 1.58-1.51 (m, 1H), 1.41-1.26 (m, 2H), 1.15 (d, 3H); LC/MS m/z (M+H)$^+$=318.3.

Preparation 22: (R)-2-(tetrahydro-2H-pyran-4-yl)propanoic acid

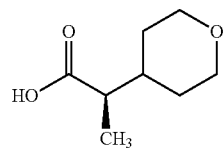

A solution of Preparation 21a (15.5 g, 48.8 mmol) in THF/H$_2$O (410 mL/255 mL) at 0° C. was treated with LiOH·H$_2$O (10.2 g, 244 mmol) and 30% aq. H$_2$O$_2$ (27.7 g, 244 mmol). The mixture was stirred at 0° C. for 1.5 h and then at 20° C. for 1.5 h. The mixture was treated with sat. aq. Na$_2$SO$_3$ (300 mL) and the organic solvent was removed in vacuo. The mixture was washed with DCM (2×200 mL) and then treated with conc. HCL until pH=1 was reached. The mixture was extracted with DCM (3×200 mL), and the extracts were combined and dried (Na$_2$SO$_4$), filtered and concentrated to give the title compound 22 (6.12 g, 79% yield). (Reference: Evans, D. A, et al. J. Am. Chem. Soc. 1984, 106, 1154-1156)
$^1$H NMR (400 MHz, CDCl$_3$) δ 4.07-3.93 (m, 2H), 3.39 (dt, 2H), 2.30 (p, 1H), 1.87-1.77 (m, 1H), 1.68-1.56 (m, 2H), 1.51-1.28 (m, 2H), 1.17 (d, 3H). [a]$^{20}_D$=−17.98 (c=0.3 g/100 mL, EtOH); Chiral SFC (MeOH/CO$_2$, Chiral Tech IG, 5 to 60% over 10 min, 250 mm×4.6 mm×5 μm) retention time=3.42 min, 97% ee.

Preparation 23: (S)-2-(tetrahydro-2H-pyran-4-yl)propanoic acid

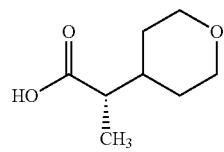

The acid was prepared in an analogous manner to Preparation 22 (R)-2-(tetrahydro-2H-pyran-4-yl)propanoic acid using (S)-4-benzyloxazolidin-2-one in Step 2. $^1$H NMR (400 MHz, CDCl$_3$) δ 4.07-3.93 (m, 2H), 3.39 (tt, 2H), 2.30 (p, 1H), 1.81 (tdt, 1H), 1.61 (dddq, 2H), 1.51-1.28 (m, 2H), 1.17 (d, 3H). [α]$^{20}_D$=+19.99 (c=0.3 g/100 mL, EtOH)

Preparation 24: Benzyl 2-bromopropanoate

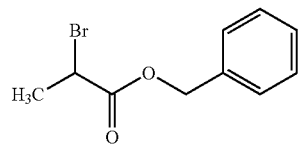

To a solution of 2-bromopropionic acid (5.0 g, 32.7 mmol) in DCM (100 mL) at 0° C. was added Et$_3$N (3.64 g, 36.0 mmol), followed by benzyl chloroformate (5.58 g, 32.7 mmol) dropwise. After 10 min, DMAP (399 mg, 3.27 mmol) was added and the mixture stirred for 4 h at 30° C. The mixture was poured into 1M HCl (15 mL) and brine (80 mL). The mixture was extracted with DCM (2×80 mL). The organic extracts were combined, dried (MgSO₄), filtered and concentrated. The crude product was purified by chromatography (silica, EtOAc/PE, 0-5%) to deliver the title compound (4.81 g, 86%). ¹H NMR (400 MHz, CDCl₃) δ 7.38-7.27 (m, 5H), 5.22-5.10 (m, 2H), 4.43-4.37 (m, 1H), 1.80 (d, 3H); LC/MS m/z (M+Na)⁺=267.0.

Preparation 25: Benzyl 2-(3-oxomorpholino)propanoate

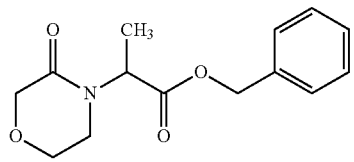 [SMILES: CC(C(=O)OCc1ccccc1)N1CCOCC1=O]

A solution of morpholin-3-one (750 mg, 7.42 mmol) in THF (49 mL) at 5° C. was treated with NaH (475 mg, 11.9 mmol). After stirring for 30 min, Preparation 24 (16 g, 8.90 mmol) was added dropwise. After stirring at 25° C. for 3 h the mixture was diluted with sat. aq. NH₄Cl (30 mL) and water (20 mL). The mixture was extracted with EtOAc (2×60 mL) and the combined extracts were dried (MgSO₄), filtered and concentrated. The crude product was purified by chromatography (silica, EtOAc/PE=0-70%) to give the title compound 25 (256 mg, 13%). ¹H NMR (400 MHz, CDCl₃) δ 7.41-7.30 (m, 5H), 5.33 (q, 1H), 5.22-5.09 (m, 2H), 4.22 (s, 2H), 3.96-3.77 (m, 2H), 3.52-3.20 (m, 2H), 1.45 (d, 3H).

Preparation 26: 2-(3-oxomorpholino)propanoic acid

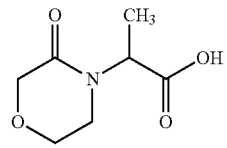

To a mixture of Preparation 25 (256 mg, 0.98 mmol) in MeOH (10 mL) was added 10% Pd/C (50% in water, 207 mg, 0.19 mmol). The mixture was stirred under H₂ (1 atm) at 25° C. for 16 h. The reaction was filtered and the solids washed with MeOH (3×20 mL). The filtrate was concentrated to give the title compound 26 (167 mg, 99%). ¹H NMR (400 MHz, CDCl₃) δ 6.15 (bs, 1H), 5.16 (d, 1H), 4.24 (d, 2H), 4.06-3.82 (m, 2H), 3.55-3.28 (m, 2H), 1.45 (dd, 3H).

Preparation 27: (S)—N-(5-chloro-2-methyl-4-nitrophenyl)-2-morpholinopropanamide

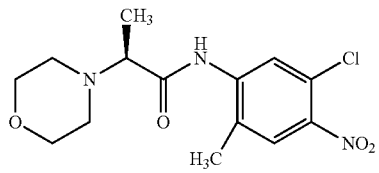 [SMILES: Cc1cc([N+](=O)[O-])c(Cl)cc1NC(=O)[C@H](C)N1CCOCC1]

To a solution of 5-chloro-2-methyl-4-nitroaniline (4.0 g, 21.4 mmol) and Preparation 19 (4.09 g 25.7 mmol) in pyridine (70 mL) was added EDCI (8.84 g, 46.1 mmol) at 20° C. The mixture was stirred at 20° C. for 16 h. The mixture was treated with sat. aq. NH₄Cl (100 mL) and extracted with EtOAc (3×100 mL). The combined organic layers were dried (Na₂SO₄), filtered and concentrated. The crude product was triturated with MTBE (100 mL) to provide the title compound (4.8 g, 68%). ¹H NMR (400 MHz, CDCl₃) δ 9.83 (s, 1H), 8.68 (s, 1H), 7.87 (s, 1H), 3.87-378 (m, 4H), 3.35-3.29 (m, 1H), 2.72-2.62 (m, 2H), 2.37 (s, 3H), 1.39-1.38 (m, 3H).

Preparation 28: (S)—N-(5-chloro-2-methyl-4-nitrophenyl)-N-methyl-2-morpholinopropanamide

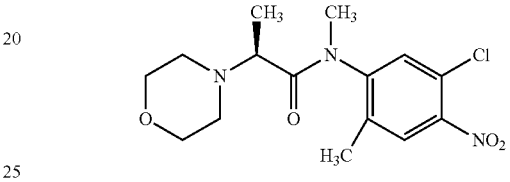

To a solution of Preparation 27 (5.50 g, 16.8 mmol) in THF (75 mL) was added KOtBu (2.07 g, 18.5 mmol) at 0° C. The mixture was stirred at 0° C. for 1 h and a solution of methyl iodide (2.62 g, 18.5 mmol) in THF (15 mL) was added dropwise at 0° C. The mixture was stirred at 25° C. for 16 h. The reaction was treated with sat. aq. NH₄Cl (100 mL) and extracted with EtOAc (2×100 mL). The combined organic layers were washed with brine, dried (Na₂SO₄), filtered and concentrated to provide the title compound (5.1 g, 89%). ¹H NMR (400 MHz, CDCl₃) δ 7.92-7.81 (m, 1H), 7.72 (s, 0.5H), 7.32 (s, 0.5H), 3.79-3.47 (m, 4H), 3.21-3.19 (m, 3H), 3.39-2.83 (m, 1H), 2.62-2.51 (m, 2H), 2.43-2.29 (m, 3H), 2.22-2.16 (m, 2H), 1.18-1.11 (m, 3H).

Preparation 29: (S)—N-(5-((4-methoxybenzyl)amino)-2-methyl-4-nitrophenyl)-N-methyl-2-morpholinopropanamide

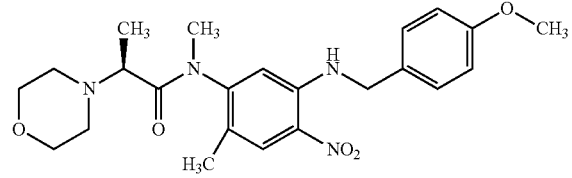 [SMILES: COc1ccc(CNc2cc(N(C)C(=O)[C@H](C)N3CCOCC3)c(C)cc2[N+](=O)[O-])cc1]

To a mixture of Preparation 28 (320 g 936.3 mmol) in 4-methoxybenzyl amine (513.7 g, 3.74 mol) was added ammonium acetate (72.2 g, 936.3 mmol). The mixture was heated at 100° C. for 16 h. The mixture was diluted with in EtOAc (1.5 L) and washed with sat. aq. NH₄Cl (3×1.5 L) and concentrated. The crude product was purified by chromatography (silica, MeOH/DCM=0-10%) to provide the title compound (261 g, 64%) as a solid. ¹H NMR (400 MHz, CDCl₃) δ 8.38-8.02 (m, 1H), 7.26-7.22 (m, 2H), 6.94-6.98 (m, 2H), 6.79-6.48 (m, 1H), 4.57-4.47 (m, 2H), 3.87-3.81 (m, 3H), 3.61-3.51 (m, 5H), 3.14-3.11 (m, 3H), 3.03-2.83 (m, 1H), 2.56-2.40 (m, 2H), 2.30-2.04 (m, 4H), 1.14-1.01 (m, 3H).

Preparation 30: (S)—N-(4,5-diamino-2-methylphenyl)-N-methyl-2-morpholinopropanamide

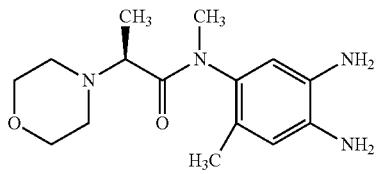 [SMILES: Cc1cc(N)c(N)cc1N(C)C(=O)[C@H](C)N1CCOCC1]

To a solution of Preparation 29 (256 g, 578.5 mmol) in DCM (1.25 L) was added TFA (1.28 L, 17.3 mol) and the mixture was stirred at 25° C. for 2 h. The mixture was concentrated and then diluted in DCM (1 L). The resulting mixture was adjusted to ~pH 9 with sat. Na$_2$CO$_3$ and then was extracted with DCM (2×1 L). The combined organic layer was washed with brine (1 L), dried over Na$_2$SO$_4$, filtered and the filtrate was concentrated. The residue was dissolved in DCM (500 mL) to which 4M HCl/dioxane (1 L) was added dropwise and stirred for 0.5 h. The mixture was concentrated and DCM (800 mL) was added. The resulting mixture was stirred for 16 h. The mixture was filtered, and the resulting filter cake was dried in vacuo to provide the HCl salt of (S)—N-(4-amino-2-methyl-5-nitrophenyl)-N-methyl-2-morpholinopropanamide (200 g) as a solid. In three separate batches, a hydrogenation vessel was charged with (S)—N-(4-amino-2-methyl-5-nitrophenyl)-N-methyl-2-morpholinopropanamide (66.6 g, 206.6 mmol) from above and MeOH (900 mL). To the reaction vessel was added 10% Pd/C (13 g, 41.32 mmol) and the mixture was purged with N$_2$ followed by H$_2$. The reaction was hydrogenated under 50 psi of H$_2$ at 40° C. for 48 h. The reaction mixture was filtered (2×) and the filtrate were washed with MeOH (3×500 mL). The filtrate was concentrated to give a residue. The residue was dissolved in MeOH (1 L) to which Na$_2$CO$_3$ (41.9 g, 395 mmol) was added and the mixture was stirred at 25° C. for 1 h. The mixture was filtered which was washed with MeOH (5×200 mL). The filtrate was concentrated. The residue was purified by chromatography (silica, DCM:MeOH 0-10% gradient) to provide the title compound (159.4 g, 89% yield). SFC method: Chiralpak IB N-5 250 mm×4.6 mm×5 µm, 5% (0.2% isopropyl amine in isopropanol/CO$_{2(g)}$) for 1 min then to 60% over 8 min, 2.5 mL/min, retention time=8.636 min, 98.42%, 96.85% ee. $^1$H NMR (400 MHz, CDCl$_3$) δ 6.60 (s, 0.5H), 6.59 (s, 0.5H), 6.56 (s, 0.5H), 6.42 (s, 0.5H), 6.56-6.42 (m, 1H), 3.71-3.60 (m, 4H), 3.40 (br s, 4H), 3.17-3.07 (m, 4H), 2.66-2.57 (m, 2H), 2.40-2.31 (m, 2H), 2.16 (s, 1.5H), 2.06 (s, 1.5H), 1.19-1.12 (m, 3H); LC/MS m/z (M+H)$^+$=293.2

Preparation 31: N-(4,5-diamino-2-methylphenyl)-N-methyl-2-morpholinopropanamide

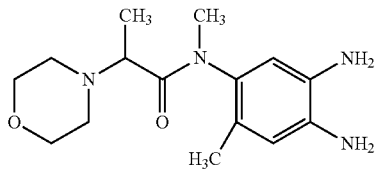 [SMILES: Cc1cc(N)c(N)cc1N(C)C(=O)C(C)N1CCOCC1]

The title compound 31 was prepared in an analogous manner to Preparation 30, starting from (±)-2-morpholinepropanoic acid; LC/MS m/z (M+H)$^+$=293.3.

Preparation 32: (S)—N-(3,4-diaminophenyl)-N-methyl-2-morpholinopropanamide

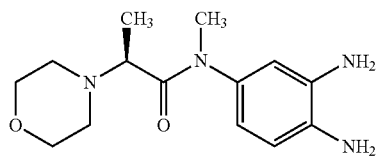

The title compound was prepared analogously to Preparation 30 starting from 3-chloro-4-nitroaniline and Preparation 19.

$^1$H NMR (400 MHz, CDCl$_3$) δ=6.68 (d, 1H), 6.60-6.47 (m, 2H), 3.75-3.61 (m, 4H), 3.54-3.37 (m, 2H), 3.26 (q, 1H), 3.21 (s, 3H), 2.64-2.55 (m, 2H), 2.47-2.35 (m, 2H), 1.15 (d, 3H)

Preparation 33: N-(5-chloro-2-ethylphenyl)acetamide

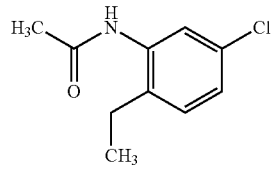

5-chloro-2-ethylaniline (405 mg, 2.6 mmol) was added to Ac$_2$O (10 mL, 110 mmol) with stirring at 25° C. The reaction mixture was stirred for 3 h and filtered to collect the precipitate. The solids were rinsed with water (3×15 mL) and dried to give the title compound (496 mg, 96%). $^1$H NMR (400 MHz, CDCl$_3$) δ 7.91 (s, 1H), 7.12 (t, 2H), 6.96 (s, 1H), 2.56 (q, 2H), 2.21 (s, 3H), 1.22 (t, 3H); LC/MS m/z (M+H)=197.9;

Preparation 34: N-(5-chloro-2-ethyl-4-nitrophenyl)acetamide

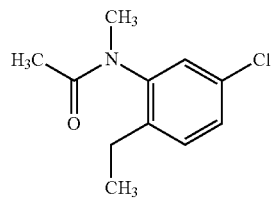

A solution of Preparation 33 (496 mg 2.51 mmol) in conc. H$_2$SO$_4$ (2 mL) was cooled at 0° C. and treated with KNO$_3$ (254 mg, 2.51 mmol) in portions and while keeping the internal temperature below 5° C. The resulting mixture was stirred for 4 h between at a temperature between 0-5° C. The mixture was poured into water (30 mL) and stirred for 10 min. The mixture was filtered and the collected solids washed with water (3×20 mL) and dried under vacuum to give the title compound (600 mg, 99%). $^1$H NMR (400 MHz, CDCl$_3$) δ 8.47 (s, 1H), 7.85 (d, 1H), 7.18 (s, 1H), 2.70-2.59 (m, 2H), 2.29 (s, 3H), 1.34 (t, 3H); LC/MS m/z (M+H)=242.9

Preparation 35: 5-chloro-2-ethyl-4-nitroaniline

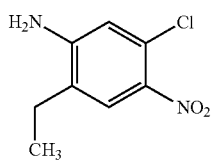

A solution of Preparation 34 (450 mg, 1.85 mmol) in EtOH (10 mL) and water (5 mL) was treated with NaOH (371 mg, 9.27 mmol) at 25° C. The resulting mixture was heated at 80° C. for 16 h. Additional NaOH (74.2 mg, 1.85 mmol) was added to the mixture and heating continued at 80° C. for an additional 16 h. The mixture was concentrated, diluted with water (20 mL) and extracted with EtOAc (2×20 mL). The combined organic layers were concentrated and purified by chromatography (silica, EtOAc/PE=0 to 15%) to give the title compound (278 mg, 74%). $^1$H NMR (400 MHz, CDCl$_3$) δ 7.88 (s, 1H), 6.70 (s, 1H), 4.29 (s, 2H), 2.54-2.43 (m, 2H), 1.29 (t, 3H); LC/MS m/z (M+H)=200.9.

Preparation 36. (S)—N-(3-fluoro-4-nitrophenyl)-2-morpholinopropanamide

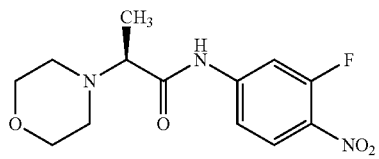 [SMILES: C[C@@H](C(=O)Nc1ccc([N+](=O)[O-])c(F)c1)N1CCOCC1]

A solution of 3-fluoro-4-nitroaniline (1.0 g, 6.41 mmol) in pyridine (20 mL) at 20° C. was treated with Preparation 19 (1.22 g, 7.69 mmol) and EDCI (1.46 g, 12.8 mmol). The mixture was stirred for 15 h, concentrated and diluted with EtOAc/H$_2$O (150 mL/50 mL). The organic layer was separated and the aqueous layer extracted with EtOAc (50 mL). The organic extracts were combined, washed with brine, dried (MgSO$_4$), filtered and concentrated. The crude product was purified by chromatography (silica, EtOAc/PE=0-100%) to deliver the title compound (1.36 g, 72%). LC/MS m/z (M+H)$^+$=298.0.

Preparation 37. (S)—N-(3-fluoro-4-nitrophenyl)-N-methyl-2-morpholinopropanamide

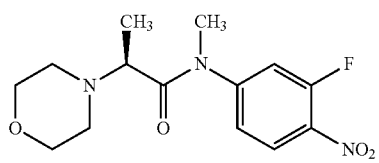 [SMILES: C[C@@H](C(=O)N(C)c1ccc([N+](=O)[O-])c(F)c1)N1CCOCC1]

A solution of Preparation 36 (1.36 g, 4.58 mmol) in THF (60 mL) at 0° C. was treated with NaH (274 mg, 6.86 mmol). After 30 min, methyl iodide (0.43 mL, 6.86 mmol) was added and the mixture stirred for 16 h. The mixture was treated with sat. aq. NH$_4$Cl (1 mL) and then partitioned between EtOAc and H$_2$O (150 mL/50 mL). The organic layer was separated and the aqueous layer extracted with EtOAc (100 mL). The organic extracts were collected, dried (MgSO$_4$), filtered and concentrated. The crude product was purified by chromatography (silica, EtOAc/PE=0-100%) to deliver the title compound (410 mg, 29%). LC/MS m/z (M+H)$^+$=312.1.

Preparation 38. (S)—N-(3-amino-4-nitrophenyl)-N-methyl-2-morpholinopropanamide

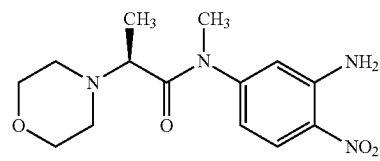

A solution of Preparation 37 (370 mg, 1.19 mmol) in EtOH (30 mL) at 20° C. was treated with conc. NH$_4$OH (10 mL). The mixture was stirred for 15 h at 70° C. and the mixture was diluted with EtOAc/H$_2$O (150/50 mL). The organic layer was separated and the aqueous layer extracted with EtOAc (50 mL). The organic extracts were combined, dried (Na$_2$SO$_4$), filtered, and concentrated to give the title compound (366 mg, 99%). LC/MS m/z (M+H)$^+$=309.1

Preparation 39: (S)—N-(5-amino-2-bromo-4-nitrophenyl)-N-methyl-2-morpholinopropanamide

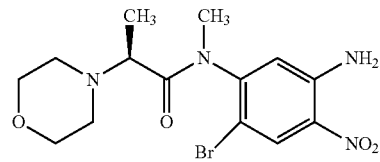 [SMILES: C[C@@H](C(=O)N(C)c1cc(N)c([N+](=O)[O-])cc1Br)N1CCOCC1]

A solution of Preparation 38 (270 mg, 0.88 mmol) in AcOH (10 mL) at 20° C. was treated with Br$_2$ (140 mg, 0.88 mmol). The mixture was stirred for 1 h and the precipitate collected by filtration. The solids were purified by prep. HPLC (Phenomenex Gemini-NX 150 mm×30 mm×5 μm, H$_2$O/CH$_3$CN (0.05% NH$_4$OH), 18-58% over 10 min) to give the title compound (65 mg, 19%). $^1$H NMR (400 MHz, DMSO-de) δ 8.25 (d, 1H), 7.69 (s, 1H), 7.57 (s, 1H), 7.23 (s, 0.6H), 7.07 (s, 0.4H), 3.54-3.46 (m, 3H), 3.37-3.33 (m, 2H), 3.04 (s, 3H), 2.41 (dt, 2H), 2.21-2.10 (m, 2H), 1.07 (d, 1.3H), 1.01 (d, 1.7H); LC/MS m/z (M+H)$^+$=388.8/390.8 ($^{79}$Br, $^{81}$Br)

Preparation 40: (S)—N-(4,5-diamino-2-bromophenyl)-N-methyl-2-morpholinopropanamide

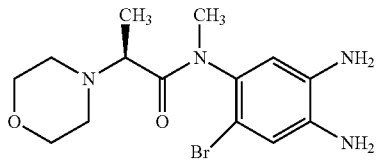

A solution of 39 (40 mg, 0.10 mmol) in EtOH (3 mL) at 20° C. was treated with sat. aq. NH$_4$Cl (0.5 mL) and iron powder (17.3 mg, 0.31 mmol). The mixture was heated to 70° C. for 1 h and filtered. The filtrate was concentrated and the residue purified by prep-HPLC (Boston Prime C18, 150×30 mm×5 μm; H$_2$O/MeCN (0.05% NH$_4$OH) 16-39% over 10 min) to give the title compound (5 mg, 10%). $^1$H NMR (400 MHz, DMSO-d$_6$) δ 6.75 (s, 0.3H), 6.72 (s, 0.7H), 6.58 (s, 0.7H), 6.47 (s, 0.3H), 4.91 (d, 2H), 4.82 (d, 2H), 3.55-3.46 (m, 4H), 3.09 (d, 2H), 2.96 (d, 3H), 1.06 (d, 1.3H), 1.01 (d, 1.7H). LC/MS m/z (M+H)=357.0/359.1 ($^{79}$Br, $^{81}$Br).

Preparation 41: tert-butyl (5-fluoro-2-methyl-4-nitrophenyl)carbamate

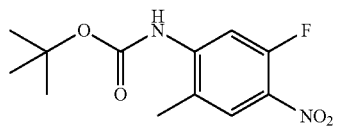 [SMILES: Cc1cc([N+](=O)[O-])c(F)cc1NC(=O)OC(C)(C)C]

A solution of 5-fluoro-2-methyl-4-nitroaniline (133 g, 781 mmol, 1 eq), DMAP (9.55 g, 78.1 mmol, 0.1 eq) and iPr$_2$NEt (202 g, 1.56 mol, 272 mL, 2 eq) in DCM (2 L) was treated with BOC$_2$O (187 g, 859 mmol) at 20° C. The mixture was stirred at 20° C. for 16 h and concentrated. The residue was dissolved in EtOAc (3 L) and washed sequentially with sat. aq. NH$_4$Cl (1 L), sat. aq. NaHCO$_3$ (1 L) and brine (1 L). The organic layer was dried (Na$_2$SO$_4$), filtered and concentrated. The residue was triturated with MeOH (3 L) and the solids collected by filtration to give the title compound (90 g, 374 mmol).

The filtrate was concentrated and the residue dissolved in MeOH (500 mL) and treated with K$_2$CO$_3$ (15.5 g). The mixture was stirred at 20° C. for 3 h. The mixture was filtered and the solids rinsed with MeOH. The filtrate was concentrated and the residue purified by chromatography (silica, EtOAc/PE=0-10%) to give additional title compound (45 g, 166 mmol).

Both batches were combined to give overall title compound (135 g, 72%). $^1$H NMR (400 MHz, CDCl$_3$) δ 8.15 (d, 1H), 7.94-7.88 (m, 1H), 6.62 (s, 1H), 2.28 (s, 3H), 1.55 (s, 9H).

Preparation 42: tert-butyl (5-fluoro-2-methyl-4-nitrophenyl)carbamate

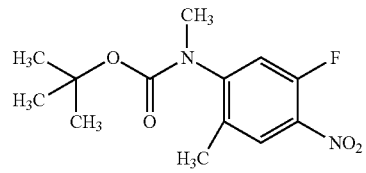

A solution of Preparation 41 (131 g, 486 mmol) in THF (1.9 L) was treated with KOtBu (81.9 g, 730 mmol) at 0° C. and the mixture was stirred at 0° C. for 1 h. Methyl iodide (61 mL, 980 mmol) was added dropwise at 0° C. The resulting mixture was stirred at 20° C. for 16 h. The reaction mixture was treated with sat. aq. NH$_4$Cl (500 mL) and extracted with EtOAc (1 L). The organic layer was washed with brine (500 mL), dried (Na$_2$SO$_4$), and concentrated to give the title compound (150 g, 95% yield). $^1$H NMR (400 MHz, CDCl$_3$) δ 7.95 (d, 1H), 7.07 (d, 1H), 3.17 (s, 3H), 2.26 (s, 3H), 1.40 (d, 9H).

Preparation 43: tert-butyl (5-amino-2-methyl-4-nitrophenyl)(methyl)carbamate

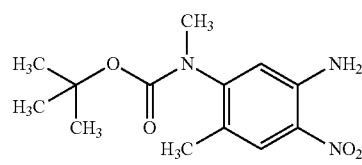

A solution of Preparation 42 (450 g, 1.38 mol, 1 eq) in 7M NH$_3$ in MeOH (7M, 5.5 L) was heated at 58° C. for 72 h. The mixture was concentrated. The residue was dissolved in EtOAc (2 L) and washed with brine (2 L). The organic layer was dried (Na$_2$SO$_4$), filtered and concentrated. The crude product was purified by chromatography (silica, EtOAc/PE=0-20%) to give the title compound (295 g, 76% yield). $^1$H NMR (400 MHz, CDCl$_3$) δ 8.00 (s, 1H), 6.62 (s, 1H), 5.95 (s, 2H), 3.15 (s, 3H), 2.15 (d, 3H), 1.41 (s, 9H); LC/MS m/z (M+H-tert butyl)=225.8.

Preparation 44: tert-butyl (4,5-diamino-2-methylphenyl)(methyl)carbamate

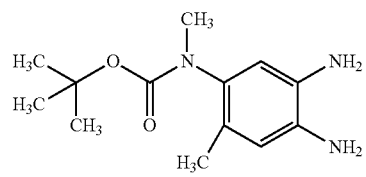 [SMILES: Cc1cc(N)c(N)cc1N(C)C(=O)OC(C)(C)C]

A solution of Preparation 43 (98 g, 349 mmol) in MeOH (1 L) was treated with 10% Pd/C (10 g). The reaction was stirred at 40° C. under H$_2$ (3 atm) for 24 h. The reaction was filtered and the solids rinsed with MeOH (3×500 mL). The filtrate was concentrated to give the title compound (68.3 g, 78%). $^1$H NMR (400 MHz, DMSO-de) δ 6.32 (s, 1H), 6.27

(s, 1H), 4.37 (s, 2H), 4.29 (s, 2H), 2.96 (d, 3H), 1.89 (d, 3H), 1.44 (s, 3H), 1.28 (s, 6H. LC/MS m/z (M+H-tert butyl)=195.9.

Preparation 45: tert-butyl methyl-(6-methyl-2-((4aS, 5aR)-5a-methyl-1-((2-(trimethylsilyl)ethoxy) methyl)-1,4,4a,5,5a,6-hexahydrocyclopropa[f]indazol-3-yl)-1H-benzo[d]imidazol-5-yl)carbamate

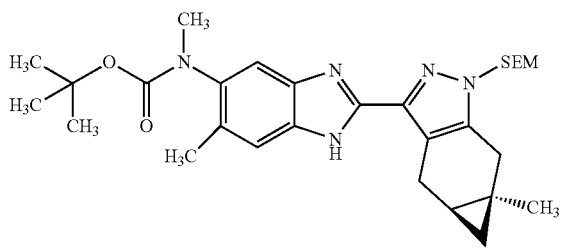 [SMILES: Cc1cc2[nH]c(-c3nn(COCC[Si](C)(C)C)c4c3C[C@@H]3C[C@]3(C)C4)nc2cc1N(C)C(=O)OC(C)(C)C]

A solution of Preparation 44 (5.53 g, 23.5 mmol) and Na₂S₂O₅ (2.24 g, 11.8 mmol) in DMF (124 mL) was treated with 9 (7.21 g, 23.5 mmol) and DMSO (4.6 g, 58.8 mmol) at RT. The mixture was heated at 110° C. for 16 h. The mixture was concentrated. The residue was diluted with EtOAc (500 mL) and washed with 3% aq. LiCl (100 mL). The organic layer was dried (MgSO₄), filtered and concentrated. The crude product was purified by chromatography (silica, EtOAc/PE=0-25%) to give the title compound (10.8 g, 86%). ¹H NMR (400 MHz, CD₃OD) δ 7.46 (t, 1H), 7.38 (s, 1H), 5.53-5.42 (m, 2H), 3.63 (t, 2H), 3.40 (d, 1H), 3.26-3.11 (m, 5H), 2.77 (d, 1H), 2.33 (s, 3H), 1.56 (s, 3H), 1.36-1.30 (m, 9H), 1.18 (dd, 1H), 0.96-0.84 (m, 2H), 0.45 (dd, 1H), 0.28 (t, 1H), −0.02 (s, 9H); LC/MS m/z (M+H)⁺=538.3.

Preparation 46: N,6-dimethyl-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-amine

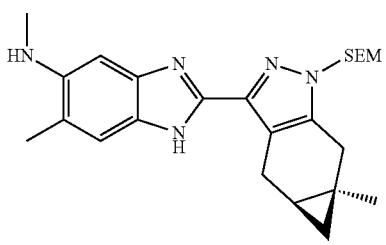 [SMILES: CNc1cc2nc(-c3nn(COCC[Si](C)(C)C)c4c3C[C@@H]3C[C@]3(C)C4)[nH]c2cc1C]

A solution of Preparation 45 (10.86 g 20.2 mmol) in DCM (135 mL) was treated with ZnBr₂ (22.7 g, 101 mmol) at 0° C. The mixture was gradually warmed to RT and stirred for 16 h. The mixture was poured into sat. aq. NaHCO₃ (200 mL) and extracted with DCM (2×200 mL). The combined organic layers dried (MgSO₄), filtered and concentrated. The crude product was purified by chromatography (silica, EtOAc/PE=0-20%) to give the title compound (7.54 q, 85.3%). Chiral SFC (Chiral Pak AS-3, 150 mm×4.6 mm×3 μm; CO₂/EtOH with 0.05% iPr₂NEt, 5 to 40% over 5.5 min) retention time=2.93 min (97.2% ee); ¹H NMR (400 MHz, CD₃OD) δ 7.32 (s, 1H), 6.76 (s, 1H), 5.51-5.42 (m, 2H), 3.38 (t, 2H), 3.40 (d, 1H), 3.31-3.28 (m, 2H), 3.22 (s, 3H), 3.17 (m, 1H), 2.27 (s, 3H), 1.32 (s, 3H), 1.18 (m, 1H), 0.88 (m, 2H), 0.45 (dd, 1H), 0.28 (t, 1H), −0.02 (s, 9H); LC/MS m/z (M+H)⁺=438.3.

Preparation 47: N-(3-fluoro-4-nitrophenyl)acetamide

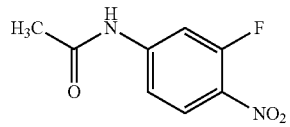

3-Fluoro-4-nitroaniline (20 g, 128.1 mmol) was treated with Ac₂O (250 mL). The mixture was stirred for 16 h at RT and then diluted with water (100 mL). The precipitate was collected by filtration. The solids were taken up in EtOAc (100 mL), dried (Na₂SO₄), filtered and concentrated to give the title compound 47 (23.0 g, 91% yield). ¹H NMR (400 MHz, CD₃OD) δ 8.09 (t, 1H), 7.86 (dd, 1H), 7.38 (dt, 1H), 2.17 (s, 3H).

Preparation 48.
N-(3-fluoro-4-nitrophenyl)-N-methylacetamide

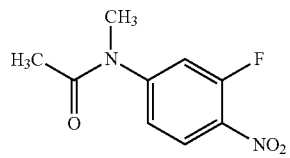

A solution of Preparation 47 (23.0 g, 116.1 mmol) in DMF (300 mL) at 0° C. was treated with NaH (6.96 g, 174 mmol) and stirred for 20 min. Methyl iodide (33.0 g, 232 mmol) was added and the mixture was stirred for 2 h. The mixture was treated with water (100 mL) and the resulting mixture extracted with 10% MeOH/EtOAc (2×200 mL). The extracts were collected, dried (Na₂SO₄), filtered and concentrated. The crude product was purified by chromatography (silica, EtOAc/PE=20-50%) to give the title compound (16.0 g, 65% yield). ¹H NMR (400 MHz, CDCl₃) δ 8.13 (t, 1H), 7.25-7.15 (m, 2H), 3.35 (s, 3H), 2.10 (s, 3H)

Preparation 49:
N-(3-amino-4-nitrophenyl)-N-methylacetamide

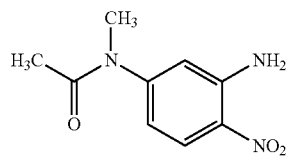

A solution of Preparation 48 (16.0 g, 75.4 mmol) in EtOH (200 mL) at RT was treated with cone. NH₄OH (13.2 g, 377 mmol). The mixture was heated at 50° C. for 3 days and the mixture concentrated. The residue was purified by chromatography (silica, EtOAc/PE=40-80%) to give the title compound (7.5 g, 48% yield). ¹H NMR (400 MHz, CDCl₃) δ

8.17 (d, 1H), 6.66 (d, 1H), 6.54 (dd, 1H), 6.18 (s, 2H), 3.27 (s, 3H), 2.02 (s, 3H); LC/MS m/z (M+H)$^+$=210.3.

Preparation 50:
N-(3,4-diaminophenyl)-N-methylacetamide

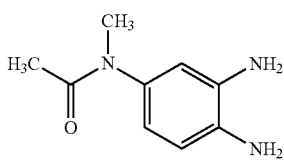

A solution of Preparation 49 (6.5 g, 31.1 mmol) in MeOH (40 mL) was treated with 10% Pd/C (1.5 g). The mixture was stirred at 20° C. under H$_2$ (2 atm) for 3 hours. The mixture was filtered and the solids rinsed with MeOH (2×50 mL). The filtrate was concentrated to give the title compound (5.38 g, 96% yield). $^1$H NMR (400 MHz, CDCl$_3$) δ 6.71-6.64 (m, 1H), 6.50 (d, 2H), 3.46 (d, 4H), 3.19 (s, 3H), 1.87 (s, 3H); LC/MS m/z (M+H)$^+$=180.3.

Preparation 51:
N-(3,5-difluoro-4-nitrophenyl)-N-methylacetamide

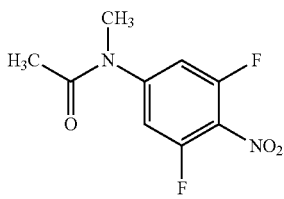 [SMILES: CC(=O)N(C)c1cc(F)c([N+](=O)[O-])c(F)c1]

A solution of 5-bromo-1,3-difluoro-2-nitrobenzene (25.0 g, 105.0 mmol) in PhCH$_3$ (250 mL) at 25° C. under N$_2$ was treated with N-methylacetamide (11.5 g, 158 mmol), Cs$_2$CO$_3$ (68.5 g, 210 mmol), Pd$_2$(dba)$_3$ (9.62 g, 10.5 mmol) XantPhos (6.08 g, 10.5 mmol) and aluminum(III)triflate (9.96 g, 21 mmol). The mixture was heated at 100° C. for 15 h. The solids were removed by filtration and the filtrate concentrated. The residue was purified by chromatography (silica, EtOAc/PE=0-100%) to give the title compound (8.75 g, 36%). $^1$H NMR (400 MHz, CDCl$_3$) δ 7.10-6.99 (m, 2H), 3.34 (s, 3H), 2.15 (s, 3H); LC/MS m/z (M+H)$^+$=230.9.

Preparation 52: N-(3-amino-5-fluoro-4-nitrophenyl)-N-methylacetamide

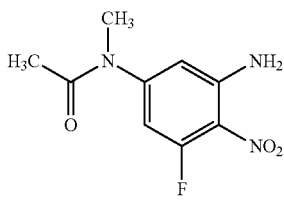 [SMILES: CC(=O)N(C)c1cc(N)c([N+](=O)[O-])c(F)c1]

A solution of Preparation 51 (8.75 g, 38.0 mmol) in EtOH (95 mL) was treated with conc. NH$_4$OH (24 mL). The mixture was stirred at RT for 16 h and treated with water (120 mL). The mixture was extracted with EtOAc (2×80 mL). The combined organic extracts were washed with brine, dried (Na$_2$SO$_4$), filtered and concentrated to give the title compound (5.70 g, 66%). $^1$H NMR (400 MHz, DMSO-d$_6$) δ 7.17 (s, 2H), 6.69 (t, 1H), 6.62 (dd, 1H), 3.15 (s, 3H), 1.99 (s, 3H). LC/MS m/z (M+H)$^+$=227.9.

Preparation 53:
N-(3,4-diamino-5-fluorophenyl)-N-methylacetamide

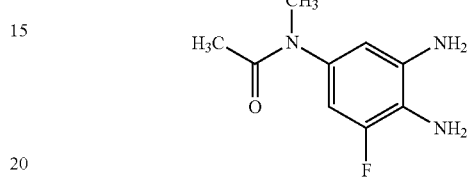

A solution Preparation 52 (5.70 g, 25.1 mmol) in EtOH (150 mL) was treated with 10% Pd/C (700 mg). The mixture was stirred under H$_2$ (1 atm) at 25° C. for 24 h. The mixture was filtered and the solids rinsed with EtOH. The filtrate was concentrated to give the title compound (4.6 g, 93%). $^1$H NMR (400 MHz, DMSO-d$_6$) δ 6.32 (dd, 1H), 6.24 (dd, 1H), 5.01 (s, 2H), 4.52 (s, 2H), 3.02 (s, 3H), 1.74 (s, 3H); LC/MS m/z (M+H)$^+$=198.1.

Preparation 54: N-methyl-N-(2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)acetamide

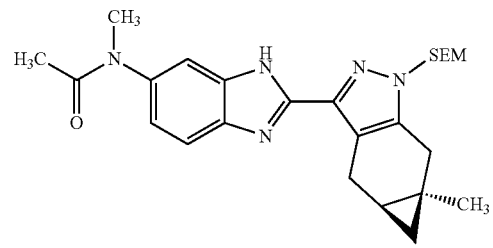 [SMILES: CC(=O)N(C)c1ccc2nc(-c3nn(COCC[Si](C)(C)C)c4c3C[C@@H]3C[C@]3(C)C4)[nH]c2c1]

A solution of Preparation 50 (5.26 g, 29.4 mmol) in DMF (147 mL) was treated with Na$_2$S$_2$O$_5$ (2.79 g, 14.7 mmol), 9 (9.0 g, 29.4 mmol) and DMSO (5.74 g, 73.4 mmol). The mixture was heated at 110° C. for 6 h and poured into 3% aq. LiCl (250 mL). The mixture was extracted with EtOAc (3×100 mL), dried (Na$_2$SO$_4$), filtered and concentrated. The crude product was purified by chromatography (silica, EtOAc/PE=0-100%) to give the title compound (13 g, 95% yield). $^1$H NMR (400 MHz, DMSO-d$_6$) rotomeric mixture δ 12.83 (s, 1H), 7.96 (s, 1H), 7.67 (d, 0.5×H), 7.59 (s, 0.5×H), 7.48 (d, 0.5×H), 7.33 (s, 0.5×H), 7.16-7.06 (m, 1H), 5.55-5.28 (m, 2H), 3.23-3.12 (m, 3H), 3.07-2.96 (m, 1H), 2.89 (s, 3H), 2.76-2.64 (m, 4H), 1.26 (s, 3H), 1.22-1.01 (m, 1H), 0.84 (dd, 2H), 0.41 (dd, 1H), 0.18-0.15 (m, 1H), −0.06 (s, 9H); LC/MS m/z (M+H)$^+$=466.2.

Preparation 55: N-methyl-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-amine

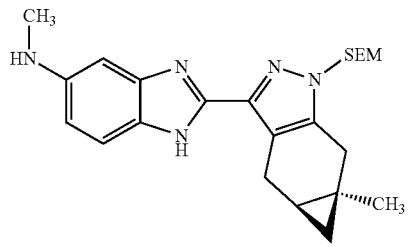 [SMILES: CNc1ccc2[nH]c(-c3nn(COCC[Si](C)(C)C)c4c3C[C@@H]3C[C@]3(C)C4)nc2c1]

A solution of Preparation 54 (2.70 g, 5.8 mmol) in EtOH (22 mL) at RT was treated with 5N NaOH (11.6 mL). The reaction was heated at 90° C. for 16 hours. Water (150 mL) was added to the mixture and the mixture was extracted with EtOAc (2×150 mL). The combined organic extracts were washed with brine (50 mL), dried (Na$_2$SO$_4$), filtered and concentrated. The crude product was purified by chromatography (silica, EtOAc/PE=50-100%) to give the title compound 55 (93 mg, 38% yield). $^1$H NMR (400 MHz, CD$_3$OD) 7.39 (d, 1H), 6.78-6.73 (m, 1H), 6.68 (dd, 1H), 5.47-5.39 (m, 2H), 3.66-3.50 (m, 2H), 3.37-3.31 (m, 1H), 3.22-3.04 (m, 2H), 2.82 (s, 3H), 2.75 (d, 1H), 1.30 (s, 3H), 1.16 (dt, 1H), 0.88 (td, 2H), 0.43 (dd, 1H), 0.25 (t, 1H), −0.03 (s, 9H); LC/MS m/z (M+H)$^+$=424.2.

Preparation 56: N-(7-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)-N-methylacetamide

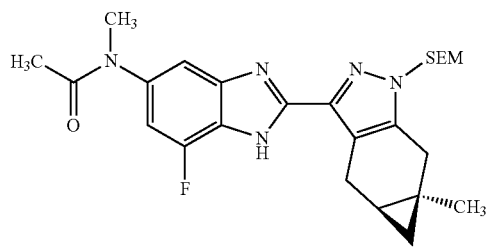 [SMILES: CC(=O)N(C)c1cc(F)c2[nH]c(-c3nn(COCC[Si](C)(C)C)c4c3C[C@@H]3C[C@]3(C)C4)nc2c1]

A solution of Preparation 9 (6.53 g, 21.3 mmol) in DMF (106 mL) at 25° C. was treated with Preparation 53 (4.20 g, 21.3 mmol), Na$_2$S$_2$O$_5$ (2.02 g, 10.6 mmol) and DMSO (4.16 g, 53.2 mmol). The mixture was heated at 110° C. for 16 h and diluted with 3% aq. LiCl (50 mL). The mixture was extracted with EtOAc (2×50 mL). The organic extracts were combined dried (Na$_2$SO$_4$), filtered and concentrated. The crude product was purified by chromatography (silica, EtOAc/PE=0-75%) to give the title compound (7.55 g, 67%). $^1$H NMR (400 MHz, CDCl$_3$) δ 9.99 (d, 1H), 7.45 (d, 0.5H), 7.12-7.03 (m, 0.5H), 6.87-6.71 (m, 1H), 5.40 (qd, 2H), 3.62-3.45 (m, 3H), 3.30 (s, 3H), 3.23-3.05 (m, 2H), 2.75 (d, 1H), 1.90 (s, 3H), 1.29 (s, 3H), 1.16 (s, 1H), 0.91 (ddd, 2H), 0.43 (dt, 1H), 0.27 (d, 1H), −0.02 (d, 9H); LC/MS m/z (M+H)$^+$=484.4.

Preparation 57: 7-fluoro-N-methyl-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-amine

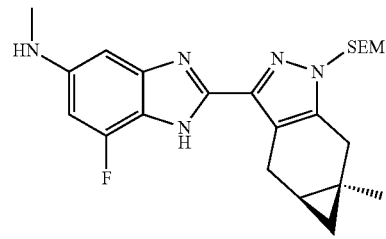 [SMILES: CNc1cc(F)c2[nH]c(-c3nn(COCC[Si](C)(C)C)c4c3C[C@@H]3C[C@]3(C)C4)nc2c1]

A solution of Preparation 56 (6.50 g, 13.44 mmol) in EtOH (51.7 mL) was treated with 5N NaOH (26.9 mL, 134 mmol). The reaction mixture was heated at 90° C. for 46 h. Water (200 mL) was added and the mixture extracted with EtOAc (2×200 mL). The organic extracts were combined, washed with brine (50 mL), dried (Na$_2$SO$_4$), filtered and concentrated. The crude product was purified by chromatography (silica, EtOAc/PE=0-50%) to give the title compound (5.2 g, 75.9%). $^1$H NMR (400 MHz, CD$_3$OD) δ 6.47 (s, 1H), 6.38 (dd, 1H), 5.48-5.38 (m, 2H), 3.60 (t, 2H), 3.37-3.30 (m, 1H), 3.21-3.08 (m, 2H), 2.83-2.72 (m, 1H), 2.80 (s, 3H), 1.29 (s, 3H), 1.15 (dt, 1H), 0.88 (td, 2H), 0.42 (dd, 1H), 0.25 (t, 1H), −0.03 (s, 9H); LC/MS m/z (M+H)$^+$=442.2.

Preparation 58: N-(5-fluoro-2-methyl-4-nitrophenyl)acetamide

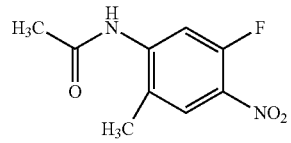

5-fluoro-2-methyl-4-nitroaniline (9.5 g, 56 mmol) was added in portions to Ac$_2$O (100 mL) at 15° C. The reaction mixture was stirred at 15° C. for 36 h. The solids were collected by filtration and rinsed with water (3×50 mL). The solids were dried to give the title compound 58 (6.3 g, 53%).

The filtrate was extracted with EtOAc (100 mL). The organic layer was washed with water (2×100 mL), sat. aq. Na$_2$HCO$_3$ (3×100 mL), dried (Na$_2$SO$_4$), filtered and concentrated. The crude product was purified by chromatography (silica, EtOAc/PE=0-100%) to give additional title compound 58 (4 g, 34%). $^1$H NMR (400 MHz, CDCl$_3$) δ 8.34 (d, 1H), 7.94 (d, 1H), 7.17 (s, 1H), 2.32 (s, 3H), 2.28 (s, 3H).

Preparation 59: N-(5-fluoro-2-methyl-4-nitrophenyl)-N-methylacetamide

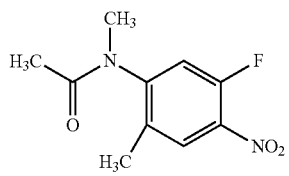 [SMILES: CC(=O)N(C)c1cc(F)c([N+](=O)[O-])cc1C]

A solution of Preparation 58 (9.3 g, 43.8 mmol) in THF (220 mL) at 0° C. was treated with KOtBu (48.2 mL, 1M THF). The mixture was stirred 1 h at 0° C. and then treated with solution of methyl iodide (6.84 g, 48.2 mmol) in THF (20 mL). The mixture was warmed to 15° C. and stirred for 16 h. The mixture was treated with sat. aq. NH$_4$Cl (50 mL). The mixture was extracted with EtOAc (2×50 mL). The combined organic extracts were washed with brine, dried (Na$_2$SO$_4$), filtered and concentrated. The crude product was purified by chromatography (silica, EtOAc/PE=20-50%) to give the title compound 59 (9.4 q. 95%). $^1$H NMR (400 MHz, CDCl$_3$) δ 8.04 (d, 1H), 7.13 (d, 1H), 3.18 (s, 3H), 2.30 (s, 3H), 1.82 (s, 3H); LC/MS m/z (M+H)$^+$=226.9.

Preparation 60: N-(5-amino-2-methyl-4-nitrophenyl)-N-methylacetamide

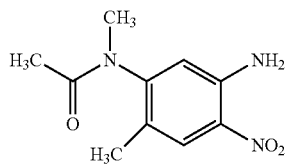 [SMILES: CC(=O)N(C)c1cc(N)c([N+](=O)[O-])cc1C]

A solution of Preparation 59 (10.3 g, 45.5 mmol) in EtOH (200 mL) at 15° C. was treated with conc. NH$_4$OH (200 mL). The mixture was heated at 50° C. and stirred for 40 h. The EtOH was removed under reduced pressure and the suspension was filtered to collect the solids. The solids were washed with water and dried to afford the title compound (9 g, 89%). $^1$H NMR (400 MHz, CDCl$_3$) δ 8.07 (s, 1H), 6.65 (s, 1H), 6.05 (s, 2H), 3.15 (s, 3H), 2.15 (s, 3H), 1.82 (s, 3H); LC/MS m/z (M+H)$^+$=224.1.

Preparation 61: N-(4,5-diamino-2-methylphenyl)-N-methylacetamide

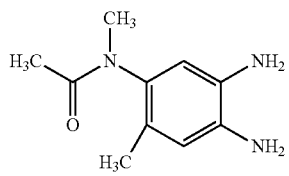

A solution of Preparation 60 (8 g, 35.8 mmol) in EtOH (10 mL) was treated with of 10% Pd/C (1.3 g). The mixture was degassed with N$_2$ and backfilled with H$_2$ three times. The reaction mixture was stirred at 15° C. under H$_2$ (1 atm) for 16 h. The mixture was filtered and the filtrate concentrated to give the title compound (7.7 g, 99%). $^1$H NMR (400 MHz, CDCl$_3$) δ 6.57 (s, 1H), 6.46 (s, 1H), 3.40 (s, 4H), 3.12 (s, 3H), 2.05 (s, 3H), 1.78 (s, 3H); LC/MS m/z (M+H)$^+$=194.3.

Preparation 62: N-methyl-N-(6-methyl-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)acetamide

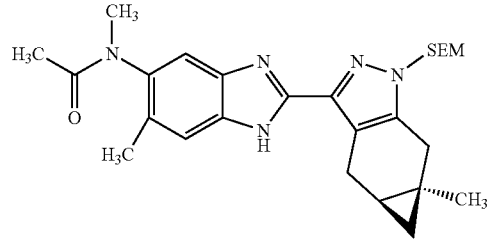 [SMILES: CC(=O)N(C)c1cc2nc(-c3nn(COCC[Si](C)(C)C)c4c3C[C@@H]3C[C@]3(C)C4)[nH]c2cc1C]

Preparation 61 (4 g, 20.7 mmol) and Na$_2$S$_2$O$_5$ (1.97 g, 10.3 mmol) were mixed with solution of Preparation 9 (6.84 g, 22.3 mmol) in DMF (100 mL) and DMSO (3.7 mL). The mixture was heated at 110° C. for 16 h. The mixture was cooled to RT and 3% aq. LiCl (150 mL) was added. The resultant solids were collected by filtration, washed with water, and dried to give the title compound (7.9 g, 80%). $^1$H NMR (400 MHz, CDCl$_3$) δ 9.88 (s, 1H), 7.58 (s, 1H), 7.31 (s, 1H), 5.50-5.26 (m, 2H), 3.55 (t, 3H), 3.23 (s, 3H), 3.20-3.05 (m, 2H), 2.74 (d, 1H), 2.32 (s, 3H), 1.79 (s, 3H), 1.29 (s, 3H), 1.16 (dt, 1H), 0.90 (dd, 2H), 0.42 (dd, 1H), 0.26 (t, 1H), −0.03 (s, 9H); LC/MS m/z (M+H)$^+$=480.4.

Preparation 63: N-(4-fluoro-2-methyl-5-nitrophenyl)acetamide

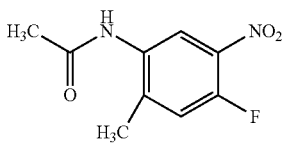

4-Fluoro-2-methyl-5-nitroaniline (16.7 g, 98.2 mmol) was added to Ac$_2$O (200 mL) with stirring at 15° C., and the mixture was stirred at 15° C. for 16 h. The mixture was treated with water (300 mL) and extracted with EtOAc (300 mL). The organic layer was washed with sat. aq. Na$_2$CO$_3$ (2×150 mL) and brine (100 mL). The organic layer was dried (Na$_2$SO$_4$), filtered and concentrated. The residue was triturated with EtOAc/PE (v/v=1:5, 100 mL). The resulting solid was collected by filtration and dried to give the title compound (15 g, 72%). $^1$H NMR (400 MHz, CDCl$_3$) δ 8.52 (d, 1H), 7.13 (br d, 2H), 2.35 (s, 3H), 2.25 (s, 3H)

Preparation 64: N-(4-amino-2-methyl-5-nitrophenyl)acetamide

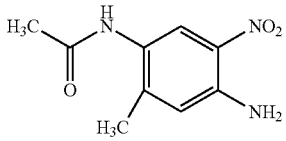

A solution of Preparation 63 (15 g, 70.7 mmol) in EtOH (300 mL) was treated with conc. NH$_4$OH (198 g) at 30° C. and the mixture was stirred at 50° C. for 16 h. Additional conc. NH$_4$OH (140 g) was added and the mixture was stirred at 50° C. for 16 h. Additional conc. NH$_4$OH (46 g) was added and the mixture was stirred at 60° C. for 16 h. The mixture was concentrated and the solids collected by filtration. The solids were washed with water (3×10 mL) and dried to deliver the title compound (14.0 g, 95%). $^1$H NMR (400 MHz, CD$_3$OD) δ 7.97 (s, 1H), 6.81 (s, 1H), 2.19 (s, 3H), 2.13 (s, 3H)

Preparation 63:
N-(4,5-diamino-2-methylphenyl)acetamide

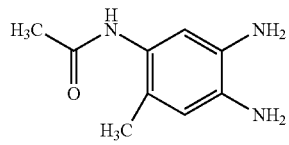

A suspension of Preparation 64 (2.50 g, 11.95 mmol) in EtOH (50 mL) was added to a suspension of 10% Pd/C (500 mg) in EtOH (10 mL). The mixture was degassed and refilled with H$_2$ three times and the reaction mixture was stirred at 15° C. under H$_2$ (1 atm) for 16 h. The mixture was filtered and the filtrate concentrated to deliver the title compound 65 (2.2 g, 103%). LC/MS m/z (M+H)$^+$=180.1.

Preparation 66: N-(6-methyl-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)acetamide

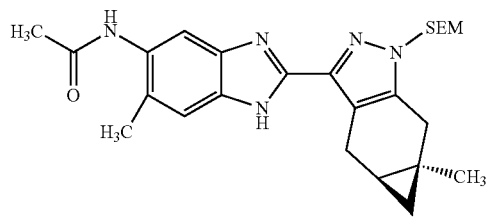 [SMILES: CC(=O)Nc1cc2nc(-c3nn(COCC[Si](C)(C)C)c4c3C[C@@H]3C[C@]3(C)C4)[nH]c2cc1C]

A solution of Preparation 65 (2.20 g, 12.28 mmol) in DMF (40 mL) was treated with Na$_2$S$_2$O$_5$ (1.17 g, 6.14 mmol), DMSO (2.18 mL, 30.7 mmol), and 9 (3.76 g, 12.3 mmol) in DMF (20 mL). The mixture was stirred at 100° C. for 16 h. The mixture was concentrated and the crude product purified by chromatography (silica, EtOAc/PE=0-100% then MeOH/DCM 0-10%) to deliver the title compound 66 (5.3 g, 92%). LC/MS m/z (M+H)$^+$=466.2.

Preparation 67: N-ethyl-6-methyl-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-amine

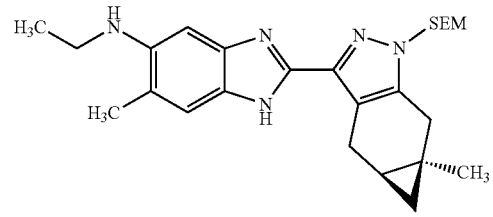 [SMILES: CCNc1cc2nc(-c3nn(COCC[Si](C)(C)C)c4c3C[C@@H]3C[C@]3(C)C4)[nH]c2cc1C]

A suspension of LiAlH$_4$ (326 mg, 8.59 mmol) in THF (33 mL) at 0° C. was treated with a solution of Preparation 66 (2 g, 4.3 mmol) in THF (10 mL) and stirred at 20° C. for 72 h. The mixture was treated with Na$_2$SO$_4$·H$_2$O, followed by MgSO$_4$ (4 g). The mixture was stirred for 30 min. The mixture was diluted with EtOAc (20 mL) and filtered. The filtrate was concentrated and the residue was purified by chromatography (silica, EtOAc/PE=0-50%) to give the title compound (1.03 g, 53%). $^1$H NMR (400 MHz, CDCl$_3$) δ 9.55 (s, 1H), 7.51 (s, 1H), 7.10 (d, 1H), 6.57 (s, 1H), 5.43-5.27 (m, 2H), 3.60-3.50 (m, 3H), 3.28-3.13 (m, 3H), 3.09 (d, 1H), 2.72 (d, 1H), 2.25 (s, 3H), 1.35 (t, 3H), 1.28 (s, 3H), 1.14 (dt, 1H), 0.96-0.84 (m, 2H), 0.39 (dd, 1H), 0.28 (t, 1H), −0.03 (s, 9H); LC/MS m/z (M+H)$^+$=452.3.

Preparation 68: (4aS,5aR)-5,5-difluoro-5a-methyl-1,4,4a,5,5a,6-hexahydrocyclopropa[f]indazole-3-carboxylic acid

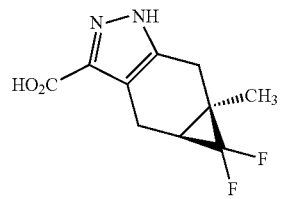 [SMILES: C[C@@]12Cc3[nH]nc(C(=O)O)c3C[C@@H]1C2(F)F]

A solution of Preparation 15 (1.0 g, 3.90 mmol) in MeOH (12 mL) and water (2.0 mL) at 20° C. was treated with NaOH (468 mg, 11.7 mmol). After 32 h, the mixture was concentrated and the residue diluted with H$_2$O (10 mL) and the pH adjusted to 4-5 with 1M HCl. The resulting suspension was filtered to collect the solids. The solids were dried to give the title compound (900 mg, 100%). $^1$H NMR (400 MHz, DMSO-d$_6$) δ 13.03 (bs, 2H), 3.16 (d, 1H), 3.03-2.97 (m, 3H), 2.76 (dd, 1H), 1.75 (d, 1H), 1.33 (d, 3H). LC/MS m/z (M+H)$^+$=228.8.

Preparation 69: (4aS,5aR)-3-(5-bromo-7-fluoro-1H-benzo[d]imidazol-2-yl)-5a-methyl-1-((2-(trimethylsilyl)ethoxy)methyl)-1,4,4a,5,5a,6-hexahydrocyclopropa[f]indazole

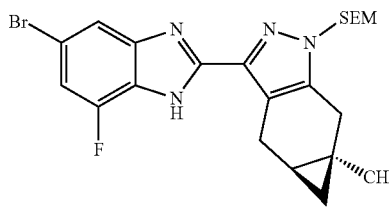

A solution of Preparation 9 (510 mg, 1.66 mmol) in DMF (20.8 mL) was treated with 5-bromo-3-fluorobenzene-1,2-diamine (358 mg, 1.75 mmol) and $Na_2S_2O_5$ (380 mg, 2.00 mmol) at RT. The vial was sealed and heated in a microwave reactor at 150° C. for 2 h. The mixture was poured into 3% aq. LiCl (40 mL) and the mixture extracted with EtOAc (2×40 mL). The organic extracts were dried ($Na_2SO_4$), filtered and concentrated. The crude product was purified by chromatography (silica, EtOAc/PE=0-25%) to give the title compound (815 g, 98%). $^1$H NMR (400 MHz, $CD_3OD$) δ 7.50 (s, 1H), 7.23-7.07 (m, 1H), 5.52-5.41 (m, 2H), 3.61 (t, 2H), 3.42-3.32 (m, 1H), 3.25-3.07 (m, 2H), 2.81-2.72 (m, 1H), 1.30 (s, 3H), 1.26-1.13 (m, 2H), 0.88 (td, 2H), 0.44 (dd, 1H), 0.25 (t, 1H), −0.04 (s, 9H). LC/MS m/z $(M+Na)^+$=514.7 ($^{79}$Br).

Preparation 70: (4aS,5aR)-3-(5-bromo-7-fluoro-1H-benzo[d]imidazol-2-yl)-5a-methyl-1,4,4a,5,5a,6-hexahydrocyclopropa[f]indazole

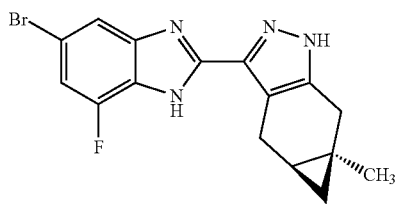

A solution of Preparation 69 (100 mg, 0.20 mmol) in TFA (2 mL) at 10° C. was treated with $Et_3SiH$ (118 mg, 1.02 mmol). The mixture was stirred at 10° C. for 3 h. The mixture was concentrated and the residue treated with sat. aq. $Na_2CO_3$. The mixture was extracted with EtOAc (3×15 mL). The organic extracts were dried ($Na_2SO_4$), filtered and concentrated. The crude product was purified by chromatography [prep HPLC, $H_2O$:MeCN (w/0.05% $NH_4OH$)] to give the title compound (27.1 mg, 37%). $^1$H NMR (400 MHz, $CD_3OD$) δ 7.53 (s, 1H), 7.16 (d, 1H), 3.36-3.31 (m, 1H), 3.13 (dd, 1H), 3.06 (d, 1H), 2.77 (d, 1H), 1.29 (s, 3H), 1.20-1.09 (m, 1H), 0.41 (dd, 1H), 0.24 (t, 1H); LC/MS m/z $(M+H)^+$=363.0 ($^{79}$Br).

Preparation 71a: (4aS,5aR)-3-(6-bromo-4-fluoro-1-((2-(trimethylsilyl)ethoxy)methyl)-1H-benzo[d]imidazol-2-yl)-5a-methyl-1-((2-(trimethylsilyl)ethoxy)methyl)-1,4,4a,5,5a,6-hexahydrocyclopropa[f]indazole

Preparation 71b: (4aS,5aR)-3-(5-bromo-7-fluoro-1-((2-(trimethylsilyl)ethoxy)methyl)-1H-benzo[d]imidazol-2-yl)-5a-methyl-1-((2-(trimethylsilyl)ethoxy)methyl)-1,4,4a,5,5a,6-hexahydrocyclopropa[f]indazole

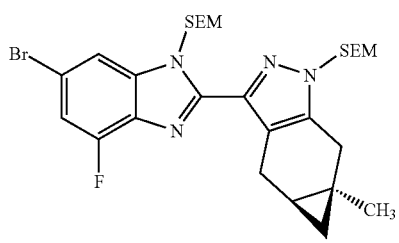

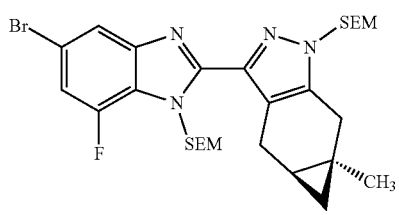 [SMILES: C[C@@]12Cc3c(c(-c4nc5cc(Br)cc(F)c5[nH]4)nn3COCC[Si](C)(C)C)C[C@@H]1C2]

A solution of Preparation 70 (1.53 g, 3.11 mmol) in THF (39 mL) at 0° C. was treated with NaH (149 mg, 3.73 mmol). After stirring for 30 min, SEM-Cl (570 mg, 3.42 mmol) was added and the mixture stirred for 2 h at 10° C. The mixture was treated with sat. aq. $NH_4Cl$ (30 mL). The mixture was extracted with EtOAc (3×40 mL) and organic extracts were combined, dried ($Na_2SO_4$), filtered and concentrated. The crude product was purified by chromatography (silica, EtOAc/PE=0-15%) to give the title compounds as a mixture (1.60 g, 83%). $^1$H NMR (400 MHz, $CD_3OD$) δ 7.69 (dd, 1H), 7.26 (ddd, 1H), 6.24-5.97 (m, 2H), 5.53-5.46 (m, 2H), 4.10 (q, 1H), 3.63 (dd, 2H), 3.53-3.36 (m, 2H), 3.28-3.17 (m, 2H), 3.16-3.03 (m, 1H), 2.78 (d, 1H), 1.31 (s, 3H), 1.24 (t, 1H), 1.15 (dt, 1H), 0.92 (td, 2H), 0.76 (dt, 2H), 0.48-0.39 (m, 1H), 0.24 (td, 1H), −0.01 (s, 9H), −0.18 (s, 9H); LC/MS m/z $(M+H)^+$=622.8 ($^{79}$Br).

Preparation 72a: tert-butyl (4-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)carbamate Preparation 72b: tert-butyl (7-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)carbamate Preparation 73a: tert-butyl (4-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)(methyl)carbamate Preparation 73b: tert-butyl (7-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)(methyl)carbamate

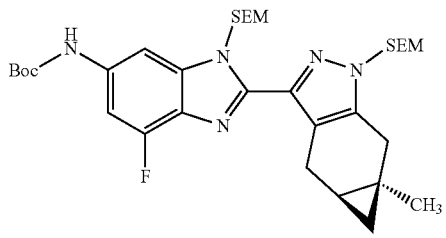

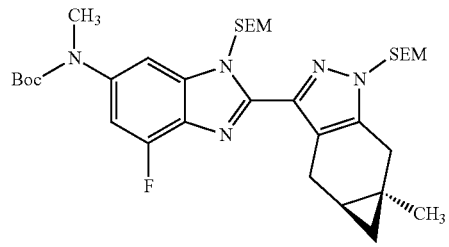

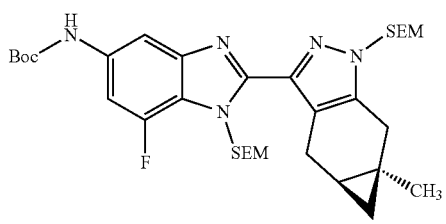

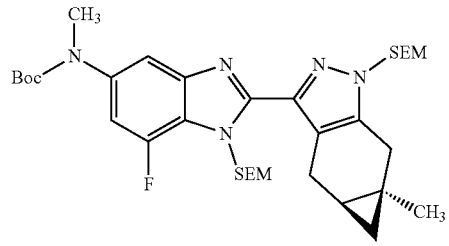

A portion of the mixture of Preparations 71a and 71b (712 mg, 1.15 mmol), tert-Butyl carbamate (161 mg, 1.37 mmol), Cs$_2$CO$_3$ (746 mg, 2.29 mmol) in tert-amyl alcohol (11.5 mL) was treated with Pd$_2$(dba)$_3$ (105 mg, 0.12 mmol) and tert-BuDavePhos (78 mg, 0.23 mmol). The reaction was heated at 100° C. for 23 h. The mixture was concentrated and the crude material purified by chromatography (silica, EtOAc/PE=0-20%) to give the title compounds as a mixture (706 mg, 93%). $^1$H NMR (400 MHz, CD$_3$OD) δ 7.72 (s, 1H), 7.40-7.21 (m, 1H), 7.07 (d, 1H), 6.08-5.89 (m, 2H), 5.48 (d, 2H), δ 3.69-3.57 (m, 2H), 3.46 (dd, 1H), 3.25-3.02 (m, 3H), 2.78 (d, 1H), 2.50 (d, 1H), 1.55 (s, 9H), 1.43 (d, 1H), 1.33-1.23 (m, 5H), 1.20-1.09 (m, 2H), 0.99-0.83 (m, 5H), 0.82-0.69 (m, 1H), 0.42 (dd, 1H), 0.25 (t, 1H), −0.00 (s, 9H), −0.13 (s, 9H). LC/MS m/z (M+H)$^+$=658.0

A portion of the mixture of Preparations 72a and 72b (235 mg, 0.36 mmol) in THF (5 mL) at 0° C. was treated with NaH (21.4 mg, 0.54 mmol). The mixture was stirred at 15° C. for 30 min and treated with methyl iodide (61 mg, 0.43 mmol). The mixture was stirred for 16 h and treated with sat. aq. NH$_4$Cl (15 mL). The mixture was extracted with EtOAc (2×20 mL). The organic extracts were collected, dried (Na$_2$SO$_4$), filtered and concentrated. The crude product was purified by chromatography (silica, EtOAc/PE=0-30%) to give the title compounds as a mixture (120 mg, 50%) $^1$H NMR (400 MHz, CD$_3$OD) δ 7.39 (d, 1H), 7.01 (dd, 1H), 6.16-5.95 (m, 2H), 5.50 (d, 2H), 3.68-3.56 (m, 2H), 3.46 (t, 2H), 3.27-3.05 (m, 4H), 2.79 (d, 1H), 1.46 (s, 9H), 1.31 (s, 3H), 1.18-1.13 (m, 1H), 0.97-0.85 (m, 2H), 0.82-0.71 (m, 2H), 0.43 (dd, 1H), 0.26 (t, 1H), −0.00 (s, 9H), −0.14 (s, 9H); LC/MS m/z (M+Na)$^+$=694.0.

Preparation 74a: 4-fluoro-N-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-amine Preparation 74b: 7-fluoro-N-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-amine Preparation 75a: tert-butyl ethyl(4-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)carbamate Preparation 75b: tert-butyl ethyl(7-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)carbamate

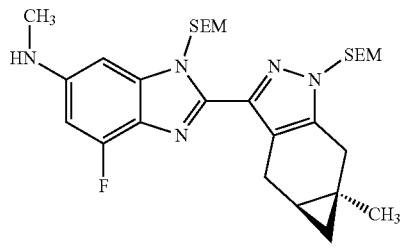

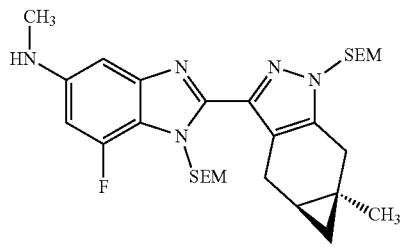

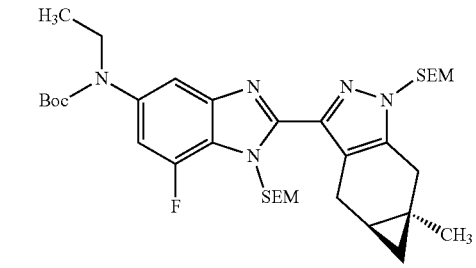

The mixture of Preparations 73a and 73b (120 mg, 0.178 mmol) in DCM (2.0 mL) at 0° C. was treated with ZnBr$_2$ (201 mg, 0.89 mmol). The mixture was stirred for 12 h then treated with sat. aq. NaHCO$_3$ (10 mL) and the mixture extracted with DCM (2×20 mL). The organic extracts were combined, dried (Na$_2$SO$_4$), filtered and concentrated to give the title compounds as a mixture (111 mg, 109%) $^1$H NMR (400 MHz, CD$_3$OD) δ 6.51 (d, 1H), 6.43 (dd, 1H), 5.97 (d, 1H), 5.86 (d, 1H), 5.47 (s, 2H), 3.62 (t, 2H), 3.41 (t, 2H), 3.25-3.03 (m, 3H), 2.84 (s, 3H), 2.82-2.75 (m, 1H), 1.30 (s, 3H), 1.17-1.10 (m, 1H), 0.92 (dd, 2H), 0.77 (t, 2H), 0.41 (dd, 1H), 0.25 (t, 1H), −0.00 (s, 9H), −0.13 (s, 9H); LC/MS m/z (M+Na)$^+$=594.0.

A mixture of Preparations 72a and 72b (10.5 g, 16.0 mmol) in THF (160 mL) at 0° C. was treated with NaH (1.27 g, 31.9 mmol). The mixture was stirred for 30 min and treated with ethyl iodide (3.30 g, 21 mmol) and the mixture stirred for 16 h. The mixture was treated with sat. aq. NH$_4$Cl (150 mL). The mixture was extracted with EtOAc (2×200 mL) and the organic layers combined, dried (Na$_2$SO$_4$), filtered and concentrated. The crude product was purified by chromatography (silica, EtOAc/PE=0-10%) to give the title compounds as a mixture (8.26 g, 75%). LC/MS m/z (M+H)$^+$=453.3.

Preparation 76a: N-ethyl-4-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-amine Preparation 76b: N-ethyl-7-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-amine

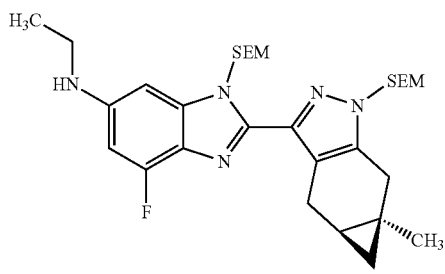

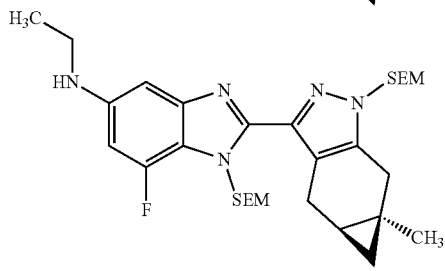

A mixture of Preparations 75a and 75b (10.39 g, 15.14 mmol) in DCM (151 mL) at 0° C. was treated with ZnBr$_2$ (17.1 g, 75.7 mmol). The reaction was warmed to 30° C. and stirred for 16 h. The mixture was poured into saturated NaHCO$_3$ (150 mL) and filtered. The filtrate was extracted with DCM (2×100 mL). The organic extracts were combined, dried (Na$_2$SO$_4$), filtered and concentrated. The crude product was purified by chromatography (silica, EtOAc/PE=0-10%) gave to give the title compounds as a mixture (6.14 g, 69.2%). LC/MS m/z (M+H)=586.2.

Preparation 77: (4aS,5aR)-3-(5-bromo-6-fluoro-1H-benzo[d]imidazol-2-yl)-5a-methyl-1-((2-(trimethylsilyl)ethoxy)methyl)-1,4,4a,5,5a,6-hexahydrocyclopropa[f]indazole

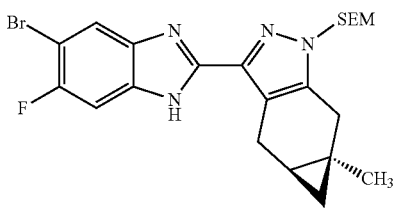 [SMILES: C[C@@]12Cc3c(c(-c4nc5cc(Br)c(F)cc5[nH]4)nn3COCC[Si](C)(C)C)C[C@@H]1C2]

A solution of Preparation 9 (467 mg, 1.52 mmol) in DMF (19 mL) was treated with 4-bromo-5-fluorobenzene-1,2-diamine (328 mg, 1.60 mmol) and Na$_2$S$_2$O$_5$ (380 mg, 2.00 mmol) at RT. The vial was sealed and heated in a microwave reactor at 150° C. for 2 h. The mixture was poured into 3% aq. LiCl (80 mL) and extracted with EtOAc (2×60 mL). The organic layers were combined, dried (Na$_2$SO$_4$), filtered and concentrated. The crude product was purified by chromatography (silica, EtOAc/PE=0-25%) to give the title compound (644 mg, 86%). $^1$H NMR (400 MHz, CDCl$_3$) δ 9.96 (s, 1H), 7.98 (s, 1H), 7.57 (s, 1H), 5.46-5.28 (m, 2H), 3.58-3.49 (m, 2H), 3.20-3.07 (m, 3H), 2.74 (d, 1H), 1.29 (s, 3H), 1.21-1.10 (m, 1H), 0.95-0.83 (m, 2H), 0.43 (dd, 1H), 0.27 (t, 1H), −0.02 (s, 9H).

Preparation 78a: tert-butyl (6-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)carbamate Preparation 78b: tert-butyl (5-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)carbamate

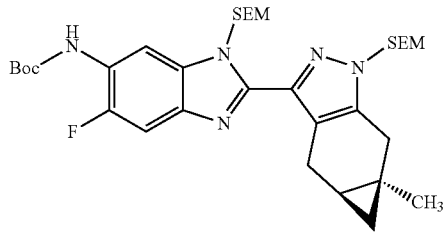

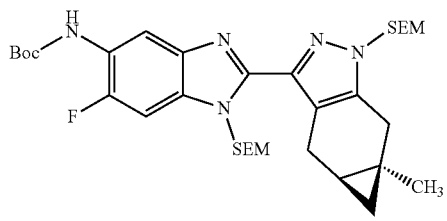

A mixture of Preparations 77 (800 mg, 1.29 mmol), f-butyl carbamate (181 mg, 1.54 mmol), and Cs$_2$CO$_3$ (838 mg, 2.57 mmol) in tert-amyl alcohol (12.9 mL) was treated with Pd$_2$(dba)$_3$ (59 mg, 0.64 mmol) and (88 mg, 0.26 mmol). The mixture was heated to 100° C. for 16 h. Additional Pd$_2$(dba)$_3$ (59 mg, 0.64 mmol) and (88 mg, 0.26 mmol) was added and heating continued at 100° C. for 16 h. The mixture was concentrated and the residue purified by chromatography (silica, EtOAc/PE=0-20%) to give the title compounds compound as a mixture (480 mg, 57%). $^1$H NMR (400 MHz, CDCl$_3$) δ 8.34 (d, 1H), 7.49 (t, 1H), 6.82 (s, 1H), 6.15-5.97 (m, 2H), 5.47-5.34 (m, 2H), 3.62-3.37 (m, 5H), 3.10 (t, 2H), 2.73 (d, 1H), 1.55 (s, 9H), 1.28 (s, 3H), 1.12 (s, 1H), 0.99-0.77 (m, 4H), 0.39 (dd, 1H), 0.26 (q, 1H), −0.02 (s, 9H), −0.13 (d, 9H); LC/MS m/z (M+H)$^+$=658.3

Preparation 79a: tert-butyl (6-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)(methyl)carbamate Preparation 79b tert-butyl (5-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)(methyl)carbamate

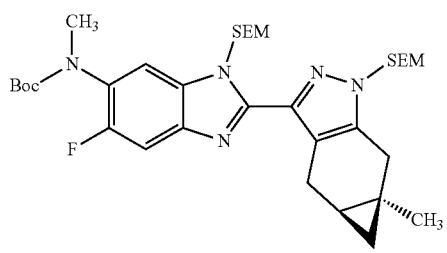

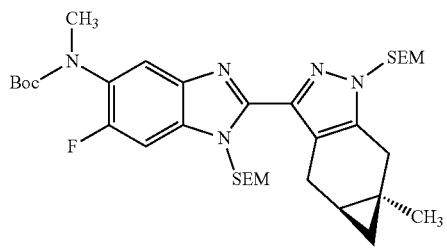

A portion of the mixture of Preparations 78a and 78b (230 mg, 0.35 mmol) in THF (4.6 mL) at 0° C. was treated with NaH (21.0 mg, 0.52 mmol). The mixture was stirred at 15° C. for 20 min and then treated with methyl iodide (124 mg, 0.87 mmol). After stirring for 16 h, the mixture was diluted with sat. aq. NH$_4$Cl (2 mL) and extracted with EtOAc (2×10 mL). The organic extracts were collected, dried (Na$_2$SO$_4$), filtered and concentrated. The crude material was purified by chromatography (silica, EtOAc/PE=0-30%) to give the title compounds as a mixture (286 mg, 100%). $^1$H NMR (400 MHz, CDCl$_3$) δ 7.63 (s, 0.5H), 7.51 (d, 0.5H), 7.40 (s, 1H), 6.10 (d, 2H), 5.50-5.37 (m, 2H), 3.64-3.53 (m, 2H), 3.56-3.43 (m, 3H), 3.28 (d, 3H), 3.20-3.07 (m, 2H), 2.76 (d, 1H), 1.38 (s, 7H), 1.30 (d, 5H), 1.15 (dt, 1H), 0.98-0.81 (m, 4H), 0.42 (dd, 1H), 0.29 (t, 1H), 0.01 (s, 9H), −0.09 (d, 9H); LC/MS m/z (M+H)$^+$=672.5

Preparation 80a: 5-fluoro-N-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-amine Preparation 80b: 6-fluoro-N-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-amine

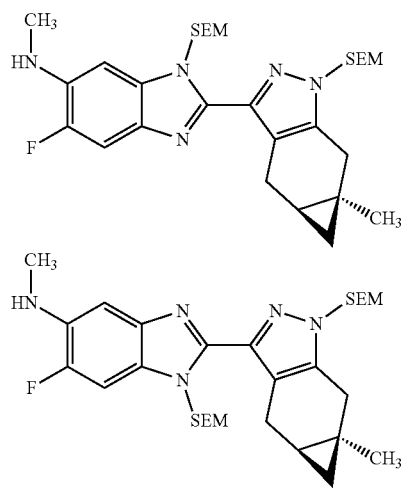

A mixture of Preparations 79a and 79b (286 mg, 0.425 mmol) in DCM (4.26 mL) at 0° C. was treated with ZnBr$_2$ (479 mg, 2.13 mmol). After stirring at 15° C. for 12 h, the mixture was poured into sat. aq. NaHCO$_3$ (20 mL) and the resulting mixture was extracted with DCM (2×20 mL). The organic extracts were collected, dried (Na$_2$SO$_4$), filtered and concentrated. The crude material was purified by chromatography (silica, EtOAc/PE=0-40%) to give the title compounds as a mixture (160 mg, 66%). $^1$H NMR (400 MHz, CDCl$_3$) δ 7.41 (d, 0.57H), 7.21 (d, 0.43H), 7.07 (d, 0.43H), 6.73 (d, 0.57H), 6.06 (d, 1H), 6.07-5.95 (m, 1H), 5.46-5.34 (m, 2H), 4.05 (s, 1H), 3.61-3.37 (m, 5H), 3.09 (t, 2H), 2.94 (d, 3H), 2.73 (d, 1H), 1.30-1.22 (m, 3H), 1.11 (d, 1H), 0.91 (t, 2H), 0.85-0.80 (m, 2H), 0.38 (dd, 1H), 0.26 (t, 1H), −0.02 (d, 9H), −0.12 (s, 9H); $^{19}$F NMR (376 MHz, CD$_3$OD) δ−131.20. LC/MS m/z (M+H)$^+$=572

Preparation 81: 4-fluoro-2-methoxy-5-nitroaniline

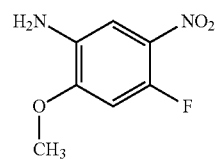

A solution of 4-fluoro-2-methoxyaniline (1590 mg, 11.27 mmol) in conc·H$_2$SO$_4$ (9.55 mL) was treated with solid KNO$_3$ (1140 mg, 11.3 mmol) in portions while keeping the internal temperature below 5° C. The resulting mixture was stirred for 2 h at 0° C. and mixture was poured into ice water (100 mL), neutralized slowly with solid Na$_2$CO$_3$ and extracted with EtOAc (2×60 mL). The organic layers were dried (Na$_2$SO$_4$), filtered and and concentrated to give the title compound (2 g, 95%). $^1$H NMR (400 MHz, CDCl$_3$) δ 7.42 (d, 1H), 6.66 (d, 1H), 3.96 (s, 3H), 1.60 (s, 2H); LC/MS m/z (M+H)$^+$=186.8.

Preparation 82: (S)—N-(4-fluoro-2-methoxy-5-nitrophenyl)-2-morpholinopropanamide

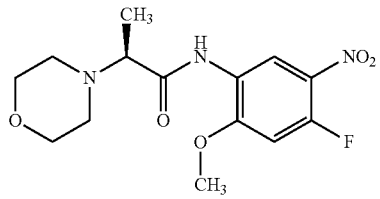 [SMILES: COc1cc(F)c([N+](=O)[O-])cc1NC(=O)[C@H](C)N1CCOCC1]

A solution of Preparation 81 (590 mg, 3.17 mmol) and preparation 19 (605 mg, 3.80 mmol) in pyridine (45.3 mL) was treated with EDCI (1.22 g, 6.34 mmol). The mixture was stirred at RT for 16 h and then poured into water (30 mL). The resulting mixture was extracted with EtOAc (2×40 mL). The organic layers were combined, washed sequentially with sat. aq. NH$_4$Cl and brine, dried (MgSO$_4$), filtered and concentrated. The crude product was purified by chromatography (silica, EtOAc/PE=0-50%) to give title compound (586 mg, 77%). $^1$H NMR (400 MHz, CDCl$_3$) δ 9.94 (s, 1H), 9.19 (d, 1H), 6.75 (d, 1H), 4.02 (s, 3H), 3.86-3.72 (m, 4H), 3.26 (q, 1H), 2.70-2.53 (m, 4H), 1.34 (d, 3H). $^{19}$F NMR (376 MHz, CDCl$_3$) 5-118.16. LC/MS m/z (M+H)=328.1; SFC method: Chiral Tech AD-3 150 mm×4.6 mm×3 μm, CO$_2$/IPA (0.05% iPr$_2$NEt) isocratic 40%, 2.5 mL/min, column temperature 40° C., RT=4.027 min (99.31%)

Preparation 83: (S)—N-(4-fluoro-2-methoxy-5-nitrophenyl)-N-methyl-2-morpholinopropanamide

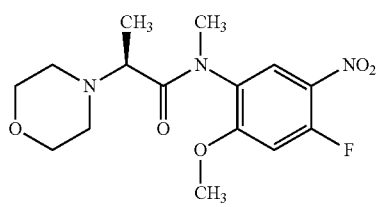 [SMILES: COc1cc(F)c([N+](=O)[O-])cc1N(C)C(=O)[C@H](C)N1CCOCC1]

A mixture of Preparation 82 (586 mg, 1.79 mmol) in THF (25 mL) at 0° C. was treated with NaH (107 mg, 2.69 mmol). The mixture was stirred at 20° C. for 30 min and treated with methyl iodide (305 mg, 2.15 mmol). After stirring for 16 h, the mixture was diluted with sat. aq. NH$_4$Cl (2 mL) and extracted with EtOAc (2×20 mL). The organic extracts were collected, dried (Na$_2$SO$_4$), filtered and concentrated. The crude material was purified by chromatography (silica, EtOAc/PE=0-100%) to give the title compound (423 mg, 69%). $^1$H NMR (400 MHz, CDCl$_3$) δ 8.30 (d, 0.5H), 7.98 (d, 0.5H), 6.86 (dd, 1H), 4.03-3.93 (m, 3H), 3.65 (t, 2H), 3.60-3.46 (m, 2H), 3.21-3.12 (m, 4H), 3.02-2.92 (m, 0.5H), 2.55 (dt, 1H), 2.48-2.37 (m, 0.5H), 2.24 (dp, 2H), 1.18 (d, 1H), 1.11 (d, 2H); LC/MS m/z (M+H)=429.1.

Preparation 84: (S)—N-(4,5-diamino-2-methoxyphenyl)-N-methyl-2-morpholinopropanamide

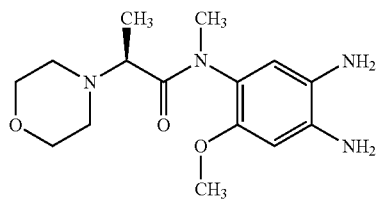 [SMILES: COc1cc(N)c(N)cc1N(C)C(=O)[C@H](C)N1CCOCC1]

A mixture of Preparation 83 (400 mg, 0.934 mmol) in MeOH (10 mL) was treated with 10% Pd/C (100 mg) and MeOH (5 mL). The mixture was degassed and refilled with Argon and H$_2$ three times and then stirred under H$_2$ (3 atm) at 25° C. for 24 h. Additional 10% Pd/C (100 mg) was added and the mixture was stirred under H$_2$ (3 atm) at 25° C. for an additional 24 h. The reaction was filtered and the filtrate concentrated. The crude product was purified by chromatography (silica, MeOH/DCM=0-10%) to give the title compound (239 mg, 83%). $^1$H NMR (400 MHz, CDCl$_3$) δ 7.41-7.29 (m, 3H), 6.60 (s, 1H), 6.35 (d, 1H), 4.46 (d, 1H), 3.74 (d, 3H), 3.72-3.60 (m, 4H), 3.18-3.12 (m, 4H), 2.63-2.52 (m, 1H), 2.51-2.39 (m, 3H), 1.19 (d, 1H), 1.14 (d, 2H); LC/MS m/z (M+H)=309.2.

Preparation 85: (S)—N-(6-bromo-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)-N-methyl-2-morpholinopropanamide

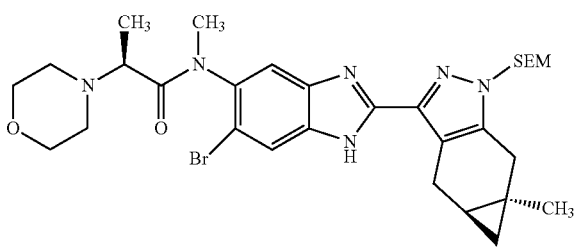 [SMILES: C[C@@H](C(=O)N(C)c1cc2nc(-c3nn(COCC[Si](C)(C)C)c4c3C[C@@H]3C[C@]3(C)C4)[nH]c2cc1Br)N1CCOCC1]

A mixture of Preparation 40 (900 mg, 2.52 mmol) in DMF (30 mL) at 20° C. was treated with 9 (722 mg, 2.52 mmol) and Na$_2$S$_2$O$_5$ (479 mg, 2.52 mmol). The mixture was heated at 110° C. for 15 h and concentrated. The crude product was purified by chromatography (silica, EtOAc/PE=0-100%) gave the title compound (703 mg, 43.4%). LC/MS m/z (M+H)$^+$=643.2/645.2 ($^{79}$Br, $^{81}$Br).

Preparation 86a: (S)—N-(6-bromo-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)-N-methyl-2-morpholinopropanamide Preparation 86a: (S)—N-(6-bromo-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)-N-methyl-2-morpholinopropanamide Preparation 87a: (S)—N-(6-cyano-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)-N-methyl-2-morpholinopropanamide Preparation 87b: (S)—N-(6-cyano-1-methyl-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)-N-methyl-2-morpholinopropanamide

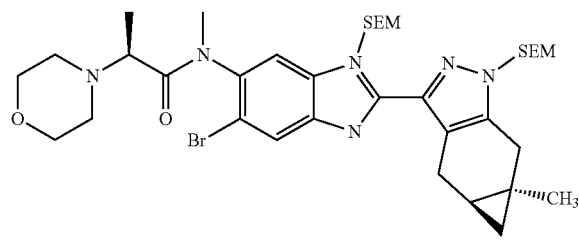

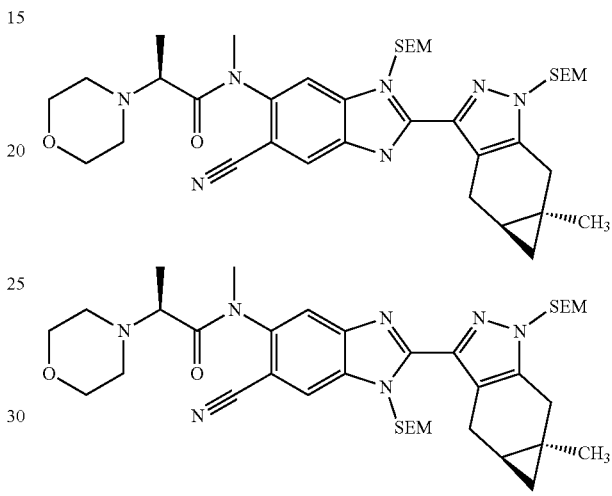

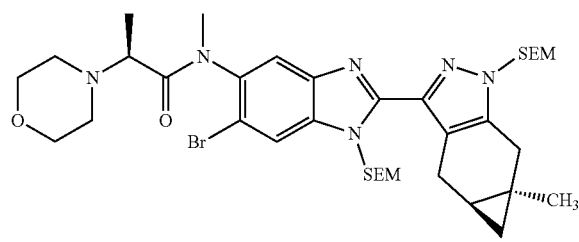

A portion of the mixture of Preparations 86a and 86b (200 mg, 0.258 mmol) in NMP (10 mL) at 20° C. was treated with Pd(PPh$_3$)$_4$ (30.0 mg, 0.026 mmol) and Zn(CN)$_2$ (152 mg, 1.29 mmol). The resulting mixture was heated in a microwave reactor at 160° C. for 1.5 h. The mixture was poured into EtOAc/H$_2$O (50/10 mL) and the organic layer collected. The aqueous layer was extracted with EtOAc (50 mL). The organic extracts were combined, washed with brine, dried (Na$_2$SO$_4$), filtered and concentrated. The crude material was purified by chromatography (silica, EtOAc/PE=0-100%) to give the title compounds as a mixture (165 mg, 89%). LC/MS m/z (M+H)$^+$=720.3.

Preparation 88. 4-bromo-2,3-difluoro-6-nitroaniline

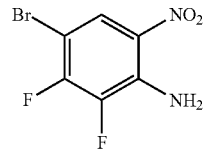 [SMILES: Nc1c([N+](=O)[O-])cc(Br)c(F)c1F]

A solution of Preparation 85 (600 mg, 0.93 mmol) in THF (30 mL) at 0° C. was treated pop-mci with NaH (48.5 mg, 1.21 mmol). After stirring for 30 min, SEM-Cl (233 mg, 1.40 mmol) was added and the mixture stirred at 20° C. for 2 h. The mixture was treated with sat. aq. NH$_4$Cl (1 mL) and diluted with 3:1 EtOAc/H$_2$O (200 mL). The organic layer was collected and the aqueous layer was extracted with EtOAc (150 mL). The organic extracts were combined, dried (Na$_2$SO$_4$), filtered and concentrated. The crude material was purified by chromatography (silica, EtOAc/PE=0-100%) to give the title compounds as a mixture (705 mg, 98%). LC/MS m/z (M+H)$^+$=773.0/775.0 ($^{79}$Br, $^{81}$Br).

A solution of 2,3-difluoro-6-nitroaniline (10.0 g, 57.4 mmol) in DMF (230 mL) at 15° C. was treated with N-bromosuccinimide (12.3 g, 68.9 mmol). The mixture was heated at 90° C. for 6 h and then cooled to RT and poured into ice water. The mixture was extracted with EtOAc (2×100 mL) and the organic extracts combined, washed with brine and dried (Na$_2$SO$_4$), filtered and concentrated. The crude material was purified by chromatography (silica, EtOAc/PE=0-20%) to give the title compound (13.5 g, 93%). ¹H NMR (400 MHz, CDCl₃) δ 8.22 (dd, 1H), 6.24 (s, 2H).

Preparation 89: 5-bromo-3,4-difluorobenzene-1,2-diamine

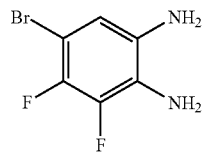

A solution of Preparation 88 (13.5 g, 53.4 mmol) in EtOH (296 mL) at 20° C. was treated with SnCl₂ (48.2 g, 213 mmol). The mixture was heated at 70° C. for 16 h and then cooled to RT. The mixture was diluted with H₂O (200 mL) and washed with sat. aq. NaHCO₃ (200 mL). The mixture was filtered and the collected solids rinsed with EtOAc (100 mL). The filtrate was concentrated. The residue was purified by chromatography (silica, EtOAc/PE=0-60%) to give the title compound (8.50 g, 71.4%). ¹H NMR (400 MHz, CDCl₃) δ 6.63 (dd, 1H), 3.49 (s, 2H), 3.35 (s, 2H); LC/MS m/z (M+H)⁺=223.1/225.0 (⁷⁹Br, ⁸¹Br).

Preparation 90: (4aS,5aR)-3-(5-bromo-6,7-difluoro-1H-benzo[d]imidazol-2-yl)-5a-methyl-1-((2-(trimethylsilyl)ethoxy)methyl)-1,4,4a,5,5a,6-hexahydrocyclopropa[f]indazole

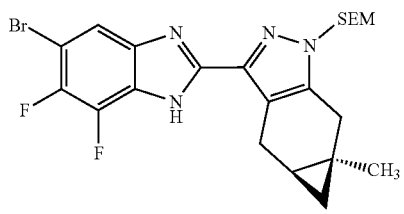 [SMILES: C[C@@]12Cc3c(c(-c4nc5cc(Br)c(F)c(F)c5[nH]4)nn3COCC[Si](C)(C)C)C[C@@H]1C2]

A solution of Preparation 89 (5.0 g, 22.42 mmol) in DMF (112 ml) at RT was treated with Preparation 9 (6.87 g, 22.4 mmol), Na₂S₂O₅ (2.13 g, 11.2 mmol) and DMSO (4.38 g, 56.0 mmol). The reaction mixture was heated at 110° C. for 16 h. The mixture was poured into 3% aq. LiCl (100 mL) and extracted with EtOAc (2×80 mL). The organic extracts were combined, dried (Na₂SO₄), filtered and concentrated. The crude material was purified by chromatography (silica, EtOAc/PE=0-20%) to give the title compound (10.17 g, 89%). LC/MS m/z (M+H)=509.3/511.3 (⁷⁹Br, ⁸¹Br).

Preparation 91a: (4aS,5aR)-3-(6-bromo-4,5-difluoro-1-((2-(trimethylsilyl)ethoxy)methyl)-1H-benzo[d]imidazol-2-yl)-5a-methyl-1-((2-(trimethylsilyl)ethoxy)methyl)-1,4,4a,5,5a,6-hexahydrocyclopropa[f]indazole

Preparation 91 b: (4aS,5aR)-3-(5-bromo-6,7-difluoro-1-((2-(trimethylsilyl)ethoxy)methyl)-1H-benzo[d]imidazol-2-yl)-5a-methyl-1-((2-(trimethylsilyl)ethoxy)methyl)-1,4,4a,5,5a,6-hexahydrocyclopropa[f]indazole

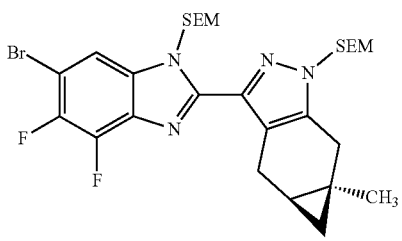

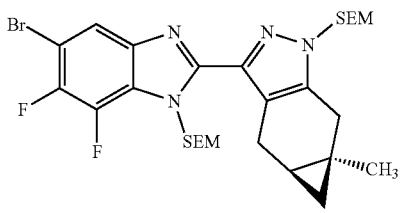

A solution of Preparation 90 (10.95 g, 2.49 mmol) in THF (269 mL) at 0° C. was added NaH (1.29 g, 32.2 mmol). After stirring for 30 min, SEM-Cl (3.94 g, 23.6 mmol) was added and the mixture stirred for 3 h at RT. The mixture was poured into sat. aq. NH₄Cl (150 mL) and extracted with EtOAc (2×100 mL). The organic extracts were collected, dried (Na₂SO₄), filtered and concentrated. The crude material was purified by chromatography (silica, EtOAc/PE=0-20%) to give the title compounds as a mixture (12.49 g, 90.8%). ¹H NMR (400 MHz, Methanol-d₄) δ 7.74 (ddd, 1H), 6.26-5.99 (m, 2H), 5.49 (d, 2H), 3.63 (t, 2H), 3.45 (dt, 2H), 3.23 (dd, 2H), 3.08 (td, 1H), 2.78 (dd, 1H), 1.31 (s, 3H), 1.15 (dt, 1H), 0.91 (td, 2H), 0.77 (ddd, 2H), 0.43 (dd, 1H), 0.24 (q, 1H), −0.01 (d, 9H), −0.14 (s, 4H), −0.17 (s, 5H).

Preparation 92a: tert-butyl (4,5-difluoro-2-((4aS, 5aR)-5a-methyl-1-((2-(trimethylsilyl)ethoxy) methyl)-1,4,4a,5,5a,6-hexahydrocyclopropa[f]indazol-3-yl)-1-((2-(trimethylsilyl)ethoxy)methyl)-1H-benzo[d]imidazol-6-yl)carbamate Preparation 92b: tert-butyl (6,7-difluoro-2-((4aS, 5aR)-5a-methyl-1-((2-(trimethylsilyl)ethoxy) methyl)-1,4,4a,5,5a,6-hexahydrocyclopropa[f]indazol-3-yl)-1-((2-(trimethylsilyl)ethoxy)methyl)-1H-benzo[d]imidazol-5-yl)carbamate

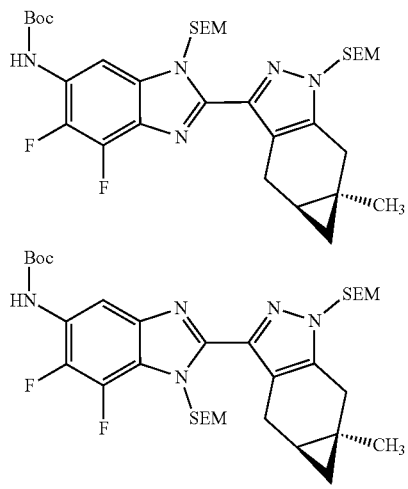

A portion of the mixture of Preparations 91a and 91b (9.45 g, 14.7 mmol) in tert-amyl alcohol (148 mL) at RT was treated with f-butyl carbamate (2.60 g, 22.2 mmol), Cs₂CO₃ (9.63 g, 29.5 mmol), Pd₂(dba)₃ (1.35 g, 1.48 mmol) and (1.01 g, 2.95 mmol). The mixture heated at 100° C. for 16 h. The mixture was concentrated and the residue purified by chromatography (silica, EtOAc/PE=0-16%) to give the title compounds as a mixture (4.24 g, 43%). LC/MS m/z (M+H)=676.3.

Preparation 93a: 4,5-difluoro-2-((4aS,5aR)-5a-methyl-1-((2-(trimethylsilyl)ethoxy)methyl)-1,4,4a, 5,5a,6-hexahydrocyclopropa[f]indazol-3-yl)-1-((2-(trimethylsilyl)ethoxy)methyl)-1H-benzo[d] imidazol-6-amine Preparation 93b: 6,7-difluoro-2-((4aS,5aR)-5a-methyl-1-((2-(trimethylsilyl)ethoxy)methyl)-1,4,4a, 5,5a,6-hexahydrocyclopropa[f]indazol-3-yl)-1-((2-(trimethylsilyl)ethoxy)methyl)-1H-benzo[d] imidazol-5-amine

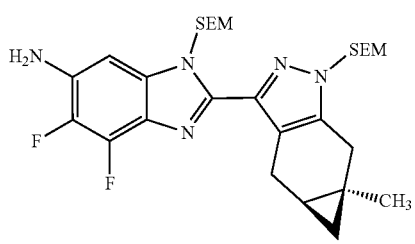

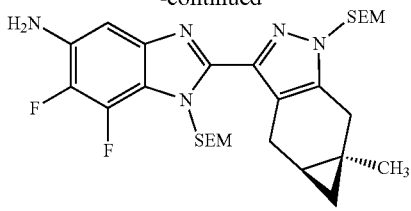

A mixture of 92a and 92b (5.27 g, 7.79 mmol) in DCM (78.0 mL) at 0° C. was treated with ZnBr₂ (8.78 g, 39.0 mmol). The mixture was stirred at 15° C. for 12 h and poured into sat. aq. NaHCO₃ (70 mL). The mixture was extracted with DCM (2×80 mL) and the organic extracts combined, dried (Na₂SO₄), filtered and concentrated. The crude material was purified by chromatography (silica, EtOAc/PE=0-25% then MeOH/EtOAc=0-15%) to give the title compounds as a mixture (2.8 g, 62.4%). LC/MS m/z (M+H)⁺=576.3.

Preparation 94a: (S)—N-(4,5-difluoro-2-((4aS,5aR)-5a-methyl-1-((2-(trimethylsilyl)ethoxy)methyl)-1,4, 4a,5,5a,6-hexahydrocyclopropa[f]indazol-3-yl)-1-((2-(trimethylsilyl)ethoxy)methyl)-1H-benzo[d] imidazol-6-yl)-2-morpholinopropanamide Preparation 94b: (S)—N-(6,7-difluoro-2-((4aS,5aR)-5a-methyl-1-((2-(trimethylsilyl)ethoxy)methyl)-1,4, 4a,5,5a,6-hexahydrocyclopropa[f]indazol-3-yl)-1-((2-(trimethylsilyl)ethoxy)methyl)-1H-benzo[d] imidazol-5-yl)-2-morpholinopropanamide

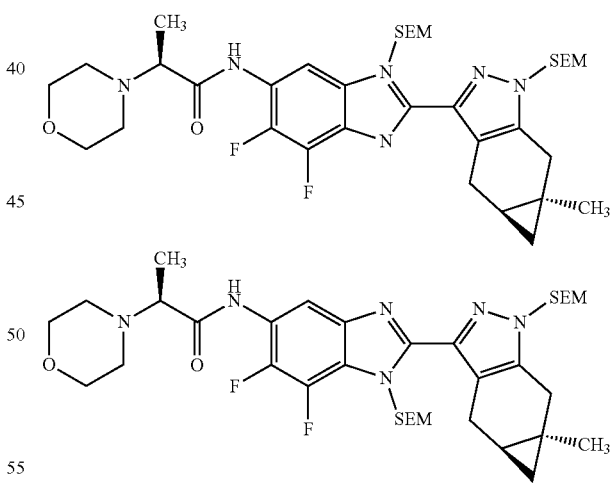

The mixture of Preparations 93a and 93b (2.80 g, 4.86 mmol) in pyridine (69.5 mL) at 0° C. was treated with Preparation 19 (1.12 g, 7.05 mmol) and EDCI (1.86 g, 9.72 mmol). The mixture was stirred at RT for 19 h, diluted with H₂O (100 mL) and extracted with EtOAc (2×100 mL). The organic extracts were combined, dried (Na₂SO₄), filtered and concentrated. The crude material was purified by chromatography (silica, EtOAc/PE=0-25%) to give the title compounds as a mixture (3.07 g, 88.1%). LC/MS m/z (M+H)=717.6.

Preparation 95a: (S)—N-(4,5-difluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-N-methyl-2-morpholinopropanamide Preparation 95b: (S)—N-(6,7-difluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)-N-methyl-2-morpholinopropanamide Preparation 96a: (S)—N-(4,5-difluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-N-ethyl-2-morpholinopropanamide Preparation 96b: (S)—N-(6,7-difluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)-N-ethyl-2-morpholinopropanamide

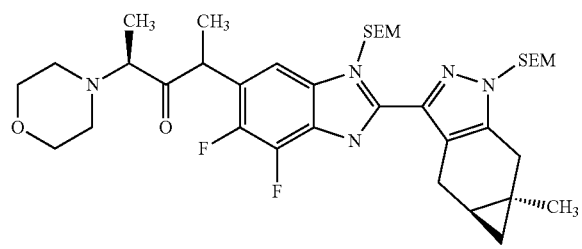

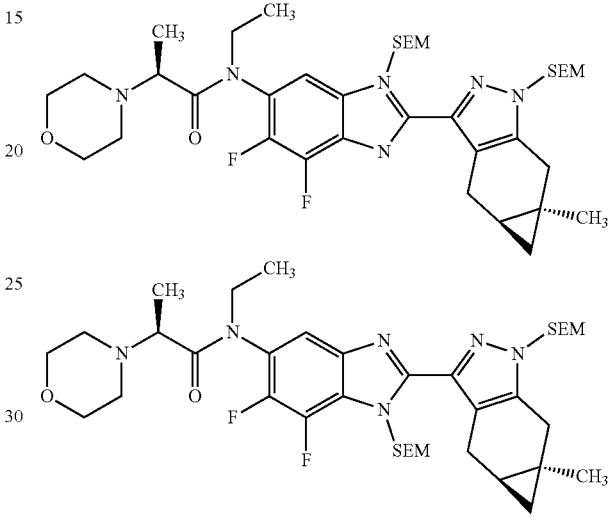

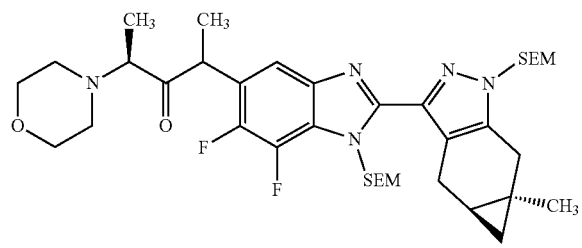

A solution of a portion of the mixture of Preparations 94a and 94b (55 mg, 0.08 mmol) in THF (1.10 mL) at 0° C. was treated with NaH (4.60 mg, 0.12 mmol). After stirring 30 min at RT, ethyl iodide (14 mg, 0.09 mmol) was added and the mixture was stirred for 22 h. The mixture was diluted with sat. aq. NH$_4$Cl (10 mL) and extracted with EtOAc (2×15 mL). The organic extracts were combined, dried (Na$_2$SO$_4$), filtered and concentrated to give the title compound as a mixture. LC/MS m/z (M+H)=745.1.

Preparation 97: N-methyl-N-(6-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)acetamide

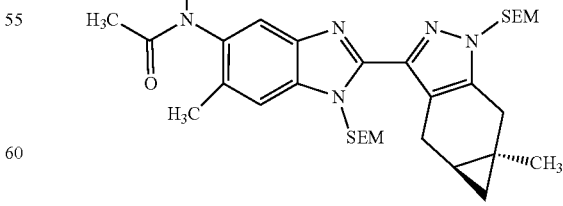

A solution of the mixture of Preparations 94a and 94b (3.07 g, 4.28 mmol) in THF (61 mL) at 0° C. was treated with NaH (257 mg, 6.42 mmol). After stirring 30 min at 15° C., methyl iodide (729 mg, 5.14 mmol) was added and the mixture stirred at RT 3 h. The mixture was diluted with sat. aq. NH$_4$Cl (80 mL) and extracted with EtOAc (2×80 mL). The organic extracts were combined, dried (Na$_2$SO$_4$), filtered and concentrated. The crude material was purified by chromatography (silica, EtOAc/PE=0-50%) to give the title compounds as a mixture (3.26 g, 100%). LC/MS m/z (M+H)=731.4.

A solution of Preparation 62 (4.74 g, 9.88 mmol) in THF (124 mL) at 0° C. was treated with NaH (474 mg, 11.9 mmol). The mixture was stirred at 0° C. for 30 min and SEM-Cl (1.81 g, 10.9 mmol) was added. The mixture was stirred at 0° C. for 1 h and warmed to 10° C. and stirred for 1.5 h. The mixture was treated with sat. aq. NH₄Cl (50 mL) and extracted with EtOAc (3×50 mL). The combined organic layers were dried (Na₂SO₄), filtered and concentrated. The crude material was purified by chromatography (silica, EtOAc/PE=0-40%) to give the title compound (2.42 g, 40%). LC/MS m/z (M+H)⁺=610.3.

Preparation 98: 2-chloro-N-methyl-N-(6-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)acetamide

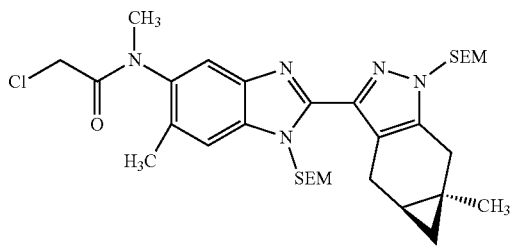 [SMILES: Cc1cc2c(cc1N(C)C(=O)CCl)nc(-c1nn(COCC[Si](C)(C)C)c3c1C[C@@H]1C[C@]1(C)C3)n2COCC[Si](C)(C)C]

A solution of Preparation 97 (848 mg, 1.39 mmol) in THF (22 mL) at −10° C. was treated with a solution of LDA (0.76 mL, 2N in THF/heptane). The mixture was stirred at −10° C. for 30 min and benzenesulfonyl chloride (577 mg, 3.27 mmol) was added. The mixture was stirred for 2 h at −10° C. and then treated with sat. aq. NH₄Cl (20 mL) and extracted with EtOAc (3×30 mL). The combined organic layers were dried (Na₂SO₄), filtered and concentrated. The crude material was purified by chromatography (silica, EtOAc/PE=0-30%) to give the title compound (404 mg, 45%). ¹H NMR (400 MHz, CDCl₃) δ 7.71 (s, 1H), 7.39 (s, 1H), 6.20-5.93 (m, 2H), 5.53-5.33 (m, 2H), 3.92-3.66 (m, 2H), 3.57 (t, 2H), 3.54-3.47 (m, 2H), 3.47-3.38 (m, 1H), 3.30 (s, 3H), 3.19-3.03 (m, 2H), 2.74 (d, 1H), 2.34 (d, 3H), 1.28 (d, 3H), 1.13 (dt, 1H), 0.91 (ddd, 2H), 0.86-0.72 (m, 2H), 0.46-0.33 (m, 1H), 0.26 (q, 1H), −0.02 (s, 9H), −0.12 (s, 9H); LC/MS m/z (M+H)⁺=644.3.

Preparation 99: (S)—N-(4-amino-3-nitrophenyl)-N-methyl-2-morpholinopropanamide

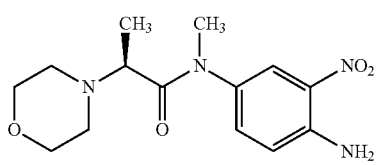

The title compound was prepared analogously to Preparation 38 starting from 4-chloro-3-nitroaniline and Preparation 19. LC/MS m/z (M+H)⁺=309.0.

Preparation 100: (S)—N-(4-amino-3-bromo-5-nitrophenyl)-N-methyl-2-morpholinopropanamide

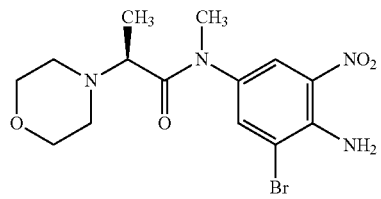 [SMILES: C[C@@H](C(=O)N(C)c1cc(Br)c(N)c([N+](=O)[O-])c1)N1CCOCC1]

A solution of Preparation 99 (1.20 g, 3.89 mmol) in DMF (20 mL) at 20° C. was treated with bromine (1.24 g, 7.78 mmol). The mixture was stirred at 20° C. for 15 h. The mixture was cooled to 0° C. and treated with of Et₃N (10 mL). The mixture was concentrated under reduced pressure and the residue was purified by chromatography (silica, EtOAc/PE=0-100%) to give the title compound (610 mg, 41%). LC/MS m/z (M+H)⁺=388.8 (⁸¹Br).

Preparation 101 (S)—N-(3,4-diamino-5-bromophenyl)-N-methyl-2-morpholinopropanamide

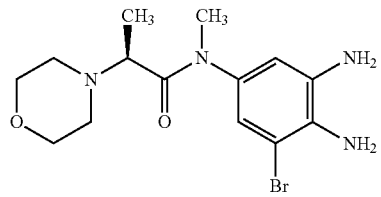 [SMILES: C[C@@H](C(=O)N(C)c1cc(N)c(N)c(Br)c1)N1CCOCC1]

A solution of Preparation 100 (900 mg, 2.32 mmol) in EtOH (80 mL) was treated with conc. HCl (1 mL) and iron powder (389 mg, 6.97 mmol). The mixture was stirred at 70° C. for 2 h. The mixture was cooled to 0° C. and adjusted to pH 7 by addition of conc. NH₄OH (2 mL). The mixture was filtered and the filtrate was concentrated. The residue was taken up in DCM (60 mL), stirred for 1 h, and filtered. The filtrate was concentrated to give the title compound (802 mg, 87%). LC/MS m/z (M+H)⁺=356.9 (⁷⁹Br).

Preparation 102: (S)—N-(7-bromo-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)-N-methyl-2-morpholinopropanamide

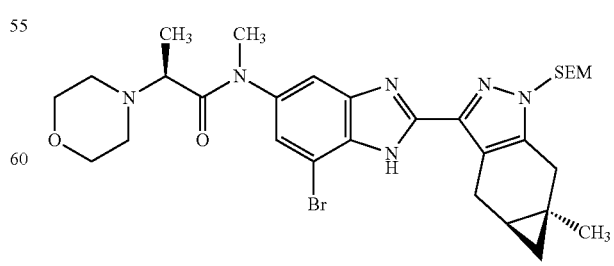

A mixture of Preparation 9 (601 mg, 1.96 mmol) in DMF (25 mL) was added to 101 (700 mg, 1.96 mmol) and Na$_2$S$_2$O$_5$ (373 mg, 1.96 mmol) and the mixture heated at 110° C. for 15 h. The mixture was concentrated and the residue was purified by chromatography (silica, EtOAc/PE=0-100%) to give the title compound (730 mg, 56%). $^1$H NMR (400 MHz, CDCl$_3$) δ 9.94 (s, 1H), 7.59 (s, 1H), 7.35 (s, 1H), 5.53-5.24 (m, 2H), 3.66 (t, 4H), 3.61-3.48 (m, 3H), 3.31 (s, 3H), 3.25-3.06 (m, 3H), 2.75 (d, 1H), 2.56 (dt, 2H), 2.38-2.23 (m, 2H), 1.30 (s, 3H), 1.14 (t, 4H), 0.92 (ddd, 2H), 0.43 (dd, 1H), 0.26 (t, 1H), −0.01 (s, 9H); LC/MS m/z (M+H)$^+$=645.0 ($^{81}$Br).

Preparation 103: (S)—N-(4-bromo-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-N-methyl-2-morpholinopropanamide

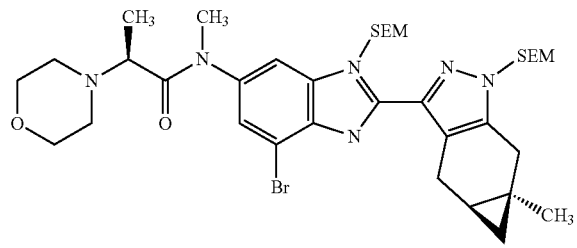

A solution of Preparation 102 (700 mg, 1.09 mmol) in THF (50 mL) at 0° C. was treated with NaH (57 mg, 1.41 mmol) and SEM-Cl (272 mg, 1.63 mmol). The mixture was warmed to RT and stirred for 2 h. The mixture was cooled to 0° C. and treated with sat. aq. NH$_4$Cl (1 mL). The mixture was diluted with water (50 mL) and extracted with EtOAc (2×150 mL). The combined organic layers were washed with brine, dried (Na$_2$SO$_4$), filtered and concentrated. The crude material was purified by chromatography (silica, EtOAc/PE=0-100%) to give the title compound (770 mg, 92%). LC/MS m/z (M+H)$^+$=775.2 ($^{81}$Br).

Preparation 104: (2-((4aS,5aR)-5a-methyl-1-((2-(trimethylsilyl)ethoxy)methyl)-1,4,4a,5,5a,6-hexahydrocyclopropa[f]indazol-3-yl)-6-((S)—N-methyl-2-morpholinopropanamide)-1-((2-(trimethylsilyl)ethoxy)methyl)-1H-benzo[d]imidazol-4-yl)boronic acid

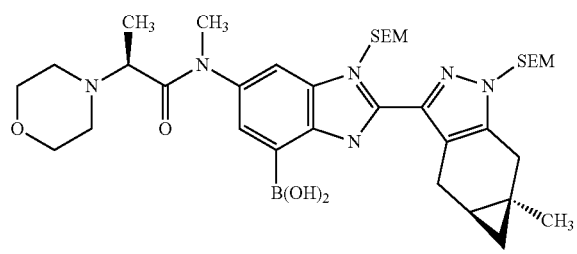

A solution of Preparation 103 (328 mg, 0.424 mmol) in 1,4-dioxane (20 mL) was treated with KOAc (125 mg, 1.27 mmol), bis(pinacolato)diboron (323 mg, 1.27 mmol), and Pd(dppf)Cl$_2$ (31 mg, 0.0424 mmol). The mixture was heated to 100° C. and stirred for 15 h. The mixture was cooled to RT and concentrated. The residue was purified by chromatography (silica, EtOAc/PE=0-100% then MeOH/EtOAc=0-100%) to give the title compound (245 mg, 86%). LC/MS m/z (M+H)$^+$=739.2 ($^{79}$Br).

Preparation 105: (S)—N-(4-hydroxy-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-N-methyl-2-morpholinopropanamide

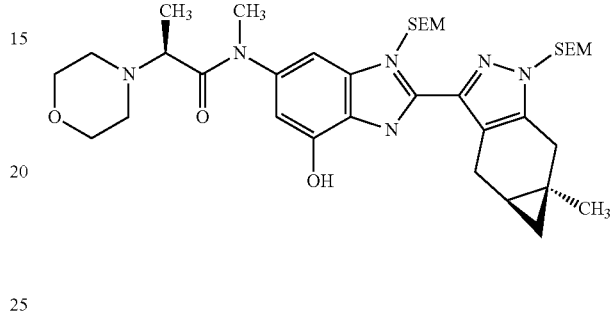

A solution of Preparation 104 (350 mg, 0.224 mmol) in THF (30 mL) at 0° C. was treated with a solution of NaBO$_3$·4H$_2$O (104 mg, 0.673 mmol) in water (10 mL). The mixture was stirred at 20° C. for 5 h. The mixture was partitioned between water (10 mL) and EtOAc (50 mL). The organic layer was separated and the aqueous layer was extracted with EtOAc (20 mL). The combined organic layers were washed with brine, dried (Na$_2$SO$_4$), filtered and concentrated to give the title compound (300 mg, 94%). LC/MS m/z (M+H)$^+$=711.3

Preparation 106: (S)—N-(4-methoxy-2-((4aS,5aR)-5a-methyl-1,4,4a,5,5a,6-hexahydrocyclopropa[f]indazol-3-yl)-1H-benzo[d]imidazol-6-yl)-N-methyl-2-morpholinopropanamide

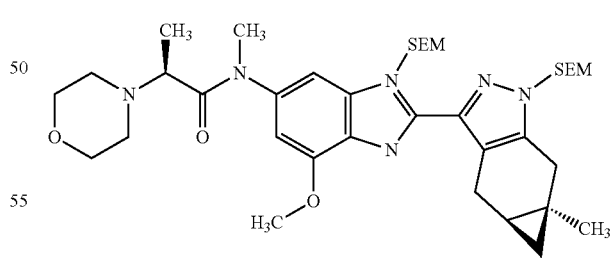

A solution of Preparation 105 (150 mg, 0.211 mmol) in DMF (3 mL) at 0° C. was treated with K$_2$CO$_3$ (88 mg, 0.63 mmol) and methyl iodide (45 mg, 0.32 mmol). The mixture was stirred at 20° C. for 2 h. The mixture was diluted with water (10 mL) and extracted with EtOAc (2×50 mL). The combined organic layers were washed with brine, dried (Na$_2$SO$_4$), filtered and concentrated to give the title compound (153 mg, 100%). LC/MS m/z (M+H)$^+$=725.3

Preparation 107: (4aS,5aR)-3-(5-bromo-7-(trifluoromethyl)-1H-benzo[d]imidazol-2-yl)-5a-methyl-1-((2-(trimethylsilyl)ethoxy)methyl)-1,4,4a,5,5a,6-hexahydrocyclopropa[f]indazole

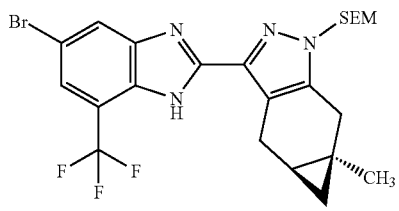 [SMILES: C[C@@]12Cc3c(c(-c4nc5cc(Br)cc(C(F)(F)F)c5[nH]4)nn3COCC[Si](C)(C)C)C[C@@H]1C2]

A solution of Preparation 9 (288 mg, 0.94 mmol) in DMF (10 mL) was treated with 5-bromo-3-(trifluoromethyl)benzene-1,2-diamine (240 mg, 0.94 mmol) and $Na_2S_2O_5$ (179 mg, 0.94 mmol). The mixture was heated at 110° C. for 15 h and concentrated. The residue was purified by chromatography (silica, EtOAc/PE=0-100%) to give the title compound (430 mg, 84%). LC/MS m/z $(M+H)^+$=543.1 ($^{81}Br$).

Preparation 108: (4aS,5aR)-3-(6-bromo-4-(trifluoromethyl)-1-((2-(trimethylsilyl)ethoxy)methyl)-1H-benzo[d]imidazol-2-yl)-5a-methyl-1-((2-(trimethylsilyl)ethoxy)methyl)-1,4,4a,5,5a,6-hexahydrocyclopropa[f]indazole

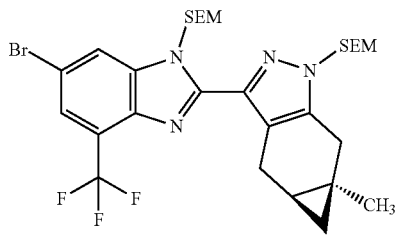 [SMILES: C[C@@]12Cc3c(c(-c4nc5c(C(F)(F)F)cc(Br)cc5n4COCC[Si](C)(C)C)nn3COCC[Si](C)(C)C)C[C@@H]1C2]

A solution of Preparation 107 (350 mg, 0.65 mmol) in THF (20 mL) at 0° C. was treated with NaH (34 mg, 0.84 mmol) and SEM-Cl (162 mg, 0.97 mmol). The mixture was warmed RT and stirred for 2 h. The mixture was cooled to 0° C. and treated with sat. aq. $NH_4Cl$ (1 mL). The mixture was diluted with water (50 mL) and extracted with EtOAc (2×150 mL). The combined organic layers were washed with brine, dried ($Na_2SO_4$), filtered and concentrated. The crude material was purified by chromatography (silica, EtOAc/PE=0-100%) to give the title compound (430 mg, 99%). LC/MS m/z $(M+H)^+$=673.0 ($^{81}Br$).

Preparation 109: tert-butyl (2-((4aS,5aR)-5a-methyl-1-((2-(trimethylsilyl)ethoxy)methyl)-1,4,4a,5,5a,6-hexahydrocyclopropa[f]indazol-3-yl)-4-(trifluoromethyl)-1-((2-(trimethylsilyl)ethoxy)methyl)-1H-benzo[d]imidazol-6-yl)carbamate

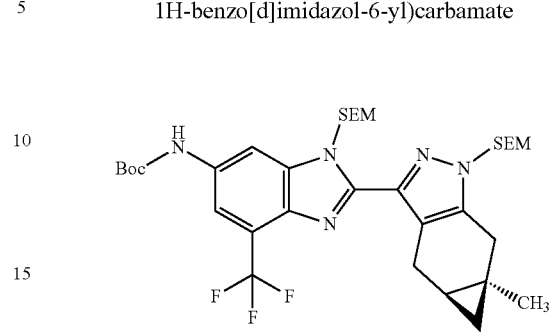

A solution of Preparation 108 (380 mg, 0.57 mmol) in 1,4-dioxane (10 mL) in tert-amyl alcohol (10 mL) was treated with $BOC_2O$ (199 mg, 1.7 mmol), $Cs_2CO_3$ (369 mg, 1.13 mmol), (77 mg, 0.23 mmol), and $Pd_2(dba)_3$ (52 mg, 0.057 mmol). The mixture was heated at 100° C. for 15 h. The mixture was cooled to RT and concentrated. The residue was purified by chromatography (silica, EtOAc/PE+0-100%) to give the title compound (223 mg, 56%). LC/MS m/z $(M+H)^+$=708.4

Preparation 110: 2-((4aS,5aR)-5a-methyl-1-((2-(trimethylsilyl)ethoxy)methyl)-1,4,4a,5,5a,6-hexahydrocyclopropa[f]indazol-3-yl)-4-(trifluoromethyl)-1-((2-(trimethylsilyl)ethoxy)methyl)-1H-benzo[d]imidazol-6-amine

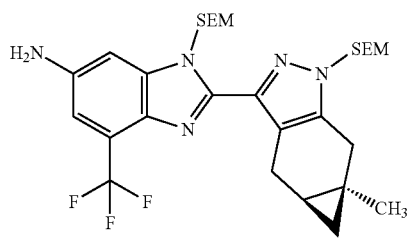 [SMILES: C[C@@]12Cc3c(c(-c4nc5c(C(F)(F)F)cc(N)cc5n4COCC[Si](C)(C)C)nn3COCC[Si](C)(C)C)C[C@@H]1C2]

A solution of Preparation 109 (220 mg, 0.31 mmol) in DCM (20 mL) was treated with $ZnBr_2$ (350 mg, 1.55 mmol). The mixture was stirred at RT for 15 h. The mixture was filtered and the filtrate was diluted with water (50 mL) and extracted with DCM (2×50 mL). The combined organic layers were washed with brine, dried ($Na_2SO_4$), filtered and concentrated to give the title compound (170 mg, 90%). LC/MS m/z $(M+H)^+$=608.2.

Preparation 111: (S)—N-(2-((4aS,5aR)-5a-methyl-1-((2-(trimethylsilyl)ethoxy)methyl)-1,4,4a,5,5a,6-hexahydrocyclopropa[f]indazol-3-yl)-4-(trifluoromethyl)-1-((2-(trimethylsilyl)ethoxy)methyl)-1H-benzo[d]imidazol-6-yl)-2-morpholinopropanamide

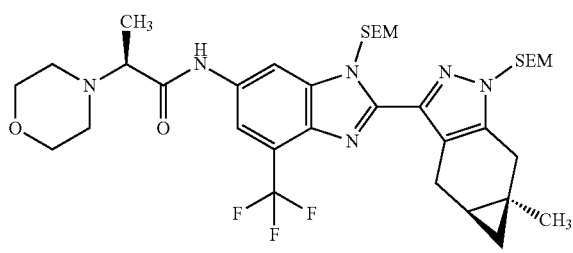 [SMILES: C[C@@H](C(=O)Nc1cc(C(F)(F)F)c2nc(-c3nn(COCC[Si](C)(C)C)c4c3C[C@@H]3C[C@]3(C)C4)n(COCC[Si](C)(C)C)c2c1)N1CCOCC1]

A solution of Preparation 110 (170 mg, 0.28 mmol) and 19 (89 mg, 0.56 mmol) in pyridine (5 mL) was treated with EDCI (107 mg, 0.56 mmol). The mixture was stirred at RT for 15 h. The mixture was diluted with water (50 mL) and extracted with EtOAc (2×50 mL). The combined organic layers were washed with brine, dried (Na$_2$SO$_4$), filtered and concentrated. The crude material was purified by chromatography (silica, EtOAc/PE=0-100%) to give the title compound (125 m, (60%). LC/MS m/z (M+H)$^+$=749.4.

Preparation 112: (S)—N-methyl-N-(2-((4aS,5aR)-5a-methyl-1-((2-(trimethylsilyl)ethoxy)methyl)-1,4,4a,5,5a,6-hexahydrocyclopropa[f]indazol-3-yl)-4-(trifluoromethyl)-1-((2-(trimethylsilyl)ethoxy)methyl)-1H-benzo[d]imidazol-6-yl)-2-morpholinopropanamide

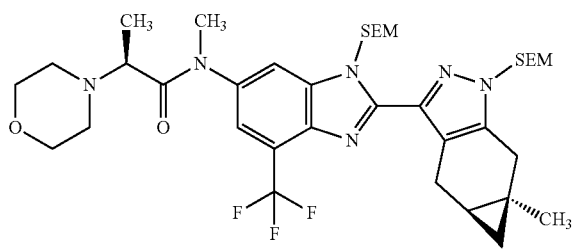 [SMILES: C[C@@H](C(=O)N(C)c1cc(C(F)(F)F)c2nc(-c3nn(COCC[Si](C)(C)C)c4c3C[C@@H]3C[C@]3(C)C4)n(COCC[Si](C)(C)C)c2c1)N1CCOCC1]

A solution of Preparation 111 (125 mg, 0.17 mmol) in THF (5 mL) at 0° C. was treated with NaH (10 mg, 0.25 mmol) followed by methyl iodide (36 mg, 0.25 mmol). The mixture was warmed to RT and stirred for 2 h. The mixture was cooled to 0° C. and treated with sat. aq. NH$_4$Cl (0.3 mL). The mixture was diluted with water (50 mL) and extracted with EtOAc (2×50 mL). The combined organic layers were washed with brine, dried (Na$_2$SO$_4$), filtered and concentrated to give the title compound (127 mg, 99%).

Preparation 113: Methyl 5-bromo-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazole-7-carboxylate

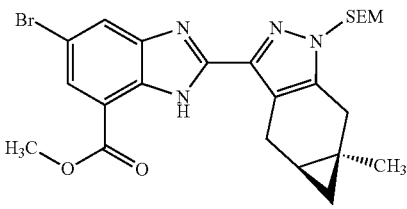

A mixture of methyl 2,3-diamino-5-bromobenzoate (720 mg, 2.94 mmol), 9 (990 mg, 3.32 mmol) and NaHSO$_3$ (336 mg, 3.23 mmol) in EtOH (14.7 mL) and water (2.5 mL) was heated at 90° C. under air for 18 h. The mixture was cooled to RT and diluted with water. The mixture was extracted with DCM (×3) and the combined organic layers were dried (MgSO$_4$), filtered and concentrated. The residue was stirred in heptane:EtOAc (1:1, 10 mL) for 18 h and the resultant solids collected by filtration to give the title compound (842 mg, 54%) of the title compound as a beige solid. $^1$H NMR (600 MHz, CDCl$_3$) δ 10.85 (s, 1H), 8.18 (s, 1H), 8.01 (d, 1H), 5.50-5.33 (m, 2H), 4.02 (s, 3H), 3.61-3.51 (m, 3H), 3.18 (dd, 1H), 3.13 (d, 1H), 2.74 (d, 1H), 1.29 (s, 3H), 1.17 (dt, 1H), 0.92 (td, 2H), 0.43 (dd, 1H), 0.27 (t, 1H), −0.02 (s, 9H); LC/MS m/z (M+H)$^+$=531.5.

Preparation 114: Methyl 6-bromo-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazole-4-carboxylate

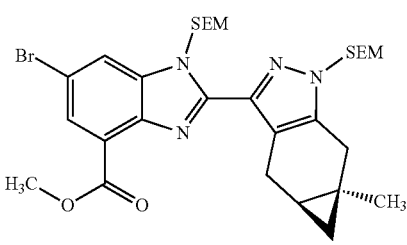

A of suspension of NaH (4147 mg, 10.4 mmol) in THF (6 mL) at 0° C. was treated with a solution of Preparation 113 (2.77 g, 5.22 mmol) in THF (24 mL). The mixture was stirred at 0° C. for 30 min and then SEM-Cl (1310 mg, 7.83 mmol) was added. The mixture was warmed to RT and stirred for 18 h. The mixture was cooled to 0° C. and treated with sat. aq. NH$_4$Cl (5 mL). The organic solvent was evaporated and the resultant mixture extracted with DCM (×4). The combined organic layers were washed with brine, dried (MgSO$_4$), filtered and concentrated. The crude material was purified by chromatography (silica, EtOAc/PE=0-60%) to give the title compound (2.88 g, 83%). $^1$H NMR (400 MHz, CDCl$_3$) δ 8.10 (d, 1H), 7.92 (d, 1H), 6.18 (d, 2H), 5.49-5.33 (m, 2H), 4.06 (s, 3H), 3.63 (d, 1H), 3.52 (dt, 4H), 3.21-3.08 (m, 2H), 2.74 (d, 1H), 1.29 (s, 3H), 1.15 (dt, 1H), 0.94-0.80 (m, 4H), 0.41 (dd, 1H), 0.29 (t, 1H), −0.02 (s, 9H), −0.12 (s, 9H).

Preparation 115: Methyl 2-((4aS,5aR)-5a-methyl-1-((2-(trimethylsilyl)ethoxy)methyl)-1,4,4a,5,5a,6-hexahydrocyclopropa[f]indazol-3-yl)-6-(methylamino)-1-((2-(trimethylsilyl)ethoxy)methyl)-1H-benzo[d]imidazole-4-carboxylate

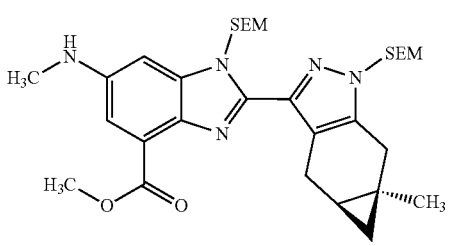

A solution of Preparation 114 (420 mg, 0.635 mmol) in DMF (4.2 mL) was added to a vial containing MeNH$_2$·HCl (64 mg, 0.95 mmol), CuI (10 mg, 0.051 mmol), N-(2,6-dimethylphenyl)-6-hydroxypicolinamide (25 mg, 0.10 mmol) and K$_3$PO$_4$ (404 mg, 1.9 mmol). The mixture was heated at 110° C. for 20 h. The mixture was cooled to RT and diluted with EtOAc. The mixture was extracted with water (×2). The organic layer was washed with brine, dried (MgSO$_4$), filtered and concentrated. The crude material was purified by chromatography (silica, EtOAc/PE=0-70%) to give the title compound (231 mg, 60%). $^1$H NMR (400 MHz, CDCl$_3$) δ 7.37 (d, 1H), 6.92 (d, 1H), 6.13 (d, 2H), 5.46-5.35 (m, 2H), 4.06 (s, 3H), 3.64-3.43 (m, 5H), 3.22-3.07 (m, 2H), 2.94 (s, 3H), 2.73 (d, 1H), 1.65 (s, 1H), 1.28 (s, 3H), 1.13 (dt, 1H), 0.94-0.87 (m, 2H), 0.86-0.76 (m, 2H), 0.39 (dd, 1H), 0.30 (t, 1H), -0.02 (s, 9H), -0.13 (s, 9H); LC/MS m/z (M+H)$^+$=612.5.

Preparation 116: 2-((4aS,5aR)-5a-methyl-1-((2-(trimethylsilyl)ethoxy)methyl)-1,4,4a,5,5a,6-hexahydrocyclopropa[f]indazol-3-yl)-6-(methylamino)-1-((2-(trimethylsilyl)ethoxy)methyl)-1H-benzo[d]imidazol-4-yl)methanol

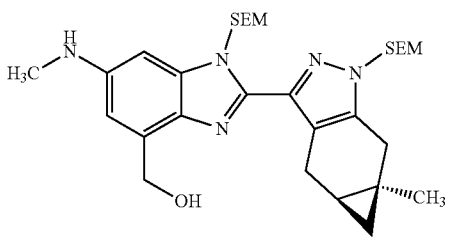

A solution of LiAlH$_4$ (15 mg, 0.39 mmol) in tetrahydrofuran (0.39 mL) at 0° C. was treated dropwise with a solution of Preparation 115 (158 mg, 0.26 mmol) in THF (1.3 mL). The mixture was warmed to RT and stirred for 1 h. The mixture was cooled to 0° C. and treated with sat. aq. Rochelle's salt (potassium sodium tartrate). The mixture was extracted with EtOAc (×2) and the combined organic layers were washed with brine, dried (MgSO$_4$), filtered and concentrated. The crude material was purified by chromatography (silica, EtOAc/heptanes=20-100%) to give the title compound (103 mg, 68%). $^1$H NMR (400 MHz, CDCl$_3$) δ 6.59 (d, 1H), 6.46 (d, 1H), 6.17-5.94 (m, 2H), 5.47-5.34 (m, 2H), 5.06 (s, 2H), 4.75 (s, 1H), 3.65-3.45 (m, 4H), 3.39 (d, 1H), 3.10 (dd, 2H), 2.89 (s, 3H), 2.76-2.65 (m, 1H), 1.27 (s, 3H), 1.10 (dt, 1H), 0.91 (ddd, 2H), 0.88-0.79 (m, 2H), 0.39 (dd, 1H), 0.25 (t, 1H), -0.02 (s, 9H), -0.11 (s, 9H).

Preparation 117: (S)—N-(4-(methoxymethyl)-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-N-methyl-2-morpholinopropanamide

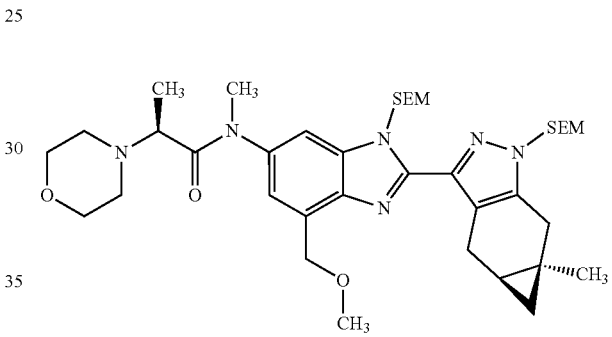

A solution of Preparation 116 (102 mg, 0.18 mmol) and 19 (42 mg, 0.262 mmol) in pyridine (1 mL) was treated with EDCI (84 mg, 0.44 mmol). The mixture was stirred at RT for 18 h. The mixture was concentrated and the residue was partitioned between EtOAc and sat. aq. NaHCO$_3$. The organic layer was separated and the aqueous layer was extracted to with EtOAc (×2). The combined organic layers were dried (Na$_2$SO$_4$), filtered and concentrated. The crude material was purified by chromatography (silica, [10:1 NH$_4$OH/MeOH]/DCM=0-16%) to provide a mixture of N- and O-acyl products. The mixture was taken up in THF (1 mL) and cooled to 0° C. NaH (18 mg, 0.45 mmol) was added and the mixture was stirred for 30 min and then treated with methyl iodide (42 mg, 0.30 mmol). The mixture was warmed to RT and stirred for 16 h. The mixture was cooled to 0° C. and treated with sat. aq. NH$_4$Cl. The mixture was diluted with water and extracted with EtOAc (×3). The combined organic layers were dried (MgSO$_4$), filtered and concentrated. The crude material was purified by chromatography (silica, EtOAc/heptanes=20-100%) to give the title compound (61 mg, 47%). $^1$H NMR (400 MHz, CDCl$_3$) δ 7.33 (s, 1H), 7.21 (s, 1H), 6.08 (d, 2H), 5.49-5.36 (m, 2H), 4.98 (d, 2H), 3.65 (t, 4H), 3.59-3.55 (m, 2H), 3.54 (s, 3H), 3.53-3.43 (m, 3H), 3.33 (s, 3H), 3.25 (q, 1H), 3.17-3.02 (m, 2H), 2.73 (d, 1H), 2.64-2.51 (m, 2H), 2.39 (dd, 2H), 1.29 (s, 3H), 1.15 (d, 3H), 1.14-1.08 (m, 1H), 0.90 (ddd, 2H), 0.85-0.76 (m, 2H), 0.41 (dd, 1H), 0.27 (t, 1H), -0.02 (s, 9H), -0.12 (s, 9H).

Preparation 118: (4aS,5aR)-3-(5-bromo-7-chloro-1H-benzo[d]imidazol-2-yl)-5a-methyl-1-((2-(trimethylsilyl)ethoxy)methyl)-1,4,4a,5,5a,6-hexahydrocyclopropa[f]indazole

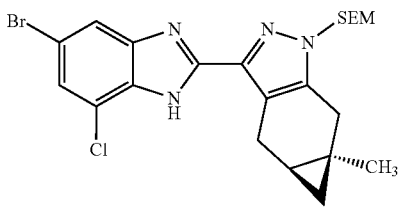 [SMILES: C[C@@]12Cc3c(c(-c4nc5cc(Br)cc(Cl)c5[nH]4)nn3COCC[Si](C)(C)C)C[C@@H]1C2]

A mixture of 1,2-diamino-5-bromo-3-chlorobenzene (200 mg, 0.90 mmol), NaHSO$_3$ (103 mg, 0.99 mmol) and Preparation 9 (304 mg, 0.99 mmol) in EtOH (3.7 mL) and water (0.8 mL) was heated at reflux for 16 h. The mixture was cooled to RT and diluted with water. After removing the EtOH under reduced pressure, the mixture was extracted with EtOAc (×3). The combined organic layers were dried (MgSO$_4$), filtered and concentrated. The crude material was purified by chromatography (silica, EtOAc/heptanes=0-30%) to give the title compound (410 mg, 89%). $^1$H NMR (400 MHz, DMSO-de) δ 13.13 (s, 1H), 7.55 (d, 1H), 7.43 (d, 1H), 5.49 (d, 1H), 5.42 (d, 1H), 3.57-3.51 (m, 2H), 3.48 (d, 1H), 3.19 (d, 1H), 3.01 (dd, 1H), 2.73 (d, 1H), 1.27 (s, 3H), 1.16 (ddd, 1H), 0.84 (td, 2H), 0.41 (dd, 1H), 0.17 (dd, 1H), −0.06 (s, 9H); LC/MS m/z (M+H)$^+$=507.4 ($^{79}$Br).

Preparation 119a: (4aS,5aR)-3-(5-bromo-7-chloro-1-((2-(trimethylsilyl)ethoxy)methyl)-1H-benzo[d]imidazol-2-yl)-5a-methyl-1-((2-(trimethylsilyl)ethoxy)methyl)-1,4,4a,5,5a,6-hexahydrocyclopropa[f]indazole Preparation 119b: (4aS,5aR)-3-(6-bromo-4-chloro-1-((2-(trimethylsilyl)ethoxy)methyl)-1H-benzo[d]imidazol-2-yl)-5a-methyl-1-((2-(trimethylsilyl)ethoxy)methyl)-1,4,4a,5,5a,6-hexahydrocyclopropa[f]indazole

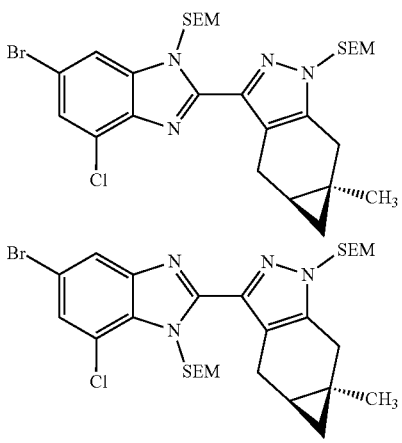

A solution of Preparation 118 (390 mg, 0.77 mmol) in THF (3.8 mL) was treated with NaH (59 mg, 1.54 mmol). The mixture was stirred at 0° C. for 30 min and SEM-Cl (205 mg, 1.23 mmol) was added. The mixture was stirred at 0° C. for 1.5 h. The mixture was cooled to 0° C. and treated with sat. aq. NH$_4$Cl. The THF was evaporated. The remaining mixture was extracted with EtOAc (×4). The combined organic layers were dried (MgSO$_4$), filtered and concentrated. The crude material was purified by chromatography (silica, EtOAc/heptanes=0-30%) to give the title compound as a mixture (425 mg, 87%). LC/MS m/z (M+H)$^+$=637.6 ($^{79}$Br).

Preparation 120: 7-chloro-N-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-amine Preparation 121: 4-chloro-N-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-amine

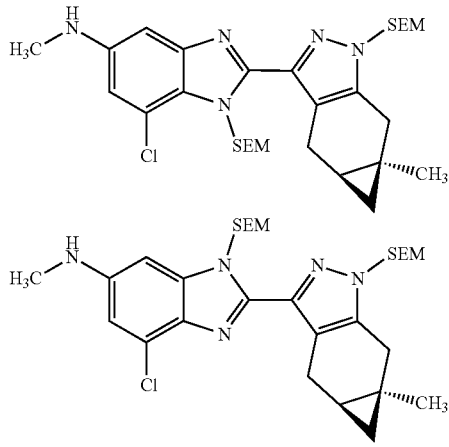

A solution of a mixture of Preparations 119a and 119b (542 mg, 0.85 mmol) in DMF (5.7 mL) was added to MeNH$_2$—HCl (86 mg, 1.27 mmol), CuI (13 mg, 0.068 mmol), N-(2,6-dimethylphenyl)-6-hydroxypicolinamide (33 mg, 0.14 mmol) and K$_3$PO$_4$ (541 mg, 2.6 mmol). The mixture was heated at 110° C. for 18 h. The mixture was diluted with EtOAc and washed with water (×3) and brine. The organic layer was dried (MgSO$_4$), filtered to and concentrated. The crude material was purified by chromatography (silica, EtOAc/heptanes=0-30%) to give the title compounds. (Reference: Bernhardson, D. J., Widlicka, D. W., Singer, R. A., *Org. Process Res. Dev.* 2019, 23, 1538-1551)

Preparation: 120: (121 mg, 24%). $^1$H NMR (400 MHz, CDCl$_3$) δ 6.66 (d, 1H), 6.58 (d, 1H), 6.03 (d, 2H), 5.44-5.34 (m, 2H), 3.59-3.44 (m, 5H), 3.11 (d, 2H), 3.07 (d, 1H), 2.89 (s, 3H), 2.71 (d, 1H), 1.28 (s, 3H), 1.11 (ddd, 1H), 0.95-0.87 (m, 2H), 0.86-0.77 (m, 2H), 0.38 (dd, 1H), 0.27 (dd, 1H), −0.02 (s, 9H), −0.12 (s, 9H). LC/MS m/z (M+H)$^+$=588.6

Preparation 121: (162 mg, 33%). $^1$H NMR (400 MHz, CDCl$_3$) δ 6.91 (d, 1H), 6.65 (d, 1H), 6.28 (d, 1H), 6.25 (d, 1H), 5.44 (d, 1H), 5.39 (d, 1H), 3.68 (brs, 1H), 3.57 (dd, 2H), 3.41-3.27 (m, 3H), 3.13 (d, 1H), 3.06 (dd, 1H), 2.88 (s, 3H), 2.73 (d, 1H), 1.28 (s, 3H), 1.10 (ddd, 1H), 0.95-0.89 (m, 2H), 0.75 (td, 2H), 0.39 (dd, 1H), 0.27 (dd, 1H), −0.01 (s, 9H), −0.16 (s, 9H). LC/MS m/z (M+H)$^+$=588.6

Preparation 122: (S)—N-(7-chloro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)-N-methyl-2-morpholinopropanamide

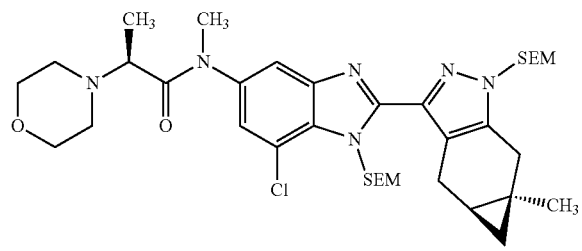 [SMILES: C[C@@H](C(=O)N(C)c1cc(Cl)c2c(c1)nc(-c1nn(COCC[Si](C)(C)C)c3c1C[C@@H]1C[C@]1(C)C3)n2COCC[Si](C)(C)C)N1CCOCC1]

A mixture of Preparation 19 (24.4 mg, 0.15 mmol), 120 (82 mg, 0.14 mmol), pyridine (0.56 mL, 0.70 mmol) and T$_3$P (50 wt % in EtOAc, 0.17 mL, 0.28 mmol) in EtOAc (0.9 mL) was stirred at RT for 18 h. The mixture was treated with DMF (0.6 mL) and the mixture was stirred at RT for an additional 24 h. The mixture was diluted with EtOAc and water. After separation of layers, the organic layer was washed with water (×2) and brine. The remaining organic fraction was dried (MgSO$_4$), filtered and concentrated. The crude material was purified by chromatography (silica, EtOAc/heptanes, 10-80% gradient) to give the title compound (42.8 mg, 42%). $^1$H NMR (400 MHz, CDCl$_3$) δ 7.55 (d, 1H), 7.21 (s, 1H), 6.38 (d, 2H), 5.45 (d, 1H), 5.41 (d, 1H), 3.65 (dd, 4H), 3.60-3.54 (m, 2H), 3.40 (d, 2H), 3.31 (s, 3H), 3.23 (q, 1H), 3.14 (d, 1H), 3.06 (dd, 1H), 2.74 (d, 1H), 2.57 (ddd, 2H), 2.32 (ddd, 2H), 1.77 (brs, 1H), 1.28 (s, 3H), 1.18-1.06 (m, 4H), 0.91 (ddd, 2H), 0.78 (td, 2H), 0.41 (dd, 1H), 0.26 (dd, 1H), −0.02 (s, 9H), −0.16 (s, 9H); LC/MS m/z (M+H)$^+$=729.7.

Preparation 123: N-(7-chloro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)-N-methylacetamide

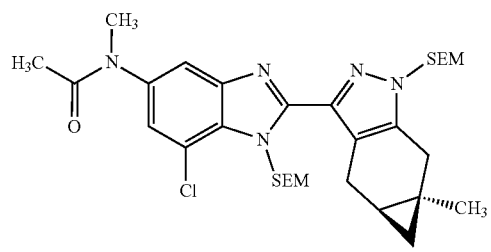 [SMILES: CC(=O)N(C)c1cc(Cl)c2c(c1)nc(-c1nn(COCC[Si](C)(C)C)c3c1C[C@@H]1C[C@]1(C)C3)n2COCC[Si](C)(C)C]

A solution of Preparation 120 (785 mg, 1.33 mmol) in DCM was cooled to 0° C. The solution was treated with Et$_3$N (0.56 mL, 4.00 mmol) and acetyl chloride (0.14 mL, 2.00 mmol). The mixture was stirred at 0° C. for 20 min and treated with sat. aq. NaHCO$_3$. The aqueous layer was extracted with DCM (×3), and the combined organic layers were dried (MgSO$_4$), filtered and concentrated. The crude material was purified by chromatography (silica, EtOAc/heptanes=0-50%) to give the title compound 123 (807 mg, 64%). LC/MS m/z (M+H)$^+$=630.5.

Preparation 124: N-methyl-N-(2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-7-vinyl-1H-benzo[d]imidazol-5-yl)acetamide

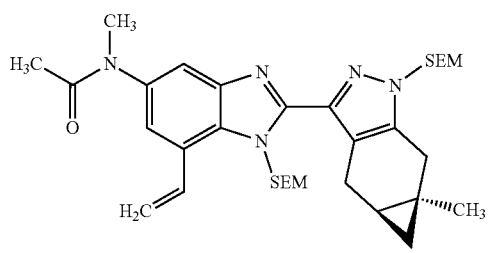 [SMILES: C=Cc1cc(N(C)C(C)=O)cc2nc(-c3nn(COCC[Si](C)(C)C)c4c3C[C@@H]3C[C@]3(C)C4)n(COCC[Si](C)(C)C)c12]

A mixture of Preparation 123 (675 mg, 1.07 mmol), 2,4,6-Trivinylcyclotriboroxane pyridine complex (297 mg, 1.24 mmol), Pd(OAc)$_2$ (9.3 mg, 0.04 mmol) and SPhos (34 mg, 0.08 mmol) in 1,4-dioxane (5.4 mL) was added 3M K$_3$PO$_4$ (0.82 mL, 2.47 mmol). The mixture was heated at 100° C. for 20 h. The mixture was filtered and the solids rinsed with EtOAc. The filtrate was diluted with water and extracted with EtOAc (×3). The combined organic extracts were dried (MgSO$_4$), filtered and concentrated. The crude material was purified by chromatography (silica, EtOAc/heptanes=0-50%) to give the title compound (391 mg, 59%). LC/MS m/z (M+H)$^+$=622.5.

Preparation 124a: N-(7-ethyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)-N-methylacetamide

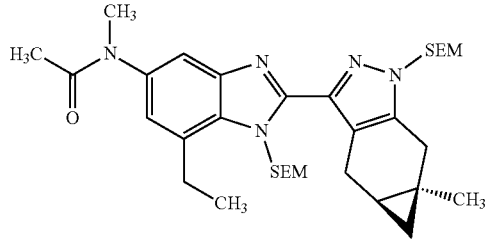 [SMILES: CCc1cc(N(C)C(C)=O)cc2nc(-c3nn(COCC[Si](C)(C)C)c4c3C[C@@H]3C[C@]3(C)C4)n(COCC[Si](C)(C)C)c12]

A solution of Preparation 124 (87 mg, 0.14 mmol) in MeOH (2 mL) was treated with 10% Pd/C (20 mg). The mixture was degassed with N$_2$ and backfilled with H$_2$ three times. The mixture was stirred at RT under H$_2$ (3 atm) for 18 h. The mixture was filtered and the filtrate concentrated to give the title compound (87 mg, quant.). $^1$H NMR (600 MHz, CDCl$_3$) δ 7.45 (d, 1H), 6.91 (d, 1H), 6.14 (q, 2H), 5.54-5.37 (m, 2H), 3.56 (t, 2H), 3.38-3.32 (m, 2H), 3.30 (s, 3H), 3.18-3.10 (m, 3H), 3.07 (dd, 1H), 2.74 (d, 1H), 1.97 (s, 1H), 1.88 (s, 3H), 1.34 (t, 3H), 1.27 (s, 3H), 1.11 (dt, 1H), 0.91 (td, 2H), 0.79-0.64 (m, 2H), 0.39 (dd, 1H), 0.24 (t, 1H), −0.02 (s, 9H), −0.18 (s, 9H).

Preparation 125: 7-ethyl-N-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-amine

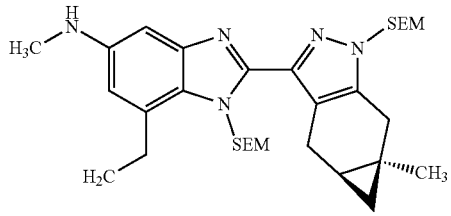

A solution of Preparation 124 (86 mg, 0.14 mmol) in 1:1 EtOH:water was treated with KOH (155 mg, 2.76 mmol). The mixture was heated at 90° C. and stirred for 72 h. The mixture was cooled to RT and diluted with water extracted with DCM (×3). The combined organic layers were dried (MgSO$_4$), filtered and concentrated. The crude material was purified by chromatography (silica, EtOAc/heptanes=0-80% gradient) to give the title. compound (37 mg, 46%). $^1$H NMR (400 MHz, CDCl$_3$) δ 6.88 (d, 1H), 6.51 (d, 1H), 6.13-5.90 (m, 2H), 5.50-5.29 (m, 2H), 3.57 (t, 2H), 3.33 (d, 1H), 3.25 (dd, 2H), 3.16-3.01 (m, 4H), 2.89 (s, 3H), 2.77-2.69 (m, 1H), 1.32 (t, 3H), 1.27 (s, 3H), 1.14-1.04 (m, 1H), 0.96-0.83 (m, 3H), 0.72 (td, 2H), 0.38 (dd, 1H), 0.26 (t, 1H), −0.01 (s, 9H), −0.16 (s, 9H); LC/MS m/z (M+H)$^+$=582.5.

Preparation 126: (S)—N-(7-ethyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)-N-methyl-2-morpholinopropanamide

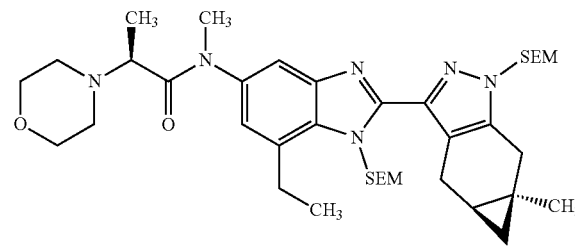

A solution of Preparation 125 (37 mg, 0.064 mmol) and Preparation 19 (15 mg, 0.095 mmol) in pyridine (1 mL) was treated with EDCI (31 mg, 0.159 mmol). The mixture was stirred at RT for 18 h. The mixture was concentrated and the residue was diluted with water. The organic layer was extracted with EtOAc (×3). The combined organic layers were dried (MgSO$_4$), filtered and concentrated to give the title compound (45 mg, 98%). $^1$H NMR (600 MHz, CDCl$_3$) δ 7.47 (s, 1H), 6.92 (s, 1H), 6.14 (s, 2H), 5.55-5.34 (m, 2H), 3.65 (dt, 4H), 3.57 (td, 2H), 3.40-3.33 (m, 2H), 3.33 (s, 3H), 3.26 (q, 1H), 3.15 (q, 3H), 3.06 (dd, 1H), 2.75 (d, 1H), 2.59-2.52 (m, 2H), 2.40 (dt, 2H), 1.34 (t, 3H), 1.29 (s, 3H), 1.25 (d, 1H), 1.17 (d, 3H), 1.15-1.06 (m, 1H), 0.92 (ddd, 2H), 0.75 (td, 2H), 0.40 (dd, 1H), 0.26 (t, 1H), −0.01 (s, 9H), −0.16 (s, 9H); LC/MS m/z (M+H)$^+$=723.7.

Preparation 127: tert-butyl (4-chloro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)(methyl)carbamate

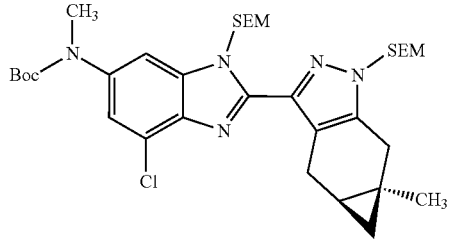

A solution of Preparation 121 (740 mg, 1.26 mmol) in THF (6.3 mL) was treated with Et$_3$N (0.35 mL, 2.52 mmol), Boc$_2$O (412 mg, 1.89 mmol) and DMAP (154 mg, 1.26 mmol) at RT. The mixture was stirred at RT for 18 h and additional Et$_3$N (0.35 mL, 2.52 mmol), Boc$_2$O (412 mg, 1.89 mmol) and DMAP (154 mg, 1.26 mmol) were added. The reaction mixture was heated to 60° C. and stirred an additional 36 h. The mixture was concentrated and the residue purified by chromatography (silica, EtOAc/heptanes=0-50%) to give the title compound (637.3 mg, 74%). $^1$H NMR (400 MHz, CDCl$_3$) δ 7.33 (d, 1H), 7.20 (d, 1H), 6.08 (d, 2H), 5.43 (d, 1H), 5.39 (d, 1H), 3.59-3.46 (m, 5H), 3.30 (s, 3H), 3.20-3.07 (m, 2H), 2.73 (d, 1H), 1.44 (s, 9H), 1.28 (s, 3H), 1.17-1.08 (m, 1H), 0.95-0.88 (m, 2H), 0.86-0.78 (m, 2H), 0.40 (dd, 1H), 0.27 (dd, 1H), −0.02 (s, 9H), −0.12 (s, 9H).

Preparation 128: tert-butyl methyl(2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-4-vinyl-1H-benzo[d]imidazol-6-yl)carbamate

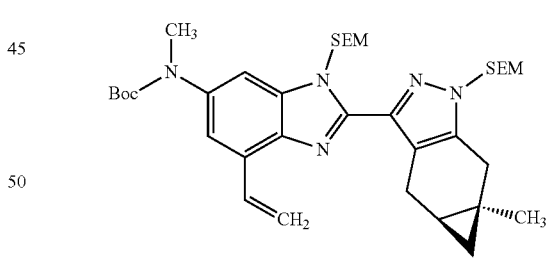

A mixture of Preparation 127 (450 mg, 0.71), vinylboronic anhydride pyridine complex (258 mg, 1.07 mmol), Pd(OAc)$_2$ (8.0 mg, 0.036 mmol) and SPhos (29.3 mg, 0.71 mmol) in 1,4-dioxane (3.6 mL) was treated with 3M K$_3$PO$_4$ (0.71 mL, 2.14 mmol). The mixture was heated at 100° C. for 20 h. The mixture was filtered and the solids rinsed with EtOAc. The filtrate was diluted with water and extracted with EtOAc (×3). The combined organic extracts were dried (MgSO$_4$), filtered and concentrated. The crude material was purified by chromatography (silica, EtOAc/heptanes=0-50%) to give the title compound (367 mg, 76%). $^1$H NMR (400 MHz, CDCl$_3$) δ 7.30 (d, 1H), 7.18 (dd, 1H), 7.15 (s, 1H), 6.62 (dd, 1H), 6.15 (d, 1H), 6.11 (d, 1H), 5.56 (dd, 1H), 5.43 (d, 1H), 5.39 (d, 1H), 3.61-3.49 (m, 5H), 3.31 (s, 3H), 3.18-3.09 (m, 2H), 2.73 (d, 1H), 1.43 (s, 9H), 1.29 (s, 3H), 1.13 (ddd, 1H), 0.91 (ddd, 2H), 0.87-0.79 (m, 2H), 0.41 (dd, 1H), 0.28 (dd, 1H), −0.02 (s, 9H), −0.12 (s, 9H).

Preparation 129: tert-butyl (4-formyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)(methyl)carbamate

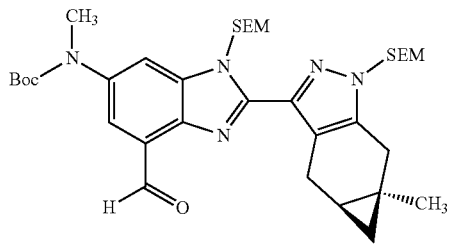 [SMILES: CN(C(=O)OC(C)(C)C)c1cc(C=O)c2nc(-c3nn(COCC[Si](C)(C)C)c4c3C[C@@H]3C[C@]3(C)C4)n(COCC[Si](C)(C)C)c2c1]

A solution of Preparation 128 (366 mg, 0.54 mmol) in pyridine (2.7 mL) and THF (2.7 mL) at 0° C. was treated with OsO₄ (4 wt % in water, 5.1 mL, 0.81 mmol). The mixture was stirred at 0° C. for 2 h and then at RT for an additional 18 h. The mixture was treated with 10% aq. NaHSO₃ (15 mL) and stirred at RT for 3 h. The mixture was concentrated and extracted with DCM (×4). The combined organic extracts were dried (Na₂SO₄), filtered and concentrated. This residue was dissolved in 2:1 THF/water (6 mL), cooled to 0° C. and treated with NaIO₄ (138 mg, 0.65 mmol). The mixture was stirred at 0° C. for 2.5 h. The mixture was filtered through Celite and MgSO₄ and the filtrate was concentrated. The residue was purified by chromatography (silica, EtOAc/heptanes=10-50% gradient) to give the title compound (163 mg, 44%). ¹H NMR (400 MHz, CDCl₃) δ 10.92 (s, 1H), 7.77-7.56 (m, 2H), 6.19 (d, 1H), 6.15 (d, 1H), 5.45 (d, 1H), 5.40 (d, 1H), 3.64-3.48 (m, 5H), 3.34 (s, 3H), 3.13 (dd, 2H), 2.74 (d, 1H), 1.44 (s, 9H), 1.29 (s, 3H), 1.21-1.08 (m, 1H), 0.91 (ddd, 2H), 0.87-0.80 (m, 2H), 0.42 (dd, 1H), 0.28 (dd, 1H), −0.02 (s, 9H), −0.12 (s, 9H).

Preparation 130: tert-butyl (4-(hydroxymethyl)-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)(methyl)carbamate

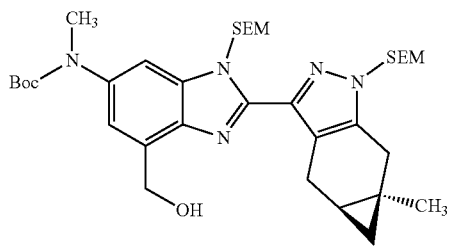 [SMILES: CN(C(=O)OC(C)(C)C)c1cc(CO)c2nc(-c3nn(COCC[Si](C)(C)C)c4c3C[C@@H]3C[C@]3(C)C4)n(COCC[Si](C)(C)C)c2c1]

A solution of Preparation 129 (30 mg, 0.044 mmol) in MeOH (1 mL) at 0° C. was treated with NaBH₄ (8 mg, 0.22 mmol). The mixture was warmed to RT and stirred 2 h. The mixture was cooled to 0° C. and diluted with brine and water. The mixture was extracted with DCM (×3) and the combined organic layers were dried (MgSO₄), filtered and concentrated to give the title compound (19 mg, 63%). ¹H NMR (400 MHz, CDCl₃) δ 7.36-7.30 (m, 1H), 7.00 (s, 1H), 6.20-6.03 (m, 2H), 5.46-5.35 (m, 2H), 5.12 (d, 2H), 4.63 (s, 1H), 3.65-3.49 (m, 4H), 3.42 (d, 1H), 3.30 (s, 3H), 3.12 (d, 2H), 2.73 (d, 1H), 1.44 (s, 9H), 1.28 (s, 3H), 1.12 (dt, 1H), 0.91 (ddd, 2H), 0.88-0.78 (m, 2H), 0.41 (dd, 1H), 0.25 (t, 1H), −0.02 (s, 9H), −0.11 (s, 9H); LC/MS m/z (M+H)⁺=684.3.

Preparation 131: (2-((4aS,5aR)-5a-methyl-1-((2-(trimethylsilyl)ethoxy)methyl)-1,4,4a,5,5a,6-hexahydrocyclopropa[f]indazol-3-yl)-6-(methylamino)-1-((2-(trimethylsilyl)ethoxy)methyl)-1H-benzo[d]imidazol-4-yl)methanol

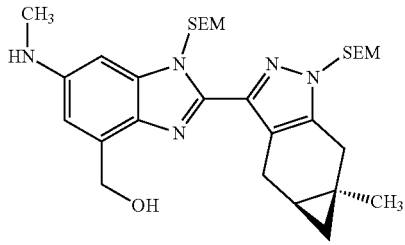

A solution of Preparation 130 (19 mg, 0.028 mmol) in DCM (1 mL) at 0° C. was treated with 2,6-lutidine (9 mg, 0.083 mmol) and TMSOTf (19 mg, 0.083 mmol). The mixture was stirred at 0° C. for 2 h and treated with sat. aq. NaHCO₃. The mixture was extracted with DCM (×3). The combined organic layers were dried (MgSO₄), filtered and concentrated to give the title compound (20 mg, quant.). ¹H NMR (600 MHz, CDCl₃) δ 6.77 (d, 1H), 6.58 (d, 1H), 6.08-5.87 (m, 2H), 5.46-5.32 (m, 2H), 5.18 (s, 2H), 3.64-3.51 (m, 3H), 3.47 (ddd, 2H), 3.38 (d, 1H), 3.09 (t, 2H), 2.91 (s, 3H), 2.71 (d, 1H), 1.64 (s, 1H), 1.28 (s, 3H), 1.11 (dq, 1H), 0.98-0.88 (m, 2H), 0.87-0.76 (m, 2H), 0.38 (dd, 1H), 0.33-0.24 (m, 1H), −0.02 (d, 9H), −0.13 (s, 9H); LC/MS m/z (M+H)⁺=584.5.

Preparation 132 (S)—N-(4-(hydroxymethyl)-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-N-methyl-2-morpholinopropanamide

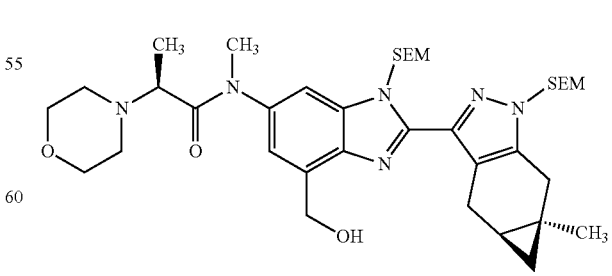

A solution of Preparation 131 (19 mg, 0.033 mmol) and Preparation 19 (10 mg, 0.065 mmol) in pyridine (1 mL) was treated with EDCI (25 mg, 0.13 mmol). The mixture was stirred at RT for 18 h. The mixture was concentrated and the residue was diluted with water and extracted with EtOAc (×3). The combined organic layers were dried (MgSO₄), filtered and concentrated to give the title compound (21 mg, 90%). ¹H NMR (600 MHz, CDCl₃) δ 7.41-7.29 (m, 1H), 6.99 (s, 1H), 6.14 (s, 2H), 5.50-5.33 (m, 2H), 5.25-5.03 (m, 2H), 4.55 (s, 1H), 3.64 (dd, 3H), 3.60-3.50 (m, 4H), 3.43 (d, 1H), 3.32 (s, 3H), 3.23 (d, 1H), 3.13 (dd, 2H), 2.74 (d, 1H), 2.63-2.47 (m, 3H), 2.37 (dt, 2H), 1.29 (s, 3H), 1.15 (d, 3H), 1.14-1.08 (m, 1H), 0.92 (td, 2H), 0.83 (dq, 2H), 0.43 (dd, 1H), 0.25 (t, 1H), −0.02 (d, 9H), −0.11 (d, 9H); LC/MS m/z (M+H)⁺=725.7.

Preparation 133: 3,4-difluoro-2-methylaniline

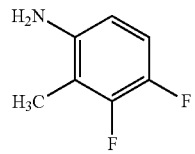

A solution of 1,2-difluoro-3-methyl-4-nitrobenzene (5 g, 28.9 mmol) in AcOH (150 mL) was treated with iron powder (9.68 g, 173 mmol) and the mixture stirred at RT for 16 h. The reaction was filtered and the filtrate was concentrated. The residue was taken up in EtOAc (300 mL) and washed with sat. aq. NaHCO₃ (500 mL). The organic layer was dried (Na₂SO₄), filtered and concentrated under reduced pressure to give the title compound (3.8 g, 92%). LC/MS m/z (M+H)⁺=143.8.

Preparation 134: (S)—N-(3,4-difluoro-2-methylphenyl)-2-morpholinopropanamide

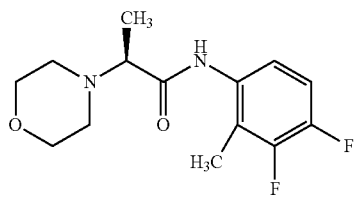 [SMILES: Cc1c(NC(=O)[C@H](C)N2CCOCC2)ccc(F)c1F]

A solution of Preparation 133 (3.8 g, 26.6 mmol) and Preparation 19 (8.45 g, 53.1 mmol) in pyridine (200 mL) was treated with EDCI (10.2 g, 53.1 mmol). The mixture was stirred at RT for 16 h. The mixture was concentrated and the residue was diluted with water and extracted with EtOAc (×3). The combined organic layers were dried (Na₂SO₄), filtered and concentrated. The crude material was purified by chromatography (silica, EtOAc/PE=0-30%) to give the title compound (6.9 g, 91%). LC/MS m/z (M+H)⁺=284.9.

Preparation 135 (S)—N-(3,4-difluoro-2-methylphenyl)-N-methyl-2-morpholinopropanamide

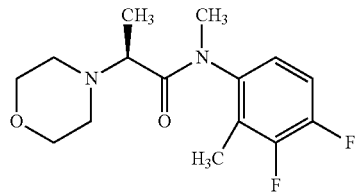 [SMILES: Cc1c(N(C)C(=O)[C@H](C)N2CCOCC2)ccc(F)c1F]

A solution of Preparation 134 (6.9 g, 24.3 mmol) in THF (150 mL) at 0° C. was treated with NaH (1.94 g, 48.5 mmol). The mixture was stirred for 30 min and methyl iodide (5.17 g, 36.4 mmol) was added. The mixture was warmed to 20° C. and stirred for 16 h. The mixture was treated with water and extracted with EtOAc (2×100 mL). The combined organic layers were dried (Na₂SO₄), filtered and concentrated. The crude material was purified by chromatography (silica, EtOAc/PE=0-60%) to give the title compound (6.6 g, 91%). LC/MS m/z (M+H)⁺=298.9.

Preparation 136: (S)—N-(3,4-difluoro-2-methyl-5-nitrophenyl)-N-methyl-2-morpholinopropanamide

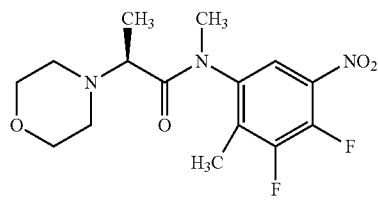 [SMILES: Cc1c(N(C)C(=O)[C@H](C)N2CCOCC2)cc([N+](=O)[O-])c(F)c1F]

A solution of Preparation 135 (5 g, 16.8 mmol) in conc. H₂SO₄ (40 mL) at 5-10° C. was treated dropwise with conc. HNO₃ (2.11 g, 33.5 mmol). The mixture was stirred at 5-10° C. fir 2 h and poured onto ice. The pH was adjusted to 7 with sat. aq. Na₂CO₃ and the mixture was extracted with EtOAc (2×100 mL). The combined organic layers were dried (Na₂SO₄), filtered and concentrated. The crude material was purified by chromatography (silica, EtOAc/PE=0-40%) to give the title compound 136 (3.5 g, 61%). LC/MS m/z (M+H)⁺=344.1.

Preparation 137: (S)—N-(4-amino-3-fluoro-2-methyl-5-nitrophenyl)-N-methyl-2-morpholinopropanamide

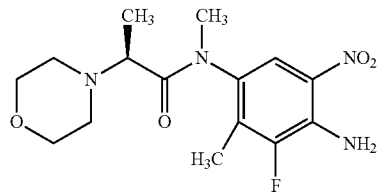 [SMILES: Cc1c(N(C)C(=O)[C@H](C)N2CCOCC2)cc([N+](=O)[O-])c(N)c1F]

A solution of Preparation 136 (3.5 g, 10.2 mmol) in THF (40 mL) at 20° C. was treated with conc. NH₄OH (40 mL). The mixture was stirred for 16 h. The mixture was extracted with EtOAc (2×200 mL). The combined organic layers were dried (Na₂SO₄), filtered and concentrated. The crude material was purified by chromatography (silica, EtOAc/PE=0-100%) to give the title compound 137 (2.2 g, 63%). LC/MS m/z (M+H)⁺=341.0.

Preparation 138: (S)—N-(4,5-diamino-3-fluoro-2-methylphenyl)-N-methyl-2-morpholinopropanamide)

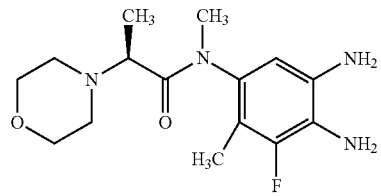

A solution of Preparation 137 (2.2 g, 6.5 mmol) in AcOH (60 mL) was treated with iron powder (2.17 g, 38.8 mmol) and the mixture stirred at RT for 16 h. The mixture was filtered and the filtrate was concentrated. The residue was taken up in EtOAc (100 mL) and washed with sat. aq. NaHCO₃ (30 mL). The organic layer was dried (Na₂SO₄), filtered and concentrated. The crude material was purified by chromatography (silica, EtOAc/PE=0-100% then 0-10% MeOH/DCM gradient) to give the title compound (1.3 g, 65%). LC/MS m/z (M+H)⁺=311.1.

Preparation 139: 3-fluoro-2-methyl-6-nitroaniline

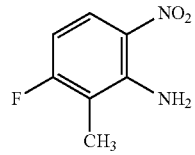

A solution of 1,3-difluoro-2-methyl-4-nitrobenzene (5 g, 28.9 mmol) in THF (100 mL) at 20° C. was treated with conc. NH₄OH (100 mL). The mixture was stirred at RT for 16 h. The mixture was extracted with EtOAc (2×200 mL). The combined organic layers were dried (Na₂SO₄), filtered and concentrated. The crude material was purified by chromatography (silica, EtOAc/PE=0-15%) to give the title compound (3 g, 61%). ¹H NMR (400 MHz, CDCl₃) δ 8.07 (dd, 1H), 6.46 (dd, 1H), 6.32 (s, 2H), 2.13 (d, 3H).

Preparation 140: 4-bromo-3-fluoro-2-methyl-6-nitroaniline

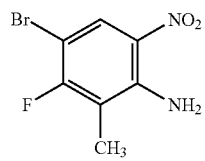

A solution of Preparation 139 (3 g, 07.6 mmol) in MeCN (20 mL) at 20° C. was treated with N-bromosuccinimide (3.77 g, 21.2 mmol). The mixture was stirred at 90° C. for 2 h. The mixture was cooled to RT and concentrated. The residue was purified by chromatography (silica, EtOAc/PE=0-15%) to give the title compound (4.3 g, 98%). ¹H NMR (400 MHz, CDCl₃) δ 8.31 (d, 1H), 6.31 (s, 2H), 2.18 (dd, 3H).

Preparation 141: 5-bromo-4-fluoro-3-methylbenzene-1,2-diamine

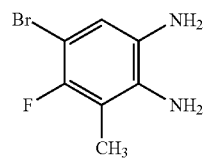

A solution of Preparation 140 (4.3 g, 17.3 mmol) in AcOH (100 mL) was treated with iron powder (5.79 g, 104 mmol) and the mixture was stirred at RT for 1 h. The reaction was filtered and the filtrate concentrated. The residue was taken up in EtOAc (300 mL) and washed with sat. aq. NaHCO₃ (50 mL). The organic layer was dried (Na₂SO₄), filtered and concentrated. The crude material was purified by chromatography (silica, EtOAc/PE=0-35%) to give the title compound 141 (3.44 g, 91%). ¹H NMR (400 MHz, CDCl₃) δ 6.74 (d, 1H), 3.36 (s, 4H), 2.12 (d, 3H).

Preparation 142: tert-butyl (4-(difluoromethyl)-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)(methyl)carbamate

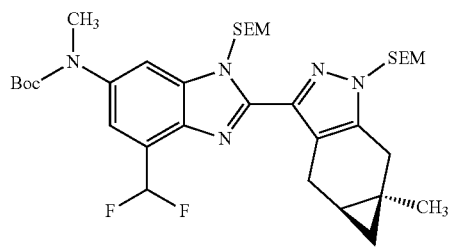 [SMILES: CN(C(=O)OC(C)(C)C)c1cc(C(F)F)c2nc(-c3nn(COCC[Si](C)(C)C)c4c3C[C@@H]3C[C@]3(C)C4)n(COCC[Si](C)(C)C)c2c1]

A solution of Preparation 129 (160 mg, 0.24 mmol) in anhydrous DCE (1.5 mL) was treated with DAST (0.047 mL, 0.35 mmol) at 0° C. The mixture was warmed to RT and stirred for 18 h. The mixture was treated with sat. aq. NaHCO₃. Additional water was added and the mixture was extracted with DCM (×3). The combined organic layers were dried (MgSO₄), filtered and concentrated. The crude material was purified by chromatography (silica, EtOAc/PE=0-40%) to give the title compound (86.0 mg, 52%).

¹H NMR (400 MHz, CDCl₃) δ 7.51 (s, 1H), 7.43 (dd, 1H), 7.42 (s, 1H), 6.14 (d, 1H), 6.10 (d, 1H), 5.44 (d, 1H), 5.39 (d, 1H), 3.61-3.50 (m, 4H), 3.48 (d, 1H), 3.34 (s, 3H), 3.17-3.05 (m, 2H), 2.73 (d, 1H), 1.44 (s, 9H), 1.29 (s, 3H), 1.13 (ddd, 1H), 0.91 (ddd, 2H), 0.87-0.79 (m, 2H), 0.41 (dd, 1H), 0.27 (dd, 1H), −0.02 (s, 9H), −0.11 (s, 9H).

Preparation 143: 4-(difluoromethyl)-N-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-amine

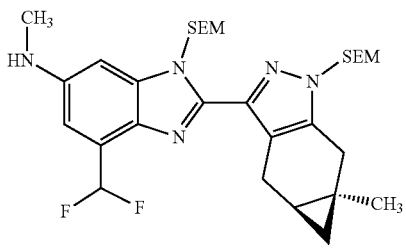

A solution of Preparation 142 (85 mg, 0.12 mmol) in DCM (1 mL) at 0° C. was treated with 2,6-lutidine (0.042 mL, 0.36 mmol) followed by TMSOTf (0.066 mL, 0.36 mmol). The mixture was stirred at 0° C. for 2 h. The mixture was treated with sat. aq. NaHCO₃. The organic phase was separated and the aqueous layer was extracted with additional DCM (×4). The combined organic extracts were dried (MgSO₄), filtered and concentrated. The crude material was purified by chromatography (silica, EtOAc/PE=0-50%) to give the title compound (61.9 mg, 85%). LC/MS m/z (M+H)⁺=604.5.

Preparation 144: (S)—N-(4-(difluoromethyl)-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-N-methyl-2-morpholinopropanamide

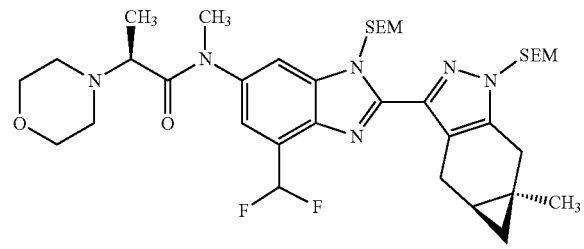 [SMILES: C[C@@H](C(=O)N(C)c1cc(C(F)F)c2nc(-c3nn(COCC[Si](C)(C)C)c4c3C[C@@H]3C[C@]3(C)C4)n(COCC[Si](C)(C)C)c2c1)N1CCOCC1]

A solution of Preparation 143 (61 mg, 0.10 mmol) and 19 (24 mg, 0.15 mmol) in pyridine (1 mL) was treated with EDCI (48 mg, 0.25 mmol). The mixture was stirred at RT for 18 h. The mixture was concentrated and the residue was taken up in water and extracted with EtOAc (×3). The combined organic layers were dried (MgSO₄), filtered and concentrated to give the title compound (72 mg, 96%). LC/MS m/z (M+H)⁺=745.7.

Preparation 145: 4-fluoro-2-(2-methoxyethoxy)-1-nitrobenzene

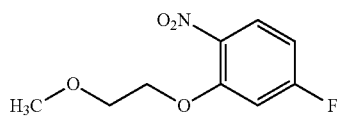

A solution of 2-methoxyethanol (2.39 g, 31.4 mmol) in THF (40 mL) at 0° C. was treated with 1M KOtBu in THF (31.4 mL, 31.4 mmol). After 30 min, a solution of 2,4-difluoro-1-nitrobenzene (5.0 g, 31.4 mmol) in THF (40 mL) was added. The mixture was stirred at 30° C. for 1 h and diluted with 1:1 H₂O:EtOAc (100 mL). The layers were separated and the aqueous layer was extracted with EtOAc (50 mL). The organic extracts were dried, filtered and concentrated to give the title compound (6.76 g, 100%). ¹H NMR (400 MHz, CDCl₃) δ 7.93 (dd, 1H), 6.82 (dd, 1H), 6.72 (ddd, 1H), 4.29-4.15 (m, 2H), 3.87-3.73 (m, 2H), 3.45 (s, 3H).

Preparation 146: 4-fluoro-2-(2-methoxyethoxy)aniline

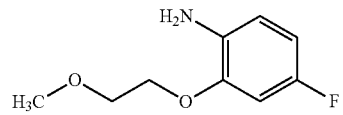

A solution of Preparation 145 (6.76 g, 31.4 mmol) in MeOH (200 mL) was treated with 10% Pd/C (600 mg,) and stirred under H₂ (1 atm) for 16 h. The mixture was filtered and the filtrate concentrated to give the title compound (4.53 g, 78%). ¹H NMR (400 MHz, CDCl₃) δ 6.66-6.48 (m, 3H), 4.16-4.06 (m, 2H), 3.81-3.66 (m, 2H), 3.44 (s, 3H).

Preparation 147: 4-fluoro-2-(2-methoxyethoxy)-5-nitroaniline

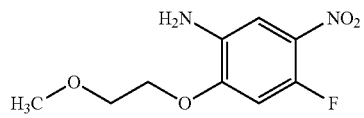

A solution of Preparation 146 (615 mg, 3.32 mmol) in conc. H₂SO₄ at 5° C. was treated with KNO₃ (336 mg, 3.32 mmol). The mixture was stirred for 2 h and poured into ice water (50 mL). The aqueous mixture was extracted with EtOAc (2×40 mL). The organic extracts were combined, dried, filtered and concentrated to give the title compound (790 mg, 103%). ¹H NMR (400 MHz, CDCl₃) δ 7.40 (d, 1H), 6.66 (d, 1H), 4.26-4.17 (m, 2H), 3.82-3.74 (m, 2H), 3.44 (s, 3H); LC/MS m/z (M+H)⁺=230.9.

Preparation 148: (S)—N-(4-fluoro-2-(2-methoxyethoxy)-5-nitrophenyl)-2-morpholinopropanamide

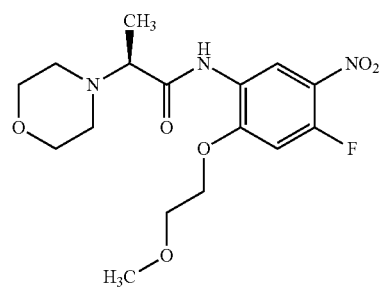 [SMILES: COCCOc1cc(F)c([N+](=O)[O-])cc1NC(=O)[C@H](C)N1CCOCC1]

A solution of Preparation 147 (590 mg, 2.56 mmol) and Preparation 19 (490 mg, 3.08 mmol) in pyridine (37 mL) at 20° C. was treated with EDCI (983 mg, 5.13 mmol). The mixture was stirred at RT for 16 h and then poured into water (40 mL). The mixture was extracted with EtOAc (2×40 mL). The organic extracts were combined, dried (Na$_2$SO$_4$), filtered and concentrated. The crude material was purified by chromatography (silica, EtOAc/PE=0-50%) to give the title compound 148 (398 mg, 42%). $^1$H NMR (400 MHz, CDCl$_3$) δ 10.01 (s, 1H), 9.29 (d, 1H), 6.76 (d, 1H), 4.33-4.21 (m, 2H), 3.91-3.78 (m, 6H), 3.46 (s, 3H), 3.27 (q, 1H), 2.72-2.50 (m, 4H), 1.34 (d, 3H); LC/MS m/z (M+H)$^+$=372.0.

Preparation 149: (S)—N-(4-fluoro-2-(2-methoxyethoxy)-5-nitrophenyl)-N-methyl-2-morpholinopropanamide

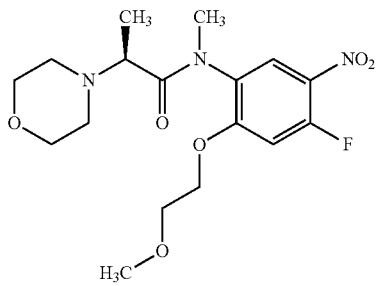 [SMILES: COCCOc1cc(F)c([N+](=O)[O-])cc1N(C)C(=O)[C@H](C)N1CCOCC1]

A solution of Preparation 148 (202 mg, 0.54 mmol) in THF (3 mL) at 0° C. was treated with KOtBu (67 mg, 0.59 mmol). After stirring for 1 hr, a solution of methyl iodide (84.7 mg, 0.59 mmol) in THF (3 mL) was added and the mixture stirred at RT for 16 h. The mixture was treated with sat. aq. NH$_4$Cl (15 mL) and the mixture extracted with EtOAc (20 mL). The organic extract was combined, dried (Na$_2$SO$_4$), filtered and concentrated. The crude material was purified by chromatography (silica, EtOAc/PE=0-100%) to give the title compound (262 mg, 92%). $^1$H NMR (400 MHz, CDCl$_3$) δ 8.28 (d, 0.5H), 6.87 (dd, 1H), 4.31-4.17 (m, 2H), 3.78-3.67 (m, 2H), 3.63 (t, 2H), 3.57-3.43 (m, 1H), 3.38 (d, 3H), 3.17 (d, 3H), 2.61-2.14 (m, 4H), 1.18 (d, 1.5H), 1.10 (d, 1.5H). $^{19}$F NMR (376 MHz, CDCl$_3$) 5-111.09. LC/MS m/z (M+H)$^+$=386.1.

Preparation 150: (S)—N-(4-amino-2-(2-methoxyethoxy)-5-nitrophenyl)-N-methyl-2-morpholinopropanamide

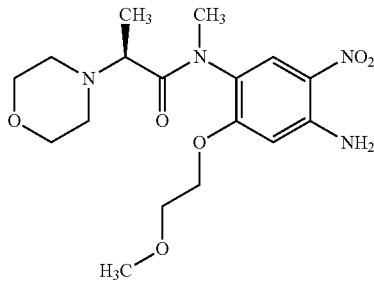

A solution of Preparation 149 (262 mg, 0.68 mmol) in EtOH (5 mL) at 15° C. was treated with conc. NH$_4$OH (4.6 g, 130 mmol). The mixture was heated at 50° C. and stirred for 16 h. The mixture was concentrated, diluted with H$_2$O (10 mL) and extracted with EtOAc (2×10 mL). The aqueous layer was further extracted with MeOH:DCM (10 mL:10 mL). The organic extracts were combined, dried, filtered and concentrated to give the title compound 150 (86 mg, 33%). LC/MS m/z (M+H)=383.1.

Preparation 151: (S)—N-(4,5-diamino-2-(2-methoxyethoxy)phenyl)-N-methyl-2-morpholinopropanamide

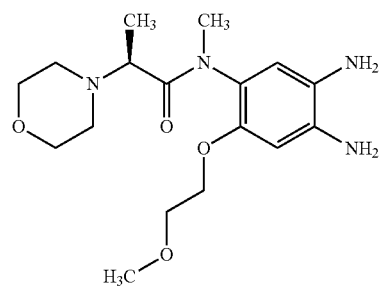 [SMILES: COCCOc1cc(N)c([N+](=O)[O-])cc1N(C)C(=O)[C@H](C)N1CCOCC1]

A solution of Preparation 150 (86 mg, 0.22 mmol) in MeOH (2 mL) was treated with 10% Pd/C (23.6 mg). The mixture was degassed with argon (×3) and then H$_2$ (3×). The mixture was then stirred under H$_2$ (1 atm) for 20 h at RT. The mixture was filtered and the solids washed with MeOH (3×). The filtrate was collected and concentrated. The residue was purified by chromatography (silica, EtOH/PE, 0-10%) to give the title compound 151 (71 mg, 73%). LC/MS m/z (M+H)$^+$=353.1.

Preparation 152: (S)—N-(6-(2-methoxyethoxy)-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)-N-methyl-2-morpholinopropanamide

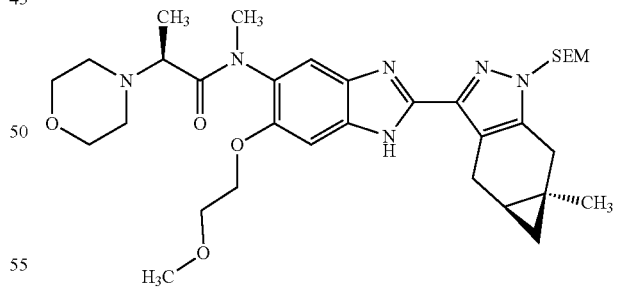

A solution of Preparation 151 (71 mg, 0.20 mmol) and Na$_2$S$_2$O$_5$ (19.1 mg, 0.10 mmol) in DMF (1.0 mL) was treated with 9 (62 mg, 0.20 mmol) and DMSO (39 mg, 0.50 mmol). The mixture was heated at 110° C. for 16 h and then poured into 3% aq. LiCl (5 mL). The mixture was extracted with EtOAc (10 mL). The organic extract was collected, dried (Na$_2$SO$_4$), filtered and concentrated. The crude material was purified by chromatography (silica, EtOAc/PE=0-100%) to give the title compound (160 mg, 120%). LC/MS m/z (M+H)$^+$=639.3.

Preparation 153: (4aS,5aR)-3-(5-bromo-7-methyl-1H-benzo[d]imidazol-2-yl)-5a-methyl-1-((2-(trimethylsilyl)ethoxy)methyl)-1,4,4a,5,5a,6-hexahydrocyclopropa[f]indazole

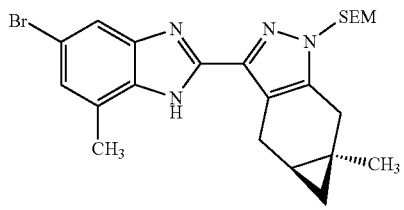 [SMILES: Cc1cc(Br)cc2nc(-c3nn(COCC[Si](C)(C)C)c4c3C[C@@H]3C[C@]3(C)C4)[nH]c12]

A solution of 5-bromo-3-methylbenzene-1,2-diamine (980 mg, 4.87 mmol) and Na$_2$S$_2$O$_5$ (463 mg, 2.44 mmol) in DMF (24 mL) were treated with 9 (1.49 g, 4.87 mmol) and DMSO (952 mg, 12.2 mmol). The mixture was heated at 110° C. for 16 h. The mixture was cooled to RT and poured into 3% aq. LiCl (100 mL). The solid was collected by filtration and the filtrate was extracted with EtOAc (2×100 mL). The organic layers were combined with the collected solid and concentrated. The residue was purified by chromatography (silica, EtOAc/PE=0-20%) to give the title compound (2.17 g, 91%). $^1$H NMR (400 MHz, CD$_3$OD) δ 7.57 (s, 1H), 7.17 (dd, 1H), 5.58-5.40 (m, 2H), 3.61 (dd, 2H), 3.38 (d, 1H), 3.26-3.02 (m, 2H), 2.82-2.68 (m, 1H), 2.58 (s, 3H), 1.30 (s, 3H), 1.17 (dt, 1H), 0.96-0.78 (m, 2H), 0.43 (dd, 1H), 0.26 (t, 1H), −0.04 (s, 9H); LC/MS m/z (M+H)$^+$=488.8.

Preparation 154: (4aS,5aR)-3-(6-bromo-4-methyl-1-((2-(trimethylsilyl)ethoxy)methyl)-1H-benzo[d]imidazol-2-yl)-5a-methyl-1-((2-(trimethylsilyl)ethoxy)methyl)-1,4,4a,5,5a,6-hexahydrocyclopropa[f]indazole

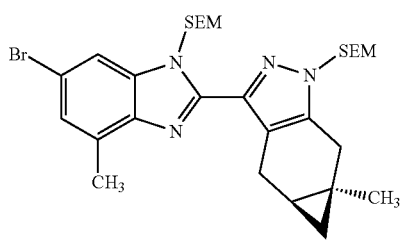 [SMILES: Cc1cc(Br)cc2c1nc(-c1nn(COCC[Si](C)(C)C)c3c1C[C@@H]1C[C@]1(C)C3)n2COCC[Si](C)(C)C]

A solution of Preparation 153 (1.87 g, 3.84 mmol) in THF (38 mL) at 0° C. was treated with NaH (184 mg, 4.6 mmol) and the mixture was stirred for 30 min. SEM-Cl (703 mg, 4.22 mmol) was added and the mixture was warmed to RT and stirred for 2.5 h. The reaction was cooled to 5° C. and treated with sat. aq. NH$_4$Cl (20 mL). The mixture was extracted with EtOAc and the organic layer was concentrated. The residue was purified by chromatography (silica, EtOAc/PE=0-10%) to give the title compound 154 (2.4 g, 92%). LC/MS m/z (M+H)$^+$=618.9.

Preparation 155: tert-butyl (4-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)carbamate

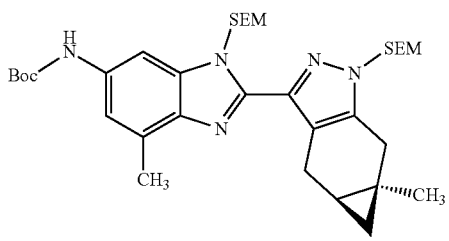 [SMILES: Cc1cc(NC(=O)OC(C)(C)C)cc2c1nc(-c1nn(COCC[Si](C)(C)C)c3c1C[C@@H]1C[C@]1(C)C3)n2COCC[Si](C)(C)C]

A solution of Preparation 154 (800 mg, 1.29 mmol) in tert-amyl alcohol (13 mL) was treated with tert-butyl carbamate (182 mg, 1.55 mmol), Cs$_2$CO$_3$ (844 mg, 2.59 mmol), QPhos (184 mg, 0.26 mmol), and Pd$_2$(dba)$_3$ (59 mg, 0.065 mmol). The mixture was heated at 100° C. for 16 h. The mixture was cooled to RT and concentrated. The residue was purified by chromatography (silica, EtOAc/PE=0-20%) to give the title compound 500 mg (59%). LC/MS m/z (M+H)$^+$=654.0.

Preparation 156: tert-butyl methyl(4-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)carbamate

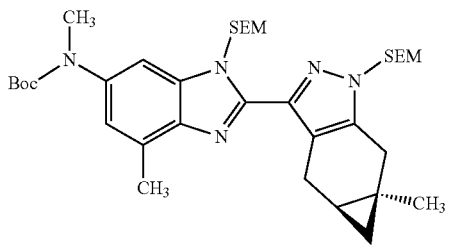 [SMILES: Cc1cc(N(C)C(=O)OC(C)(C)C)cc2c1nc(-c1nn(COCC[Si](C)(C)C)c3c1C[C@@H]1C[C@]1(C)C3)n2COCC[Si](C)(C)C]

A solution of Preparation 155 (500 mg, 0.77 mmol) in THF (11 mL) at 0° C. was treated with NaH (122 mg, 3.1 mmol). The mixture was stirred for 30 min and methyl iodide (130 mg, 0.92 mmol) was added. The mixture was warmed to 15° C. and stirred for 16 h. The mixture was treated with of sat. aq. NH$_4$Cl and extracted with EtOAc (2×10 mL). The combined organic layers were concentrated. The residue was purified by chromatography (silica, EtOAc/PE=0-20%) to give the title compound (308 mg, 74%). LC/MS m/z (M+H)$^+$=668.0.

Preparation 157: N,4-dimethyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-amine

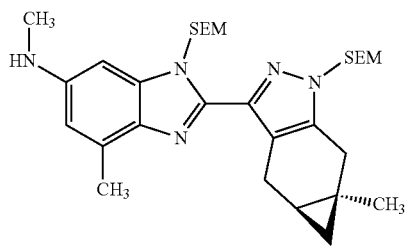

A solution of Preparation 156 (380 mg, 0.57 mmol) in DCM (11 mL) at 0° C. was treated with ZnBr$_2$ (641 mg, 2.84 mmol). The mixture was stirred at RT for 18 h. The mixture was poured into sat. aq. NaHCO$_3$ (20 mL) and extracted with DCM (2×20 mL). The combined organic layers were concentrated to give the title compound (170 mg, 90%). LC/MS m/z (M+H)$^+$=567.9.

Preparation 158: (S)—N-methyl-N-(4-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-2-morpholinopropanamide

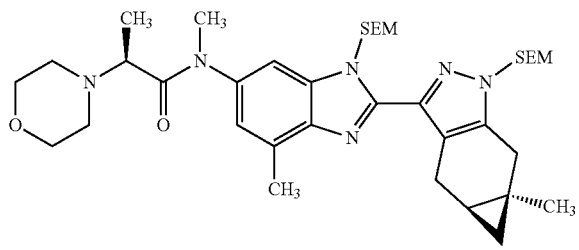 [SMILES: Cc1cc(N(C)C(=O)[C@H](C)N2CCOCC2)cc2c1nc(-c1nn(COCC[Si](C)(C)C)c3c1C[C@@H]1C[C@]1(C)C3)n2COCC[Si](C)(C)C]

A solution of Preparation 157 (300 mg, 0.53 mmol) and Preparation 19 (124 mg, 0.63 mmol) in pyridine (7.6 mL) was treated with EDCI (203 mg, 1.1 mmol). The mixture was stirred at RT for 16 h. The mixture was partitioned between water (50 mL) and EtOAc (50 mL). The organic layer was separated and the organic layer concentrated to give the title compound (380 mg, quant.). LC/MS m/z (M+H)$^+$=709.0.

Preparation 159: 2-bromo-4-fluoro-5-nitrobenzonitrile

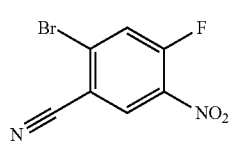 [SMILES: N#Cc1cc([N+](=O)[O-])c(F)cc1Br]

To a solution of 2-bromo-4-fluorobenzonitrile (1.0 g, 5.0 mmol) in conc. H$_2$SO$_4$ (5.0 mL) was added KNO$_3$ (556 mg, 5.50 mmol) in portions at 0° C., and then stirred at 25° C. for 2 h. The reaction mixture was poured into ice water and the mixture was extracted with ethyl acetate (3×10 mL). The combined organic layers were washed with brine (10 mL) dried (Na$_2$SO$_4$) and concentrated to give the title compound (1.2 g, 98%). $^1$H NMR (400 MHz, CDCl$_3$) δ 8.45 (d, J=7.3 Hz, 1H), 7.75 (d, J=9.5 Hz, 1H).

Preparation 160: 4-amino-2-bromo-5-nitrobenzonitrile

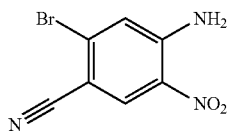 [SMILES: N#Cc1cc([N+](=O)[O-])c(N)cc1Br]

To a solution of Preparation 159 (1.10 g, 4.490 mmol) in THF (40 mL) was added conc. NH$_4$OH (0.63 mL, 4.49 mmol) at 0° C. The reaction was stirred at 25° C. for 1 h. The mixture was filtered, and the filtrate concentrated to give the title compound (1.02 g, 94%). $^1$H NMR (400 MHz, DMSO-d$_6$) δ 8.51 (s, 1H), 8.17 (s, 2H), 7.40 (s, 1H).

Preparation 161: 4,5-diamino-2-bromobenzonitrile

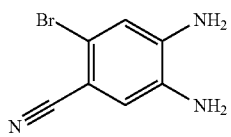 [SMILES: N#Cc1cc(N)c(N)cc1Br]

To a solution of Preparation 160 (1.11 g, 4.58 mmol) in EtOH (20 mL) and H$_2$O (20 mL) was added NH$_4$Cl (1.23 g, 22.9 mmol) at 25° C. followed by iron powder (1.28 g, 22.9 mmol). The mixture was stirred at 25° C. for 16 h. The reaction mixture was filtered through diatomaceous earth and filter cake was rinsed with EtOH (2×20 mL), and the filtrate concentrated. The residue was dissolved in EtOAc and washed with brine and the aqueous phase was extracted with EtOAc (2×20 mL), the combined organic extracts were dried (Na$_2$SO$_4$), filtered and concentrated to give title compound (860 mg, 88%). $^1$H NMR (400 MHz, CDCl$_3$) δ 6.86 (s, 1H), 6.82 (s, 1H), 3.86 (s, 2H), 3.34 (s, 2H).

Preparation 162: 6-bromo-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazole-5-carbonitrile

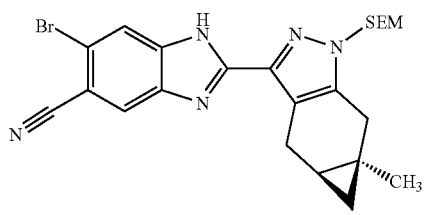 [SMILES: C[C@@]12Cc3c(c(-c4nc5cc(C#N)c(Br)cc5[nH]4)nn3COCC[Si](C)(C)C)C[C@@H]1C2]

To a solution of Preparation 161 (760 mg, 3.58 mmol) in DMF (15 mL) was added Na$_2$S$_2$O$_5$ (341 mg, 1.79 mmol), DMSO (700 mg, 8.96 mmol) and a solution of Preparation 17 (1.21 g, 3.94 mmol) in DMF (3.0 mL). The reaction mixture was stirred at 110° C. for 16 h, then concentrated. The crude product was purified by silica gel chromatography (silica, EtOAc/PE=0-30%) to give the title compound (1.38 g, 68%). LC/MS m/z (M+H)$^+$=499.1

Preparation 163: 6-Bromo-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazole-5-carbonitrile and 5-bromo-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazole-6-carbonitrile

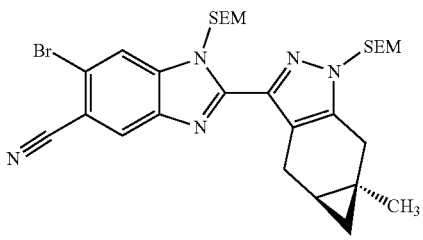

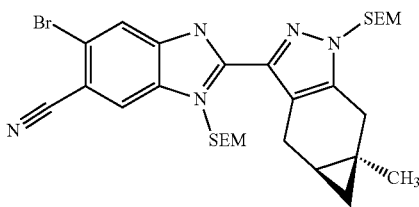

To a suspension of NaH (133 mg, 3.32 mmol) in THF (5.0 mL) was added a solution of Preparation 162 (1.380 g, 2.76 mmol) in THF (10 mL) at 0° C. After stirring at 0° C. for 15 min, SEM-Cl (0.69 g, 4.15 mmol) was added dropwise and reaction mixture was stirred at 20° C. for 2 h. The reaction mixture was poured onto ice and the mixture was extracted to with EtOAc (3×10 mL). The combined organic layers were washed with brine (10 mL) dried (Na$_2$SO$_4$) and concentrated. The crude product was purified by chromatography (silica, EtOAc/PE=0-30%) to give the title compounds as a mixture (1.14 g, 66%). $^1$H NMR (400 MHz, CDCl$_3$) δ 8.08 (d, 1H), 7.93 (d, 1H), 6.23-6.11 (m, 2H), 5.50-5.38 (m, 2H), 3.68-3.50 (m, 4H), 3.49 (m, 1H), 3.21-3.07 (m, 2H), 2.77 (d, J=16.3 Hz, 1H), 1.32 (s, 3H), 1.17 (dt, J=10.0, 5.5 Hz, 1H), 1.00-0.89 (m, 2H), 0.92-0.81 (m, 2H), 0.45 (dd, J=8.8, 4.7 Hz, 1H), 0.28 (t, J=5.1 Hz, 1H), 0.01 (s, 9H), −0.08 (d, J=2.7 Hz, 9H); LC/MS m/z (M+H)$^+$=629.1.

Preparation 164: 2-((4aS,5aR)-5a-methyl-1-((2-(trimethylsilyl)ethoxy)methyl)-1,4,4a,5,5a,6-hexahydrocyclopropa[f]indazol-3-yl)-6-(methylamino)-1-((2-(trimethylsilyl)ethoxy)methyl)-1H-benzo[d]imidazole-5-carbonitrile and 2-((4aS,5aR)-5a-methyl-1-((2-(trimethylsilyl)ethoxy)methyl)-1,4,4a,5,5a,6-hexahydrocyclopropa[f]indazol-3-yl)-5-(methylamino)-1-((2-(trimethylsilyl)ethoxy)methyl)-1H-benzo[d]imidazole-6-carbonitrile

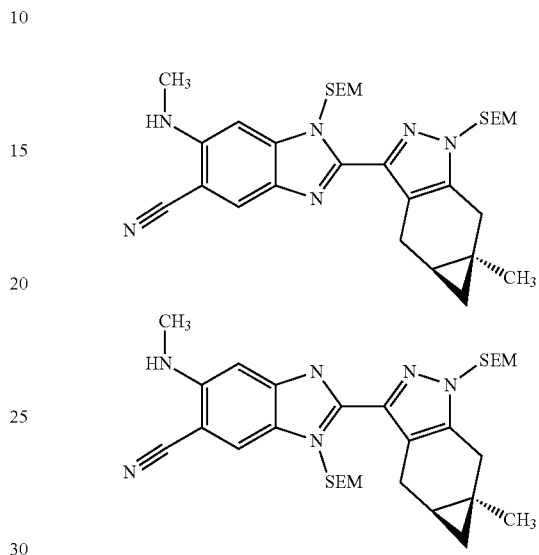

A solution of Preparation 163 (1.01 g, 1.61 mmol) in DMF (8 mL) was degassed with nitrogen. The solution was treated with N-(2,6-dimethylphenyl)-6-hydroxypicolinamide (156 mg, 0.64 mmol), K$_3$PO$_4$ (1.02 g, 4.82 mmol), CuI (153 mg, 0.80 mmol) and 2M CH$_3$NH$_2$ in THF (99.8 mg, 3.21 mmol) at 20° C. The reaction vial was sealed and heated at 110° C. for 16 h. The reaction mixture was concentrated. The crude product was purified by chromatography (silica, EtOAc/PE=0-10%) to give the title compound as a mixture (670 mg, 68.7%). $^1$H NMR (400 MHz, CDCl$_3$) δ 7.87 (s, 0.5H), 7.65 (s, 0.5H), 7.01 (s, 0.5H), 6.67 (s, 0.5H), 6.15-6.01 (m, 2H), 5.49-5.36 (m, 2H), 4.64 (s, OH), 3.63-3.49 (m, 5H), 3.53-3.40 (m, 1H), 3.11 (t, J=18.0 Hz, 2H), 2.99 (d, J=5.6 Hz, 3H), 2.75 (d, J=16.9 Hz, 1H), 1.30 (s, 3H), 1.14 (dt, J=9.8, 5.3 Hz, 1H), 0.98-0.89 (m, 2H), 0.89-0.80 (m, 2H), 0.46-0.38 (m, 1H), 0.27 (t, J=5.0 Hz, 1H), −0.00 (d, J=0.8 Hz, 9H), −0.09 (d, J=4.3 Hz, 9H); LC/MS m/z (M+H)$^+$=579.3.

Preparation 165: Step 1. methyl 6-bromo-2-((4aS, 5aR)-5a-methyl-1-((2-(trimethylsilyl)ethoxy)methyl)-1,4,4a,5,5a,6-hexahydrocyclopropa[f]indazol-3-yl)-1H-benzo[d]imidazole-4-carboxylate

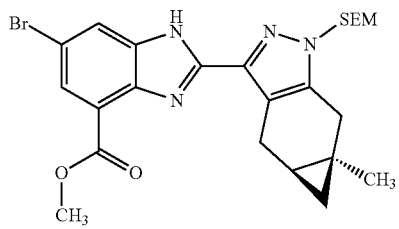 [SMILES: COC(=O)c1cc(Br)cc2[nH]c(-c3nn(COCC[Si](C)(C)C)c4c3C[C@@H]3C[C@]3(C)C4)nc12]

To a solution of methyl 2,3-diamino-5-bromobenzoate (1.57 g, 6.41 mmol) in DMF (30 mL) at 20° C. was added Preparation 9 (1.96 g, 6.41 mmol) and Na$_2$S$_2$O$_5$ (1.2 g, 6.40 mmol). The mixture was heated at 110° C. for 16 h then cooled to RT and concentrated. The crude product was purified by chromatography (silica, EtOAc/PE=0-75%) to give the title compound (1.23 g, 36%). LC/MS m/z (M+H)$^+$=533.1 ($^{81}$Br).

Preparation 166: methyl 6-bromo-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazole-4-carboxylate

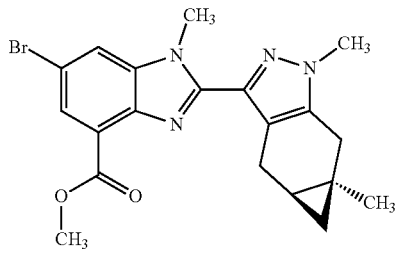 [SMILES: COC(=O)c1cc(Br)cc2c1nc(-c1nn(C)c3c1C[C@@H]1C[C@]1(C)C3)n2C]

To a solution of Preparation 165 (1.20 g, 2.26 mmol) in THF (50 mL) at 0° C. was added NaH (117 mg, 2.93 mmol) and SEM-Cl (565 mg, 3.39 mmol). The mixture was stirred for 20 h at RT. The reaction was treated with sat. aq. NH$_4$Cl (1.0 mL) and water (50 mL). The mixture was extracted with EtOAc (2×150 mL). The combined organic extracts were washed with brine, dried (Na$_2$SO$_4$) and concentrated to give the title compound (1.49 g, 99%). LC/MS m/z (M+H)$^+$=663.1 ($^{81}$Br).

Preparation 167: 6-bromo-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazole-4-carboxylic acid

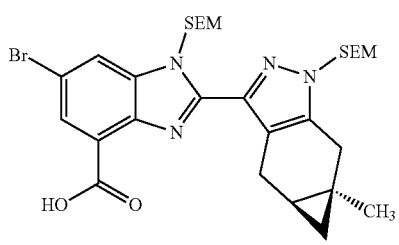 [SMILES: C[C@@]12Cc3c(c(-c4nc5c(C(=O)O)cc(Br)cc5n4COCC[Si](C)(C)C)nn3COCC[Si](C)(C)C)C[C@@H]1C2]

To a solution of Preparation 166 (900 mg, 1.36 mmol) in MeOH (50 mL) at RT was added 10% NaOH (5 mL). The mixture was stirred at RT for 15 h, cooled to 0° C. and acidified to with 1N HCl to a pH 1. The mixture was then diluted with water (50 mL) and extracted with EtOAc (3×50 mL). The organic extracts were combined, dried (Na$_2$SO$_4$) and concentrated to give the title compound (880 mg, 100%). LC/MS m/z (M+H)$^+$=649.1 ($^{81}$Br).

Preparation 168: 6-bromo-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazole-4-carboxamide

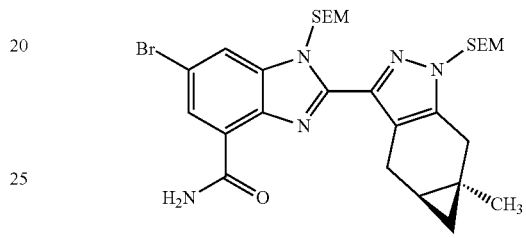

To a solution of Preparation 167 (850 mg, 1.31 mmol) in DMF (10 mL) at RT was added HATU (649 mg, 1.71 mmol), Et$_3$N (1 mL) and NH$_4$Cl (211 mg, 3.94 mmol). The mixture was stirred at RT for 15 h. The mixture was diluted with water (50 mL) and extracted with EtOAc (3×50 mL). The organic extracts were combined, dried (Na$_2$SO$_4$) and concentrated. The crude product was purified by chromatography (silica, EtOAc/PE=0-50%) to give the title compound (400 mg, 47%). LC/MS m/z (M+H)$^+$=648.1 ($^{81}$Br).

Preparation 169: 6-bromo-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazole-4-carbonitrile

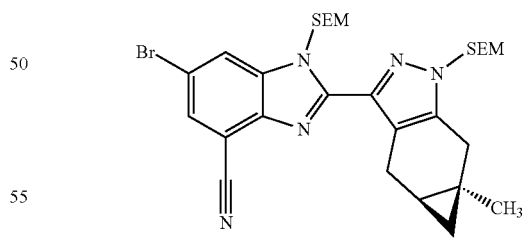

To a solution of Preparation 168 (400 mg, 0.62 mmol) in THF (20 mL) at 0° C. was added Et$_3$N (375 mg, 3.71 mmol) and TFAA (390 mg, 1.86 mmol). The mixture was stirred at RT for 15 h. The mixture was diluted with 1:1 water/DCM (100 mL) and the layers separated. The aqueous layer was extracted with DCM (50 mL). The combined organic extracts were washed with brine (50 mL), dried (Na$_2$SO$_4$), filtered and concentrated to give the title compound (389 mg, 100%). LC/MS m/z (M+H)$^+$=630.1 ($^{81}$Br).

Preparation 170: tert-butyl (4-cyano-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)carbamate

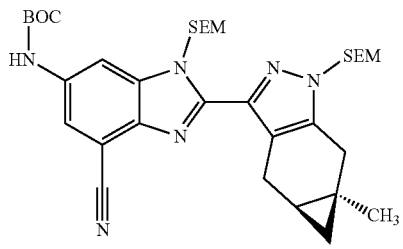 [SMILES: CC(C)(C)OC(=O)Nc1cc(C#N)c2nc(-c3nn(COCC[Si](C)(C)C)c4c3C[C@@H]3C[C@]3(C)C4)n(COCC[Si](C)(C)C)c2c1]

To a solution of Preparation 169 (389 mg, 0.62 mmol) in tert-amyl alcohol (10 mL) and dioxane (10 mL) under $N_2$ was added tert-butyl carbamate (217 mg, 1.86 mmol), $Cs_2CO_3$ (403 mg, 1.24 mmol), tert-BuDavePhos (84.5 mg, 0.25 mmol) and $Pd_2(dba)_3$ (57 mg, 0.06 mmol). The mixture was stirred at 100° C. for 15 h. The reaction was cooled to RT and concentrated. The crude product was purified by chromatography (silica, EtOAc/PE=0-75%) to give the title compound (320 mg, 78%). LC/MS m/z $(M+H)^+=665.3$

Preparation 171: 6-amino-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazole-4-carbonitrile

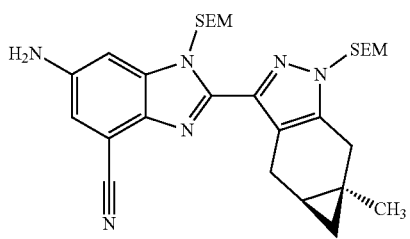 [SMILES: C[C@@]12Cc3c(c(-c4nc5c(C#N)cc(N)cc5n4COCC[Si](C)(C)C)nn3COCC[Si](C)(C)C)C[C@@H]1C2]

A solution of Preparation 170 (540 mg, 0.81 mmol) in DCM (50 mL) was treated with $ZnBr_2$ (914 mg, 4.06 mmol). The mixture was stirred at RT for 15 h. The reaction was filtered and the filtrate was taken up in DCM (150 mL) and washed with sat. aq. $NaHCO_3$ (50 mL). The layers were separated, and the aqueous layer extracted with DCM (50 mL). The combined organic extracts were washed with brine, dried ($Na_2SO_4$) filtered and concentrated to give the title compound (155 mg, 34%). LC/MS m/z $(M+H)^+=565.3$

Preparation 172: (R)—N-(4-cyano-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-2-(tetrahydro-2H-pyran-4-yl)propenamide

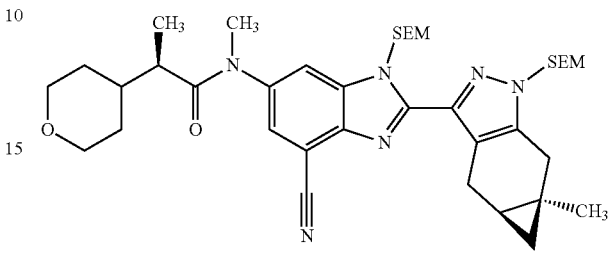

To a solution of Preparation 171 (70 mg, 0.12 mmol) in THF (10 mL) at RT was added Preparation 22 (39 mg, 0.25 mmol), 2-chloro-1-methylpyridinium iodide (63 mg, 0.25 mmol) and iPr$_2$NEt (80 mg, 0.62 mmol). The mixture was stirred at 60° C. for 15 h. The reaction mixture was cooled to RT and concentrated. The crude product was purified by chromatography (silica, EtOAc/PE=0-100%) to give the title compound (80 mg, 92%). LC/MS m/z $(M+H)^+=705.3$

Preparation 173: (R)—N-(4-cyano-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-N-methyl-2-(tetrahydro-2H-pyran-4-yl)propenamide

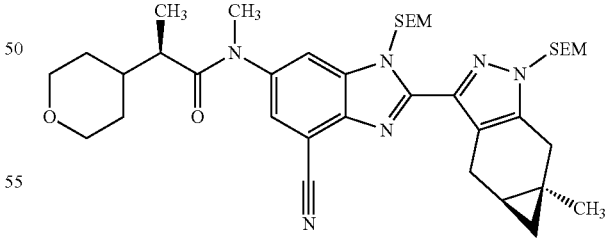

A solution of Preparation 172 (80 mg, 0.11 mmol) in THF (5 mL) at 0° C. was treated with NaH (6.81 mg, 0.17 mmol) and then MeI (24.2 mg, 0.17 mmol). The mixture was stirred at RT for 2 h. The mixture was treated with sat. aq. $NH_4Cl$ (0.3 mL) and water (50 mL) and extracted with EtOAc (2×50 mL). The combined organic extracts were washed with brine, dried ($Na_2SO_4$) and concentrated to give the title compound (82 mg, 100%). LC/MS m/z $(M+H)^+=719.4$.

EXAMPLES

Example 1: (S)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide

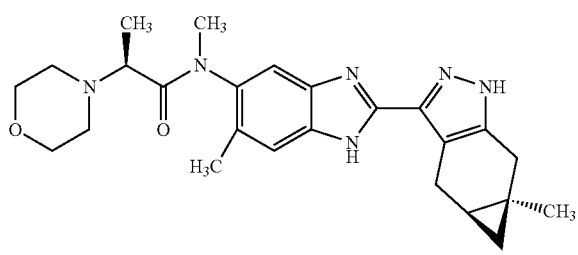 [SMILES: Cc1cc2[nH]c(-c3n[nH]c4c3C[C@@H]3C[C@]3(C)C4)nc2cc1N(C)C(=O)[C@H](C)N1CCOCC1]

Step 1: (S)—N-methyl-N-(6-methyl-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)-2-morpholinopropanamide

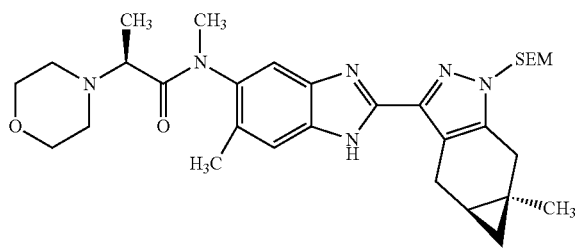 [SMILES: Cc1cc2[nH]c(-c3nn(COCC[Si](C)(C)C)c4c3C[C@@H]3C[C@]3(C)C4)nc2cc1N(C)C(=O)[C@H](C)N1CCOCC1]

A mixture of Preparation 9 (20.2 g, 66.2 mmol) and Na$_2$S$_2$O$_5$ (6.2 g, 32.6 mmol) was treated with a solution of Preparation 30 (20 g, 65.3 mmol), in DMF (114 mL). The mixture was treated with DMSO (11.6 mL, 163 mmol) and heated at 80° C. for 16 h. The mixture was cooled to RT and poured into ice-water. The pH of the mixture was adjusted to pH 7-8 using sat. aq. NaHCO$_3$ and the mixture was stirred for additional 2 h. The solids were collected by filtration. The solids were dissolved in DCM, washed with brine, water and dried (MgSO$_4$), filtered and concentrated. The crude material was purified by chromatography (silica, MeOH/EtOAc=0-10%) to give the Step 1 title compound (32.0 g, 85%). $^1$H NMR (400 MHz, CD$_3$OD) δ 7.69-7.32 (m, 2H), 5.53-5.40 (m, 2H), 3.77-3.55 (m, 4H), 3.52-3.36 (m, 1H), 3.27-3.20 (m, 3H), 3.19-3.03 (m, 3H), 2.81-2.72 (m, 1H), 2.63-2.49 (m, 2H), 2.44-2.31 (m, 3H), 2.30-2.20 (m, 2H), 1.22-1.14 (m, 3H), 1.13-1.08 (m, 1H), 0.94-0.84 (m, 7H), 0.49-0.41 (m, 1H), 0.30-0.22 (m, 1H), 0.02-0.10 (m, 9H); LC/MS m/z (M+H)$^+$=579.4.

Step 2: (S)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide

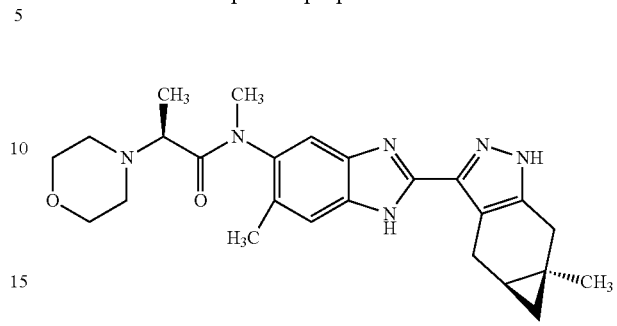

A solution of the silyl ether of Step 1 (30.4 g, 52.6 mmol) in DCM (50 mL) was cooled to 0° C. A premixed solution of TFA (76.4 mL, 1 mol) in DCM (150 mL) was added dropwise over 30 min. The mixture was warmed to RT and then stirred for 16 h. The mixture was treated with toluene (100 mL) and concentrated. The resultant residue was azeotroped with toluene (2×250 mL). The residue was dissolved in EtOH (210 mL), cooled to 0° C. and treated with conc. NH$_4$OH (138 mL) dropwise over 30 min. The mixture was warmed to RT and stirred for 2 h. The solvent was concentrated and azeotroped with heptanes (2×200 mL). The residue was dissolved in DCM and washed sequentially with aq. 1 N HaOH, brine, water, and then dried (MgSO$_4$), filtered and concentrated. The resultant solid was azeotroped with diethyl ether (×2). The resulting solid was recrystallized with 25% water/MeCN (300 mL), filtered and dried to give the title compound as a crystalline white solid (17.45 g, 74%). $^1$H NMR (400 MHz, CD$_3$OD) δ 7.68-7.32 (m, 2H), 3.79-3.56 (m, 4H), 3.51-3.33 (m, 1H), 3.27-3.20 (m, 3H), 3.16-3.01 (m, 3H), 2.81-2.72 (m, 1H), 2.61-2.49 (m, 2H), 2.45-2.31 (m, 3H), 2.32-2.22 (m, 2H), 1.34-1.25 (m, 3H), 1.23-1.01 (m, 4H), 0.45-0.35 (m, 1H), 0.30-0.21 (m, 1H); $^1$H NMR (500 MHz, 140° C., DMF-d$_7$) δ 12.52 (s, 1H), 12.09 (s, 1H), 7.58 (s, 1,5H), 7.46 (s, 0.5H), 3.68-3.60 (m, 4H), 3.61-3.52 (m, 1H), 3.38-3.25 (br, s, 3H), 3.17 (d, 2H), 2.88 (t, 2H), 2.74-2.65 (m, 2H), 2.64-2.61 (br, s, 3H), 2.43-2.31 (m, 2H), 1.41 (s, 3H), 1.29-1.11 (m, 4H), 0.56-0.50 (m, 1H), 0.37-0.32 (m, 1H); SFC method: Chiral Tech AD-H 250 mm×4.6 mm×5 μm, 10 to 60% with 0.2% isopropyl amine in MeOH/CO$_{2(g)}$, 3.0 mL/min, column temperature 15° C., retention time=6.59 min (40.9%) and 9.54 min (59.1%), 100% ee. LC/MS m/z (M+H)$^+$=449.1.

Example 1.1: (S)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide, dihydrate (crystal Form 1)

A solution of the silyl ether of Example 1 Step 1 (8.90 g, 15.4 mmol) in DCM (59 mL) and TFA (29 mL) was stirred for 16 h. The mixture was concentrated and the residue was azeotroped with toluene (2×100 mL). The residue was dissolved in a 3:2 (v/v) mixture of EtOH/conc. NH$_4$OH (125 mL). The mixture was stirred at RT for 2 h. The solvent was concentrated and azeotroped with heptanes (2×50 mL). The residue was dissolved in DCM and washed sequentially with water and brine. The aqueous phase was extracted with DCM (3×), dried (MgSO$_4$), filtered and concentrated. The residue was purified by SFC (Princeton PPU 250 mm×50 mm, 5 µm; Isocratic elution 75% CO$_2$/25% (0.2% 7N MeOH/MeOH); 80 mL/min) to deliver solids (5.3 g). The solids (5.3 g) were dissolved in DCM (200 mL) and washed with (2×50 mL) deionized water. The aqueous layers were combined and extracted with DCM (2×50 mL). The combined DCM layers were dried (MgSO$_4$), filtered through Celite®, concentrated and dried under vacuum to provide solids (4.5 g). The solids (4.5 g) were suspended in MeCN (90.4 mL) at RT, treated with water (22.3 mL) and the mixture was stirred at 58° C. for 1 h until all the solids were dissolved. The mixture was allowed to cool to RT over 18 h and then stirred at RT for 24 h. The solids were collected by filtration and dried under vacuum at 60° C. for 60 h to provide the title compound (3.55 g, 51%). NMR for the title compound was consistent with that for Example 1.

Powder X-Ray Diffraction (PXRD)

PXRD analysis was conducted using a Bruker AXS D8 Endeavor diffractometer equipped with a Cu radiation source. The divergence slit was set at 11 mm continuous illumination. Diffracted radiation was detected by a PSD-Lynx Eye detector, with the detector PSD opening set at 2.949 degrees. The X-ray tube voltage and amperage were set to 40 kV and 40 mA respectively. Data was collected in the Theta-Theta goniometer at the Cu wavelength from 3.0 to 40.0 degrees 2-Theta using a step size of 0.016 degrees and a step time of 0.3 second. The antiscatter screen was set to a fixed distance of 1.5 mm. Samples were rotated at 15/min during collection. Samples were prepared by placing them in a silicon low background sample holder and rotated during collection. Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked and peak positions were adjusted to the peak maximum. Peaks with relative intensity of ≥3% were generally chosen. The peaks which were not resolved or were consistent with noise were not selected. A typical error associated with the peak position from PXRD stated in USP is up to +/−0.2° 2-Theta (USP-941). The PXRD pattern for the title compound is provided in FIG. 1 and the corresponding peak list is found in Table 1 below.

Thermogravimetric Analysis (TGA)

Figure 6:
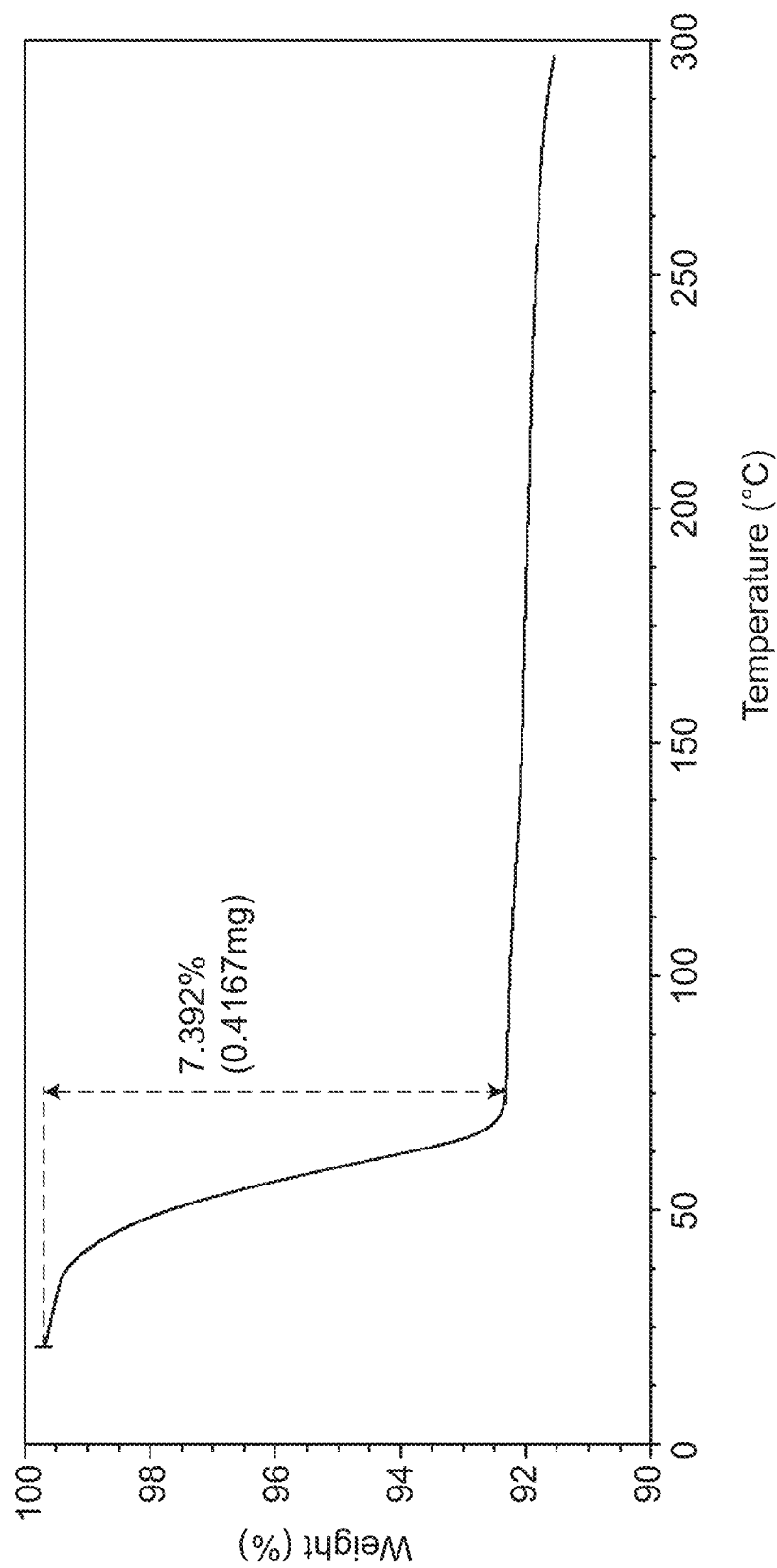
FIG. 6 is the TGA for the compound of Example 1.1 (crystal Form 1).

TGA was conducted using a Discovery TGA (TA instruments) thermogravimetric analyzer. Samples of approximately 10 mg were weighed into aluminum pans and heated from ambient temperature to 250° C. at 10° C./minute heating rate under nitrogen purge (10 mL/min for both sample chamber and balance). TGA for the title compound is provided in FIG. 6. The observed weight loss of 7.4% is consistent with a theoretical weight loss of 7.4% for Form 1 dihydrate.

Example 1,2a: (S)—N-methyl-N-(6-methyl-2-((4aS, 5aR)-5a-methyl-1,4,4a,5,5a,6-hexahydrocyclopropa [f]indazol-3-yl)-1H-benzo[d]imidazol-5-yl)-2-morpholinopropanamide, dihydrate (crystal Form 2)

A solution of the silyl ether of Example 1 Step 1 (30.4 g, 52.6 mmol) in DCM (50 mL) was cooled to 0° C. A premixed solution of TFA (76.4 mL, 1 mol) in DCM (150 mL) was added dropwise over 30 min. The mixture was warmed to RT and then stirred for 16 h. The mixture was treated with toluene (100 mL) and concentrated. The resultant residue was azeotroped with toluene (2×250 mL). The residue was dissolved in EtOH (210 mL), cooled to 0° C. and treated with conc. NH$_4$OH (138 mL) dropwise over 30 min. The mixture was warmed to RT and stirred for 2 h. The solvent was concentrated and azeotroped with heptanes (2×200 mL). The residue was dissolved in DCM and washed sequentially with aq. 1 N NaOH, brine, water, and then dried (MgSO$_4$), filtered and concentrated. The resultant solid was azeotroped with diethyl ether (×2) to afford solids (24 g). A suspension of these solids (24 g) in MeCN (240 mL) and water (60 mL) was heated at a temperature between 60° C. and 70 for 30 min. Undissolved solids were removed by filtration and the filtrate was cooled slowly to RT. Seed crystals (Example 1.1, Form 1) were added and the mixture was stirred at RT for about 24 h. The solids were collected by filtration and dried under vacuum at 50° C. to provide the title compound (17.45 g, 74%).

$^1$H NMR (400 MHz, CD$_3$OD) δ 7.68-7.32 (m, 2H), 3.79-3.56 (m, 4H), 3.51-3.33 (m, 1H), 3.27-3.20 (m, 3H), 3.16-3.01 (m, 3H), 2.81-2.72 (m, 1H), 2.61-2.49 (m, 2H), 2.45-2.31 (m, 3H), 2.32-2.22 (m, 2H), 1.34-1.25 (m, 3H), 1.23-1.01 (m, 4H), 0.45-0.35 (m, 1H), 0.30-0.21 (m, 1H); $^1$H NMR (500 MHz, 140° C., DMF-d$_7$) δ 12.52 (s, 1H), 12.09 (s, 1H), 7.58 (s, 1,5H), 7.46 (s, 0.5H), 3.68-3.60 (m, 4H), 3.61-3.52 (m, 1H), 3.38-3.25 (br, s, 3H), 3.17 (d, 2H), 2.88 (t, 2H), 2.74-2.65 (m, 2H), 2.64-2.61 (br, s, 3H), 2.43-2.31 (m, 2H), 1.41 (s, 3H), 1.29-1.11 (m, 4H), 0.56-0.50 (m, 1H), 0.37-0.32 (m, 1H); SFC method: Chiral Tech AD-H 250 mm×4.6 mm×5 µm, 10 to 60% with 0.2% isopropyl amine in MeOH/CO$_{2(g)}$, 3.0 mL/min, column temperature 15° C., retention time=6.59 min (40.9%) and 9.54 min (59.1%), 100% ee. LC/MS m/z (M+H)$^+$=449.1.

PXRD

Figure 2:
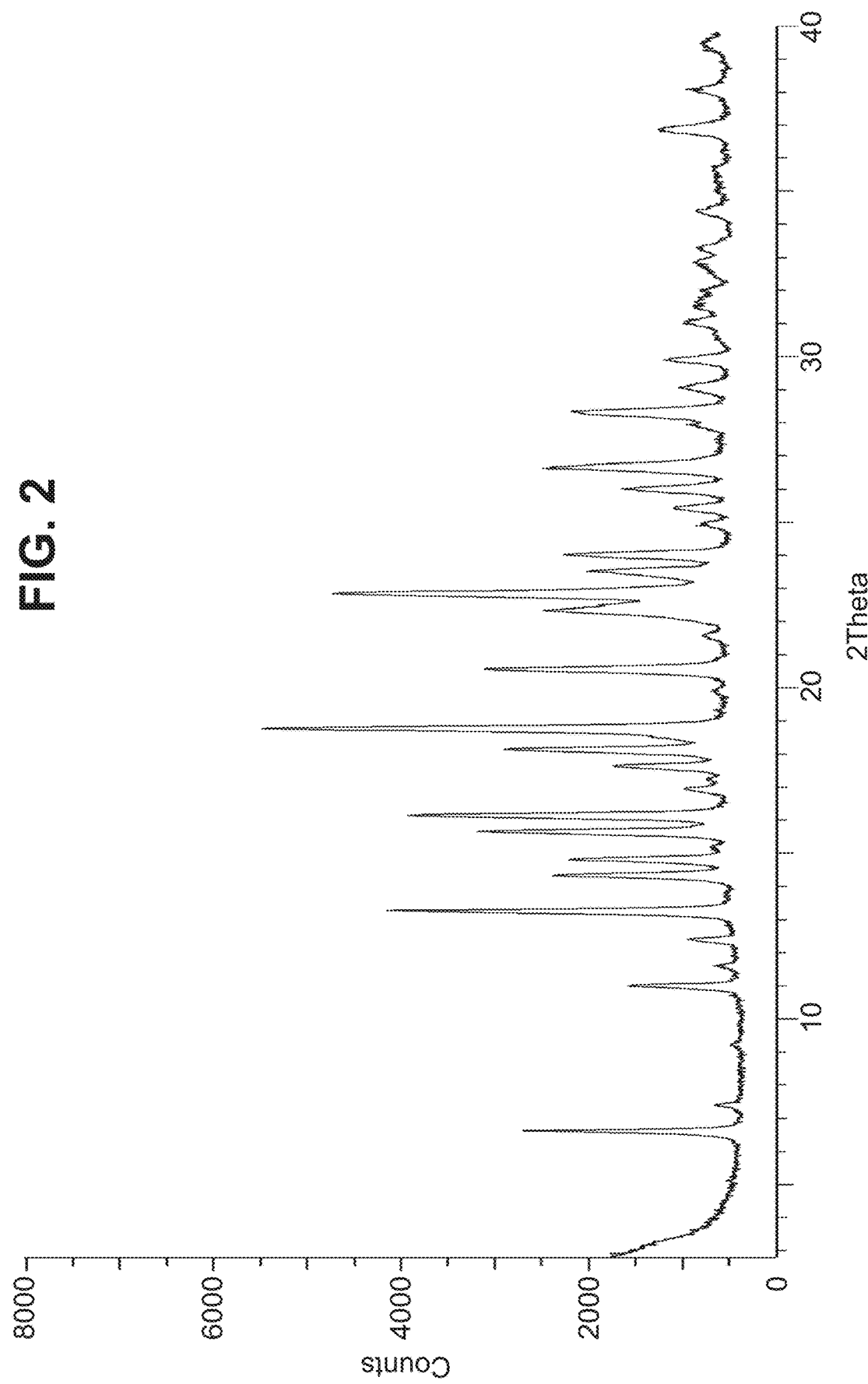
FIG. 2 is the PXRD pattern for the compound of Example 1.2a (crystal Form 2).

PXRD was carried out according to the procedure set out for Example 1.1 (Form 1), but with the divergence slit set at 10 mm, the detector PSD opening set at 2.99 degrees, and a step size of 0.02 degrees. The PXRD pattern for the title compound is provided in FIG. 2 and has been aligned with the calculated powder pattern generated from the single crystal solution of Example 1.4 below. The corresponding peak list is found in Table 1 below.

Example 1.2b: (S)—N-methyl-N-(6-methyl-2-((4aS, 5aR)-5a-methyl-1,4,4a,5,5a,6-hexahydrocyclopropa [f]indazol-3-yl)-1H-benzo[d]imidazol-5-yl)-2-morpholinopropanamide, dihydrate (crystal Form 2)

A solution of the silyl ether of Example 1 Step 1 (70.0 g, 120.9 mmol) in DCM (150 mL) at about 0° C. was treated dropwise with a mixture of 1:1 (v/v) DCM/TFA (342 mL). The reaction mixture was warmed to RT and stirred for about 16 h. The mixture was concentrated and the residue was azeotroped with toluene (2×). The residue was dissolved in ethanol (300 mL) and treated dropwise with conc. NH$_4$OH (300 mL). The mixture was stirred at RT for about 24 h. The solvent was concentrated. The residue was dissolved in DCM and washed sequentially with brine and water. The DCM extract was dried (MgSO$_4$), filtered and concentrated. The residue was purified by chromatography (silica, EtOAc/PE=50-100% then MeOH/EtOAc 0-3%) to deliver the solids (batch 1, 31 g). A solution of the collected solids (2.0 g) in ethanol (12 mL) was heated to about 75° C. and water (18 mL) was added at a rate to keep the internal temperature above 70° C. The mixture was cooled to about 60° C. and treated with additional solids (100 mg). The mixture was stirred at about 60° C. for about 2 h and then stirred at about 30° C. for about 18 h. The mixture was cooled to about 5° C. and stirred for about 1 h. The solids were collected by filtration, rinsed with 1:2 (v/v) ethanol/water and dried to provide solids (batch 2, 1.1 g). The remaining batch 1 solids (29 g) were suspended in MTBE (150 mL) and stirred at about 30° C. for about 48 h. The solids were collected by filtration, rinsed with MTBE and dried to provide solids (batch 3, 23 g). The combined batch 2 and batch 3 solids (24.1 g) were suspended in ethanol (150 mL) and heated to about 75° C. and water (220 mL) was added at a rate to keep the internal temperature above 70° C. The solution was stirred at about 65° C. for about 1 h, at about 55° C. for about 1 h, at 45° C. for about 3 h and then at about 35° C. for about 48 h. The solids were collected by filtration, rinsed with 1:2 (v/v) ethanol/water and dried under vacuum to provide the title compound (20.5 g, 38%). NMR and PXRD for the title compound were consistent with that for Example 1,2a Example 1.3: (S)—N-methyl-N-(6-methyl-2-((4aS, 5aR)-5a-methyl-1,4,4a,5,5a,6-hexahydrocyclopropa[f]indazol-3-yl)-1H-benzo[d]imidazol-5-yl)-2-morpholinopropanamide, hemihydrate (crystal Form 3)

(S)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide, dihydrate (crystal Form 2) (400 mg) was suspended in MeCN (4 mL) and stirred at RT for about 18 h. The solids were collected by filtration and rinsed with MeCN (about 3 mL). The collected solids were dried under vacuum at 50° C. for 1.5 h to provide the title compound (300 mg, 89%).

TGA and PXRD

Figure 3:
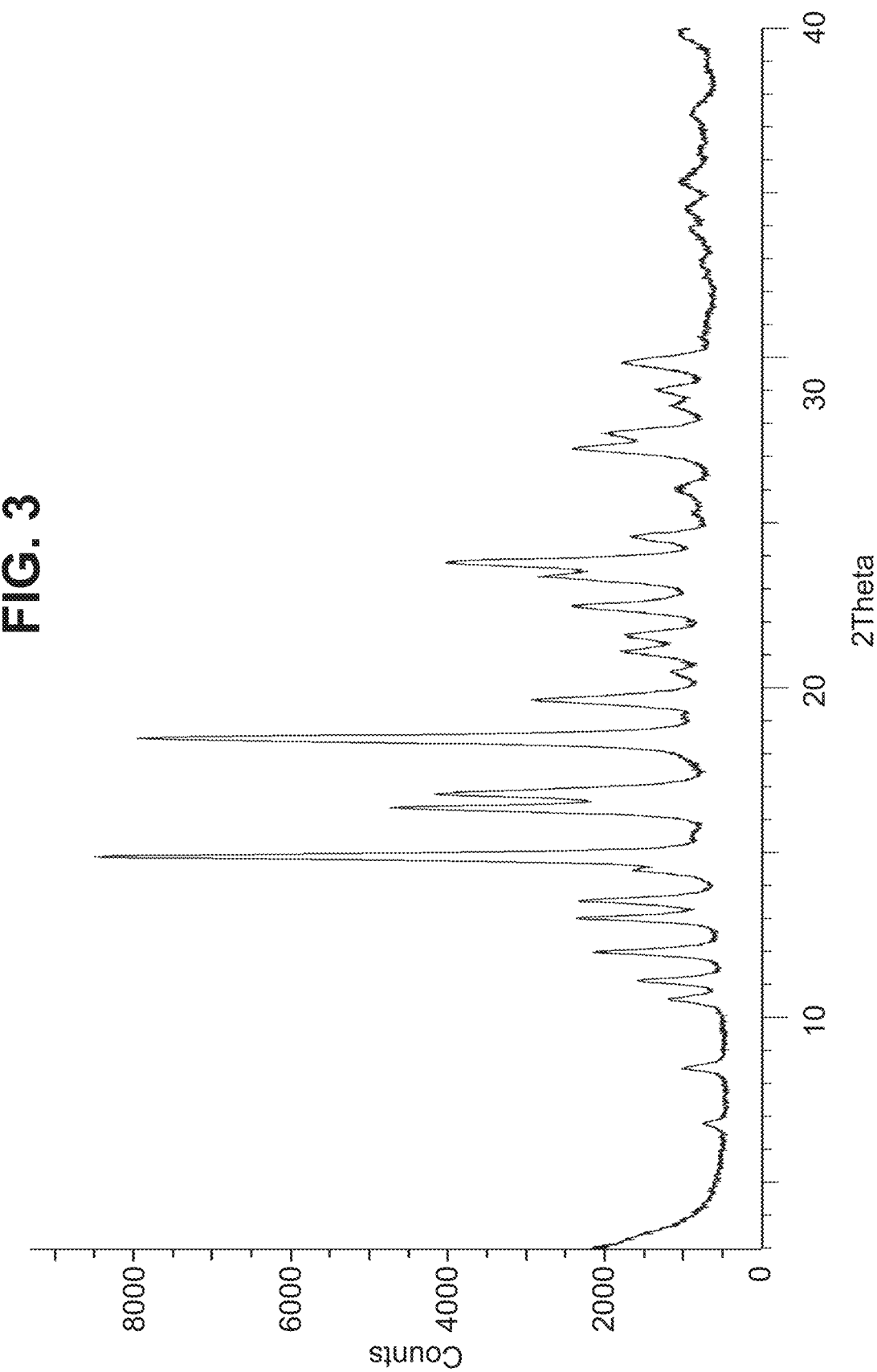
FIG. 3 is the PXRD pattern for the compound of Example 1.3 (crystal Form 3).
Figure 7:
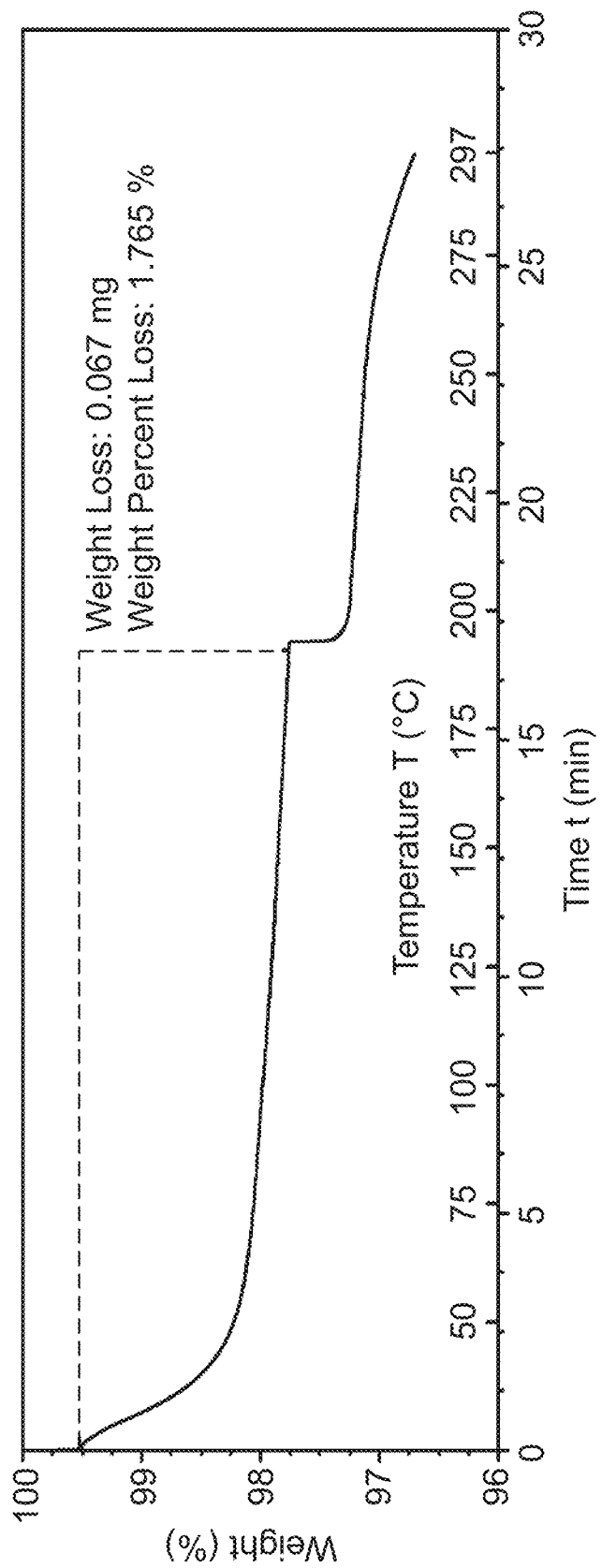
FIG. 7 is the TGA for the compound of Example 1.3 (crystal Form 3).

TGA and PXRD were respectively carried out according to the procedures set out in Examples 1.1 (Form 1) and 1.2a (Form 2). The PXRD pattern for the title compound is provided in FIG. 3 and the corresponding peak list is found in Table 1 below. TGA for the title compound is provided in FIG. 7. The observed weight loss of 1.8% is consistent with a theoretical weight loss of 2% for Form 3 hemi-hydrate.

TABLE 1

PXRD peak list for crystal Forms 1, 2 and 3 of, respectively, Examples 1.1, 1.2a and 1.3

| Form 1 | | Form 2 [1] | | Form 3 | |
|---|---|---|---|---|---|
| Angle, °2θ (°2-Theta) | Relative Intensity, % | Angle, °2θ (°2-Theta) | Relative Intensity, % | Angle, °2θ (°2-Theta) | Relative Intensity, % |
| 8.6 | 12 | 6.6 | 46 | 6.8 | 3 |
| 9.2 | 5 | 7.4 | 6 | 8.5 | 6 |
| 10.1 | 53 | 11.0 | 24 | 10.6 | 9 |
| 12.6 | 100 | 11.6 | 5 | 11.1 | 13 |
| 13.7 | 5 | 12.4 | 10 | 12.0 | 17 |
| 14.4 | 74 | 13.3 | 76 | 13.0 | 22 |
| 15.0 | 65 | 14.4 | 38 | 13.5 | 21 |
| 16.2 | 78 | 14.8 | 34 | 14.5 | 12 |
| 16.8 | 9 | 15.2 | 3 | 14.9 | 100 |
| 17.0 | 10 | 15.7 | 54 | 16.4 | 51 |
| 18.6 | 57 | 16.2 | 70 | 16.8 | 43 |
| 18.9 | 55 | 17.0 | 8 | 18.5 | 91 |
| 19.4 | 44 | 17.2 | 4 | 19.6 | 26 |
| 19.9 | 23 | 17.7 | 23 | 20.5 | 4 |
| 20.3 | 13 | 18.2 | 48 | 21.1 | 12 |
| 21.0 | 35 | 18.8 | 100 | 21.6 | 11 |
| 22.1 | 31 | 19.9 | 3 | 22.5 | 20 |
| 22.5 | 41 | 20.6 | 52 | 23.4 | 27 |
| 22.9 | 9 | 21.6 | 5 | 23.8 | 42 |
| 23.5 | 43 | 22.4 | 40 | 24.6 | 12 |
| 23.9 | 21 | 22.9 | 87 | 26.0 | 4 |
| 24.6 | 8 | 23.6 | 30 | 27.3 | 22 |
| 25.7 | 8 | 24.0 | 36 | 27.7 | 15 |
| 26.0 | 39 | 25.0 | 4 | 28.6 | 6 |
| 26.4 | 31 | 25.5 | 11 | 29.0 | 8 |
| 27.2 | 12 | 26.0 | 22 | 29.9 | 13 |
| 27.6 | 3 | 26.7 | 39 | 33.9 | 3 |
| 29.2 | 12 | 28.0 | 6 | 34.5 | 4 |
| 29.4 | 16 | 28.4 | 32 | 35.4 | 5 |
| 29.8 | 9 | 29.1 | 10 | 37.4 | 3 |
| 30.7 | 22 | 29.9 | 13 | | |
| 31.2 | 7 | 30.7 | 3 | | |
| 31.8 | 6 | 31.1 | 8 | | |
| 32.7 | 6 | 31.5 | 6 | | |
| 33.6 | 7 | 32.0 | 6 | | |
| 35.0 | 7 | 32.6 | 4 | | |
| 35.4 | 15 | 32.9 | 8 | | |
| 36.4 | 8 | 33.3 | 5 | | |
| 37.7 | 5 | 34.4 | 7 | | |
| 38.3 | 4 | 35.7 | 3 | | |
| | | 36.9 | 15 | | |
| | | 38.1 | 9 | | |
| | | 39.4 | 3 | | |
| | | 39.5 | 4 | | |

[1] The PXRD pattern for Form 2 has been aligned with the calculated powder pattern generated from the single crystal solution of Example 1.4 below.

Example 1.4: (S)—N-methyl-N-(6-methyl-2-((4aS, 5aR)-5a-methyl-1,4,4a,5,5a,6-hexahydrocyclopropa[f]indazol-3-yl)-1H-benzo[d]imidazol-5-yl)-2-morpholinopropanamide, dihydrate (crystal Form 2)

(S)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide, dihydrate (crystal Form 2) (30 mg) was dissolved in EtOAc (10 mL) in a 20 mL scintillation vial. The vial was covered with a cap but not tightened. The vial was left undisturbed at RT for about 26 days. During the elapsed time most of the solvent had evaporated leaving approximately 1 mL of EtOAc and the title compound.

Single Crystal X-Ray Diffraction (SXRD)

SXRD was performed on a Bruker D8 Venture diffractometer at room temperature. Data collection consisted of omega and phi scans. The structure was solved by intrinsic phasing using SHELX software suite in the Orthorhombic space group $P2_12_12_1$. The structure was subsequently refined by the full-matrix least squares method. All non-hydrogen atoms were found and refined using anisotropic displacement parameters. The final R-index was 3.92%. A final difference Fourier revealed no missing or misplaced electron density. Table 2 contains structural data from the SXRD analysis.

TABLE 2

Crystal structure data for the crystalline form of Example 1.4 (Form 2)

| | |
|---|---|
| Empirical formula | $C_{25}H_{36}N_6O_4$ |
| Formula weight | 484.60 |
| Temperature | 296(2) K |

TABLE 2-continued

Crystal structure data for the crystalline form of Example 1.4 (Form 2)

| | |
|---|---|
| Wavelength | 1.54178 Å |
| Crystal system | Orthorhombic |
| Space group | P212121 |
| Unit cell dimensions | a = 6.6838(2) Å   α = 90° |
| | b = 16.0450(4) Å   β = 90° |
| | c = 23.8703(6) Å   γ = 90° |
| Volume | 2559.89(12) Å3 |
| Z | 4 |
| Density (calculated) | 1.257 Mg/m3 |
| Goodness-of-fit on F2 | 1.043 |
| Final R indices [I > 2sigma(I)] | R1 = 0.0392, wR2 = 0.1026 |
| R indices (all data) | R1 = 0.0451, wR2 = 0.1048 |

Figure 4:
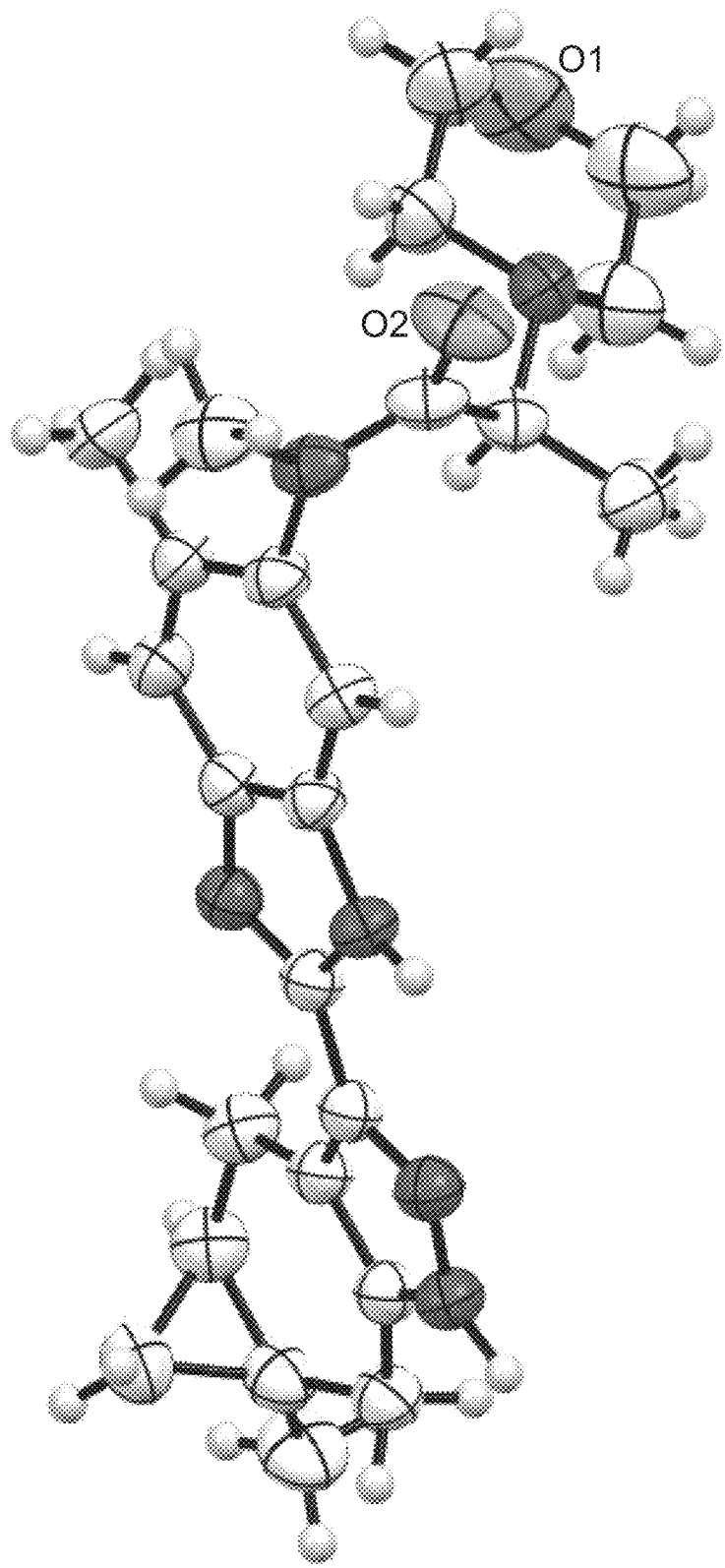
FIG. 4 is an ORTEP diagram for the compound of Example 1.4 (crystal Form 2), drawn with displacement parameters at 50% probability and water molecules omitted for clarity.
Figure 5:
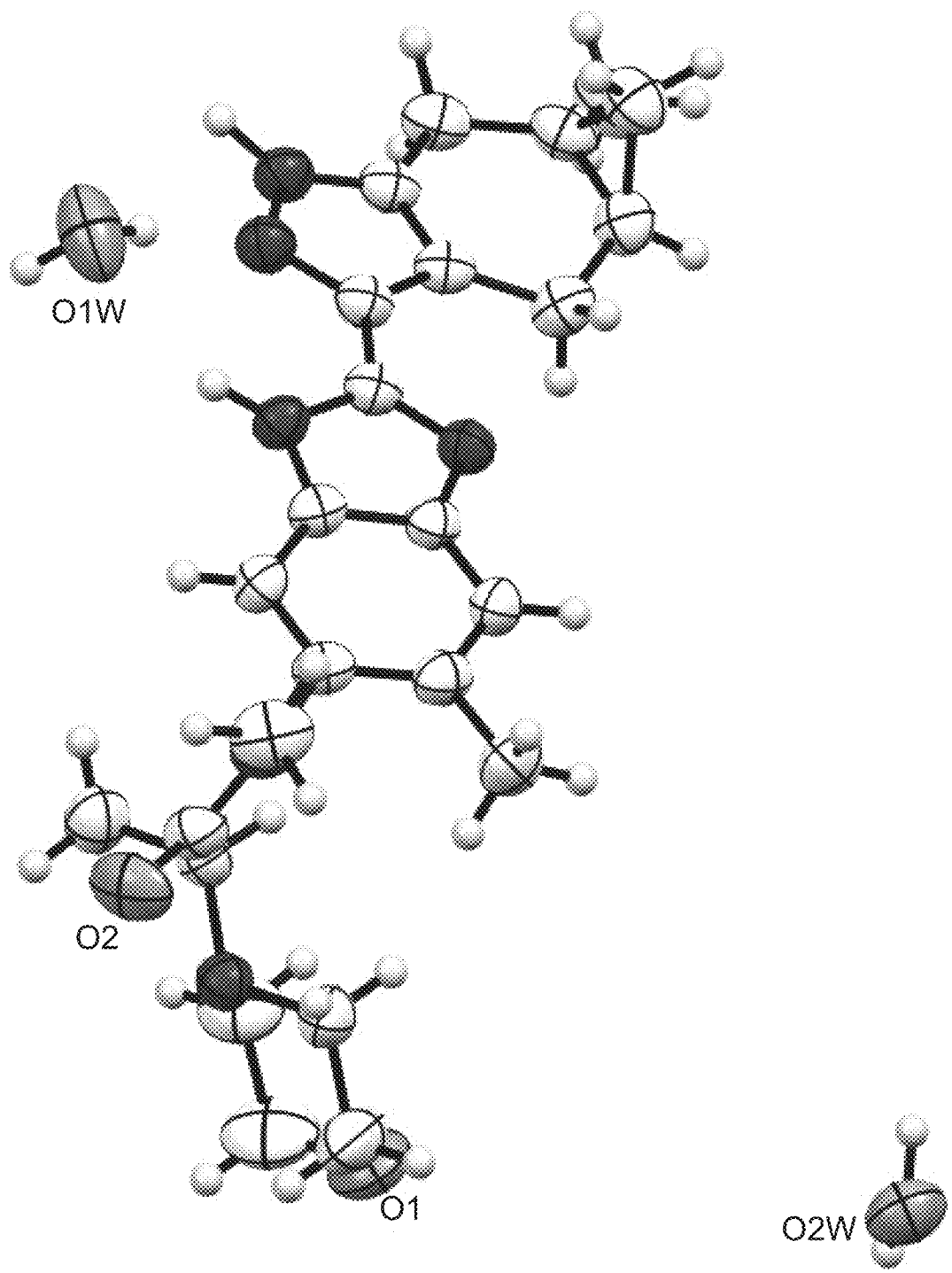
FIG. 5 is an ORTEP diagram for the compound of Example 1.4 (crystal Form 2), drawn with displacement parameters at 50% probability and water molecules shown.

The ORTEP diagram for one of the molecules in the asymmetric unit for the solution is presented in FIG. 4, with displacement parameters at 50% probability and water molecules omitted from the figure for clarity. FIG. 5 is an ORTEP diagram drawn with displacement parameters at 50% probability and water molecules shown.

The PXRD peak list from the calculated powder pattern for Form 2 is given in Table 3.

TABLE 3

Calculated PXRD peak list from the SXRD data for (Form 2)

| Angle (2-theta) | Relative Intensity (%) | Angle (2-theta) | Relative Intensity (%) |
|---|---|---|---|
| 6.6 | 59 | 24.0 | 31 |
| 7.4 | 8 | 25.0 | 4 |
| 9.2 | 3 | 25.5 | 10 |
| 11.0 | 28 | 26.0 | 17 |
| 11.6 | 5 | 26.6 | 26 |
| 12.4 | 11 | 26.7 | 18 |
| 13.3 | 64 | 27.0 | 3 |
| 14.3 | 49 | 27.9 | 5 |
| 14.8 | 39 | 28.3 | 15 |
| 15.2 | 4 | 28.4 | 26 |
| 15.7 | 51 | 29.1 | 6 |
| 16.2 | 81 | 29.2 | 6 |
| 17.0 | 8 | 29.9 | 10 |
| 17.3 | 3 | 31.1 | 6 |
| 17.7 | 24 | 31.5 | 4 |
| 18.2 | 41 | 31.8 | 4 |
| 18.5 | 12 | 32.0 | 4 |
| 18.8 | 100 | 32.6 | 4 |
| 20.6 | 51 | 32.9 | 6 |
| 21.6 | 4 | 33.3 | 5 |
| 22.1 | 9 | 34.4 | 4 |
| 22.3 | 33 | 36.9 | 9 |
| 22.5 | 20 | 37.0 | 6 |
| 22.9 | 73 | 38.1 | 7 |
| 23.0 | 18 | 39.5 | 3 |

Comparison of the experimental PXRD data in Table 1 of crystal Form 2 (Example 1,2a) with the data in Table 3 for the calculated PXRD pattern of crystal Form 2 (Example 1.4) obtained from single crystal structure determination shows good peak correlation.

Example 2: N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide

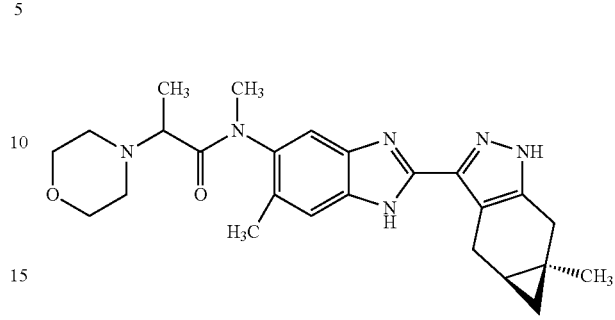

Example 2 was prepared following the procedure described for Example 1 from Preparation 31 (292 mg) and Preparation 9 (306 mg) to deliver 110 mg of the title compound. SFC method: Chiral Tech AD-H 250 mm×4.6 mm×5 μm, $CO_2$/MeOH (0.2% isopropyl amine) 5 to 60%, 3.0 mL/min, column temperature 15° C., retention time=6.33 min (13.42%), 6.74 min (24.37%), 8.35 min (35.92%), and 9.76 min (24.37%); LC/MS m/z $(M+H)^+$=449.5.

Example 3: (R)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide

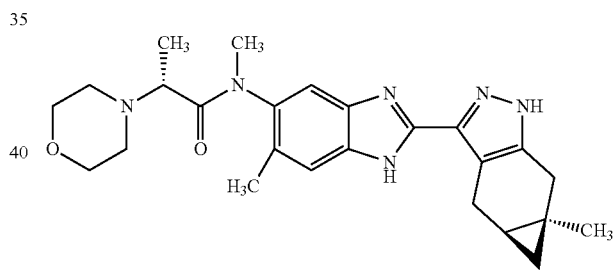

Step 1: (R)—N-methyl-N-(6-methyl-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)-2-morpholinopropanamide

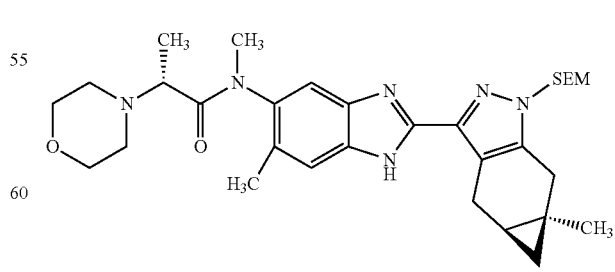

A mixture of Preparation 46 (219 mg, 0.5 mmol), (R)-2-morpholinepropanoic acid (398 mg, 2.50 mmol), EDCI (959 mg, 5.00 mmol) in pyridine (10.0 mL) was heated at 80° C.

for 16 h. The mixture was cooled to RT and diluted with EtOAc/water. The organic layer was separated and washed sequentially with sat. aqueous NH₄Cl, brine, dried (MgSO₄), filtered and concentrated. The crude material was purified by chromatography (silica, 0-10% MeOH/EtOAc) to give the title compound 160 (150 mg, 50%). ¹H NMR (400 MHz, CD₃OD) δ 7.68 (s, 1H), 7.53 (s, 1H), 5.62-5.38 (m, 2H), 3.71-3.57 (m, 6H), 3.43 (d, 1H), 3.28 (d, 3H), 3.24-3.04 (m, 3H), 2.81 (d, 1H), 2.67-2.49 (m, 2H), 2.47 (s, 2H), 2.36 (s, 1H), 2.31 (dd, 2H), 1.34 (d, 4H), 1.22 (d, 2H), 1.13 (dd, 1H), 0.98-0.88 (m, 2H), 0.48 (dd, 1H), 0.30 (t, 1H), 0.02--0.02 (m, 9H); LC/MS m/z (M+H)⁺=579.6.

Step 2: (R)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide

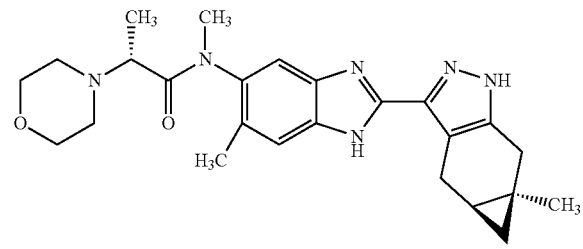 [SMILES: Cc1cc2[nH]c(-c3n[nH]c4c3C[C@@H]3C[C@]3(C)C4)nc2cc1N(C)C(=O)[C@@H](C)N1CCOCC1]

A solution of the silyl ether of Step 1 (150 mg, 0.259 mmol) in TFA (2 mL) was treated with Et₃SiH (151 mg, 1.3 mmol). The mixture was stirred at room temperature for 1 h. The mixture was concentrated and the residue triturated with toluene (2×10 mL). The residue was dissolved in EtOH (8 mL) and treated with conc. NH₄OH (2 mL). The mixture was stirred at RT for 2 h and concentrated. The residue was dissolved in DCM and washed sequentially with water and brine, dried (MgSO₄), filtered and concentrated. The crude material was purified by chromatography (silica, MeOH-EtOAc=0-10%) to give the title compound (100 mg, 86%). SFC method: Chiral Tech AD-H 250 mm×4.6 mm×5 µm, CO₂/MeOH (0.2% isopropyl amine) 5 to 60%, 3.0 mL/min, column temperature 15° C., RT=6.29 min (30.15%) and 8.38 min (69.20%), 99.37% ee; ¹H NMR (400 MHz, CD₃OD) δ 7.65 (s, 1H), 7.51 (s, 1H), 3.70-3.56 (m, 4H), 3.42-3.34 (m, 1H), 3.26 (d, 3H), 3.19-3.02 (m, 3H), 2.79 (d, 1H), 2.64-2.49 (m, 2H), 2.45 (s, 2H), 2.35 (s, 1H), 2.34-2.22 (m, 2H), 1.31 (s, 3H), 1.25-1.15 (m, 2H), 1.12 (d, 2H), 0.44 (dd, 1H), 0.27 (t, 1H); LC/MS m/z (M+H)⁺=449.5.

Example 4: (R)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide

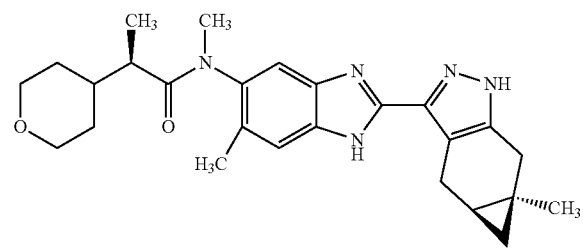 [SMILES: Cc1cc2[nH]c(-c3n[nH]c4c3C[C@@H]3C[C@]3(C)C4)nc2cc1N(C)C(=O)[C@H](C)C1CCOCC1]

Step 1: (R)—N-methyl-N-(6-methyl-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)-2-(tetrahydro-2H-pyran-4-yl)propanamide

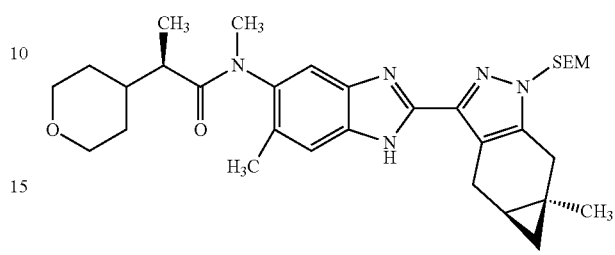

A solution of Preparation 46 (120 mg, 0.274 mmol) in THF (5 mL) was treated with iPr₂NEt (100 µL, 0.55 mmol), Preparation 22 (86.8 mg, 0.55 mmol) and 2-chloro-1-methylpyridinium iodide (140 mg, 0.548 mmol). The mixture was heated at 60° C. for 16 h. Water (10 mL) was added and the mixture extracted with EtOAc (2×20 mL). The combined organic extracts were concentrated and the residue purified by silica gel chromatography (silica, EtOAc/PE=0-85%) to give the title compound (165 mg, quant.).
¹H NMR (400 MHz, CD₃OD) δ 7.52 (s, 2H), 5.55-5.43 (m, 2H), 3.91 (t, 2H), 3.64 (t, 2H), 3.48-3.34 (m, 3H), 3.25 (dd, 3H), 3.21-3.11 (m, 3H), 2.79 (d, 1H), 2.42-2.35 (m, 3H), 2.20-2.10 (m, 1H), 2.01-1.91 (m, 1H), 1.82-1.72 (m, 1H), 1.60 (t, 2H), 1.33 (s, 3H), 1.17 (dd, 1H), 1.12 (d, 1H), 1.06-0.99 (m, 2H), 0.95-0.85 (m, 2H), 0.46 (dd, 1H), 0.28 (t, 1H), −0.02 (d, 9H); LC/MS m/z (M+H)⁺=578.3.

Step 2: (R)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide

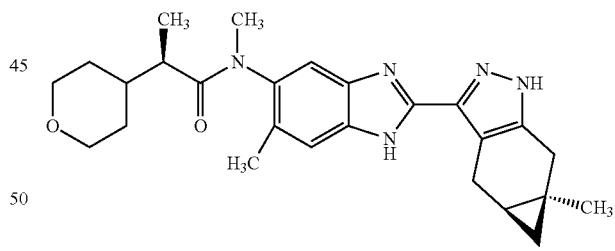

A mixture of the silyl ether of Step 1 (3.7 g, 6.4 mmol) in TFA (45.7 mL) and Et₃SiH (3.72 g, 32.0 mmol) was stirred at RT for 3 h and the mixture was concentrated. The residue was treated with sat. aq. NaHCO₃ until the pH=8 and extracted with EtOAc (2×30 mL). The extracts were combined, dried (MgSO₄), filtered and concentrated. The crude product was purified by prep HPLC (YMC triart C18 250×50 mm×7 µM, water (0.05% NH₄OH)/MeCN from 26 to 66% over 10 min, 60 ml/min) to give the title compound (1.86 g, 64.9%). SFC method: Chiral Tech OD-3 100 mm×4.6 mm×3 µm, CO₂/EtOH (0.05%) 5 to 40%, 1.5 mL/min, column temperature 35° C., retention time=3.47 min (41.5%) and 3.55 min (58.5%), 100% ee; ¹H NMR (400 MHz, CD₃OD) δ 7.52 (s, 2H), 3.99-3.66 (m, 2H), 3.46-3.34

(m, 3H), 3.26 (d, 3H), 3.20-3.11 (m, 2H), 3.08 (d, 1H), 2.79 (d, 1H), 2.38 (d, 3H), 2.16 (t, 0.5H), 1.99 (dd, 0.5H), 1.78 (ddt, 1H), 1.60 (t, 2H), 1.31 (s, 3H), 1.18 (dt, 1H), 1.12 (d, 1H), 1.07-0.95 (m, 3H), 0.43 (dd, 1H), 0.27 (t, 1H); LC/MS m/z (M+H)+=448.3.

Example 5: N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide

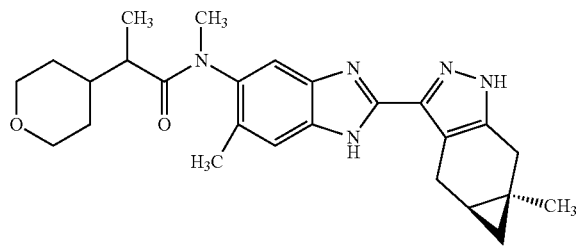 [SMILES: Cc1cc2[nH]c(-c3n[nH]c4c3C[C@@H]3C[C@]3(C)C4)nc2cc1N(C)C(=O)C(C)C1CCOCC1]

Example 5 was prepared analogously to Example 4 from Preparation 46 (100 mg) and 72 mg (±)-2-(tetrahydro-2H-pyran-4-yl)propanoic acid and purified by Prep-HPLC (Phenomenex Gemini-NX C18 150 mm×30 mm×5 μM, Water (0.04% NH₄OH)/MeCN from 26 to 66% over 9 min, 25 ml/min) to give the title compound (63 mg, 51%). SFC method: Chiral Tech OD-3 100 mm×4.6 mm×3 μm, CO₂/EtOH (0.05%) 5 to 40%, 2.8 mL/min, column temperature 35° C., retention time=3.39 min (15.8%), 3.46 min (26.0%), 3.54 min (35.6%) and 3.76 min (22.43%); ¹H NMR (400 MHz, CD₃OD) δ 7.57 (d, 1H), 7.47 (d, 1H), 4.00-3.80 (m, 2H), 3.47-3.35 (m, 4H), 3.29-3.22 (m, 3H), 3.15 (dd, 1H), 3.08 (d, 1H), 2.79 (d, 1H), 2.38 (d, 3H), 2.16 (dd, 0.5H), 1.99 (t, 0.5H), 1.90-1.69 (m, 1H), 1.60 (t, 2H), 1.31 (m, 4H), 1.17 (dq, 1H), 1.11 (dd, 1H), 1.03 (d, 2H), 0.43 (dd, 1H), 0.27 (q, 1H); LC/MS m/z (M+H)=448.3.

Example 6: (S)—N-ethyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide

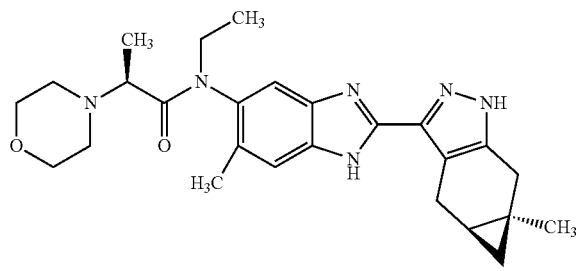 [SMILES: CCN(C(=O)[C@H](C)N1CCOCC1)c1cc2nc(-c3n[nH]c4c3C[C@@H]3C[C@]3(C)C4)[nH]c2cc1C]

Step 1: (S)—N-ethyl-N-(6-methyl-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)-2-morpholinopropanamide

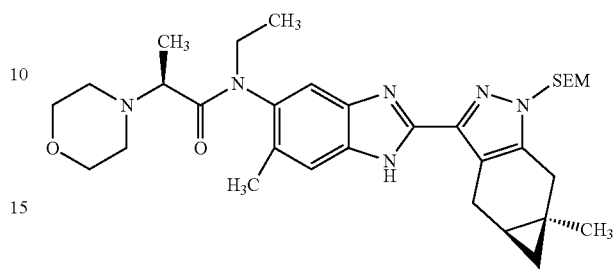

A solution of Preparation 67 (200 mg, 0.44 mmol) in pyridine (4.43 mL) at was treated with Preparation 19 (162 mg, 1.02 mmol) and EDCI (170 mg, 0.89 mmol). The mixture was stirred for 96 h, then was heated at 80° C. for an additional 24 h. The mixture was diluted with water and the mixture extracted with EtOAc (2×20 mL). The organic extracts were combined, dried (Na₂SO₄), filtered and concentrated. The crude material was purified by chromatography (silica, EtOAc/PE 0-100% then MeOH/DCM=0-10%) to give the title compound (78 mg, 30%). LC/MS m/z (M+H)+=593.5.

Step 2: (S)—N-ethyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide

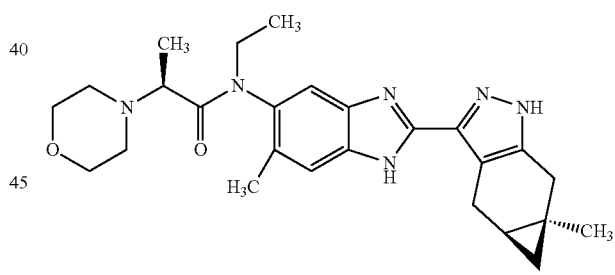

A solution of the silyl ether of Step 1 (78 mg, 0.132 mmol) in TFA (1.5 mL) at 0-5° C. was treated with Et₃SiH (80 mg, 0.69 mmol). After stirring at 15° C. for 2 h, the solvent was removed and the reaction made basic with sat. aq. Na₂CO₃. The mixture was extracted with premixed DCM/MeOH (10:1.8 mL×3) and the extracts combined. The concentrated and the residue purified by prep HPLC [YMC-Actus Triart Prep C18 150 mm×30 mm×5 μM, water (0.05% NH4OH)/MeCN from 43 to 63% over 10 min, 35 ml/min] to give the title compound (35 mg, 57%). SFC method: Chiral Tech AD-3 50 mm×4.6 mm×3 μm, CO₂/EtOH (0.05%) isocratic 40%, 4 mL/min, column temperature 35° C., retention time=0.45 min (51.01%) and 1.39 (48.99%), 100% ee; ¹H NMR (400 MHz, DMSO-de) δ 12.88 (s, 1H), 12.60 (d, 1H), 7.69-7.46 (m, 0.75H), 7.41-7.33 (m, 1.25H), 4.11 (tq, 1H), 3.51-3.42 (m, 2H), 3.11-2.94 (m, 5H), 2.74 (d, 1H), 2.46 (s, 2H), 2.35 (s, 3H), 2.22 (d, 2H), 2.12-2.04 (m, 1H), 2.02 (s, 1H), 1.25 (s, 3H), 1.13-0.91 (m, 7H), 0.37 (dd, 1H), 0.16 (d, 1H); LC/MS m/z (M+H)⁺=463.2.

Example 7: (R)—N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide

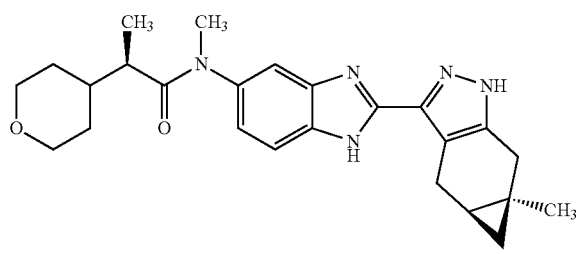 [SMILES: C[C@@H](C(=O)N(C)c1ccc2[nH]c(-c3n[nH]c4c3C[C@@H]3C[C@]3(C)C4)nc2c1)C1CCOCC1]

Step 1: (R)—N-methyl-N-(2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)-2-(tetrahydro-2H-pyran-4-yl)propanamide

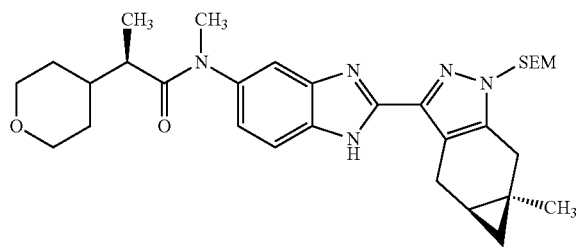 [SMILES: C[C@@H](C(=O)N(C)c1ccc2[nH]c(-c3nn(COCC[Si](C)(C)C)c4c3C[C@@H]3C[C@]3(C)C4)nc2c1)C1CCOCC1]

A solution of Preparation 55 (6.9 g, 16.3 mmol) and Preparation 22 (2.83 g, 17.9 mmol) in pyridine (163 mL) at RT was added EDCI (6.24 g, 32.6 mmol). The mixture was stirred at 25° C. for 16 h and diluted with water (150 mL) and brine (150 mL). The resulting aqueous mixture was extracted with EtOAc (2×300 mL) and the extracts dried (Na₂SO₄), filtered and concentrated. The crude material was purified by chromatography (silica, EtOAc/PE=0-90%) to give the title compound (6.9 g, 75% yield). ¹H NMR (400 MHz, CD₃OD) δ 7.77 (s, 0.5H), 7.65-7.51 (m, 1H), 7.40 (s, 0.5H), 7.14 (bs, 1H), 5.56-5.37 (m, 2H), 3.94-3.77 (m, 2H), 3.63 (t, 2H), 3.45-3.06 (m, 8H), 2.78 (d, 1H), 2.31-2.10 (m, 1H), 1.83-1.68 (m, 1H), 1.60 (d, 2H), 1.32 (s, 3H), 1.28-1.11 (m, 2H), 1.05 (d, 3H), 0.98-0.87 (m, 3H), 0.45 (dd, 1H), 0.27 (t, 1H), −0.03 (s, 9H); LC/MS m/z (M+H)⁺=564.2.

Step 2: (R)—N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide

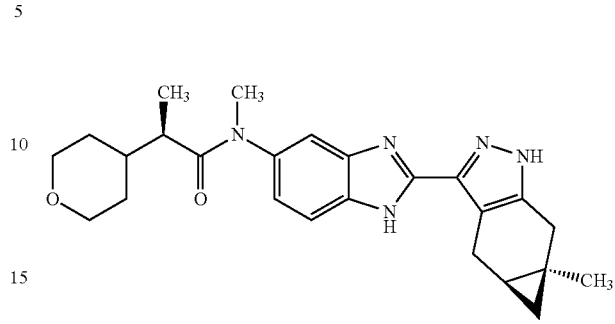

A solution of the silyl ether of Step 1 (6.9 g, 12.2 mmol) in TFA (122 mL) at 25° C. was treated with Et₃SiH (7.12 g, 61.2 mmol). After stirring for 3 h, the mixture was concentrated and made basic with sat. sq. NaHCO₃. The resulting mixture was extracted with EtOAc (2×100 mL). The organic extracts were dried (Na₂SO₄), filtered and concentrated. The crude material was purified by chromatography (silica, EtOAc/PE, 10-100%). The resultant material was purified further by chiral SFC (CO₂/MeOH+ 1% NH₄OH, Daicel OJ, 250 mm×50 mm×10 μm) to give the final product (3.43 g, 64.6%).

¹H NMR (400 MHz, CD₃OD) δ 7.79-7.41 (m, 2H), 7.17-7.05 (m, 1H), 3.87 (td, 2H), 3.41-3.28 (m, 6H), 3.20-3.00 (m, 2H), 2.78 (d, 1H), 2.22 (dq, 1H), 1.75 (q, 1H), 1.60 (d, 2H), 1.29 (s, 3H), 1.24-1.12 (m, 2H), 1.05 (d, 3H), 1.00-0.88 (m, 1H), 0.42 (dd, 1H), 0.26 (t, 1H). LC/MS m/z (M+H)⁺=434.3; analytical SFC (ChiralCel OJ-H 150 mm×4.6 mm×5 μm, CO₂/EtOH (0.05% DEA), 5 to 40%), retention time=4.91 min (100%).

Example 8: N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide

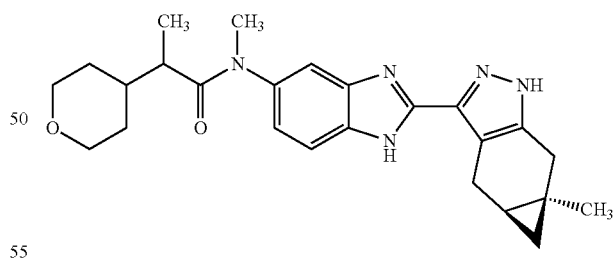

Example 8 was prepared analogously to Example 7 from Preparation 55 (350 mg) and (±)-2-(tetrahydro-2H-pyran-4-yl)propanoic acid (131 mg) and purified by prep HPLC (YMC-Actus Triart C18, 100×30 mm×5 μm, H₂O/MeCN+ 0.05% NH₄OH, 38%-58% over 10 min) to deliver the title compound (150 mg, 39.4%). ¹H NMR (400 MHz, CD₃OD) δ 7.79-7.38 (m, 2H), 7.13 (dd, 1H), 3.87 (t, 2H), 3.41-3.33 (m, 3H), 3.31 (s, 3H), 3.19-3.10 (m, 1H), 3.07 (d, 1H), 2.78 (d, 1H), 2.21 (dq, 1H), 1.84-1.68 (m, 1H), 1.60 (d, 2H), 1.29 (s, 3H), 1.27-1.10 (m, 2H), 1.05 (d, 3H), 0.95 (qd, 1H), 0.42 (dd, 1H), 0.26 (t, 1H). LC/MS m/z (M+H)⁺=434.3.

Example 9: (S)—N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide

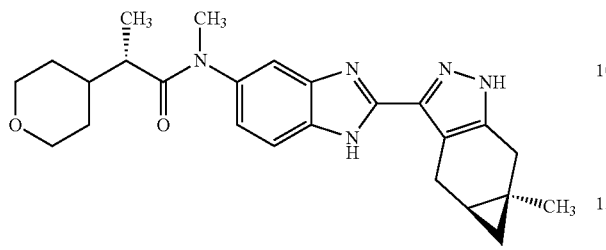

Example 9 was prepared analogously to Example 7 from Preparation 55 (296 mg) and (S)-2-(tetrahydro-2H-pyran-4-yl)propanoic acid (111 mg) and purified by Prep-HPLC (YMC-Actus triart C18, 100× 30 mm×5 µm, H₂O/MeCN (0.05% NH₄OH), 38 to 58% over 10 min) to give the title compound (102 mg). $^1$H NMR (400 MHz, CD₃OD) δ 7.81-7.34 (m, 2H), 7.11 (dd, 1H), 3.86 (ddd, 2H), 3.41-3.31 (m, 3H), 3.31 (s, 3H), 3.13 (dd, 1H), 3.05 (d, 1H), 2.76 (d, 1H), 2.20 (dq, 1H), 1.73 (td, 1H), 1.58 (dd, 2H), 1.28 (s, 3H), 1.25-1.10 (m, 2H), 1.03 (d, 3H), 0.93 (qd, 1H), 0.40 (dd, 1H), 0.24 (t, 1H). Chiral SFC (ChiralCel OJ-H 150×4.6 mm×5 µm, CO₂/EtOH (0.05% DEA), 5 to 40%), retention time=3.60 min.

Example 10: N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)acetamide

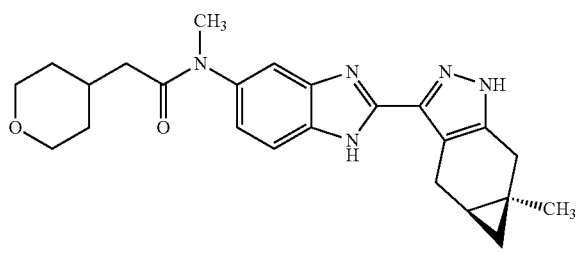 [SMILES: CN(C(=O)CC1CCOCC1)c1ccc2[nH]c(-c3n[nH]c4c3C[C@@H]3C[C@]3(C)C4)nc2c1]

Example 10 was prepared analogously to Example 7 from Preparation 55 (200 mg) and 2-(tetrahydro-2H-pyran-4-yl)acetic acid (82 mg) and purified by chiral SFC (Daicel Chiralcel OJ-H (250 mm×30 mm×5 µm), CO₂/EtOH w/0.1% NH₄OH, 25% isocratic) to give the title compound (71 mg). $^1$H NMR (400 MHz, CD₃OD) δ 7.75-7.39 (m, 2H), 7.13 (d, 1H), 3.83 (dd, 2H), 3.41-3.32 (m, 4H), 3.14 (dd, 1H), 3.07 (d, 1H), 2.78 (d, 1H), 2.15-1.92 (m, 3H), 1.57 (d, 2H), 1.30 (s, 3H), 1.23-0.99 (m, 3H), 0.42 (dd, 1H), 0.26 (t, 1H); LC/MS m/z (M+H)⁺=420.3.

Example 11: 2,2-difluoro-N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)acetamide

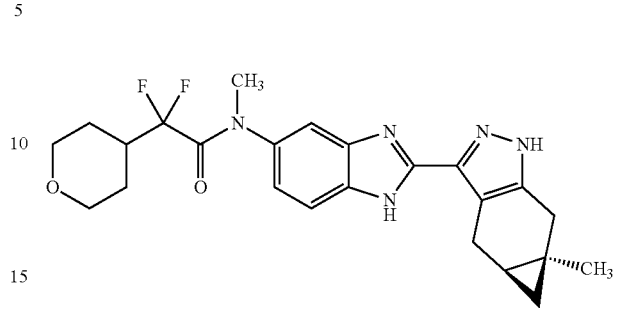

Example 11 was prepared analogously to Example 7 from Preparation 55 (200 mg) and 2,2-difluoro-2-(tetrahydro-2H-pyran-4-yl)acetic acid (170 mg) and purified by chiral SFC (Daicel Chiralcel OJ-H, 250 mm×30 mm×5 µm; CO₂/EtOH (0.1% NH₄OH), 25% isocratic) to give the title compound (60 mg). $^1$H NMR (400 MHz, DMSO-d₆) δ 12.89 (s, 1H), 12.73 (d, 1H), 7.62 (d, 0.5H), 7.55 (d, 0.5H), 7.42 (d, 0.5H), 7.31 (s, 0.5H), 7.13-7.04 (m, 1H), 3.87-3.74 (m, 2H), 3.47-3.31 (m, 2H), 3.25 (s, 3H), 3.18 (t, 2H), 3.04-2.92 (m, 2H), 2.72 (d, 1H), 2.35-2.14 (m, 1H), 1.49 (d, 2H), 1.31-1.19 (m, 5H), 1.15-1.00 (m, 1H), 0.36 (dd, 1H), 0.14 (t, 1H). LC/MS m/z (M+H)⁺=582.3.

Example 12: (R)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-(tetrahydro-2H-pyran-4-yl)propanamide

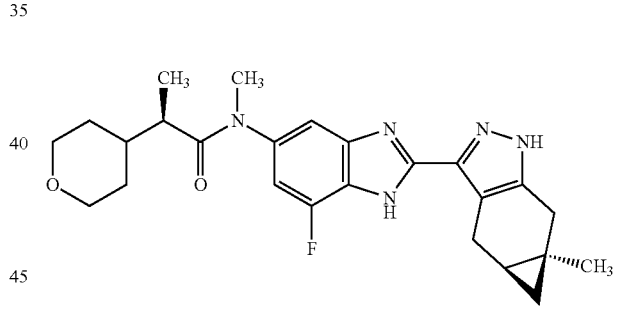

Step 1: (R)—N-(7-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)-N-methyl-2-(tetrahydro-2H-pyran-4-yl)propanamide

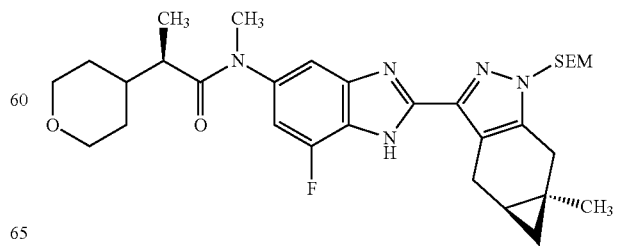

A solution of Preparation 57 (3.0 g, 6.79 mmol) in pyridine (67.9 mL) at 25° C. was added Preparation 22 (1.50 g, 9.51 mmol) and EDCI (2.87 g, 14.9 mmol). The mixture was stirred at 25° C. for 16 h and concentrated. The residue was diluted with water and extracted with EtOAc (5×100 mL). The organic extracts were combined, dried (Na$_2$SO$_4$), filtered and concentrated. The crude material was purified by chromatography (silica, EtOAc/PE=0-50%) to give the title compound (2.3 g, 58.2%). $^1$H NMR (400 MHz, CD$_3$OD) δ 7.26 (bs, 1H), 6.97 (d, J=10.9 Hz, 1H), 5.59-5.37 (m, 2H), 3.89 (td, J=12.4, 11.9, 4.1 Hz, 2H), 3.63 (t, J=7.9 Hz, 2H), 3.49-3.30 (m, 6H), 3.25-3.09 (m, 2H), 2.78 (d, J=16.3 Hz, 1H), 2.24 (dq, J=9.2, 6.7 Hz, 1H), 1.84-1.67 (m, 1H), 1.61 (d, J=13.2 Hz, 2H), 1.36-1.13 (m, 6H), 1.07 (d, J=6.8 Hz, 3H), 0.94-0.85 (m, 2H), 0.45 (dd, J=8.9, 4.6 Hz, 1H), 0.27 (t, J=5.1 Hz, 1H), −0.02 (s, 9H); LC/MS m/z (M+H)$^+$=582.3.

Step 2: (R)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-(tetrahydro-2H-pyran-4-yl)propanamide

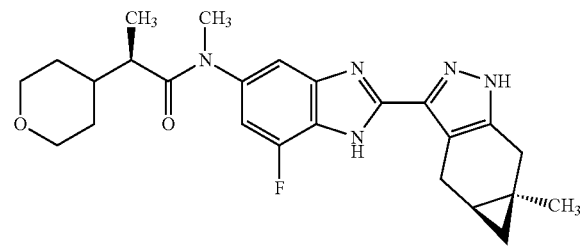 [SMILES: C[C@@H](C(=O)N(C)c1cc(F)c2[nH]c(-c3n[nH]c4c3C[C@@H]3C[C@]3(C)C4)nc2c1)C1CCOCC1]

A solution of the silyl ether of step 1 (2.30 g, 3.95 mmol) in TFA (39.5 mL) at 5° C. was treated with Et$_3$SiH (2.30 g, 19.8 mmol). After stirring 3 h at RT, the mixture was concentrated and the residue diluted with sat. aq Na$_2$CO$_3$. The mixture was extracted with EtOAc (2×30 mL) and the organic extracts combined, dried (Na$_2$SO$_4$), filtered and concentrated. The crude material was purified by chromatography (silica, EtOAc/PE=20-100%). The compound was taken up in MeCN (10 mL), EtOH (10 mL) and H$_2$O (150 mL) and lyophilized to give the title compound (1.78 g, 99%). $^1$H NMR (400 MHz, CD$_3$OD) 7.25 (s, 1H), 6.95 (d, 1H), 3.95-3.78 (m, 2H), 3.43-3.25 (m, 6H), 3.20-3.11 (m, 1H), 3.07 (d, 1H), 2.78 (d, 1H), 2.30-2.12 (m, 1H), 1.75 (q, 1H), 1.60 (t, 2H), 1.30 (s, 3H), 1.25-1.11 (m, 2H), 1.06 (d, 3H), 0.98 (dt, 1H), 0.42 (dd, 1H), 0.25 (t, 1H). LC/MS m/z (M+H)=452.3.

Example 13: (S)—N-(2-((4aS,5aR)-5,5-difluoro-5a-methyl-1,4,4a,5,5a,6-hexahydrocyclopropa[f]indazol-3-yl)-1H-benzo[d]imidazol-5-yl)-N-methyl-2-morpholinopropanamide

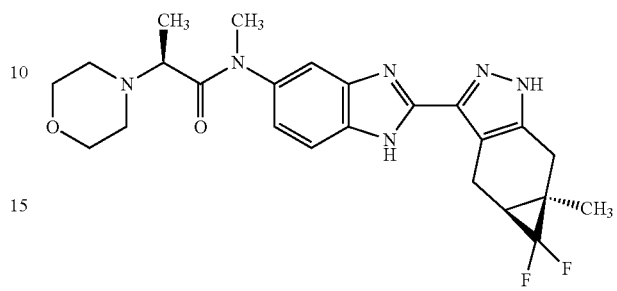

Step 1: (4aS,5aR)—N-(2-amino-5-((S)—N-methyl-2-morpholinopropanamide)phenyl)-5,5-difluoro-5a-methyl-1,4,4a,5,5a,6-hexahydrocyclopropa[f]indazole-3-carboxamide

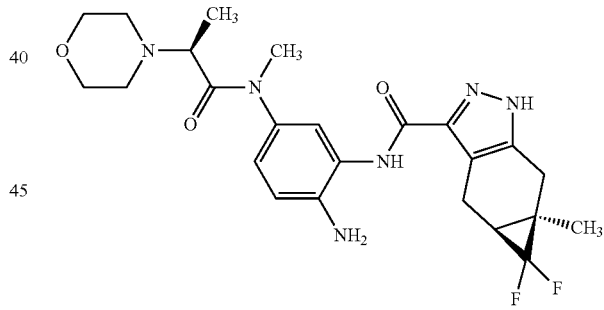

To a solution of Preparation 68 (700 mg, 3.07 mmol) in DMF (40 mL) at RT was treated with HBTU (1.75 g, 4.60 mmol), DMAP (37.5 mg, 0.31 mmol), iPr$_2$NEt (1.19 mg, 9.2 mmol) and 32 (854 mg, 3.07 mmol). The mixture was stirred at 80° C. for 16 h and diluted with sat. aq. NaHCO$_3$ (100 mL). The aqueous was extracted with EtOAc (4×100 mL) and the organic layers combined, dried (Na$_2$SO$_4$), filtered and concentrated. The crude product was purified by chromatography (silica, EtOAc/PE=0-100%, then EtOAc/EtOH 3:1) to give the title compound (850 mg, 57%). LC/MS m/z (M+H)$^+$=488.9.

Step 2: (S)—N-(2-((4aS,5aR)-5,5-difluoro-5a-methyl-1,4,4a,5,5a,6-hexahydrocyclopropa[f]indazol-3-yl)-1H-benzo[d]imidazol-5-yl)-N-methyl-2-morpholinopropanamide

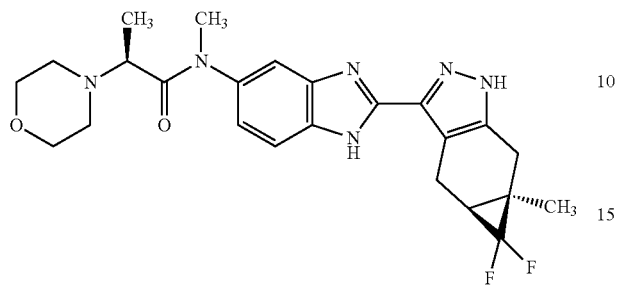

A mixture of the amide of step 1 (850 mg, 1.74 mmol) and AcOH (50 mL) was stirred at 90° C. for 16 h and concentrated. The residue was diluted with EtOAc (50 mL) and washed with saturated Na₂CO₃. The aqueous layer was extracted with EtOAc (4×100 mL). The organic extracts were combined and concentrated. The residue was purified by prep-HPLC (Xtimiate C-18 150×25 mm×5 μm, H₂O/CH₃CN (0.225% FA), 20-40% over 8 min) to give the title compound (289 mg, 35%). $^1$H NMR (400 MHz, CD₃OD) δ 7.75-7.49 (m, 2H), 7.18 (d, 1H), 3.70-3.56 (m, 4H), 3.33 (s, 3H), 3.23 (q, 1H), 3.14 (d, 1H), 2.86 (dd, 1H), 2.56 (dt, 2H), 2.40 (dd, 2H), 1.83-1.67 (m, 1H), 1.43 (d, 3H), 1.18 (d, 3H); LC/MS m/z (M+H)$^+$=435.3.

Example 14: (S)—N-methyl-N-(2-((4aS,5aR)-5a-methyl-1,4,4a,5,5a,6-hexahydrocyclopropa[f]indazol-3-yl)-1H-benzo[d]imidazol-5-yl)-2-morpholinopropanamide

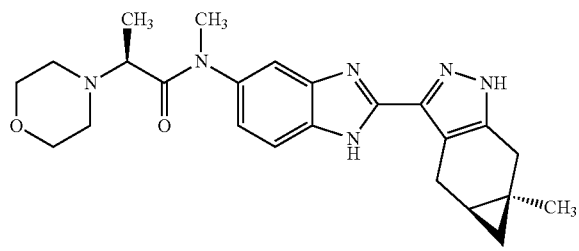 [SMILES: C[C@@H](C(=O)N(C)c1ccc2[nH]c(-c3n[nH]c4c3C[C@@H]3C[C@]3(C)C4)nc2c1)N1CCOCC1]

Step 1: (S)—N-methyl-N-(2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)-2-morpholinopropanamide

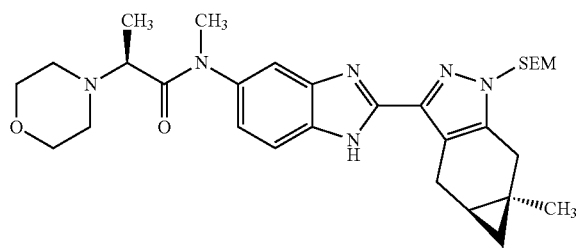 [SMILES: C[C@@H](C(=O)N(C)c1ccc2[nH]c(-c3nn(COCC[Si](C)(C)C)c4c3C[C@@H]3C[C@]3(C)C4)nc2c1)N1CCOCC1]

A mixture of Preparation 32 (1.53 g, 5.5 mmol), Preparation 9 (1.69 g, 5.5 mmol) in EtOH (27.5 mL) and water (2.75 mL) was treated with Na₂S2O3 (1.14 g, 11.0 mml). The mixture was heated at 90° C. for 2 h. The mixture was concentrated and residue diluted with EtOAc and H₂O. The layers were separated and the aqueous layer extracted with EtOAc (2×). The organic extracts were combined, dried (Na₂SO₄), filtered and concentrated. The crude product was purified by chromatography (silica, EtOAc/Heptanes=10-100%, then EtOAc/MeOH=0-15%) to give the title compound (2.41 g, 78%). LC/MS m/z (M+H)$^+$=565.5.

Step 2: (S)—N-methyl-N-(2-((4aS,5aR)-5a-methyl-1,4,4a,5,5a,6-hexahydrocyclopropa[f]indazol-3-yl)-1H-benzo[d]imidazol-5-yl)-2-morpholinopropanamide

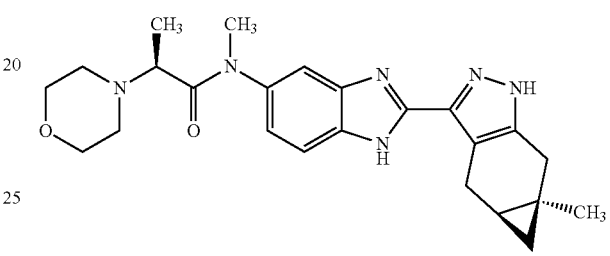

A solution of the silyl ether of step 1 (2.41 g, 4.26 mmol) in DCM (12.8 mL) at 0° C. was treated with TFA (8.61 mL) and stirred at RT for 18 h. The mixture was concentrated and the residue dissolved in THF/MeOH and the pH adjusted to 10 with solid K₂CO₃. The mixture was diluted in 10% MeOH in DCM and washed with brine. The aqueous layer was extracted with 10% MeOH in DCM. The organic extracts were combined, dried, filtered and concentrated. The crude product was purified by chiral SFC (Chiralcel OJ, 30 mm×250 mm×5 μm, CO₂/MeOH (0.2% NH₃), isocratic 25% over 10 min) to give the title compound (0.89 g, 48%). $^1$H NMR (400 MHz, DMSO-de) δ 12.93-12.87 (m, 1H), 12.73 (d, J=5.9 Hz, 1H), 7.63 (d, J=8.4 Hz, 0.5H), 7.55 (s, 0.5H), 7.44 (d, J=8.3 Hz, 0.5H), 7.35 (s, 0.5H), 7.07 (t, J=9.9 Hz, 1H), 3.50-3.41 (m, 5H), 3.23-3.13 (m, 4H), 2.98 (dd, J=16.2, 8.6 Hz, 2H), 2.72 (d, J=16.1 Hz, 1H), 2.46-2.35 (m, 2H), 2.31-2.11 (m, 2H), 1.23 (s, 3H), 1.15-0.88 (m, 4H), 0.36 (dd, J=8.8, 4.3 Hz, 1H), 0.14 (s, 1H). LC/MS m/z (M+H)$^+$=435.3. Chiral SFC (Lux Cellulose-2, 150×4.6 mm×3 μm, CO₂/EtOH (0.1% ethanolamine, 1 to 40% EtOH) retention time=2.96 min Example 15: (S)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

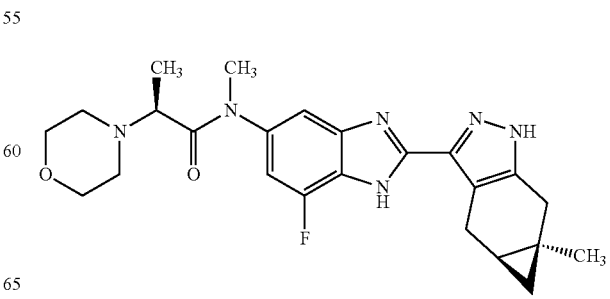

Step 1: (S)—N-(4-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-N-methyl-2-morpholinopropanamide and (S)—N-(7-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)-N-methyl-2-morpholinopropanamide

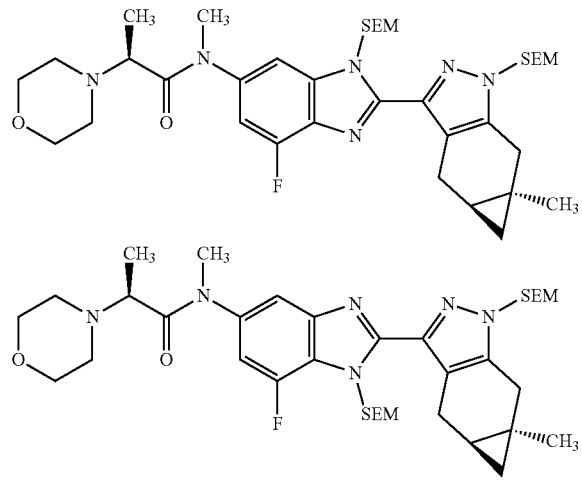

A mixture of Preparations 74a and 74b (mg, 0.19 mmol) in pyridine (2.77 mL) at 15° C. was treated with 19 (45.6 mg, 0.23 mmol) and EDCI (74.4 mg, 0.39 mmol). The mixture was stirred for 16 h. The mixture was diluted with water and extracted with EtOAc (2×20 mL). The organic extracts were combined, dried (Na$_2$SO$_4$), filtered and concentrated to give the title compounds as a mixture (131 mg, 95%). LC/MS m/z (M+Na)$^+$=735.1

Step 2: (S)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

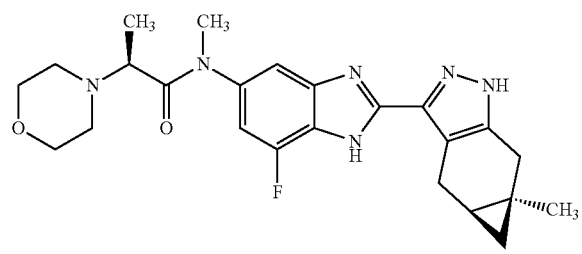 [SMILES: C[C@@H](C(=O)N(C)c1cc(F)c2[nH]c(-c3n[nH]c4c3C[C@@H]3C[C@]3(C)C4)nc2c1)N1CCOCC1]

A mixture of the silyl ethers of step 1 (131 mg, 0.18 mmol) in TFA (1.84 mL) at 10° C. was treated with Et$_3$SiH (107 mg, 0.92 mmol). After stirring 3 h, the mixture was concentrated and the residue made basic with sat. aq. Na$_2$CO$_3$. The mixture was extracted with EtOAc (3×15 mL) and the extracts combined. The solvent was removed and the residue was purified by prep HPLC (H$_2$O: MeCN, 0.05% TFA) to give the title compound (37 mg, 45%).

$^1$H NMR (400 MHz, CD$_3$OD) δ 7.34 (s, 1H), 7.04 (d, 1H), 4.61 (s, 1H), 3.62 (ddd, 4H), 3.30 (s, 3H), 3.37 (d, 1H), 3.23 (q, 1H), 3.19-3.10 (m, 1H), 3.07 (d, 1H), 2.78 (d, 1H), 2.54 (dt, 2H), 2.36 (dt, 2H), 1.30 (s, 3H), 1.17 (d, 3H), 0.42 (dd, 1H), 0.25 (t, 1H); LC/MS m/z (M+H)$^+$=453.3

Example 16: (S)—N-ethyl-N-(7-fluoro-2-((4aS,5aR)-5a-methyl-1,4,4a,5,5a,6-hexahydrocyclopropa[f]indazol-3-yl)-1H-benzo[d]imidazol-5-yl)-2-morpholinopropanamide

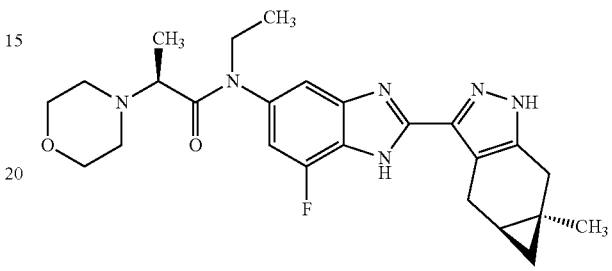

Step 1: (S)—N-ethyl-N-(4-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-2-morpholinopropanamide and (S)—N-ethyl-N-(7-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)-2-morpholinopropanamide

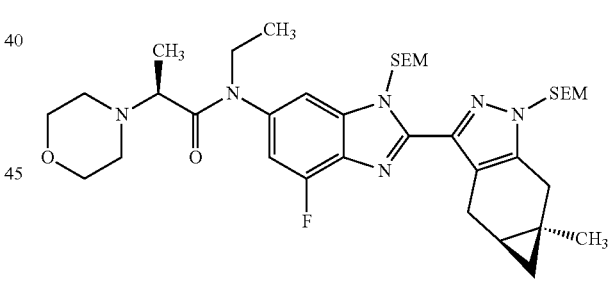

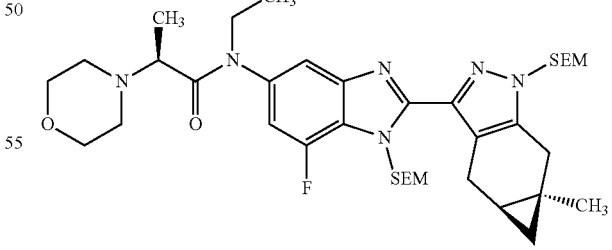

A mixture of Preparations 76a and 76b (6.14 g, 10.48 mmol) and 19 (1.46 g, 9.17 mmol) in pyridine (70 mL) at 30° C. was treated with EDCI (4.02 g, 21.0 mmol). After stirring for 16 h the solvent was removed and water was (80 mL) was added. The mixture was extracted with EtOAc (2×80 mL) and the organic extracts combined, dried (Na$_2$SO$_4$), filtered and concentrated. The crude product was purified by chromatography (silica, EtOAc/PE=0-50%) to give the title compounds as a mixture (5.13 g, 67%). LC/MS m/z (M+H)=727.4

Step 2: (S)—N-ethyl-N-(7-fluoro-2-((4aS,5aR)-5a-methyl-1,4,4a,5,5a,6-hexahydrocyclopropa[f]indazol-3-yl)-1H-benzo[d]imidazol-5-yl)-2-morpholinopropanamide

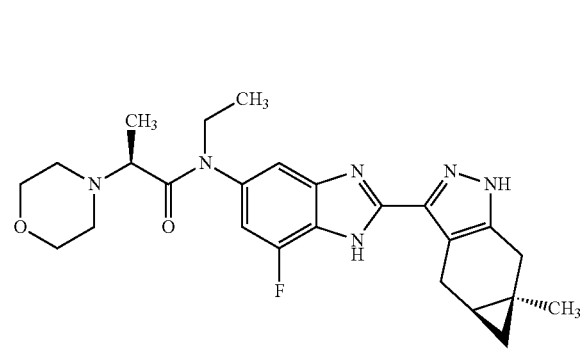 [SMILES: CCN(C(=O)[C@H](C)N1CCOCC1)c1cc(F)c2[nH]c(-c3n[nH]c4c3C[C@@H]3C[C@]3(C)C4)nc2c1]

A mixture of the silyl ethers of step 1 (5.13 g, 7.06 mmol) in TFA (35 mL) at 0° C. was treated with Et₃SiH (4.1 g, 35.3 mmol). The mixture was stirred at 30° C. for 3 h. The mixture was concentrated and the residue diluted with sat. aq. NaHCO₃. The mixture was extracted with EtOAc (2×100 mL) and the organic extracts combined, dried (Na₂SO₄), filtered and concentrated. The crude product was chromatographed (silica, EtOAc/PE=0-50%. (2.66 g, 81%). The mixture was further purified by chiral SFC (Daicel Chiralpak AD, 250 mm×50 mm×10 μm; CO₂/EtOH (0.1% NH₄OH), 50% isocratic) to give the title compound (1.72 g, 52%). ¹H NMR (400 MHz, CD₃OD) δ 7.31 (bs, 1H), 7.05-6.93 (m, 1H), 3.78 (s, 2H), 3.61 (ddd, 4H), 3.38 (d, 1H), 3.14 (dt, 2H), 3.06 (d, 1H), 2.76 (d, 1H), 2.53 (dt, 2H), 2.35 (dt, 2H), 1.28 (s, 3H), 1.20-1.11 (m, 7H), 0.40 (dd, 1H), 0.24 (t, 1H); LC/MS m/z (M+H)⁺=467.1.

Example 17: (S)—N-(6-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

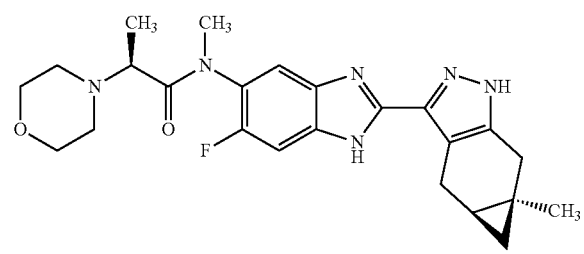 [SMILES: C[C@@H](C(=O)N(C)c1cc2nc(-c3n[nH]c4c3C[C@@H]3C[C@]3(C)C4)[nH]c2cc1F)N1CCOCC1]

Step 1: (S)—N-(6-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)-N-methyl-2-morpholinopropanamide and (S)—N-(5-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-N-methyl-2-morpholinopropanamide A mixture of Preparations 80a and 80b (170 mg, 0.29 mmol) in pyridine (4.95 mL) at 15° C. was treated with 19 (71 mg, 0.45 mmol) and EDCI (114 mg, 0.6 mmol). The mixture was stirred for 2 days then diluted with water and extracted with EtOAc (2×20 mL). The organic extracts were collected, dried (Na₂SO₄), filtered and concentrated to give the title compounds as a mixture (180 mg, 85%). LC/MS m/z (M+H)⁺=713.5

Step 2: (S)—N-(6-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide A mixture of the silyl ethers of step 1 (180 mg, 0.25 mmol) in TFA (2.52 mL) at 10° C. was treated withe Et₃SiH (147 mg, 1.26 mmol). The mixture was stirred for 3 h and concentrated. The mixture was made basic with sat. aq. Na₂CO₃ and extracted with EtOAc (3×8 mL). The combined extracts were concentrated and the residue was purified by prep HPLC (YMC-Triart Prep C18 150 mm×40 mm×7 μM, water (0.05% NH₄OH)/MeCN from 42 to 62% over 10 min, 25 ml/min) to give the title compound (38 mg, 34%). ¹H NMR (400 MHz, CD₃OD) δ 7.72-7.39 (m, 2H), 3.69-3.50 (m, 4H), 3.39 (d, 1H), 3.30 (d, 3H), 3.27-3.04 (m, 3H), 2.79 (d, 1H), 2.54 (dt, 1H), 2.41 (dd, 2H), 2.27 (ddd, 1H), 1.31 (s, 3H), 1.23-1.12 (m, 4H), 0.44 (dd, 1H), 0.27 (t, 1H); LC/MS m/z (M+H)⁺=453.2.

Example 18: (S)—N-(6-ethyl-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

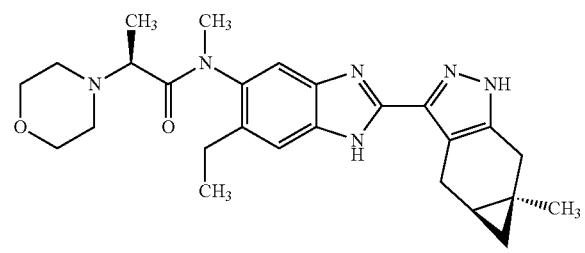 [SMILES: CCc1cc2[nH]c(-c3n[nH]c4c3C[C@@H]3C[C@]3(C)C4)nc2cc1N(C)C(=O)[C@H](C)N1CCOCC1]

Example 18 was prepared analogously to Example 1 from 5-chloro-2-ethyl-4-nitroaniline to deliver the title compound (50 mg, 57%). 1H NMR (400 MHz, CD₃OD) δ 7.54 (s, 2H), 3.69-3.58 (m, 4H), 3.38 (d, 1H), 3.27 (d, 3H), 3.20-3.01 (m, 3H), 2.87-2.72 (m, 1H), 2.67 (q, 2H), 2.56 (d, 2H), 2.35-2.27 (m, 2H), 1.37 (dt, 3H), 1.31 (s, 3H), 1.19 (t, 2H), 1.11 (dd, J=6.6, 1.7 Hz, 2H), 0.44 (dd, 1H), 0.28 (d, J=5.6 Hz, 1H). LC/MS m/z (M+H)⁺=463.4.

Example 19: (S)—N-(6-methoxy-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

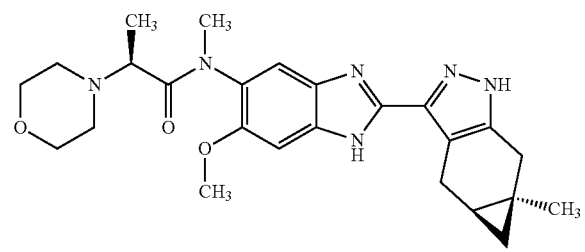 [SMILES: COc1cc2[nH]c(-c3n[nH]c4c3C[C@@H]3C[C@]3(C)C4)nc2cc1N(C)C(=O)[C@H](C)N1CCOCC1]

Step 1: (S)—N-(6-methoxy-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)-N-methyl-2-morpholinopropanamide

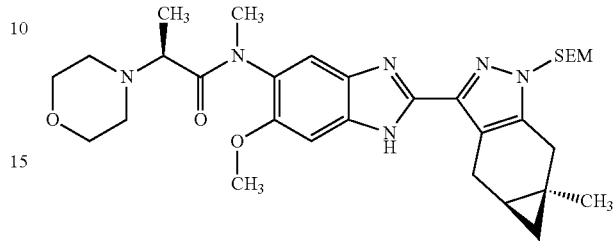

A mixture of Preparation 84 (189 mg, 0.61 mmol), Na₂S₂O₅ (126 mg, 0.66 mmol) in DMF (7.3 mL) was treated with Preparation 9 (157 mg, 0.51 mmol). The mixture was heated in a microwave reactor at 150° C. for 2 h and poured into 3% aq. LiCl (20 mL) and EtOAc (30 mL). The layers were separated and the aqueous layer extracted with EtOAc (30 mL). The organic layers were collected, dried (Na₂SO₄), filtered and concentrated. The crude product was chromatographed (silica, EtOAc/PE=0-100%) to give the title compound (201 mg, 44%). LC/MS m/z (M+H)⁺=595.3.

Step 2: (S)—N-(6-methoxy-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

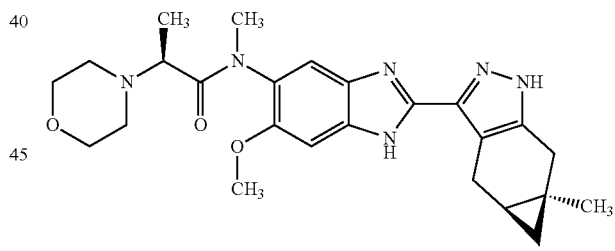

A solution of the silyl ether of step 1 (201 mg, 0.338 mmol) in TFA (3.38 mL) at 0-5° C. was treated with Et₃SiH (196 mg, 1.69 mmol). The mixture was stirred at RT for 2 h and concentrated. The residue was made basic with sat. aq NaHCO₃. The mixture was extracted with EtOAc (2×20 mL) and the extracts and concentrated. The residue was purified by prep HPLC (YMC Triart C18 150 mm×30 mm×7 μM, Water (0.05% NH₄OH)/MeCN from 25 to 75% over 10 min, 25 ml/min) to give the title compound (87 mg, 55%). ¹H NMR (400 MHz, CD₃OD) δ 7.56 (s, 1H), 7.28 (s, 1H), 3.94 (d, 3H), 3.63 (tq, 4H), 3.41-3.34 (m, 1H), 3.23 (d, 3H), 3.20-3.08 (m, 2H), 3.08-2.97 (m, 1H), 2.79 (d, 1H), 2.54 (dt, 1H), 2.44 (dt, 3H), 1.31 (s, 3H), 1.26-1.10 (m, 4H), 0.43 (dd, 1H), 0.27 (t, 1H); LC/MS m/z (M+H)⁺=465.2.

Example 20: (S)—N-(6-bromo-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

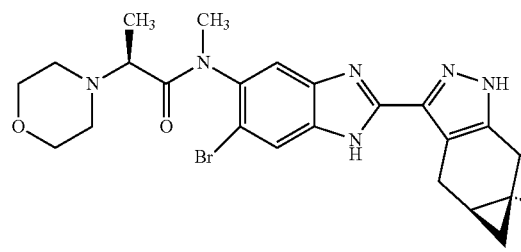

A solution of Preparation 85 (100 mg, 0.155 mmol) in TFA (5.0 mL) at 0° C. was treated with Et$_3$SiH (90.3 mg, 0.77 mmol). The mixture was stirred for 2 h and concentrated. The residue was dissolved in MeOH (10 mL) and treated with conc. NH$_4$OH (1 mL). The mixture was stirred at RT for 1 h and concentrated. The residue was purified by prep-HPLC (Boston Prime C18, 150×30 mm×5 μm, H$_2$O/MeCN (0.05% NH$_4$OH) 10-70% over 10 min) to give the title compound (61 mg, 76%). $^1$H NMR (400 MHz, DMSO-d$_6$) δ 13.09-12.65 (m, 2H), 7.99-7.63 (m, 2H), 3.58-3.38 (m, 5H), 3.18-3.09 (m, 3H), 3.08-2.86 (m, 2H), 2.81-2.60 (m, 1H), 2.46-2.28 (m, 2H), 2.24-1.91 (m, 2H), 1.24 (s, 3H), 1.17-0.90 (m, 4H), 0.37 (dd, 1H), 0.15 (t, 1H). LC/MS m/z (M+H)$^+$=513.3/515.5 ($^{79}$Br, $^{81}$Br).

Example 21. (S)—N-(6-cyano-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

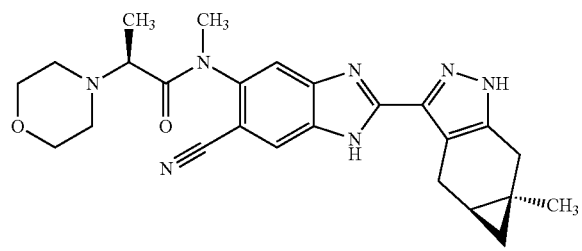 [SMILES: C[C@@H](C(=O)N(C)c1cc2nc(-c3n[nH]c4c3C[C@@H]3C[C@]3(C)C4)[nH]c2cc1C#N)N1CCOCC1]

A mixture of Preparations 87a and 87b (150 mg, 0.21 mmol) in TFA (5 mL) was treated with Et$_3$SiH (121 mg, 1.04 mmol) at 0° C. The mixture was stirred for 2 h and concentrated. The residue was dissolved in MeOH (10 mL) and conc. NH$_4$OH (1 mL) was added. The mixture was stirred 1 h and the mixture was concentrated. The residue was purified by prep-HPLC (Boston Prime C18, 150×30 mm×5 μm; H$_2$O/MeCN (0.2% FA), 23-45% over 10 min) to give the title compound (34 mg, 35%). $^1$H NMR (400 MHz, DMSO-d$_6$) δ 13.22-13.05 (m, 2H), 8.35-7.36 (m, 2H), 3.58-3.25 (m, 5H), 3.22 (d, 3H), 3.01 (dd, 2H), 2.80-2.56 (m, 2H), 2.44-2.27 (m, 2H), 2.12-1.90 (m, 2H), 1.25 (s, 3H), 1.18-0.95 (m, 34H), 0.38 (dd, 1H), 0.16 (t, 1H); LC/MS m/z (M+H)$^+$=460.2.

Example 22: (S)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-(3-oxomorpholino)propanamide; and Example 23: (R)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-(3-oxomorpholino)propanamide

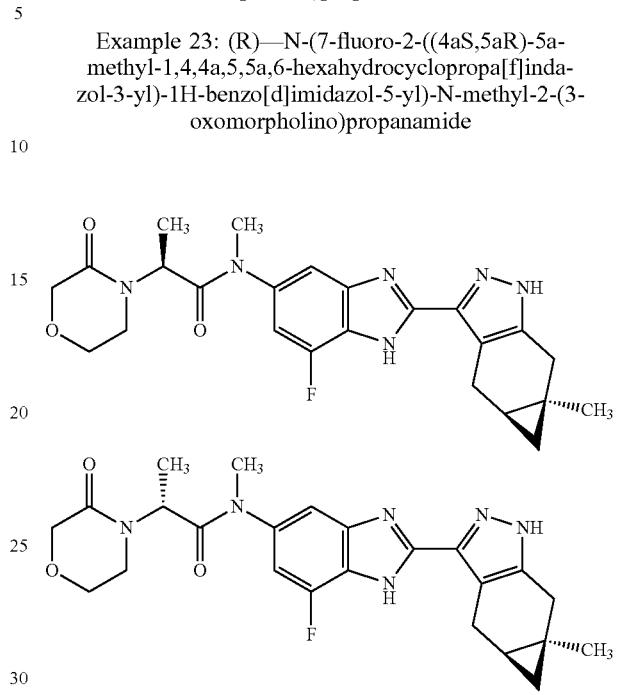

Step 1: N-(4-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-N-methyl-2-(3-oxomorpholino)propanamide and N-(7-fluoro-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)-N-methyl-2-(3-oxomorpholino)propanamide

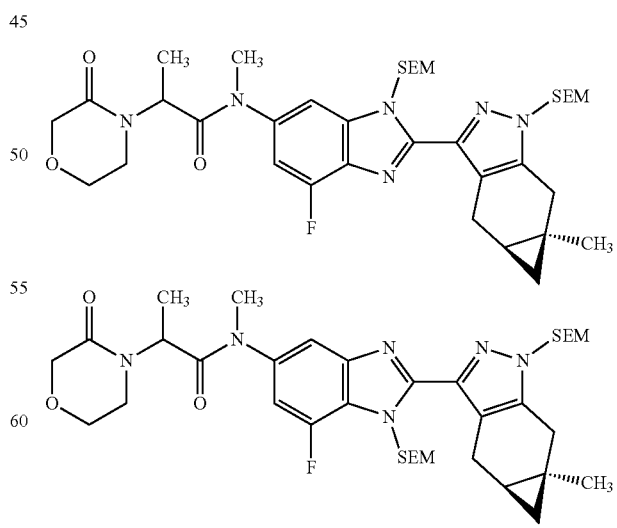

A mixture of Preparations 74a and 74b (150 mg, 0.26 mmol) and Preparation 26 (54.5 mg, 0.32 mmol) in pyridine (3.75 mL) at 25° C. was treated with EDCI (101 mg, 0.53 mmol). The mixture was stirred for 48 h and diluted with water (20 mL). The mixture was extracted with EtOAc (3×20 mL). The organic extracts were combined, dried and concentrated to give the title compounds as a mixture (60 mg, 31%). LC/MS m/z (M+H)$^+$=727.3.

Step 2: (S1-N-(7-fluoro-2-((4aS,5aR)-5a-methyl-1, 4,4a,5,5a,6-hexahydrocyclopropa[f]indazol-3-yl)-1H-benzo[d]imidazol-5-yl)-N-methyl-2-(3-oxomorpholino)propanamide and (R)—N-(7-fluoro-2-((4aS, 5aR)-5a-methyl-1,4,4a,5,5a,6-hexahydrocyclopropa [f]indazol-3-yl)-1H-benzo[d]imidazol-5-yl)-N-methyl-2-(3-oxomorpholino)propanamide

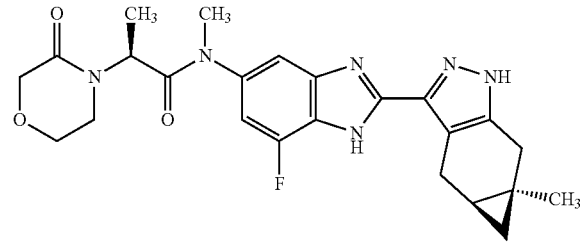

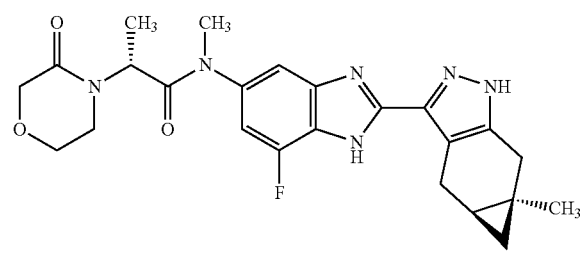

A mixture of the silyl enol ethers of step 1 (85.0 mg, 0.12 mmol) in TFA (1.2 mL) at 5° C. was treated with Et$_3$SiH (68.0 mg, 0.58 mmol). The mixture was stirred for 2 h and concentrated. The mixture was treated with sat. aq. NaHCO$_3$ and extracted with EtOAc (3×8 mL). The organic extracts were combined, dried, filtered and concentrated and the residue was which was purified by prep-HPLC (Phenomenex Gemini NX-C18, 75×30 mm×3 μm MeCN/H$_2$O (0.225% FA), 29-49% over 10 min). The mixture was separated by chiral SFC (Daicel ChiralPak AD, 250 mm×30 mm×10 μm, CO$_2$/EtOH (0.1% NH$_4$OH), 55% isocratic) to give the title compounds with absolute stereochemistry at C-2 methyl defined arbitrarily.

Example 22: $^1$H NMR (400 MHz, CD$_3$OD) δ 7.44-7.40 (m 1H), 7.08 (d, 1H), 5.14-5.07 (m, 1H), 4.03-3.85 (m, 3H), 3.81-3.71 (m, 1H), 3.56-3.44 (m, 1H), 3.38-3.25 (m, 4H), 3.14 (dd, 1H), 3.06 (d, 1H), 2.77 (d, 1H), 1.29 (s, 3H), 1.25 (d, 3H), 1.16 (dt, 1H), 0.41 (dd, 1H), 0.25 (t, 1H); LC/MS m/z (M+H)$^+$=467.1.

Example 23: $^1$H NMR (400 MHz, CD$_3$OD) δ 7.42 (s, 1H), 7.08 (d, 1H), 5.13-5.08 (m, 1H), 4.00-3.86 (m, 3H), 3.82-3.70 (m, 1H), 3.56-3.45 (m, 1H), 3.39-3.24 (m, 4H), 3.14 (dd, 1H), 3.06 (d, 1H), 2.77 (d, 1H), 1.29 (s, 3H), 1.25 (d, 3H), 1.16 (dt, 1H), 0.41 (dd, 1H), 0.25 (t, 1H); LC/MS m/z (M+H)$^+$=467.1.

Example 24: (S)—N-(6,7-difluoro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

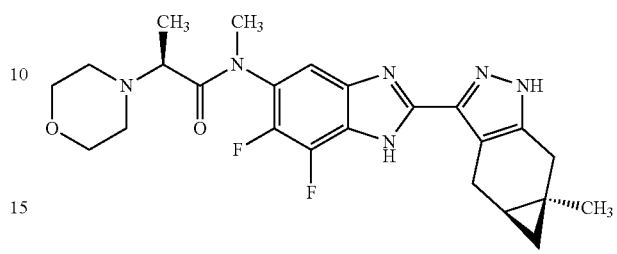

A mixture of Preparations 95a and 95b (3.26 g, 4.47 mmol) in TFA (45 mL) at 0° C. was treated with Et$_3$SiH (2.60 g, 22.3 mmol). The mixture was stirred for 5 h and concentrated. The mixture was treated with sat. aq. NaHCO$_3$ and extracted with DCM (3×30 mL). The organic extracts were combined, dried, filtered and concentrated. The residue was chromatographed (silica, MeOH/EtOAc=0-7%) and the isolated material dissolved in MeOH (30 mL)/H$_2$O (50 mL). The solvent was removed by lyophilization to give the title compound (1.56 q. 69%). $^1$H NMR (400 MHz, CD$_3$OD) δ 7.56-7.30 (m, 1H), 3.67-3.46 (m, 4H), 3.44-3.22 (m, 5H), 3.22-3.09 (m, 1H), 3.06 (d, 1H), 2.77 (d, 1H), 2.58-2.29 (m, 3H), 2.19 (ddd, 1H), 1.29 (s, 3H), 1.15 (dd, 4H), 0.42 (dd, 1H), 0.24 (t, 1H). $^{19}$F NMR (377 MHz, CD$_3$OD) 5-153.83.

Example 25: (S)—N-(6,7-difluoro-2-((4aS,5aR)-5a-methyl-1,4,4a,5,5a,6-hexahydrocyclopropa[f]indazol-3-yl)-1H-benzo[d]imidazol-5-yl)-N-ethyl-2-morpholinopropanamide

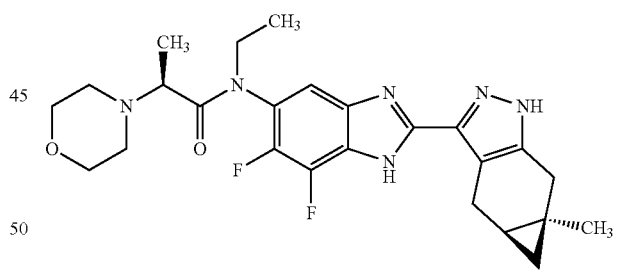

A mixture of Preparations 96a and 96b (120 mg, 0.16 mmol) in TFA (1.6 mL) at 5° C. was treated with Et$_3$SiH (93.6 mg, 0.81 mmol). The mixture was stirred 2 h and concentrated. The residue was diluted with sat. aq. NaHCO$_3$ (5 mL) and extracted with EtOAc (3×8 mL) The organic extracts were collected, dried, filtered and concentrated. The residue was purified by prep-HPLC (YMC Triart, 30×150 mm×7 μm, CH$_3$CN/H$_2$O (0.05% NH$_{40}$H), 46-66% over 10 min) to give the title compound (7.2 mg, 9%). $^1$H NMR (400 MHz, Methanol-d$_4$) δ 7.41-7.26 (m, 1H), 3.90-3.66 (m, 1H), 3.65-3.46 (m, 4H), 3.44-3.32 (m, 1H), 3.23-3.10 (m, 1H), 3.07 (d, 1H), 2.78 (d, 1H), 2.56-2.41 (m, 2H), 2.38-2.19 (m, 1H), 1.30 (s, 3H), 1.19-1.14 (m, 6H), 0.42 (dd, 1H), 0.25 (t, 1H); LC/MS m/z (M+H)$^+$=485.1.

Example 26: 2-((S)-2-(hydroxymethyl)morpholino)-N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)acetamide

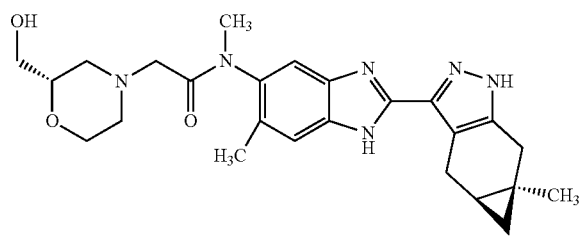 [SMILES: Cc1cc2[nH]c(-c3n[nH]c4c3C[C@@H]3C[C@]3(C)C4)nc2cc1N(C)C(=O)CN1CCO[C@H](CO)C1]

Step 1: 2-((S)-2-(hydroxymethyl)morpholino)-N-methyl-N-(6-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)acetamide

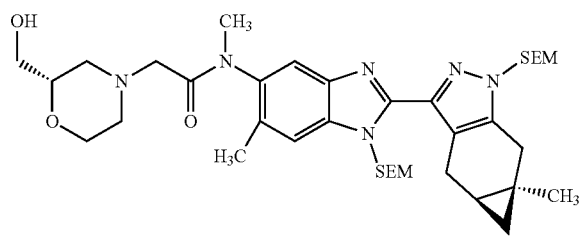 [SMILES: Cc1cc2c(cc1N(C)C(=O)CN1CCO[C@H](CO)C1)nc(-c1nn(COCC[Si](C)(C)C)c3c1C[C@@H]1C[C@]1(C)C3)n2COCC[Si](C)(C)C]

A solution of Preparation 98 (130 mg, 0.20 mmol) and (S)-morpholin-2-ylmethanol (26 mg, 0.22 mmol) in MeCN (5 mL) was treated with NaI (40 mg, 0.27 mmol) and $K_2CO_3$ (40 mg, 0.29 mmol). The mixture was heated at 80° C. for 16 h. The mixture was cooled to RT and concentrated. The residue was purified by chromatography (silica, EtOAc/PE=0-100%, then MeOH/EtOAc=0-20%) to give the title compound (108 mg, 74%). $^1$H NMR (400 MHz, Chloroform-d) δ 7.71 (s, 1H), 7.36 (d, 1H), 6.22-6.07 (m, 1H), 6.09-5.93 (m, 1H), 5.42 (q, 2H), 3.94-3.73 (m, 4H), 3.71-3.37 (m, 8H), 3.26 (s, 3H), 3.19-3.01 (m, 2H), 2.96-2.68 (m, 4H), 2.34 (s, 4H), 1.38-1.27 (m, 3H), 1.17-1.01 (m, 2H), 0.91 (t, 2H), 0.87-0.73 (m, 2H), 0.40 (s, 1H), 0.26 (d, 1H), −0.02 (s, 9H), −0.11 (t, 9H); LC/MS m/z $(M+H)^+$=725.4.

Step 2: 2-((S)-2-(hydroxymethyl)morpholino)-N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)acetamide

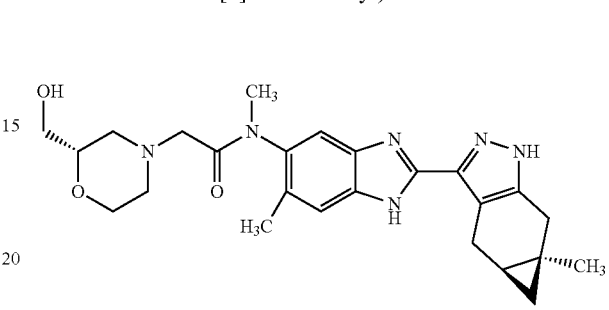

A solution of the silyl ether of step 1 (108 mg, 0.149 mmol) in DCM (5 mL) at 15° C. was treated with TFA (1.5 mL). The mixture was stirred at 15° C. for 2 h and concentrated. The residue was taken up in MeOH (5 mL) and treated with conc. $NH_4OH$ (2 mL). The mixture was stirred at RT for 2 h. The mixture was concentrated and the residue purified by preparative HPLC (Welch Xtimate 75 mm×40 mm×3 μm, 16 to 56% MeCN in 0.05% $NH_4OH$/water, 25 mL/min, 10 min) to give the title compound (16 mg, 23%). $^1$H NMR (400 MHz, $CD_3OD$) δ 7.68-7.39 (m, 2H), 3.77 (d, 1H), 3.72-3.52 (m, 2H), 3.52-3.40 (m, 2H), 3.40-3.33 (m, 2H), 3.24 (s, 3H), 3.19-2.93 (m, 3H), 2.86-2.59 (m, 4H), 2.35 (s, 3H), 2.19-2.04 (m, 1H), 1.85 (dt, 1H), 1.29 (s, 3H), 1.24-1.05 (m, 1H), 0.42 (dt, 1H), 0.24 (t, 1H); LC/MS m/z $(M+H)^+$=465.3.

The title compounds in the table below were prepared by the procedure described in Example 18, or a procedure analogous thereto (by employing DIPEA+$K_2CO_3$/NaI), from the appropriate amine and 2-chloro-N-methyl-N-(6-methyl-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)acetamide (Preparation 98).

| Ex | Structure and Name | Analytical Data |
|---|---|---|
| 27 | ![structure] 2-(2-(Hydroxymethyl)morpholino)-N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)acetamide | Prep HPLC Method 1.17 mg (18%). $^1$H NMR (400 MHz, $CD_3OD$) δ 7.69-7.26 (m, 2H), 3.77 (d, 1H), 3.72-3.53 (m, 2H), 3.50-3.36 (m, 2H), 3.37-3.30 (m, 2H), 3.24 (s, 3H), 3.19-2.95 (m, 3H), 2.85-2.68 (m, 3H), 2.64 (d, 1H), 2.35 (s, 3H), 2.16-2.02 (m, 1H), 1.84 (dt, 1H), 1.29 (s, 3H), 1.16 (dt, 1H), 0.42 (dd, 1H), 0.25 (t, 1H); LC/MS m/z $(M + H)^+$ = 465.1. |

| Ex | Structure and Name | Analytical Data |
|---|---|---|
| 28 | 2-((R)-2-(Hydroxymethyl)morpholino)-N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)acetamide | Prep HPLC conditions: Method 2. 66 mg (25%). $^1$H NMR (400 MHz, CD$_3$OD) δ 7.74-7.24 (m, 2H), 3.77 (d, 1H), 3.70-3.49 (m, 2H), 3.50-3.36 (m, 2H), 3.32 (d, 2H), 3.24 (s, 3H), 3.19-2.88 (m, 3H), 2.86-2.56 (m, 4H), 2.35 (s, 3H), 2.17-1.99 (m, 1H), 1.84 (dt, 1H), 1.29 (s, 3H), 1.22-1.10 (m, 1H), 0.42 (dd, 1H), 0.25 (s, 1H); LC/MS m/z (M + H)$^+$ = 465.2. |
| 29 | 2-(2,2-Dimethylmorpholino)-N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)acetamide | Prep HPLC conditions: Method 3; 53 mg (42%). $^1$H NMR (400 MHz, CD$_3$OD) δ 7.56 (s, 1H), 7.49 (s, 1H), 3.71 (d, 2H), 3.40-3.32 (m, 2H), 3.25 (s, 3H), 3.18-3.01 (m, 2H), 2.79 (t, 2H), 2.42 (s, 2H), 2.35 (s, 3H), 2.34-2.23 (m, 2H), 1.29 (s, 3H), 1.21 (s, 6H), 1.17-1.11 (m, 1H), 0.48-0.34 (m, 1H), 0.30-0.18 (m, 1H); LCMS m/z (M + H)$^+$ = 463.2. |
| 30 | N-Methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-((R)-2-methylmorpholino)acetamide | Prep HPLC conditions: Method 4; 5 mg (8%). $^1$H NMR (400 MHz, CD$_3$OD) δ 7.57 (s, 1H), 7.53-7.40 (m, 1H), 3.98-3.59 (m, 3H), 3.39-3.33 (m, 2H), 3.26 (s, 3H), 3.18-3.10 (m, 1H), 3.07 (d, 1H), 2.95-2.83 (m, 3H), 2.77 (d, 1H), 2.35 (s, 3H), 2.32-2.13 (m, 1H), 2.05-1.86 (m, 1H), 1.29 (s, 3H), 1.16 (dt, 1H), 1.07 (dd, 3H), 0.42 (dd, 1H), 0.25 (q, 1H); LC/MS m/z (M + H)$^+$ = 449.3. |
| 31 | N-Methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-((S)-2-methylmorpholino)acetamide | Prep HPLC conditions: Method 5; 19 mg (28%). $^1$H NMR (400 MHz, CD$_3$OD) δ 7.57 (s, 1H), 7.49 (S, 2H), 3.79 (dd, 1H), 3.75-3.60 (m, 2H), 3.44-3.33 (m, 2H), 3.26 (s, 3H), 3.18-3.10 (m, 1H), 3.07 (d, 1H), 2.99-2.81 (m, 2H), 2.77 (d, 1H), 2.35 (s, 3H), 2.32-2.16 (m, 1H), 2.01 (d, 1H), 1.29 (s, 3H), 1.16 (dt, 1H), 1.07 (dd, 3H), 0.42 (dd, 1H), 0.25 (td, 1H); LC/MS m/z (M + H)$^+$ = 449.3. |

| Ex | Structure and Name | Analytical Data |
|---|---|---|
| 32 | 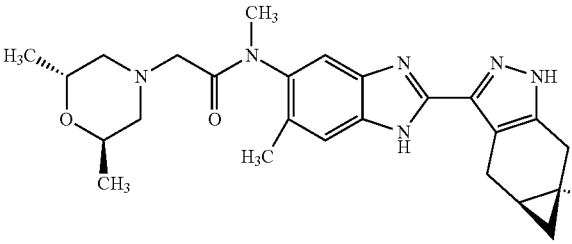<br>2-((2R,6R)-2,6-Dimethylmorpholino)-N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)acetamide | Prep HPLC conditions: Method 3; 24 mg (34%). $^1$H NMR (400 MHz, CD$_3$OD) δ 7.56 (s, 1H), 7.49 (s, 1H), 3.99 (d, 2H), 3.50-3.33 (m, 2H), 3.26 (d, 3H), 3.18-3.10 (m, 1H), 3.07 (d, 1H), 2.93-2.68 (m, 2H), 2.53 (s, 2H), 2.35 (d, 1H), 2.34-2.17 (m, 2H), 1.29 (s, 3H), 1.27-1.11 (m, 7H), 0.42 (dd, 1H), 0.30-0.19 (m, 1H); LC/MS m/z (M + H)$^+$ = 463.2. |
| 33 | 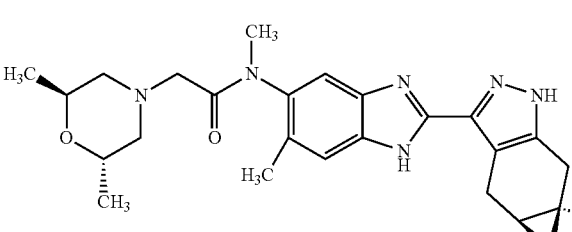<br>2-((2S,6S)-2,6-Dimethylmorpholino)-N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)acetamide | Prep HPLC conditions: Method 6; 28 mg (39%). $^1$H NMR (400 MHz, CD$_3$OD) δ 7.56 (s, 1H), 7.48 (d, 1H), 3.97 (tt, 2H), 3.42-3.33 (m, 1H), 3.25 (s, 3H), 3.18-3.10 (m, 1H), 3.07 (d, 1H), 2.98 (dd, 1H), 2.84-2.64 (m, 2H), 2.52-2.37 (m, 2H), 2.35 (d, 3H), 2.16 (dd, 2H), 1.29 (s, 3H), 1.18 (t, 7H), 0.42 (dd, 1H), 0.24 (td, 1H); LC/MS m/z (M + H)$^+$ = 463.2. |

Prep HPLC Conditions: Method 1: Welch Xtimate C18 100 mm×40 mm×3 μm, 22 to 52% MeCN in 0.05% NH$_4$OH/water, 25 mL/min, 10 min; Method 2 Welch Xtimate C18 100 mm×40 mm×3 μm, 32 to 52% MeCN in 0.05 NH$_4$OH/water, 25 mL/min, 10 min; Method 3: YMC-Actus Triart C18 100 mm×30 mm×5 μm, 42 to 62% MeCN in 0.05% NH$_4$OH/water, 35 mL/min, 10 min; Method 4: YMC-Actus Triart C18 100 mm×30 mm×5 μm, 38 to 48% MeCN in 0.05% NH$_4$OH/water, 35 mL/min, 10 min; Method 5: YMC-Actus Triart C18 100 mm×30 mm×5 μm, 40 to 60% MeCN in 0.05% NH$_4$OH/water, 35 mL/min, 10 min; Method 6: Welch Xtimate C18 150 mm×40 mm×10 μm, 21 to 61% MeCN in 0.225% formic acid in water, 60 mL/min, 10 min.

The title compounds in the table below were prepared by the procedure described for Example 3, from the appropriate acid and Preparation 46.

| Ex | Structure and Name | Analytical data |
|---|---|---|
| 34 | 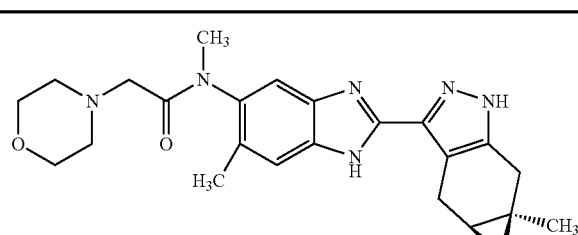<br>N-Methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinoacetamide | Prep HPLC conditions: Method 7; 44 mg (44%). $^1$H NMR (400 MHz, CD$_3$OD) δ 7.73-7.24 (m, 2H), 3.64 (t, 4H), 3.35 (d, 1H), 3.24 (d, 3H), 3.20-3.09 (m, 1H), 3.06 (d, 1H), 3.00 (dd, 1H), 2.75 (dd, 2H), 2.39 (s, 4H), 2.34 (s, 3H), 1.29 (s, 3H), 1.16 (dt, 1H), 0.42 (dd, 1H), 0.25 (t, 1H); |

| Ex | Structure and Name | Analytical data |
|---|---|---|
| 35 | 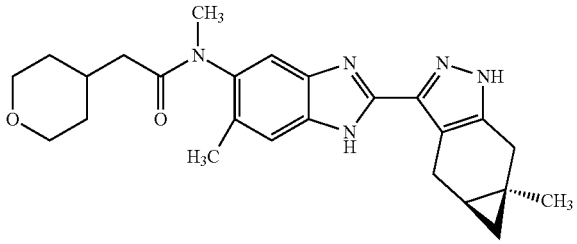 [SMILES: Cc1cc2[nH]c(-c3n[nH]c4c3C[C@@H]3C[C@]3(C)C4)nc2cc1N(C)C(=O)CC1CCOCC1]<br>N-Methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)acetamide | Prep HPLC conditions; Method 8; 36 mg (62%). $^1$H NMR (400 MHz, CD$_3$OD) δ 7.48 (s, 2H), 3.94-3.75 (m, 2H), 3.43-3.33 (m, 3H), 3.24 (d, 3H), 3.13 (dd, 1H), 3.06 (d, 1H), 2.77 (d, 1H), 2.32 (s, 3H), 2.05 (d, 2H), 1.87 (q, 1H), 1.68-1.46 (m, 2H), 1.29 (s, 3H), 1.13 (ddd, 3H), 0.42 (dd, 1H), 0.25 (t, 1H); LC/MS m/z (M + H)$^+$ = 434.3. |
| 36 | 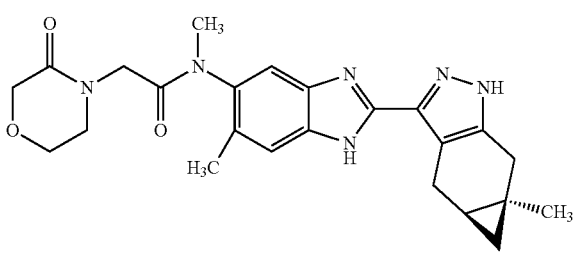 [SMILES: Cc1cc2[nH]c(-c3n[nH]c4c3C[C@@H]3C[C@]3(C)C4)nc2cc1N(C)C(=O)CN1CCOCC1=O]<br>N-Methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-(3-oxomorpholino)acetamide | Prep HPLC conditions: Method 9, retention time 2.30. LC/MS m/z (M + H)$^+$ = 449.0 |

Prep HPLC conditions: Method 7: Phenomenex Gemini-NX 150 mm×30 mm×5 μm, 19 to 59% 0.05% NH$_4$OH in MeCN/water, 30 mL/min, 10 min. Method 8: YMC-Actus Triart C18 100 mm×30 mm×5 μm, 40 to 60% MeCN in 0.05% NH$_4$OH/water, 35 mL/min, 10 min. Method 9: Agela Durashell C18 150 mm×25 mm×5 μm, i5-55% 0.225% formic acid in MeCN/water, 35 mL/min, 8 min gradient.

Example 37: (S)—N-(7-bromo-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

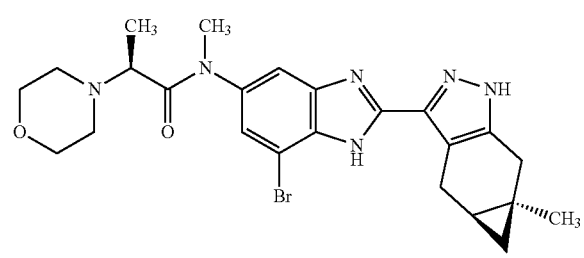 [SMILES: C[C@@H](C(=O)N(C)c1cc(Br)c2[nH]c(-c3n[nH]c4c3C[C@@H]3C[C@]3(C)C4)nc2c1)N1CCOCC1]

A solution of Et$_3$SiH (117 mg, 1.01 mmol) in TFA (5 mL) at 0° C. was treated with Preparation 102 (130 mg, 0.202 mmol). The mixture was stirred at 0° C. for 2 h and concentrated. The residue was taken up in MeOH, cooled to 0° C. and treated with conc. NH$_4$OH (1 mL). The mixture was concentrated and the residue was purified by preparative HPLC (Boston Prime C18 150 mm×30 mm×5 μm, 35 to 55% MeCN in 0.05% NH$_4$OH/water, 25 mL/min, 10 min) to give the title compound (38 mg, 36%). $^1$H NMR (400 MHz, DMSO-de) δ 13.05 (s, 1H), 12.96 (s, 1H), 7.42 (s, 1H), 7.40 (s, 1H), 3.48 (d, 5H), 3.31-3.23 (m, 1H), 3.19 (s, 3H), 3.16 (d, 1H), 3.00 (td, 2H), 2.74 (d, 1H), 2.47-2.36 (m, 1H), 2.23-2.01 (m, 2H), 1.25 (s, 3H), 1.13 (dt, 1H), 0.99 (d, 3H), 0.38 (dd, 1H), 0.17 (t, 1H); LC/MS m/z (M+H)$^+$=514.9 ($^{81}$Br).

Example 38: (S)—N-(7-cyano-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

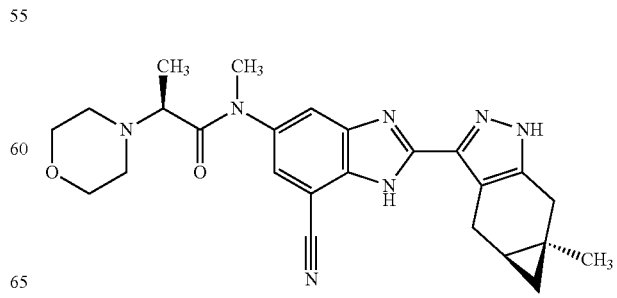

Step 1: (S)—N-(4-cyano-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-N-methyl-2-morpholinopropanamide

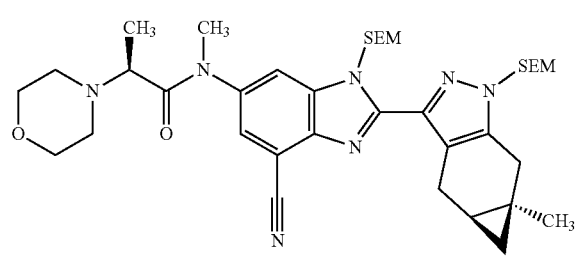 [SMILES: C[C@@H](C(=O)N(C)c1cc(C#N)c2nc(-c3nn(COCC[Si](C)(C)C)c4c3C[C@@H]3C[C@]3(C)C4)n(COCC[Si](C)(C)C)c2c1)N1CCOCC1]

A solution of Preparation 103 (160 mg, 0.207 mmol) in NMP (10 mL) was treated with Pd(Ph₃P)₄ (24 m, 0.021 mmol) and Zn(CN)₂ (121 mg, 1.03 mmol). The mixture was heated in a microwave reactor at 160° C. for 1 h. The mixture was cooled to RT and partitioned between water (10 mL) and EtOAc (50 mL). The organic layer was separated and the aqueous layer was extracted with additional EtOAc (50 mL). The combined organic layers were washed with brine, dried (Na₂SO₄), filtered and concentrated. The crude material was purified by chromatography (silica, EtOAc/PE=0-100%) to give the title compound (120 mg, 81%). LC/MS m/z (M+H)⁺=720.4.

Step 2: (S)—N-(7-cyano-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

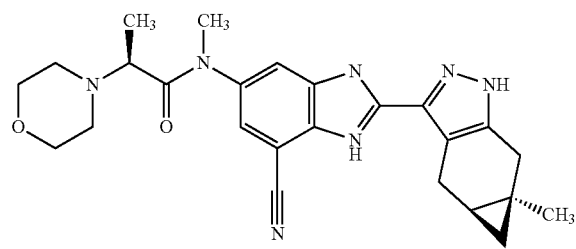 [SMILES: C[C@@H](C(=O)N(C)c1cc(C#N)c2nc(-c3n[nH]c4c3C[C@@H]3C[C@]3(C)C4)[nH]c2c1)N1CCOCC1]

A solution of Et₃SiH (81 mg, 0.694 mmol) in TFA (5 mL) at 0° C. was treated with the silyl ether of step 1 (100 mg, 0.139 mmol). The mixture was stirred at 0° C. for 2 h and concentrated. The residue was taken up in MeOH and cooled to 0° C. NH₄OH (1 mL) was added. The mixture was concentrated and the residue was purified by preparative HPLC (Boston Prime C18 150 mm×30 mm×5 μm, 22 to 47% MeCN in 0.2% formic acid in water, 25 mL/min, 10 min) to give the title compound (27 mg, 42%). ¹H NMR (400 MHz, DMSO-d₆) δ 13.35 (s, 1H), 13.09 (s, 1H), 7.73 (s, 2H), 3.53-3.40 (m, 5H), 3.20 (s, 3H), 3.14 (d, 1H), 3.02 (d, 2H), 2.75 (d, 1H), 2.37 (dd, 2H), 2.07 (s, 1H), 1.26 (s, 3H), 1.14 (s, 1H), 0.98 (d, 3H), 0.38 (dd, 1H), 0.17 (t, 1H); LC/MS m/z (M+H)⁺=460.2.

Example 39: (S)—N-(7-hydroxy-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

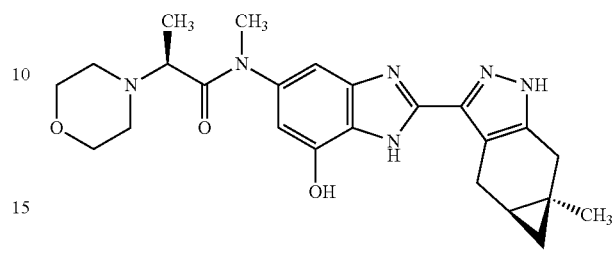

A solution of Et₃SiH (196 mg, 1.69 mmol) in TFA (5 mL) at 0° C. was treated with Preparation 105 (120 mg, 0.169 mmol). The mixture was stirred at 20° C. for 2 h and concentrated. The residue was taken up in MeOH, cooled to 0° C. and treated with conc. NH₄OH (1 mL). The mixture was concentrated and the residue was purified by preparative HPLC (Boston Prime C18 150 mm×30 mm×5 μm, 25 to 45% MeCN in 0.05% NH₄OH in water, 25 mL/min, 10 min) to give the title compound (28 mg, 37%). Analytical chiral SFC Column: Chiralpak AS-3 100 mm×4.6 mm×3 μm; Mobile phase: A/B: CO₂/EtOH (0.05% Et₂NH); Gradient: 5% to 40% of B in 4 min and hold 40% for 2.5 min, then 5% of B for 1.5 min; Flow rate: 2.8 mL/min Column temp.: 35° C. retention time=2.760 min; LC/MS m/z (M+H)⁺=451.2.

Example 40: (S)—N-(7-methoxy-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

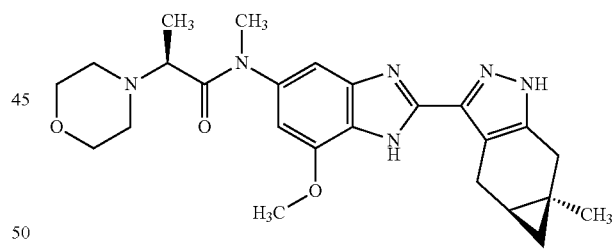

A solution of Et₃SiH (120 mg, 1.03 mmol) in TFA (5 mL) at 0° C. was treated with Preparation 106 (150 mg, 0.207 mmol). The mixture was stirred at 0° C. for 2 h and concentrated. The residue was taken up in MeOH and cooled to 0° C. The mixture was treated with conc. NH₄OH (1 mL), concentrated and the residue was purified by preparative HPLC (Boston Prime C18 150 mm×30 mm×5 μm, 32 to 55% MeCN in 0.05% NH₄OH/water, 25 mL/min, 10 min) to give the title compound (11.4 mg, 12%). ¹H NMR (400 MHz, DMSO-de) δ 12.84 (s, 1H), 12.70 (s, 1H), 6.96 (s, 1H), 6.60 (s, 1H), 3.96 (s, 3H), 3.49 (d, 5H), 3.39 (d, OH), 3.29 (td, 1H), 3.27-3.19 (m, 1H), 3.19 (s, 3H), 3.10-2.89 (m, 2H), 2.73 (d, 1H), 2.47-2.38 (m, 1H), 2.24 (d, 2H), 1.25 (s, 3H), 1.16-1.04 (m, 1H), 1.03 (d, 3H), 0.37 (dd, 1H), 0.16 (s, 1H); LC/MS m/z (M+H)⁺=465.1.

Example 41: (S)—N-methyl-N-(2-((4aS,5aR)-5a-methyl-1,4,4a,5,5a,6-hexahydrocyclopropa[f]indazol-3-yl)-7-(trifluoromethyl)-1H-benzo[d]imidazol-5-yl)-2-morpholinopropanamide

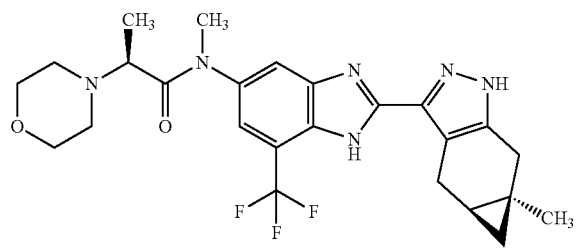 [SMILES: C[C@@H](C(=O)N(C)c1cc(C(F)(F)F)c2[nH]c(-c3n[nH]c4c3C[C@@H]3C[C@]3(C)C4)nc2c1)N1CCOCC1]

A solution of Et₃SiH (183 mg, 1.57 mmol) in TFA (5 mL) at 0° C. was treated with Preparation 112 (120 mg, 0.157 mmol). The mixture was stirred at RT for 2 h and concentrated. The residue was taken up in MeOH and cooled to 0° C. The mixture was treated with conc. NH₄OH (1 mL), concentrated and the residue was purified by preparative HPLC (Boston Prime C18 150 mm×30 mm×5 μm, 43 to 65% MeCN in 0.05% NH₄OH/water, 25 mL/min, 10 min) to give the title compound (50 mg, 63%). $^1$H NMR (400 MHz, DMSO-de) δ 13.23 (s, 1H), 13.02 (s, 1H), 7.68 (s, 1H), 7.50 (s, 1H), 3.55-3.37 (m, 4H), 3.30 (s, 2H), 3.22 (s, 3H), 3.13 (q, 1H), 3.08-2.90 (m, 2H), 2.75 (d, 1H), 2.45-2.30 (m, 1H), 2.14-1.93 (m, 2H), 1.25 (s, 3H), 1.12 (dd, 1H), 0.97 (d, 3H), 0.37 (dd, 1H), 0.17 (t, 1H); LC/MS m/z (M+H)⁺=503.1.

Example 42: (S)—N-(7-(methoxymethyl)-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

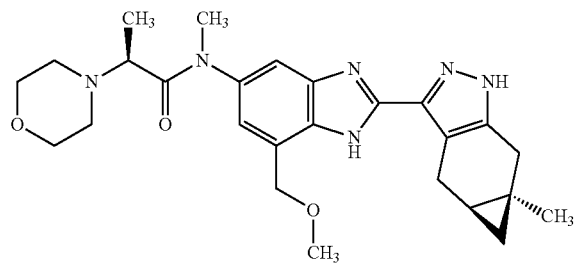 [SMILES: COCc1cc(N(C)C(=O)[C@H](C)N2CCOCC2)cc2nc(-c3n[nH]c4c3C[C@@H]3C[C@]3(C)C4)[nH]c12]

A solution of Preparation 117 (61 mg, 0.083 mmol) in DCE (0.7 mL) at RT was treated with TFA (0.6 mL). The mixture was stirred for 16 h and concentrated. The residue was taken up in EtOH (0.7 mL) and cooled to 0° C. The mixture was treated with conc. NH₄OH (0.2 mL) dropwise and the mixture was stirred at RT for 4 h. The mixture was diluted with water and extracted with 85:15% isopropanol/DCM (×3). The combined organic layers were dried (Na₂SO₄), filtered and concentrated. The residue was purified by preparative HPLC (XBridge C18 19 mm×100 mm×5 μm, 5-95% MeCN (0.03% NH₄OH)/water, 8.5 min, hold at 95% for 1.5 min, 25 mL/min) to give the title compound (23 mg, 59%). Retention time=1.74 min; LC/MS m/z (M+H)⁺=479.5.

Example 43: (S)—N-(7-chloro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

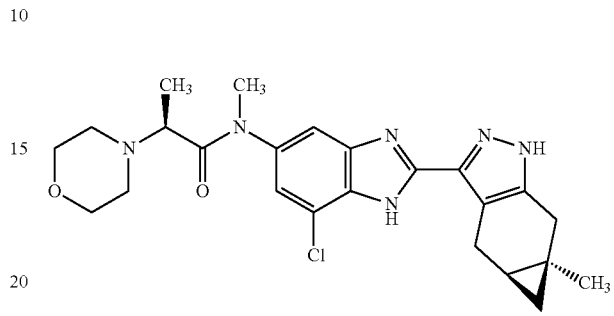

A solution of Preparation 122 (42 mg, 0.085 mmol) in TFA (0.6 mL) and DCE (0.5 mL) was stirred at RT for 2 h and treated with Et₃SiH (0.046 mL, 0.29 mmol). The mixture was stirred at RT for an additional 2 h. The mixture was concentrated and the residue was diluted with sat. aq. NaHCO₃. The mixture was extracted with EtOAc (×3). The combined organic extracts were dried (MgSO₄), filtered and concentrated. The crude material was purified by preparative HPLC (XBridge C18 19 mm×100 mm×5 μm, 5-95% MeCN (0.03% NH₄OH)/water, 8.5 min, hold at 95% for 1.5 min, 25 mL/min) to give the title compound (17.3 mg, 63%). Retention time=2.04 min; LC/MS m/z (M+H)⁺=469.6.

Example 44: (S)—N-(7-ethyl-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

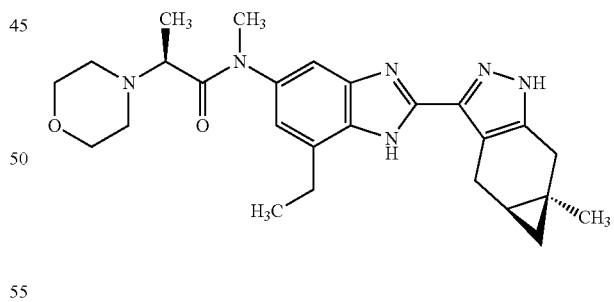

A solution of Preparation 126 (45 mg, 0.062 mmol) in DCE (0.5 mL) at RT was treated with TFA (0.2 mL) and Et₃SiH (24 mg, 0.21 mmol). The mixture was stirred for 16 h and concentrated. The residue was taken up in DCM and sat. aq. NaHCO₃. The layers were separated and the aqueous layer was extracted with EtOAc (×2). The combined organic layers were dried (MgSO₄), filtered and concentrated. The residue was purified preparative HPLC (XBridge C18 19 mm×100 mm×5 μm, 5-95% MeCN (0.03% NH₄OH)/water, 8.5 min, hold at 95% for 1.5 min, 25 mL/min) to give the title compound (6.1 mg, 21%). LC/MS m/z (M+H)⁺=463.6; Retention time 1.78 min.

Example 45: (S)—N-(7-(hydroxymethyl)-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

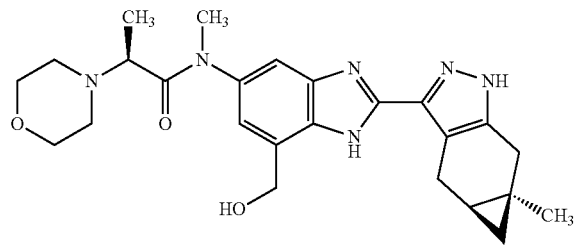 [SMILES: C[C@@H](C(=O)N(C)c1cc(CO)c2[nH]c(-c3n[nH]c4c3C[C@@H]3C[C@]3(C)C4)nc2c1)N1CCOCC1]

A solution of Preparation 132 (20 mg, 0.028 mmol) in DCE (0.3 mL) at 0° C. was treated with TFA (157 mg, 1.38 mmol). The mixture was warmed to RT and stirred for 20 h. The mixture was concentrated and taken up in EtOH, cooled to 0° C., treated with conc. NH$_4$OH (0.2 mL) and the mixture stirred for 3 h. The mixture was diluted with water and extracted with DCM (×4) and 15% isopropanol/DCM (×3). The combined organic layers were dried (Na$_2$SO$_4$), filtered and concentrated. The residue was purified by preparative HPLC (XBridge C18 19 mm×100 mm×5 μm, 5-95% MeCN (0.03% NH$_4$OH)/water, 8.5 min, hold at 95% for 1.5 min, 25 mL/min) to give the title compound (4.9 mg, 38%). Retention time=1.59; LC/MS m/z (M+H)$^+$=465.6.

Example 46: (S)—N-(7-fluoro-6-methyl-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

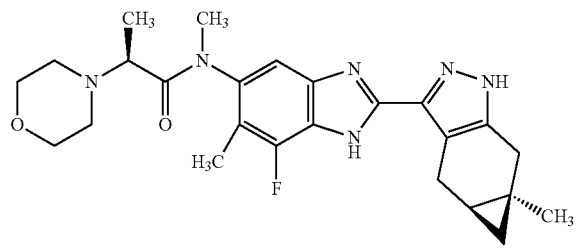 [SMILES: Cc1c(N(C)C(=O)[C@H](C)N2CCOCC2)cc2nc(-c3n[nH]c4c3C[C@@H]3C[C@]3(C)C4)[nH]c2c1F]

The title compound was prepared analogously to Example 1 from 138 (2.1 g, 3.52 mmol) and purified by prep HPLC (Chiralpak AD-3 50 mm×6 mm×3 μm, 40% isocratic (0.05% diethylamine in Et$_0$H/CO$_{2(g)}$) 4 mL/min, column temp=35° C.) to give the title compound (1.3 g, 79%). Retention time=0.38 min and 1.46 min; LC/MS m/z (M+H)$^+$=467.1.

Example 47: (S)—N-(6-fluoro-7-methyl-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

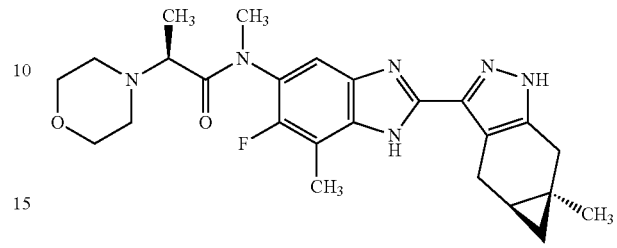

The title compound was prepared analogously to Example 41 from 5-bromo-4-fluoro-3-methylbenzene-1,2-diamine. Purified by prep HPLC conditions: Welch Xtimate 75 mm×40 mm×3 μm, 42 to 62% MeCN in 0.05% NH$_4$OH in water, 25 mL/min, 10 min) to give the title compound (234 mg, 74%). Analytical SFC (Chiralpak AS-3 100 mm×4.6 mm×3 μm, A: CO$_{2(g)}$; B: 0.05% diethylamine in EtOH; Gradient 5-40% B over 4 min, hold 40% B 2.5 min, 5% B for 1.5 min; 2.8 mL/min, column temp=35° C.), retention time=2.70 min; LC/MS m/z (M+H)$^+$=467.2.

Example 48: (S)—N-(7-(difluoromethyl)-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

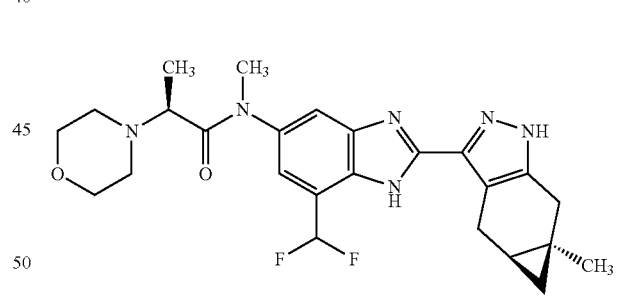

A solution of Preparation 144 (72 mg, 0.097 mmol) in DCE (0.6 mL) was treated with TFA (0.37 mL). The mixture was stirred at RT for 20 h. The mixture was concentrated and the resulting residue was dissolved in EtOH (1 mL), cooled to 0° C. and treated with conc. NH$_4$OH (0.7 mL). The mixture was stirred at RT for 3 h. The mixture was diluted with water and extracted with DCM (×4) followed by 15% isopropanol/DCM (×3). The combined organic extracts were dried (Na$_2$SO$_4$), filtered and concentrated. The residue was purified by prep HPLC (XBridge C18 19 mm×100 mm×5 μm, 5-95% MeCN (0.03% NH$_4$OH)/water, 8.5 min, hold at 95% for 1.5 min, 25 mL/min) to provide the title compound (27 mg, 57%). Retention time=2.16 min; LC/MS m/z (M+H)$^+$=485.6.

Example 49: (S)—N-(6-(2-methoxyethoxy)-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide

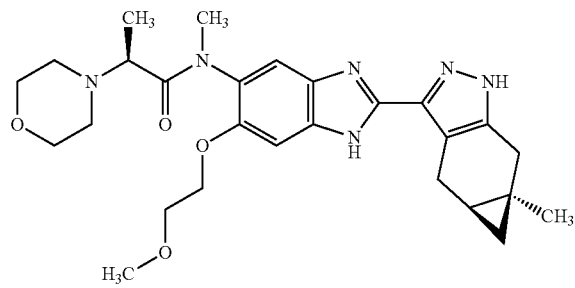 [SMILES: COCCOc1cc2[nH]c(-c3n[nH]c4c3C[C@@H]3C[C@]3(C)C4)nc2cc1N(C)C(=O)[C@H](C)N1CCOCC1]

A solution of Preparation 152 (160 mg, 0.25 mmol) in TFA (2.5 mL) at 5° C. was treated with Et₃SiH (146 mg, 1.25 mmol). The mixture was stirred 2 h and the mixture was concentrated. The residue was diluted with sat. aq. NaHCO₃ and extracted with EtOAc (3×8 mL). The organic extracts were combined, dried, filtered and concentrated. The residue was purified by prep-HPLC (Phenomenex Gemini, NX-C18, 75×30 mm×3 μm, water/CH₃CN (0.05% NH₄OH), 10-50% over 11 min) to give the title compound (2.5 mg, 2%). $^1$H NMR (400 MHz, CD₃OD) δ 7.67-7.16 (m, 2H), 4.26-4.18 (m, 2H), 3.81-3.72 (m, 2H), 3.65-357 (m, 4H), 3.40 (s, 3H), 3.24 (d, 3H), 3.19-3.01 (m, 2H), 2.77 (d, 1H), 2.57-2.36 (m, 4H), 1.30 (s, 3H), 1.27-1.08 (m, 3H), 0.42 (dd, 1H), 0.25 (t, 1H). LC/MS m/z (M+H)⁺=509.3.

Example 50: (S)—N-methyl-N-(7-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide

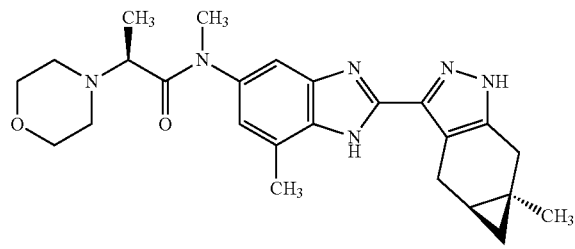 [SMILES: Cc1cc(N(C)C(=O)[C@H](C)N2CCOCC2)cc2nc(-c3n[nH]c4c3C[C@@H]3C[C@]3(C)C4)[nH]c12]

A solution of Preparation 158 (380 mg, 0.54 mmol) in TFA (5.4 mL) at RT was treated with Et₃SiH (321 mg, 2.7 mmol). The mixture was stirred at RT for 3 h and concentrated. The residue was made basic with sat. aq. NaHCO₃ and extracted with EtOAc (3×15 mL). The combined organic layers were concentrated. The residue was purified by preparative HPLC (YMC Triart 150 mm×30 mm×5 μm, 27 to 67% MeCN in 0.05% NH₄OH/water, 25 mL/min, 10 min) to give the title compound (108 mg, 45%). $^1$H NMR (400 MHz, CD₃OD) δ 7.36 (s, 1H), 6.99 (s, 1H), 3.62 (ddd, 4H), 3.36 (d, 1H), 3.31 (s, 3H), 3.26-3.10 (m, 2H), 3.07 (d, 1H), 2.78 (d, 1H), 2.63 (s, 3H), 2.54 (dt, 2H), 2.38 (dt, 2H), 1.30 (s, 3H), 1.20-1.14 (m, 3H), 1.16-1.13 (m, 1H), 0.41 (dd, 1H), 0.26 (t, 1H); LC/MS m/z (M+H)⁺=448.9.

Example 51: (S)—N-(2-((4aS,5aR)-5,5-difluoro-5a-methyl-1,4,4a,5,5a,6-hexahydrocyclopropa[f]indazol-3-yl)-7-methyl-1H-benzo[d]imidazol-5-yl)-N-methyl-2-morpholinopropanamide

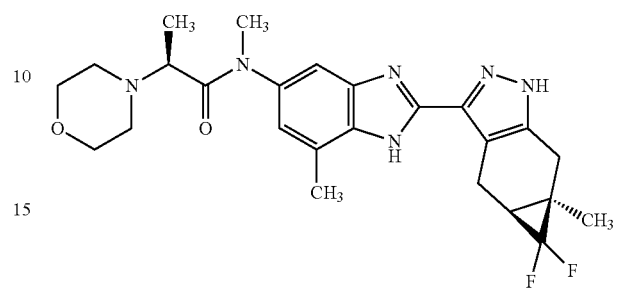

The title compound was prepared analogously to Example 41 from 5-bromo-3-methylbenzene-1,2-diamine and Preparation 17. Preparative HPLC conditions: Phenomenex Gemini-NX 150 mm×30 mm×5 μm, 24 to 64% MeCN in 0.05% NH₄OH/water, 25 mL/min, 9 min) to give the title compound (56 mg, 39%). $^1$H NMR (400 MHz, CD₃OD) δ 7.48-7.25 (m, 1H), 7.07-6.95 (m, 1H), 3.72-3.57 (m, 4H), 3.26-3.19 (m, 1H), 3.14 (br d, 1H), 2.87 (dd, 1H), 2.69-2.52 (m, 5H), 2.46-2.35 (m, 2H), 1.80-1.71 (m, 1H), 1.44 (s, 3H), 1.18 (d, 3H); LC/MS m/z (M+H)⁺=485.2.

Example 52: (S)—N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide

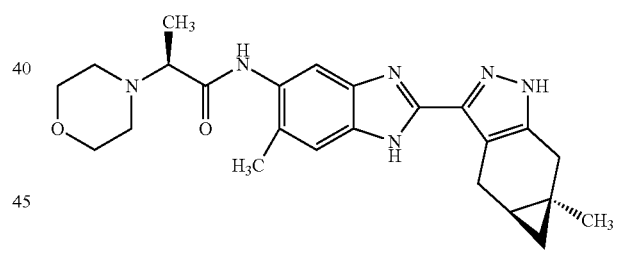

Step 1: 6-methyl-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-amine

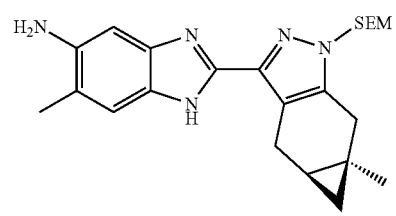 [SMILES: Cc1cc2[nH]c(-c3nn(COCC[Si](C)(C)C)c4c3C[C@@H]3C[C@]3(C)C4)nc2cc1N]

A solution of Preparation 66 (1.50 g, 3.22 mmol) in ethanol (20 mL) was treated with aq. NaOH (10M, 6.44 mL, 64.4 mmol) at 15° C. The mixture was stirred at 90° C. for 18 h. The mixture was concentrated and the residue was extracted with EtOAc (3×100 mL). The combined organic layers were concentrated and crude product purified by chromatography (silica, EtOAc/PE=30-50%) to deliver the title compound (984 g, 72%). LC/MS m/z (M+H)$^+$=423.9.

Step 2: (S)—N-(6-methyl-2-((4aS,5aR)-5a-methyl-1-((2-(trimethylsilyl)ethoxy)methyl)-1,4,4a,5,5a,6-hexahydrocyclopropa[f]indazol-3-yl)-1H-benzo[d]imidazol-5-yl)-2-morpholinopropanamide

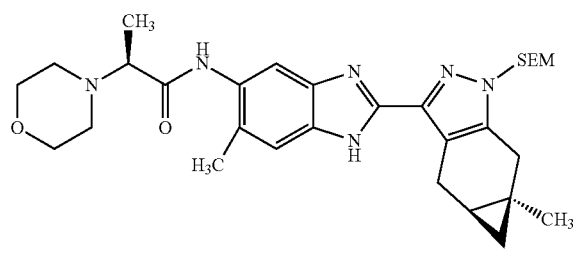 [SMILES: Cc1cc2[nH]c(-c3nn(COCC[Si](C)(C)C)c4c3C[C@@H]3C[C@]3(C)C4)nc2cc1NC(=O)[C@H](C)N1CCOCC1]

Title compound was prepared analogously to Example 6 Step 1 from Preparation 16 (115 mg, 0.59 mmol) and silyl ether of step 1 (208 mg, 0.491 mmol) to deliver the title compound (216 mg. 78%). 1H NMR (400 MHz, CDCl$_3$) δ 9.62-9.51 (m, 1H), 8.41-7.62 (m, 1H), 5.42-5.35 (m, 2H), 3.85-3.78 (m, 3H), 3.59-3.55 (m, 2H), 3.27-3.17 (m, 2H), 2.75-2.60 (m, 9H), 2.44-2.40 (m, 2H), 1.40-1.15 (m, 8H), 0.92-0.85 (m, 2H), 0.42-0.38 (m, 1H), 0.01--0.08 (m, 9H); LC/MS m/z (M+H)$^+$=565.1. Step 3: (S)—N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide

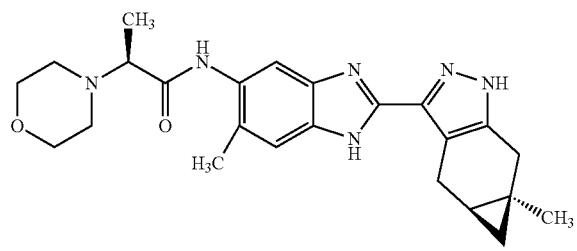 [SMILES: Cc1cc2[nH]c(-c3n[nH]c4c3C[C@@H]3C[C@]3(C)C4)nc2cc1NC(=O)[C@H](C)N1CCOCC1]

Title compound was prepared analogously to Example 6 Step 2 using silyl ether of step 2 (0.216 g, 0.382 mmol) and was purified by prep HPLC (Phenomenex Gemini NX-C18 30 mm×74 mm×3 μm, 17-57% MeCN (0.05% NH$_4$OH)/water, 11 min, 25 mL/min) to provide the title compound (81 mg, 49%). $^1$H NMR (400 MHz, CD$_3$OD) δ 7.91 (s, 1H), 7.45 (br. s, 1H), 3.85-3.78 (m, 4H), 3.30-3.25 (m, 1H), 3.17-3.13 (m, 1H), 3.09-2.76 (m, 2H), 2.72-2.64 (m, 4H), 2.43 (s, 3H), 1.41-1.39 (m, 3H), 1.30 (m, 3H), 1.19-1.15 (m, 1H), 0.44-0.39 (m, 1H), 0.26-0.24 (m, 1H); LC/MS m/z (M+H)$^+$=435.1.

Example 53: (S)—N-(2-((4aS,5aR)-5,5-difluoro-5a-methyl-1,4,4a,5,5a,6-hexahydrocyclopropa[f]indazol-3-yl)-5-methyl-1H-benzo[d]imidazol-6-yl)-N-methyl-2-morpholinopropanamide

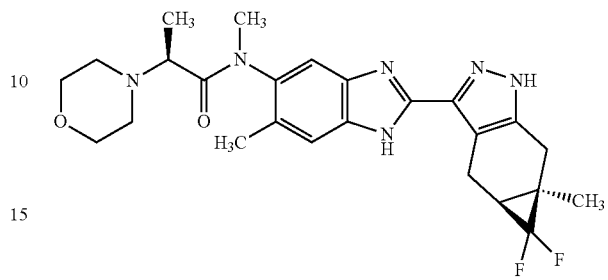

Step 1: (S)—N-(2-((4aS,5aR)-5,5-difluoro-5a-methyl-1-((2-(trimethylsilyl)ethoxy)methyl)-1,4,4a,5,5a,6-hexahydrocyclopropa[f]indazol-3-yl)-5-methyl-1H-benzo[d]imidazol-6-yl)-N-methyl-2-morpholinopropanamide

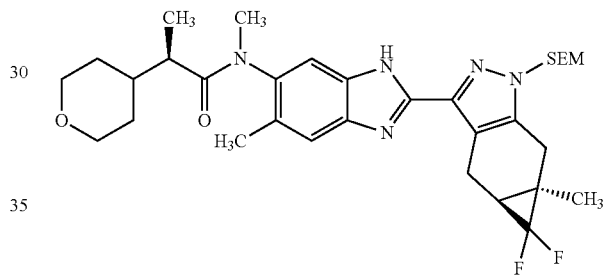

A mixture of preparation 17 (260 mg, 0.75 mmol) and Na$_2$S$_2$O$_5$ (65 mg, 0.34 mmol) was treated with a solution of preparation 32 (200 mg, 0.68 mmol), in DMF (5 mL). The mixture was treated with DMSO (1 mL) and heated at 110° C. for 18 h. The mixture was cooled to RT and poured into ice-water and extracted using EtOAc. The layers were separated and the organic phase washed with brine, dried (MgSO$_4$), filtered and concentrated to give Step 1 title compound (550 mg). LC/MS m/z (M+H)$^+$=615.3, Step 2: (S)—N-(2-((4aS,5aR)-5,5-difluoro-5a-methyl-1,4,4a,5,5a,6-hexahydrocyclopropa[f]indazol-3-yl)-5-methyl-1H-benzo[d]imidazol-6-yl)-N-methyl-2-morpholinopropanamide

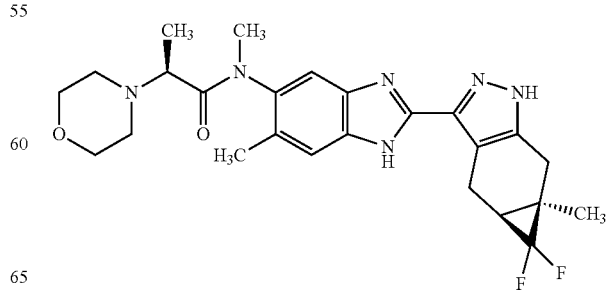

To silyl ether from Step 1 (0.55 g, 0.72 mmol) cooled to 0° C. was added TFA (10 mL) followed by Et₃SiH (0.83 mg, 7.16 mmol). The mixture was warmed to RT and stirred for 1.5 h. The mixture was concentrated, neutralized using aq. sat. NaHCO₃ (20 mL), then extracted using EtOAc. The organic layers were combined, washed with brine, dried (MgSO₄), filtered and concentrated. The crude product was purified by reverse phase HPLC (Phenomenex Gemini C18, 250×50 mm×7 µM, water (0.05% NH₄OH)/MeCN from 30 to 50% over 10 min, 35 ml/min) to give title compound (0.19 g, 55%). SFC method: Chiral Tech OD-3, 50 mm×4.6 mm×3 µm, 5 to 40% with 0.05% diethyl amine in EtOH/CO$_{2(g)}$, 4.0 mL/min, column temperature 35° C., retention time=1.58 min (43.1%) and 1.65 min (56.8%), 100% ee. LC/MS m/z (M+H)⁺=485.3.

Example 54: N-(6-cyano-2-((4aS,5aR)-5a-methyl-1,4,4a,5,5a,6-hexahydrocyclopropa[f]indazol-3-yl)-1H-benzo[d]imidazol-5-yl)-N-methyl-2-(tetrahydro-2H-pyran-4-yl)acetamide

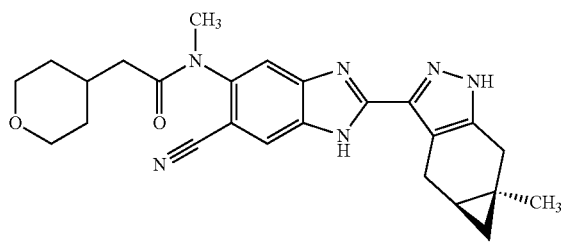 [SMILES: CN(C(=O)CC1CCOCC1)c1cc2nc(-c3n[nH]c4c3C[C@@H]3C[C@]3(C)C4)[nH]c2cc1C#N]

Step 1: N-(5-cyano-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-6-yl)-N-methyl-2-(tetrahydro-2H-pyran-4-yl)acetamide and N-(6-cyano-2-((4aS,5aR)-5a-methyl-1-((2-(trimethylsilyl)ethoxy)methyl)-1,4,4a,5,5a,6-hexahydrocyclopropa[f]indazol-3-yl)-1-((2-(trimethylsilyl)ethoxy)methyl)-1H-benzo[d]imidazol-5-yl)-N-methyl-2-(tetrahydro-2H-pyran-4-yl)acetamide

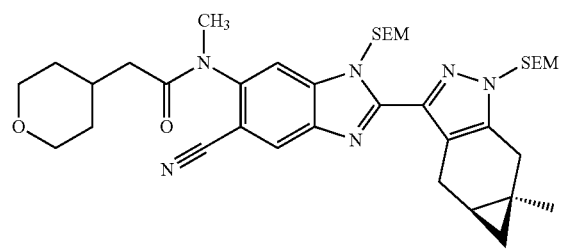

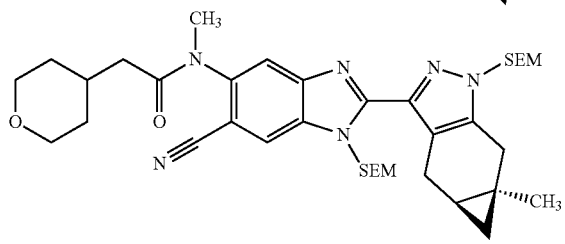

To a solution of Preparation 164 (100.0 mg, 0.1727 mmol) in DMF (5.0 mL) was added 2-(tetrahydro-2H-pyran-4-yl) acetic acid (25 mg 0.17 mmol), N,N,N',N'-tetramethylchloroformamidinium hexafluorophosphate (72.7 mg, 0.259 mmol) and N-methylimidazole; (28.4 mg, 0.345 mmol) at RT, then the reaction mixture was stirred at 60 C for 16 h. The reaction mixture was treated with 3% aq. LiCl (10 mL) and extracted with EtOAc (3×5 mL). The combined organic layers were washed with brine (10 mL) and concentrated. The crude product was purified by chromatography (silica, EtOAc/PE=0-100%) to give the title compounds as a mixture (104 mg, 85%). LC/MS m/z (M+H)⁺=705.3

Step 2: N-(6-cyano-2-((4aS,5aR)-5a-methyl-1,4,4a,5,5a,6-hexahydrocyclopropa[f]indazol-3-yl)-1H-benzo[d]imidazol-5-yl)-N-methyl-2-(tetrahydro-2H-pyran-4-yl)acetamide

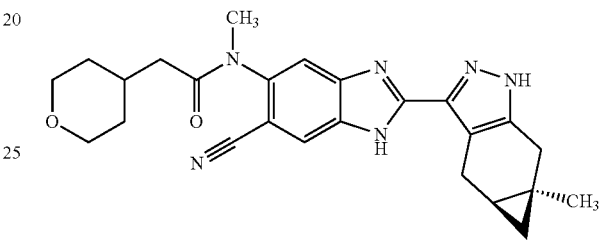

A solution of the silyl ethers from step 1 (40 mg, 0.07 mmol) in TFA (2.0 mL) was cooled to 0° C. and Et₃SiH (41 mg, 0.35 mmol) was added. The reaction was stirred at 0° C. for 2 h. The mixture was concentrated, neutralized with conc. NH₄OH (20 mL) and extracted with EtOAc (×2). The combined organic extracts were washed with brine, then dried (MgSO₄), filtered and concentrated. The crude product was purified by reverse phase HPLC (Phenomenex Gemini NX, 75×30 mm×3 µM, water (0.05% NH₄OH)/MeCN from 13 to 53% over 9 min, 30 ml/min) to give the title compound (14.86 mg, 48%). SFC method: Chiral Tech OD-3, 50 mm×4.6 mm×3 µm, 5 to 40% with 0.05% diethyl amine in EtOH/CO$_{2(g)}$, 2.8 mL/min, column temperature 35° C., retention time=5.03 min (100%), 100% ee. ¹H NMR (400 MHz, DMSO-de) δ 13.09 (s, 1H), 13.04 (s, 1H), 8.27 (s, 0.5H), 8.13 (s, 0.5H), 7.95 (s, 0.5H), 7.55 (0.5H), 3.83 (d, 5H), 3.31 (m, 1H), 3.03 (d, 2H), 2.83 (d, 2H), 2.76 (d, 1H), 2.17 (s, 1H), 1.67 (d, 2H), 1.34 (qd, 2H), 1.26 (s, 4H), 1.23 (s, 1H), 1.13 (s, 1H), 0.42-0.35 (m, 1H), 0.18 (s, 1H); LC/MS m/z (M+H)⁺=445.2

Example 55: (R)—N-(7-cyano-2-((4aS,5aR)-5a-methyl-1,4,4a,5,5a,6-hexahydrocyclopropa[f]indazol-3-yl)-1H-benzo[d]imidazol-5-yl)-N-methyl-2-(tetrahydro-2H-pyran-4-yl)propanamide

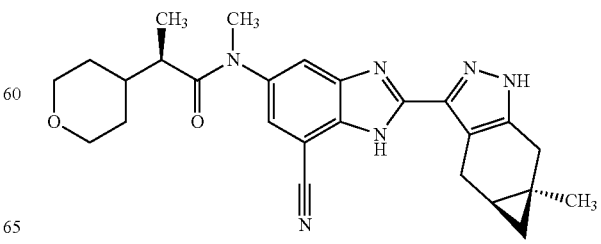

To a Preparation 173 (82 mg, 0.18 mmol) cooled to 0° C. was added a mixture of TFA (5 mL) and Et$_3$SiH (206 mg, 1.77 mmol). The mixture was stirred at RT for 15 h and the solvent was removed. The residue was dissolved in MeOH (10 mL) and treated with NH$_4$OH (1 mL). The solvent was removed, and the crude material purified by prep-HPLC (Boston Prime C-18 150×30 mm×5 μm, H$_2$O/CH$_3$CN with 0.05% NH$_4$OH, 40-65% over 10 min, 25 mL/min) to give the title compound (35 mg, 68%). $^1$H NMR (400 MHz, DMSO-d$_6$) δ 7.66 (bs, 1H), 7.58 (s, 1H), 3.76 (t, 2H), 3.48 (d, 1H), 3.35-3.26 (m, 2H), 3.20 (s, 4H), 3.02 (d, 2H), 2.76 (d, 1H), 2.11-1.95 (m, 1H), 1.66-1.58 (m, 1H), 1.48 (d, 2H), 1.26 (s, 3H), 1.19-0.97 (m, 1H), 0.93 (d, 3H), 0.88-0.80 (m, 1H), 0.39 (dd, 1H), 0.17 (t, 1H). Chiral SFC (Chiralpak AD-3, 50×4.6 mm, 3 μm, CO$_2$/iPrOH with 0.05% Et$_2$NH, 5 to 40% 2 min, hold 1.2 min, 4 mL/min, T=35° C.) Rt=1.785 min (100% ee). LC/MS m/z (M+H)$^+$=459.1.

Example 56: (S)—N-(methyl-$^{13}$C-d$_3$)-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide

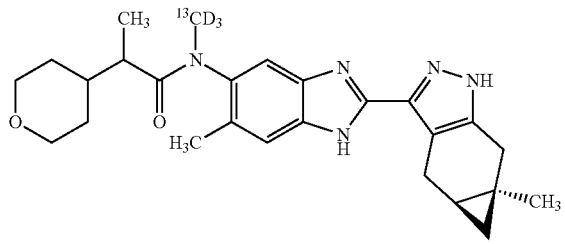

Example 56 was prepared following the procedure described for Example 1 with iodomethane-$^{13}$CD$_3$ in place of iodomethane to deliver 550 mg of the title compound. Analytical HPLC method: Eclipse XDB-C18 150 mm×4.6 mm×3.5 μm; H$_2$O/MeCN: 10-90% over 10 min, 1.0 mL/min, retention time=7.605 min (99.6%), LC/MS m/z (M+H)$^+$=453.2.

Biological Assays

In Vitro Studies
IL-2-Inducible T-Cell Kinase (ITK) Activity, IC$_{50}$ (nM)
ITK activity was determined by measuring the effect of a test compound in an ITK enzyme assay.

1.0M HEPES Buffer pH 7.5 solution was prepared as follows: 238.3 g HEPES free acid (Sigma) and 800 mL of water were combined, and the mixture was stirred until complete dissolution. The pH was adjusted to 7.5 via titration with 5N NaOH and the volume adjusted to 1000 mL. The solution was filtered and sterilized.

ITK assay buffer was prepared as follows: 50 mL of HPLC-grade water was treated with 2 mL of 1.0M HEPES Buffer, 500 μL of 2% Gelatin (Sigma), 1.0 mL of aqueous MgCl$_2$ solution (1.0M), and 1.0 mL of aqueous glutathione solution (0.5M), and the solution was mixed. The solution was brought to 99 mL in a graduated cylinder by addition of water and sterilized through a 0.2 μm filter. 0.1 mL of Brij-35™ Surfact-Amps™ Detergent Solution (10% w/v aqueous solution, ThermoFisher) and 1.0 mL of ATP (Teknova,100 mM) were added and the solution was mixed.

Preparation of 1.33× ITK enzyme solution was as follows: 49.99 mL of ITK assay buffer was treated with 4.1 μL of ITK enzyme (ITK FL (N-Flag and C-His tagged, ~72 kDa) Lake Pharma, 0.25 mg/ml in a buffer containing 25 mM Tris pH 7.8, 150 mM NaCl, 10% glycerol and 2 mM TCEP) and the mixture was gently agitated. The resulting solution was stored on ice. 30 Minutes prior to use, the enzyme solution was removed from ice and equilibrated to RT by incubation in a RT water bath.

Preparation of 4× ITK substrate solution was as follows: 50 mL of ITK assay buffer was treated with 100 μL of BTK peptide (China Peptide Company, 2 mM stock solution in DMSO). The tube was capped, mixed by gently inverting the tube, and then stored on ice. 30 Minutes prior to use, the substrate solution was removed from ice and equilibrated to RT by incubation in a RT water bath.

At the time of assay, 7.5 μL of the 1.33× ITK enzyme solution was added to plate wells containing 0.1 μL of varying concentrations of test compound in DMSO. The plate was incubated 30 min at RT. The plate wells were each treated with 2.5 uL of the 4× ITK substrate solution and the plate was sealed (TopSeal™, Perkin Elmer). The plate was spun at 1000 rpm for 30 sec and then incubated for 60 min at RT. The seal was removed, and each well was treated with 10 μL of Stop/Detect Buffer (20 mM HEPES pH 7.5, 0.01% gelatin, 1 nM LANCE PT66 (Perkin Elmer), 16.5 μg/ml Surelight APC (Perkin Elmer), 10 mM EDTA, 250 mM NaCl). The plate was again covered and was spun at 1000 rpm for seconds. The plate was allowed to incubate overnight at RT and in a closed carrier to reduce dehydration. The seal was removed, and the fluorescence was read with a plate reader with an excitation wavelength of 665 nm and an emission wavelength of 615 nm. The concentrations and resulting effect values for the tested compound were plotted and the concentration of compound required for 50% effect (IC$_{50}$) was determined with the four-parameter logistic dose response equation.

IC$_{50}$ (uM) values for compounds of the invention are presented in the Table that follows.

IL-2-Inhibition Activity, IC$_{50}$ (uM)
IL-2 inhibition activity in supernatants from activated CD$_4$+ human T-cells was determined by measuring the effect of a test compound on the activity using the cisbio HTRF™ technology.

Human CD$_4$+ T cells were activated with CD$_3$/CD$_{28}$ for 3 days and expanded for an additional 4-6 days (7 to 9 days total). On day 0, frozen CD$_4$+ T cells were thawed, treated with CD$_3$/CD28 Dynabeads, and incubated at 37° C./5% CO$_2$. On day 3, the beads were removed, and the cells were diluted to 5×10$^5$ cells/cm$^2$, placed in G-Rex10 flask, and incubated at 37° C./5% CO$_2$. On day 7 to day 9 the cells were removed from the G-Rex flasks, counted and diluted back to 1×10$^6$ cells/ml in standard tissue culture flask.

The expanded CD$_4$+ T-cells were centrifuged at 300×g for 10 minutes and resuspended to 0.5 million cells per ml (30,000 cells/well). 60 μl of CD$_4$+ T cells were added per well to a 384 well plate containing 0.1 μL of varying concentrations of test compound in DMSO. The plates were incubated for 15 min at 37° C./5% CO$_2$. 20 μl of diluted ImmunoCult™ (STEMCELL Technologies, 1:12.5 in T cell assay media) were added to all wells of the plate (1:50 final assay concentration). The plates were incubated for an additional 20 to 24 hrs at 37° C./5% CO$_2$. The plates were centrifuged at 300×g for 10 minutes. 16 μL of supernatant was removed and combined with 4 μl of IL-2 HTRF Abs. (cisbio kit). Plates were incubated for 3 hours at RT and read with an EnVision plate reader at 665 nm and 615 nm wavelengths. The concentrations and resulting effect values for the tested compound were plotted and the concentration of compound required for 50% effect ($IC_{50}$) was determined with the four-parameter logistic dose response equation.

$IC_{50}$ (uM) values for compounds of the invention are presented in the Table that follows.

Tropomyosin Receptor Kinase a (TRKA) Activity, % Inhibition

Assays to determine TRKA activity are known in the art; e.g. see those described in:

Skerratt S E, et al. J. Med. Chem. (2016), 59(22): 10084-10099 PMID: 27766865. DPI: 10.1021/acs.jmedchem.6b00850

Bagal S K, et al. J. Med. Chem. (2018), 61(15):6779-6800 PMID: 29944371. DPI: 10.1021/acs.jmedchem.8b00633

TRKA, also known as neurotrophic tyrosine kinase receptor type 1 (NTKR1) activity was determined by measuring the effect of a test compound on the activity against the NTRK1 enzyme using the ThermoFisher Z'-LYTE Assay fluorescence-based coupled enzyme format (www.thermofisher.com/selectscreen). Test compounds were screened at a fixed concentration of 1 uM and the % inhibition was determined compared to controls at a fixed ATP concentration of 1 mM. The resulting effect value for the tested compound was compared to the assay controls to determine the % inhibition (%).

% Inhibition (%) values for compounds of the invention are presented in the Table that follows.

TABLE

In Vitro Study Data

| Ex # | ITK $IC_{50}$ (uM)[1] | ITK count (n) | IL-2 $IC_{50}$ (uM)[2] | IL-2 count (n) | TRKA % inhibition (%)[3] | TRKA count (n) |
|---|---|---|---|---|---|---|
| 1 | 0.006 | 13 | 0.039 | 14 | 108 | 2 |
| 2 | NT | | NT | | NT | |
| 3 | 0.016 | 3 | 0.113 | 3 | 97 | 2 |
| 4 | 0.003 | 3 | 0.022 | 3 | 95 | 2 |
| 5 | 0.005 | 2 | 0.027 | 2 | NT | |
| 6 | 0.011 | 3 | 0.101 | 3 | 102 | 2 |
| 7 | 0.002 | 9 | 0.013 | 7 | 106 | 2 |
| 8 | 0.005 | 2 | 0.026 | 2 | NT | |
| 9 | 0.020 | 2 | 0.099 | 3 | 99 | 2 |
| 10 | 0.007 | 3 | 0.067 | 3 | 104 | 2 |
| 11 | 0.003 | 3 | 0.034 | 3 | 107 | 2 |
| 12 | 0.003 | 3 | 0.025 | 4 | 94 | 2 |
| 13 | 0.001 | 63 | 0.003 | 6 | 99 | 6 |
| 14 | 0.003 | 61 | 0.042 | 7 | 92 | 4 |
| 15 | 0.004 | 4 | 0.042 | 4 | 107 | 2 |
| 16 | 0.005 | 4 | 0.065 | 6 | 116 | 2 |
| 17 | 0.005 | 2 | 0.045 | 3 | NT | |
| 18 | 0.009 | 3 | 0.091 | 3 | 100 | 2 |
| 19 | 0.009 | 3 | 0.057 | 3 | 98 | 4 |
| 20 | 0.005 | 3 | 0.053 | 3 | 98 | 2 |
| 21 | 0.009 | 3 | 0.098 | 3 | 91 | 2 |
| 22 | 0.044 | 3 | 0.340 | 3 | 93 | 2 |
| 23 | 0.124 | 3 | 0.304 | 3 | 101 | 2 |
| 24 | 0.008 | 3 | 0.106 | 4 | 105 | 2 |
| 25 | 0.013 | 3 | 0.101 | 3 | 101 | 2 |
| 26 | 0.012 | 4 | 0.212 | 2 | 99 | 2 |
| 27 | 0.017 | 3 | 0.289 | 2 | NT | |
| 28 | 0.019 | 3 | 0.305 | 3 | NT | |
| 29 | 0.012 | 3 | 0.058 | 4 | NT | |
| 30 | 0.015 | 3 | 0.082 | 4 | NT | |
| 31 | 0.013 | 3 | 0.075 | 4 | 99 | 2 |
| 32 | 0.016 | 3 | 0.083 | 4 | 99 | 2 |
| 33 | 0.011 | 3 | 0.068 | 4 | NT | |
| 34 | 0.010 | 2 | 0.103 | 3 | 98 | 2 |
| 35 | 0.006 | 3 | 0.050 | 3 | NT | |
| 36 | 0.005 | 3 | 0.096 | 3 | 97 | 2 |

TABLE-continued

In Vitro Study Data

| Ex # | ITK $IC_{50}$ (uM)[1] | ITK count (n) | IL-2 $IC_{50}$ (uM)[2] | IL-2 count (n) | TRKA % inhibition (%)[3] | TRKA count (n) |
|---|---|---|---|---|---|---|
| 37 | 0.009 | 2 | 0.130 | 3 | 96 | 2 |
| 38 | 0.007 | 3 | 0.085 | 3 | 96 | 2 |
| 39 | 0.008 | 3 | 0.082 | 3 | 97 | 2 |
| 40 | 0.019 | 3 | 0.103 | 3 | 96 | 2 |
| 41 | 0.034 | 4 | 0.176 | 4 | 96 | 2 |
| 42 | 0.038 | 3 | 0.200 | 4 | 98 | 2 |
| 43 | 0.016 | 3 | 0.171 | 3 | 96 | 2 |
| 44 | 0.028 | 4 | 0.219 | 3 | 94 | 4 |
| 45 | 0.017 | 4 | 0.365 | 3 | 97 | 2 |
| 46 | 0.006 | 3 | 0.047 | 4 | 95 | 4 |
| 47 | 0.029 | 3 | 0.161 | 3 | 98 | 2 |
| 48 | 0.017 | 4 | 0.207 | 3 | 95 | 2 |
| 49 | 0.012 | 2 | 0.100 | 2 | 98 | 2 |
| 50 | 0.016 | 5 | 0.126 | 3 | 97 | 2 |
| 51 | 0.002 | 4 | 0.019 | 4 | 97 | 2 |
| 52 | 0.121 | 3 | 0.274 | 3 | 109 | 2 |
| 53 | 0.001 | 3 | 0.010 | 4 | 96 | 2 |
| 54 | 0.272 | 3 | 4.570 | 2 | NT | |
| 55 | 0.005 | 4 | 0.041 | 3 | 89 | 2 |
| 56 | NT | | NT | | NT | |

Key:
[1]ITK $IC_{50}$ values are presented as a geometric mean of count n
[2]IL-2 $IC_{50}$ values are presented as a geometric mean of count n
[3]TRKA % inhibition values are presented as an arithmetic mean of count n
NT means not tested All references mentioned hereinabove are incorporated by reference in their entirety.

The invention claimed is:

1. A compound of Formula (I)

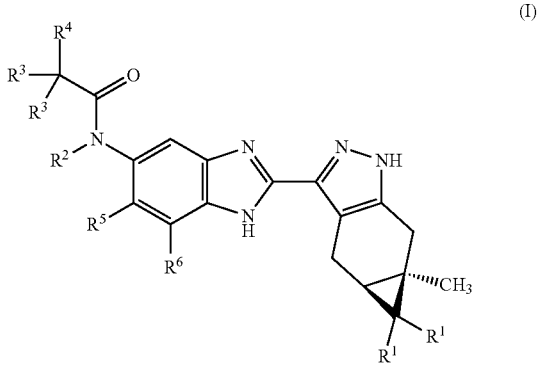

or a pharmaceutically acceptable salt thereof, or a pharmaceutically acceptable solvate of said compound or said salt, wherein:

each $R^1$ is independently H or F;

$R^2$ is H, $(C_1-C_4)$alkyl, hydroxy$(C_1-C_4)$alkyl, $(C_1-C_4)$alkoxy$(C_1-C_4)$alkyl or $(C_1-C_4)$alkyl substituted by one, two or three F;

each $R^3$ is independently H, F, $(C_3-C_5)$cycloalkyl, $(C_1-C_4)$alkyl or $(C_1-C_4)$alkyl substituted by one, two or three F; or both $R^3$ taken together with the carbon atom to which they are attached form $(C_3-C_5)$cycloalkyl;

R⁴ is selected from

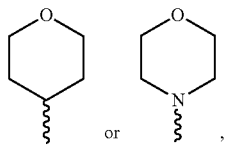

wherein each heterocycle is optionally substituted by one or two substituents independently selected from oxo, (C1-C4) alkyl, hydroxy(C1-C4)alkyl and (C1-C4)alkyl substituted by one, two or three F; and R⁵ and R⁶ are independently H; halogen; OH; CN; ($C_1$-$C_6$)alkyl; hydroxy($C_1$-$C_6$)alkyl; ($C_1$-$C_4$)alkoxy($C_1$-$C_6$)alkyl; ($C_1$-$C_6$)alkyl substituted by one, two or three F; ($C_1$-$C_6$)alkoxy; or ($C_1$-$C_6$)alkoxy substituted by ($C_1$-$C_4$)alkoxy.

2. A compound according to claim 1, or a pharmaceutically acceptable salt thereof, or a pharmaceutically acceptable solvate of said compound or said salt, wherein each $R^1$ is H.

3. A compound according to claim 1, or a pharmaceutically acceptable salt thereof, or a pharmaceutically acceptable solvate of said compound or said salt, wherein $R^2$ is H or (C1-C4)alkyl.

4. A compound according to claim 3, or a pharmaceutically acceptable salt thereof, or a pharmaceutically acceptable solvate of said compound or said salt, wherein $R^2$ is methyl.

5. A compound according to claim 1, or a pharmaceutically acceptable salt thereof, or a pharmaceutically acceptable solvate of said compound or said salt, wherein each $R^3$ is independently H, F or ($C_1$-$C_4$)alkyl.

6. A compound according to claim 5, or a pharmaceutically acceptable salt thereof, or a pharmaceutically acceptable solvate of said compound or said salt, wherein each $R^3$ is independently H, F or methyl.

7. A compound according to claim 6, or a pharmaceutically acceptable salt thereof, or a pharmaceutically acceptable solvate of said compound or said salt, wherein one $R^3$ is H and the other $R^3$ is methyl.

8. A compound according to claim 7 of Formula (Ia)

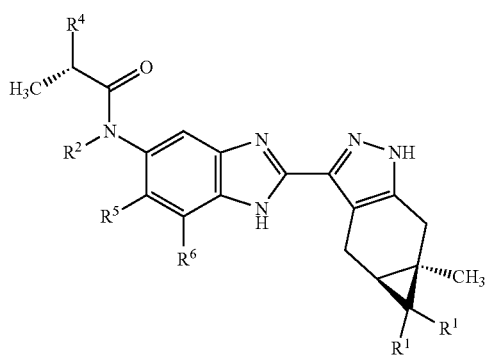

(Ia)

or a pharmaceutically acceptable salt thereof, or a pharmaceutically acceptable solvate of said compound or said salt.

9. A compound according to claim 1, or a pharmaceutically acceptable salt thereof, or a pharmaceutically acceptable solvate of said compound or said salt, wherein $R^4$ is

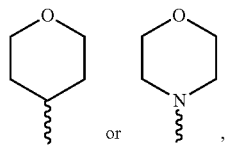

optionally substituted by one or two substituents independently selected from oxo, ($C_1$-$C_4$)alkyl and hydroxy(C1-C4) alkyl.

10. A compound according to claim 9, or a pharmaceutically acceptable salt thereof, or a pharmaceutically acceptable solvate of said compound or said salt, wherein $R^4$ is

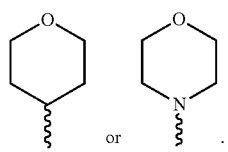

11. A compound according to claim 10, or a pharmaceutically acceptable salt thereof, or a pharmaceutically acceptable solvate of said compound or said salt, wherein $R^4$ is

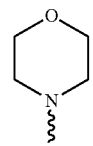

12. A compound according to claim 1, or a pharmaceutically acceptable salt thereof, or a pharmaceutically acceptable solvate of said compound or said salt, wherein $R^5$ and $R^6$ are independently H; halogen; OH; CN; ($C_1$-$C_3$)alkyl; hydroxy($C_1$-$C_3$)alkyl; (C1-C3)alkoxy(C1-C3)alkyl; (C1-C3)alkyl substituted by one, two or three F; (C1-C3)alkoxy; or (C1-C3)alkoxy substituted by (C1-C3)alkoxy.

13. A compound according to claim 12, or a pharmaceutically acceptable salt thereof, or a pharmaceutically acceptable solvate of said compound or said salt, wherein $R^5$ is H, halogen, CN, ($C_1$-$C_3$)alkyl, ($C_1$-$C_3$)alkoxy or ($C_1$-$C_3$)alkoxy substituted by ($C_1$-$C_3$)alkoxy.

14. A compound according to claim 13, or a pharmaceutically acceptable salt thereof, or a pharmaceutically acceptable solvate of said compound or said salt, wherein $R^6$ is H; halogen; OH; CN; ($C_1$-$C_3$)alkyl; hydroxy($C_1$-$C_3$)alkyl; ($C_1$-$C_3$)alkoxy($C_1$-$C_3$)alkyl; ($C_1$-$C_3$)alkyl substituted by one, two or three F; or ($C_1$-$C_3$)alkoxy.

15. A compound according to claim 1, or a pharmaceutically acceptable salt thereof, or a pharmaceutically acceptable solvate of said compound or said salt, selected from:
(S)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide;
(R)—N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl-)propanamide;
(R)—N-(7-fluoro-2-(4aS,5aR)-5a-methyl-1,4,4a,5,5a,6-hexahydrocyclopropa[f]indazol-3-yl)-1H-benzo[d]imidazol-5-yl)-N-methyl-2-(tetrahydro-2H-pyran-4-yl) propanamide;

(S)—N-(7-fluoro-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

(S)—N-ethyl-N-(7-fluoro-2-((4aS,5aR)-5a-methyl-1,4,4a,5,5a,6-hexahydrocyclopropa[f]indazol-3-yl)-1H-benzo[d]imidazol-5-yl)-2-morpholinopropanamide;

(S)—N-(6,7-difluoro-2-(4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide;

(S)—N-(6,7-difluoro-2-(4aS,5aR)-5a-methyl-1,4,4a,5,5a,6-hexahydrocyclopropa[f]indazol-3-yl)-1H-benzo[d]imidazol-5-yl)-N-ethyl-2-morpholinopropanamide;

(S)—N-(7-fluoro-6-methyl-2-((4aS,5aR)-5a-methyl-1,4,4a,5,5a,6-hexahydrocyclopropa[f]indazol-3-yl)-1H-benzo[d]imidazol-5-yl)-N-methyl-2-morpholinopropanamide; and (S)—N-methyl-N-(7-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide.

16. The compound according to claim 15 which is (S)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide, or a pharmaceutically acceptable salt thereof, or a pharmaceutically acceptable solvate of said compound or said salt.

17. The compound according to claim 15 which is (R)—N-methyl-N-(2-((4aS,5aR)-5a-methyl-1,4,4a,5,5a,6-hexahydrocyclopropa[f]indazol-3-yl)-1H-benzo[d]imidazol-5-yl)-2-(tetrahydro-2H-pyran-4-yl)propanamide, or a pharmaceutically acceptable salt thereof, or a pharmaceutically acceptable solvate of said compound or said salt.

18. The compound according to claim 16 which is (S)—N-methyl-N-(6-methyl-2-((4aS,5aR)-5a-methyl-1,4,4a,5,5a,6-hexahydrocyclopropa[f]indazol-3-yl)-1H-benzo[d]imidazol-5-yl)-2-morpholinopropanamide, or a hydrate thereof.

19. A compound which is (S)—N-methyl-N-(6-methyl-2-(4aS,5aR)-5a-methyl-1,4,4a,5,5a,6-hexahydrocyclopropa[f]indazol-3-yl)-1H-benzo[d]imidazol-5-yl)-2-morpholinopropanamide, dihydrate.

20. A compound which is

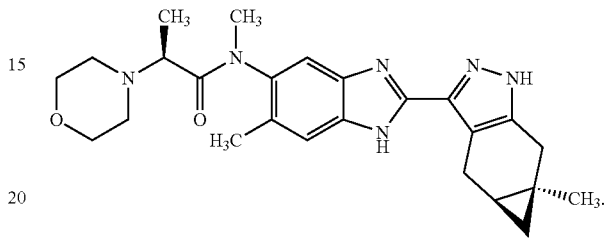

21. A pharmaceutical composition comprising a compound according to claim 1 and a pharmaceutically acceptable excipient.

22. The pharmaceutical composition according to claim 21 adapted for topical administration.

23. The pharmaceutical composition according to claim 22 including one or more additional therapeutic agents.

* * * * *